US009045381B2

(12) United States Patent
Milstein et al.

(10) Patent No.: US 9,045,381 B2
(45) Date of Patent: Jun. 2, 2015

(54) RUTHENIUM COMPLEXES AND THEIR USES IN PROCESSES FOR FORMATION AND/OR HYDROGENATION OF ESTERS, AMIDES AND DERIVATIVES THEREOF

(75) Inventors: David Milstein, Rehovot (IL); Ekambaram Balaraman, Rehovot (IL); Chidambaram Gunanathan, Rehovot (IL); Boopathy Gnanaprakasam, Rehovot (IL); Jing Zhang, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/880,328

(22) PCT Filed: Oct. 11, 2011

(86) PCT No.: PCT/IL2011/000817
§ 371 (c)(1),
(2), (4) Date: Jun. 11, 2013

(87) PCT Pub. No.: WO2012/052996
PCT Pub. Date: Apr. 26, 2012

(65) Prior Publication Data
US 2013/0281664 A1  Oct. 24, 2013

Related U.S. Application Data

(60) Provisional application No. 61/394,387, filed on Oct. 19, 2010.

(51) Int. Cl.
| | |
|---|---|
| *B01J 31/18* | (2006.01) |
| *C07B 41/08* | (2006.01) |
| *C07C 29/136* | (2006.01) |
| *C07C 29/149* | (2006.01) |
| *C07C 29/17* | (2006.01) |
| *C07C 41/16* | (2006.01) |

(Continued)

(52) U.S. Cl.
CPC ............... *C07B 41/08* (2013.01); *B01J 31/18* (2013.01); *B01J 31/189* (2013.01); *B01J 2231/40* (2013.01); *B01J 2231/643* (2013.01); *B01J 2531/0244* (2013.01); *B01J 2531/821* (2013.01); *C07C 29/136* (2013.01); *C07C 29/149* (2013.01); *C07C 29/177* (2013.01); *C07C 41/16* (2013.01); *C07C 45/006* (2013.01); *C07C 51/23* (2013.01); *C07C 67/00* (2013.01); *C07C 67/03* (2013.01); *C07C 209/62* (2013.01); *C07C 213/00* (2013.01); *C07C 231/02* (2013.01); *C07C 231/10* (2013.01); *C07C 2101/10* (2013.01); *C07C 2101/14* (2013.01); *C07D 207/08* (2013.01); *C07D 213/38* (2013.01); *C07D 241/08* (2013.01); *C07D 241/12* (2013.01); *C07D 295/023* (2013.01); *C07D 307/14* (2013.01);

*C07D 307/33* (2013.01); *C07D 307/83* (2013.01); *C07D 309/30* (2013.01); *C07D 487/14* (2013.01); *C07F 9/582* (2013.01); *C07F 15/0046* (2013.01); *C07F 15/0053* (2013.01); *C08G 69/00* (2013.01); *C07C 51/02* (2013.01); *C07C 51/295* (2013.01); *C07B 41/02* (2013.01); *C07B 41/12* (2013.01); *C07B 43/06* (2013.01); *C07C 45/002* (2013.01); *C07C 209/00* (2013.01); *C07C 213/02* (2013.01); *C07F 9/65583* (2013.01); *C07K 1/00* (2013.01)

(58) Field of Classification Search
None
See application file for complete search history.

(56) References Cited

U.S. PATENT DOCUMENTS

| | | | |
|---|---|---|---|
| 4,788,289 A | 11/1988 | Su et al. | |
| 4,855,431 A | 8/1989 | Chang et al. | |

(Continued)

FOREIGN PATENT DOCUMENTS

| | | |
|---|---|---|
| CN | 1569813 | 1/2005 |
| CN | 1820850 | 8/2006 |

(Continued)

OTHER PUBLICATIONS

Chardon-Noblat, Silvie et al; "Electroshnthesis, physico-chemical and electrocatalytic properties of a novel electroactive ru(0) material based on the (ru(terpy)(co)) fram (terpy-2,2":6',2"-terpyridine)." J. Electroanal. Chem. (2002) 529 p. 135-144.*

(Continued)

*Primary Examiner* — Maury Audet
*Assistant Examiner* — Fred Reynolds
(74) *Attorney, Agent, or Firm* — Winston & Strawn LLP

(57) ABSTRACT

The present invention relates to novel Ruthenium catalysts and related borohydride complexes, and the use of such catalysts, inter alia, for (1) hydrogenation of amides (including polyamides) to alcohols and amines; (2) preparing amides from alcohols with amines (including the preparation of polyamides (e.g., polypeptides) by reacting dialcohols and diamines and/or by polymerization of amino alcohols); (3) hydrogenation of esters to alcohols (including hydrogenation of cyclic esters (lactones) or cyclic di-esters (di-lactones) or polyesters); (4) hydrogenation of organic carbonates (including polycarbonates) to alcohols and hydrogenation of carbamates (including polycarbamates) or urea derivatives to alcohols and amines; (5) dehydrogenative coupling of alcohols to esters; (6) hydrogenation of secondary alcohols to ketones; (7) amidation of esters (i.e., synthesis of amides from esters and amines); (8) acylation of alcohols using esters; (9) coupling of alcohols with water to form carboxylic acids; and (10) dehydrogenation of beta-amino alcohols to form pyrazines. The present invention further relates to the novel uses of certain pyridine Ruthenium catalysts.

21 Claims, 8 Drawing Sheets

(51) Int. Cl.

| | | |
|---|---|---|
| C07C 45/00 | (2006.01) | |
| C07C 51/23 | (2006.01) | |
| C07C 67/00 | (2006.01) | |
| C07C 67/03 | (2006.01) | |
| C07C 209/62 | (2006.01) | |
| C07C 213/00 | (2006.01) | |
| C07C 231/02 | (2006.01) | |
| C07C 231/10 | (2006.01) | |
| C07D 207/08 | (2006.01) | |
| C07D 213/38 | (2006.01) | |
| C07D 241/08 | (2006.01) | |
| C07D 241/12 | (2006.01) | |
| C07D 295/023 | (2006.01) | |
| C07D 307/14 | (2006.01) | |
| C07D 307/33 | (2006.01) | |
| C07D 307/83 | (2006.01) | |
| C07D 309/30 | (2006.01) | |
| C07D 487/14 | (2006.01) | |
| C07F 9/58 | (2006.01) | |
| C07F 15/00 | (2006.01) | |
| C08G 69/00 | (2006.01) | |
| C07C 51/02 | (2006.01) | |
| C07C 51/295 | (2006.01) | |
| C07B 41/02 | (2006.01) | |
| C07B 41/12 | (2006.01) | |
| C07B 43/06 | (2006.01) | |
| C07C 209/00 | (2006.01) | |
| C07C 213/02 | (2006.01) | |
| C07F 9/6558 | (2006.01) | |
| C07K 1/00 | (2006.01) | |

(56) References Cited

U.S. PATENT DOCUMENTS

| 7,709,689 | B2 | 5/2010 | Kilner |
|---|---|---|---|
| 2009/0112005 | A1 | 4/2009 | Milstein et al. |
| 2011/0042227 | A1 | 2/2011 | Corbea |
| 2012/0253042 | A1 | 10/2012 | Milstein |

FOREIGN PATENT DOCUMENTS

| CN | 1850330 | 10/2006 |
|---|---|---|
| CN | 101587779 | 11/2009 |
| CN | 101602015 | 12/2009 |
| CN | 101961661 | 2/2011 |
| CN | 102010447 | 4/2011 |
| CN | 102030657 | 4/2011 |
| CN | 102489315 | 6/2012 |
| CN | 102600888 | 7/2012 |
| CN | 202356105 | 8/2012 |
| CN | 102690162 | 9/2012 |
| CN | 103420796 | 12/2013 |
| CN | 103420797 | 12/2013 |
| EP | 0286280 | 10/1988 |
| EP | 2 161 251 A1 | 3/2010 |
| JP | 2003146966 | 5/2003 |
| JP | 2004345964 | 12/2004 |
| JP | 2006063050 | 3/2006 |
| JP | 2008285454 | 11/2008 |
| JP | 2010063986 | 3/2010 |
| WO | 03093208 | 11/2003 |
| WO | 2008035123 | 3/2008 |
| WO | 2010/018570 A1 | 2/2010 |

OTHER PUBLICATIONS

Ziessel, Raymond et al; "Co-ordinative properties of a hybrid phosphine-bipyridine ligand." J. Chem. Soc. Dalton Trans. (1997) p. 3777-3784.*

Hino et al, Chem. Lett. (2004) 33(12) p. 1596-1597.*
Masaoka et al, Chem. Lett. (2009) 38(2) p. 182-183.*
Naota et al., (1991) "Ruthenium-Catalyzed Transformations of Amino Alcohols to Lactams," Synlett, (10):693-694.
Nordstrom et al., (2008) "Amide Synthesis from Alcohols and Amines by the Extrusion of Dihydrogen," J. Am. Chem. Soc., 130(52):17672-17673.
Núñez Magro et al., (2007) "The synthesis of amines by the homogeneous hydrogenation of secondary and primary amides," Chem. Commun., 3154-3156.
Owston et al., (2007) "Iridium-Catalyzed Conversion of Alcohols into Amides via Oximes," Organic Letters, 9(1):73-75.
Pérez-Picaso et al., (2009) "Efficient Microwave Assisted Syntheses of 2,5-Diketopiperazines in Aqueous Media," Molecules, 14(8):2836-2849.
Rannard et al., (2000) "The Selective Reaction of Primary Amines with Carbonyl Imidazole Containing Compounds: Selective Amide and Carbamate Synthesis," Organic Letters, 2(14):2117-2120.
Sandoval et al., (2003) "Mechanism of Asymmetric Hydrogenation of Ketones Catalyzed by BINAP/1,2-Diamine-Ruthenium(II) Complexes," J. Am. Chem. Soc., 125(44):13490-13503.
Shimizu et al., (2009) "Direct Dehydrogenative Amide Synthesis from Alcohols and Amines Catalyzed by γ-Alumina Supported Silver Cluster," Chem. Eur. J., 15:9977-9980.
Smith et al., (2002) "Efficient Synthesis of Halomethyl-2,2'-Bipyridines: 4,4'-Bis(Chloromethyl)-2,2'-Bipyridine," Organic Syntheses, 78:82-90.
Statler et al., (1984) "Alkyl, hydrido-, and Related Compounds of Ruthenium(II) with Trimethylphosphine. X-Ray Crystal Structures of Hydrido(tetrahydroborato-HH')tris(trimethylphosphine)ruthenium(II), tri-µ-chloro-bis[tris(trimethylphosphine)ruthenium(II)] Tetrafluoroborate, and Bis[cis-methyltetrakis(trimethylphosphine)ruthenio]mercury(II)-Tetrahydrofuran(1/1)," J. Chem. Soc., Dalton Trans., 1731-1738.
Tamaru et al., (1983) "Direct Oxidative Transformation of Aldehydes to Amides by Palladium Catalysis," Synthesis 1983(6):474-476.
Tillack et al., (2001) "Catalytic Amination of Aldehydes to Amides," Eur. J. Org. Chem., 2001:523-528.
Tillack et al., (2006) "A novel ruthenium-catalyzed amination of primary and secondary alcohols," Tetrahedron Letters, 47(50):8881-8885.
Watanabe et al., (1984) "Ruthenium-Catalyzed N-Alkylation and N-Benzylation of Aminoarenes with Alcohols," J. Org. Chem., 49:3359-3363.
Watson et al., (2009) "Ruthenium-Catalyzed Oxidation of Alcohols into Amides," Organic Letters, 11(12):2667-2670.
Williams et al., (1998) "Variable NMR Spin-Lattice Relaxation Times in Secondary Amides: Effect of Ramachandran Angles on Librational Dynamics," J. Phys. Chem. B, 102:6248-6259.
Zeng et al., (2011) "Direct Synthesis of Polyamides via Catalytic Dehydrogenation of Diols and Diamines," J. Am. Chem. Soc., 133(5):1159-1161.
Zhang et al., (2004) "Electron-Rich, Bulky Ruthenium PNP-Type Complexes. Acceptorless Catalytic Alcohol Dehydrogenation," Organometallics, 23(17):4026-4033.
Zhang et al., (2005) "Facile Conversion of Alcohols into Esters and Dihydrogen Catalyzed by New Ruthenium Complexes," J. Am. Chem. Soc., 127(31):10840-10841.
Zhang et al., (2006) "Efficient Homogeneous Catalytic Hydrogenation of Esters to Alcohols," Angew. Chem. Int. Ed., 45(7):1113-1115.
Zhang et al., (2007) "Electron-rich, bulky PNN-type ruthenium complexes: synthesis, characterization and catalysis of alcohol dehydrogenation," Dalton Trans., 1:107-113.
Zhang et al., (2011) "Electron-Rich PNP- and PNN-Type Ruthenium(II) Hydrido Borohydride Pincer Complexes. Synthesis, Structure, and Catalytic Dehydrogenation of Alcohols and Hydrogenation of Esters," Organometallics, 30(21):5716-5724.
Zhao et al., (2005) "Acceptorless, Neat, Ruthenium-Catalyzed Dehydrogenative Cyclization of Diols to Lactones," Organometallics, 24(10):2441-2446.
Ziessel et al., (1997) "Co-ordinative properties of a hybrid phosphine-bipyridine ligand," J. Chem. Soc., Dalton Trans., 20:3777-3784.

(56) References Cited

OTHER PUBLICATIONS

Zweifel et al., (2009) "Catalyzed Dehydrogenative Coupling of Primary Alcohols with Water, Methanol, or Amines," Angew. Chem., 121(3):567-571.
Abbenhuis et al., (1998) "Ruthenium-Complex-Catalyzed N-(Cyclo)alkylation of Aromatic Amines with Diols. Selective Synthesis of N-(ω-Hydroxyalkyl)anilines of Type PhNH(CH2)nOH and of Some Bioactive Arylpiperazines," J. Org. Chem., 63:4282-4290.
Adair et al., (2005) "Oxidant-free oxidation: ruthenium catalysed dehydrogenation of alcohols," Tetrahedron Letters, 46(47):8233-8235.
Ahmad et al., (1974) "Complexes of Ruthenium, Osmium, Rhodium, and Iridium Containing Hydride Carbonyl, or Nitrosyl Ligands," Inorganic Syntheses, John Wiley & Sons, Inc., Hoboken, NJ, USA, vol. 15, pp. 45-64.
Albrecht et al., (2001) "Platinum Group Organometallics Based on 'Pincer' Complexes: Sensors, Switches, and Catalysts," Angew. Chem. Int. Ed., 40(20):3750-3781.
Balaraman et al., (2010) "Direct Hydrogenation of Amides to Alcohols and Amines under Mild Conditions," J. Am. Chem. Soc., 132(47):16756-16758.
Balaraman et al., (2011) "Efficient hydrogenation of organic carbonates, carbamates and formates indicates alternative routes to methanol based on CO2 and CO," Nature Chemistry, 3(8):609-614.
Beamson et al., (2010) "Selective hydrogenation of amides using Rh/Mo catalysts," Journal of Catalysis, 269(1):93-102.
Beamson et al., (2010) "Selective Hydrogenation of Amides using Ruthenium/Molybdenum Catalysts," Adv. Synth. Catal., 352(5):869-883.
Ben-Ari et al., (2006) "Metal-Ligand Cooperation in C—H and H2 Activation by an Electron-Rich PNP Ir(I) System: Facile Ligand Dearomatization-Aromatization as Key Steps," J. Am. Chem. Soc., 128:15390-15391.
Blum et al., (1985) "Catalytically reactive (η4-tetracyclone)(CO)2(H)2Ru and related complexes in dehydrogenation of alcohols to esters," Journal of Organometallic Chemistry, 282(1):C7-C10.
Bonnet et al., (2005) "Lanthanide mono(borohydride) complexes of diamide-diamine donor ligands: novel single site catalysts for the polymerisation of methyl methacrylate," Dalton Trans., 7(3):421-423.
Bray, (2003) "Large-scale manufacture of peptide therapeutics by chemical synthesis," Nature Reviews, 2(7):587-593.
Cantillo, (2011) "Mechanistic Insights on the Ruthenium-Catalyzed Hydrogenation of Amides—C—N vs. C—O Cleavage," Eur. J. Inorg. Chem., 2011(19):3008-3013.
Cassidy et al., (2006) "Practical Synthesis of Amides from In Situ Generated Copper(I) Acetylides and Sulfonyl Azides," Angew. Chem. Int. Ed., 45(19):3154-3157.
Chaignaud et al., (2008) "New highlights in the synthesis and reactivity of 1,4-dihydropyrazine derivatives," Tetrahedron, 64(35):8059-8066.
Chan et al., (2006) "Oxidative Amide Synthesis and N-Terminal α-Amino Group Ligation of Peptides in Aqueous Medium," J. Am. Chem. Soc., 128(46):14796-14797.
Cho et al., (2005) "Copper-Catalyzed Hydrative Amide Synthesis with Terminal Alkyne, Sulfonyl Azide, and Water," J. Am. Chem. Soc., 127(46):16046-16047.
Cobley et al., (2000) "Platinum catalysed hydrolytic amidation of unactivated nitriles," Tetrahedron Letters, 41(14):2467-2470.
Das et al., (2010) "Zinc-Catalyzed Reduction of Amides: Unprecedented Selectivity and Functional Group Tolerance," J. Am. Chem. Soc., 132(6):1770-1771.
Dobson et al., (1977) "Complexes of the Platinum Metals. 7. Homogeneous Ruthenium and Osmium Catalysts for the Dehydrogenation of Primary and Secondary Alcohols," Inorganic Chemistry, 16(1):137-142.
Fernandes et al., (2007) "Reduction of amides with silanes catalyzed by MoO2Cl2," Journal of Molecular Catalysis A: Chemical, 272(1-2):60-63.

Fogler et al., (2011) "New CNN-Type Ruthenium Pincer NHC Complexes. Mild, Efficient Catalytic Hydrogenation of Esters," Organometallics, 30(14):3826-3833.
Fujita et al., (2004) "Synthesis of Five-, Six-, and Seven-Membered Ring Lactams by Cp*Rh Complex-Catalyzed Oxidative N-Heterocyclization of Amino Alcohols," Organic Letters, 6(16):2785-2788.
Ghosh et al., (2009) "Direct Amide Synthesis from Alcohols and Amines by Phosphine-Free Ruthenium Catalyst Systems," Adv. Synth. Catal., 351(16):2643-2649.
Gibson et al., (2004) "Synthesis and Characterization of Ruthenium(II) Hydrido and Hydroxo Complexes Bearing the 2,6-Bis(di-tert-butylphosphinomethyl)pyridine Ligand," Organometallics, 23(10):2510-2513.
Gnanaprakasam et al., (2010) "Direct Synthesis of Imines from Alcohols and Amines with Liberation of H2," Angew. Chem. Int. Ed., 49(8):1468-1471.
Gunanathan et al., (2008) "Selective Synthesis of Primary Amines Directly from Alcohols and Ammonia," Angew. Chem. Int. Ed., 47(45):8661-8664.
Gunanathan et al., (2007) "Direct Synthesis of Amides from Alcohols and Amines with Liberation of H2," Science, 317(5839):790-792.
Gunanathan et al., (2009) "Direct Conversion of Alcohols to Acetals and H2 Catalyzed by an Acridine-Based Ruthenium Pincer Complex," J. Am. Chem. Soc., 131(9):3146-3147.
Guo et al., (2005) "Applications of Ruthenium Hydride Borohydride Complexes Containing Phosphinite and Diamine Ligands to Asymmetric Catalytic Reactions," Organic Letters, 7(9):1757-1759.
Haniti et al., (2007) "Ruthenium catalysed N-alkylation of amines with alcohols," Chem. Commun., (7):725-727.
Hirosawa et al., (1996) "Hydrogenation of Amides by the Use of Bimetallic Catalysts Consisting of Group 8 to 10, and Group 6 or 7 Metals," Tetrahedron Letters, 37(37):6749-6752.
Ito et al., (1982) "Selective Dimerization of Aldehydes to Esters Catalyzed by Hydridoruthenium Complexes," Bull. Chem. Soc. Jpn., 55(2):504-512.
Ito et al., (2009) "Hydrogenation of N-Acylcarbamates and N-Acylsulfonamides Catalyzed by a Bifunctional [Cp*Ru (PN)] Complex," Angew. Chem. Int. Ed., 48(7):1324-1327.
Jansen et al., (1999) "Synthesis of Hemilabile P,N Ligands: ω-2-Pyridyl-n-alkylphosphines," Monatshefte für Chemie, 130(6):783-794.
Jensen et al., (1986) "Transition Metal Tetrahydridoborates as Models of Methane Activation: Synthesis and Structure of Ti(BH4)3(PMe3)2," J. Chem. Soc., Chem. Commun., 15:1160-1162.
Jensen et al., (1988) "Titanium(III) Tetrahydroborates. Preparation and Crystal Structure of Ti(BH4)3(PMe3)2 Containing an Unusual Ti—H—B Agostic Interaction," J. Am. Chem. Soc., 110(15):4977-4982.
Jia et al., (1997) "Synthesis, Characterization, and Acidity Properties of [MCl(H2)(L)(PMP)]BF4 (M=Ru, L=PPh3, CO; M=Os, L=PPh3; PMP=2,6-(Ph2PCH2)2C5H3N)," Organometallics, 16:3941-3949.
Jung et al., (1982) "Dehydrogenation of Alcohols and Hydrogenation of Aldehydes Using Homogeneous Ruthenium Catalysts," Organometallics, 1(4):658-666.
Kohl et al., (2009) "Consecutive Thermal H2 and Light-Induced O2 Evolution from Water Promoted by a Metal Complex," Science, 324(5923):74-77.
Swamy et al., (2009) "Mitsunobu and Related Reactions: Advances and Applications," Chem. Rev., 109(6):2551-2651.
Lee et al., (1984) "Hydroboration of Alkenes and Alkynes with Sodium Borohydride Catalyzed by Titanium Complex," Chemistry Letters, 13(3):363-366.
Lee et al., (1984) Regio- and Stereo-Selectivities in the Titanium Complex Catalyzed Hydroboration of Carbon-Carbon Double Bonds in Various Unsaturated Compounds, Chemistry Letters, 13(5):673-676.
Letts et al., (1982) "The Synthesis, Characterization, and Reactivity of an Unusual, Amphoteric (Tetrahydroborato) ruthenium Hydride Complex of a Chelating Triphosphine, Ru(H)(η2-BH4)(ttp)," J. Am. Chem. Soc., 104(14):3898-3905.

(56) References Cited

OTHER PUBLICATIONS

Ligthart et al., (2003) "Highly sustainable catalytic dehydrogenation of alcohols with evolution of hydrogen gas," Tetrahedron Letters, 44(7):1507-1509.
Lin et al., (1992) "A convenient lactonization of diols to γ- and σ-lactones catalysed by transition metal polyhydrides," Journal of Organometallic Chemistry, 429(2):269-274.
Menashe et al., (1991) "Catalytic Disproportionation of Aldehydes with Ruthenium Complexes," Organometallics, 10(11):3885-3891.
Milstein, (2010) "Discovery of Environmentally Benign Catalytic Reactions of Alcohols Catalyzed by Pyridine-Based Pincer Ru Complexes, Based on Metal-Ligand Cooperation," Top Catal 53(13-14):915-923.
Murahashi et al., (1986) "Ruthenium-Catalyzed Amidation of Nitriles with Amines. A Novel, Facile Route to Amides and Polyamides," J. Am. Chem. Soc., 108(24):7846-7847.
Murahashi et al., (1992) "Ruthenium-Catalyzed Hydration of Nitriles and Transformation of σ-Keto Nitriles to Ene-Lactams," J. Org. Chem., 57(9):2521-2523.
Balaraman et al., (2011) Unprecedented catalytic hydrogenation of urea derivatives to amines and methanol. Angewandte Chemie, International Edition 50(49): 11702-11705, and supporting information S11702/1-S11702/7.
Barrios-Francisco et al., (2013) Pnn ruthenium pincer complexes based on phosphinated 2,2'-dipyridinemethane and 2,2'-oxobispyridine. Metal-Ligand Cooperation in Cyclometalation and Catalysis. Organometallics 32(10): 2973-2982.
Benet-Buchholz et al., (2009) Iron vs. ruthenium—a comparison of the stereoselectivity in catalytic olefin epoxidation. Dalton Transactions (30): 5910-5923.
Benet-Buchholz et al., (2010) The Ru(IV)=O-catalyzed sulfoxidation: a gated mechanism where O to S linkage isomerization switches between different efficiencies. Dalton Transactions 39(13): 3315-3320.
Boelrijk et al., (1995) Oxidation of octyl α-d-glucopyranoside to octyl α-d-glucuronic acid, catalyzed by several ruthenium complexes, containing a 2-(phenyl)azopyridine or a 2-(nitrophenyl)azopyridine ligand. Journal of Molecular Catalysis A: Chemical 103(2): 73-85.
Catalano et al., (1998) Steric modulation of electrocatalytic benzyl alcohol oxidation by [Ru(trpy)(R2dppi)(O)]2+ complexes. Inorganic Chemistry 37(9): 2150-2157.
Catalano et al., (2000) Synthesis, characterization, and electrocatalytic oxidation of benzyl alcohol by a pair of geometric isomers of [Ru(trpy)(4,4'-Me2dppi)(OH2)]2+ where 4,4'-dppi is 3,6-di-(4-methylpyrid-2-yl)pyridazine. Polyhedron 19(9): 1049-1055.
Chanda et al., (2002) Ruthenium monoterpyridine complexes incorporating α,α'-diimine based ancillary functions. Synthesis, crystal structure, spectroelectrochemical properties and catalytic aspect. Polyhedron 21(20): 2033-2043.
Chatterjee and Mitra (2008) Kinetics and catalysis of oxidation of phenol by ruthenium(IV)-oxo complex Original Research Article. Journal of Molecular Catalysis A: Chemical 282(1-2): 124-128.
Chatterjee et al., (2006) Oxidation of catechol and I-ascorbic acid by [RuIII(tpy)(pic)(OH)]+ (tpy=2,2'6',2"-terpyridine; pic-=picolinate): Kinetic and mechanistic studies. Inorganic Chemistry Communications 9(12): 1219-1222.
Chatterjee et al., (2007) Synthesis, characterization and reactivity of a novel ruthenium(II) complex containing polypyridyl ligand. Polyhedron 26(1): 178-183.
Chi-tung Yeunget al., (2010) Chiral C1-symmetric 2,2':6',2"-terpyridine ligands: synthesis, characterization, complexation with copper(II), rhodium(III) and ruthenium(II) ions and use of the complexes in catalytic cyclopropanation of styrene. Polyhedron 29(5): 1497-1507.
Claustro et al., (2003) Synthesis, spectroscopic and electrochemical properties of ruthenium-2-(2'-hydroxyphenyl)-benzoxazole complexes. Crystal structure of [Ru(terpy)(HPB)Cl]. Inorganica Chimica Acta 342: 29-36.
Concepcion et al., (2008) One site is enough. Catalytic water oxidation by [Ru(tpy)(bpm)(OH2)]2+ and [Ru(tpy)(bpz)(OH2)]2+. Journal of the American Chemical Society 130(49): 16462-16463.
Concepcion et al., (2009) Catalytic and surface-electrocatalytic water oxidation by redox mediator-catalyst assemblies. Angewandte Chem., International Edition 48 (50): 9473-9476, and supporting information S9473/1-S9473/11.
Concepcion et al., (2010) Catalytic water oxidation by single-site ruthenium catalysts. Inorganic Chemistry 49(4):1277-1279.
Concepcion et al., (2010) Mechanism of water oxidation by single-site ruthenium complex catalysts. Journal of the American Chemical Society 132(5): 1545-1557.
Dakkach et al., (2010) New Ru(II) complexes with anionic and neutral N-donor ligands as epoxidation catalysts: an evaluation of geometrical and electronic effects. Inorganic Chemistry 49(15): 7072-7079.
Diao et al., (2000) Studies on ruthenium catalyst with a ligand of copolymer and its performance in catalytic hydrogenation. Huaxue Tongbao (12): 34-37. Translated abstract.
Duan et al., (2009) Isolated seven-coordinate Ru(IV) dimer complex with [HOHOH](−) bridging ligand as an intermediate for catalytic water oxidation. Journal of the American Chemical Society 131(30): 10397-10399.
Francas et al., (2009) A Ru-Hbpp-based water-oxidation catalyst anchored on rutile TiO2. ChemSusChem 2(4):321-329.
Gnanaprakasam (2011) Direct synthesis of imines from alcohols and amines with liberation of H2. Abstracts of Papers, 241st ACS National Meeting and Exposition, Anaheim, CA, United States, Mar. 27-31, 2011, ORGN-152. American Chemical Society: Washington, D. C.
Gnanaprakasam et al., (2010) Ruthenium pincer-catalyzed acylation of alcohols using esters with liberation of hydrogen under neutral conditions. Advanced Synthesis and Catalysis 352(18): 3169-3173.
Gnanaprakasam et al., (2011) Synthesis of peptides and pyrazines from β-amino alcohols through extrusion of H2 catalyzed by ruthenium pincer complexes: ligand-controlled selectivity. Angewandte Chemie, International Edition 50(51): 12240-12244, and supporting information S12240/1-S12240/9.
Gunanathan and Milstein (2011) Bond activation by metal-ligand cooperation: design of "green" catalytic reactions based on aromatization-dearomatization of pincer complexes. Topics in Organometallic Chemistry 37(Bifunctional Molecular Catalysis): 55-84.
Gunanathan et al., (2011) Metal-ligand cooperation by aromatization-dearomatization: a new paradigm in bond activation and "green" catalysis. Accounts of Chemical Research 44(8): 588-602.
Gunanathan et al., (2011) Reduction of nitriles to amines with H2 catalyzed by nonclassical ruthenium hydrides—water-promoted selectivity for primary amines and mechanistic investigations. European Journal of Inorganic Chemistry 2011(22): 3381-3386.
Ho et al., (1996) Double-helical ruthenium complexes of 2,2' : 6',''',2''':6''',2''''-quinquepyridine (qpy) for multi-electron oxidation reactions. Chemical Communications (10): 1197-1198.
Huang et al., (2005) A novel method to immobilize Ru nanoparticles on SBA-15 firmly by ionic liquid and hydrogenation of arene. Catalysis Letters 103(1-2): 59-62.
Huff and Sanford (2011) Cascade catalysis for the homogeneous hydrogenation of CO2 to methanol. Journal of the American Chemical Society 133(45): 18122-18125.
Kelson and Phengsy (2000) Synthesis and structure of a ruthenium(II) complex incorporating κN bound 2-pyridonato ligands; a new catalytic system for transfer hydrogenation of ketones. Dalton (22): 4023-4024.
Langer et al., (2013) Stepwise metal-ligand cooperation by a reversible aromatization/deconjugation sequence in Ruthenium complexes with a tetradentate phenanthroline-based ligand. Chemistry—A European Journal 19(10):3407-3414.
Liao et al., (2013) Hydrophilicity modification of MCM-41 with zirconia and supported ruthenium-lanthanum for benzene hydrogenation to cyclohexene. Synthesis and Reactivity in Inorganic, Metal-Organic and Nano-Metal Chemistry 43(9):1206-1211.

(56) References Cited

OTHER PUBLICATIONS

Liao et al., (2014) Benzene hydrogenation over oxide-modified MCM-41 supported ruthenium—lanthanum catalyst: The influence of zirconia crystal form and surface hydrophilicity. Chemical Engineering Journal 243: 207-216.
Liu et al., (2011) Synthesis of PVP-stabilized Pt/Ru colloidal nanoparticles by ethanol reduction and their catalytic properties for selective hydrogenation of ortho-chloronitrobenzene. Journal of Catalysis 278(1): 1-7.
Livanov et al. (2011) Photocatalytic splitting of CS2 to S8 and a carbon—sulfur polymer catalyzed by a bimetallic Ruthenium(II) compound with a tertiary amine binding site: toward photocatalytic splitting of CO2? Inorganic Chemistry 50(22): 11273-5.
Miao et al., (2005) Ru nanoparticles immobilized on montmorillonite by ionic liquids: a highly efficient heterogeneous catalyst for the hydrogenation of benzene. Angewandte Chemie, International Edition 45(2): 266-269.
Mola et al., (2008) Ru-hbpp-based water-oxidation catalysts anchored on conducting solid supports. Angewandte Chemie, International Edition 47(31): 5830-5832.
Mulfort and Tiede (2010) Supramolecular cobaloxime assemblies for H2 photocatalysis: an initial solution state structure-function analysis. Journal of Physical Chemistry B 114(45): 14572-14581.
Muthusamy et al., (2007) New approach to the synthesis of macrocyclic tetralactones via ring-closing metathesis using Grubbs' first-generation catalyst. Journal of Organic Chemistry 72(4): 1495-1498.
Navarro et al., (1996) Redox and spectral properties of [Ru(trpy)L(H2O)](ClO4)2 [trpy=2,2':6' 2"-terpyridine; L=4,4'-(OMe)2bpy; 4,4'-(NO2)2bpy]: A comparative computational study. Polyhedron 15(9): 1531-7.
Pefkianakis et al., (2009) End-functionalization of semiconducting species with dendronized terpyridine-Ru(II)-terpyridine complexes. Journal of Polymer Science, Part A: Polymer Chemistry 47(7): 1939-1952.
Pitet (2013) Sequential ROMP of cyclooctenes as a route to linear polyethylene block copolymers. Dalton Transactions (Cambridge, England:2003) 42(25): 9079-88.
Pramanik and Bhattacharya (1997) Chemical oxidation of water to dioxygen. Homogeneous catalysis by a ruthenium aquo-complex. Transition Metal Chemistry (London) 22(5): 524-526.
Pramanik et al., (1998) Chemistry of [Ru(tpy)(pap)(L')n+ (tpy=2,2',6',2"-terpyridine; pap=2-(phenylazo)pyridine; L'=Cl-, H2O, CH3CN, 4-picoline, N3-; n=1,2). X-ray crystal structure of [Ru(tpy)(pap)(CH3CN)](ClO4)2 and catalytic oxidation of water to dioxygen by [Ru(tpy)(pap)(H2O)]2+. Polyhedron 17(9): 1525-1534.
Prechtl et al., (2012) Direct coupling of alcohols to form esters and amides with evolution of H2 using in situ formed ruthenium catalysts. Catalysis Science and Technology 2(10): 2039-2042.
Ramos Sende et al., (1995) Electrocatalysis of CO2 reduction in aqueous media at electrodes modified with electropolymerized films of vinylterpyridine complexes of transition metals. Inorganic Chemistry 34(12): 3339-48.
Sala et al., (2007) The Spectroscopic, Electrochemical and Structural Characterization of a Family of Ru Complexes Containing the C2-Symmetric Didentate Chiral 1,3-Oxazoline Ligand and Their Catalytic Activity. European Journal of Inorganic Chemistry (33): 5207-5214.
Schwalbe et al., (2009) Ruthenium polypyridine complexes of tris-(2-pyridyl)-1,3,5-triazine-unusual building blocks for the synthesis of photochemical molecular devices. Dalton Transactions (20): 4012-4022.
Seckin et al., (2009) Preparation and catalytic properties of a Ru(II) coordinated polyimide supported by a ligand containing terpyridine units. Journal of Inorganic and Organometallic Polymers and Materials 19(2): 143-151.
Sens et al., (2003) Synthesis, structure, and acid-base and redox properties of a family of new Ru(II) isomeric complexes containing the Trpy and the dinucleating Hbpp ligands. Inorganic Chemistry 42(25): 8385-8394.

Sens et al., (2004) A new Ru complex capable of catalytically oxidizing water to molecular dioxygen. Journal of the American Chemical Society 126(25): 7798-7799.
Seok et al., (1998) The comparative study in the oxygen atom transfer reaction by Ruthenium mono-oxo complexes. Bulletin of the Korean Chemical Society 19(10): 1084-1090.
Serrano et al., (2007) Synthesis, structure, redox properties, and catalytic activity of new ruthenium complexes containing neutral or anionic and facial or meridional ligands: an evaluation of electronic and geometrical effects. Inorganic Chemistry 46(13): 5381-5389.
Sussuchi et al., (2006) Effect of the cis- and trans-[1,2-bis(diphenylphosphino)ethylene] ligands in the properties of diphosphine-polypyridyl complexes of ruthenium(II): Application to electrocatalytic oxidations of organic compounds. Journal of Molecular Catalysis A: Chemical 259(1-2): 302-308.
Sussuchi et al., (2006) Synthesis and electrochemical, spectral and catalytic properties of diphosphine-polypyridyl ruthenium complexes. Polyhedron 25(6): 1457-1463.
Taher et al., (2009) Acid-, water- and high-temperature-stable ruthenium complexes for the total catalytic deoxygenation of glycerol to propane. Chemistry—A European Journal 15(39): 10132-10143, and supporting information S10132/1-S10132/26.
Tanaka et al., (2008) Reversible conversion between chemical and electrical energies catalyzed by Ru complexes aimed to construct sustainable society. Preprints of Symposia—American Chemical Society, Division of Fuel Chemistry 53(1): 236-237.
Tse et al., (2006) Synthetic, spectral and catalytic activity studies of ruthenium bipyridine and terpyridine complexes: Implications in the mechanism of the ruthenium(pyridine-2,6-bisoxazoline)(pyridine-2,6-dicarboxylate)-catalyzed asymmetric epoxidation of olefins utilizing H2O2. Journal of Organometallic Chemistry 691(21): 4419-4433.
Tseng et al., (2008) Mononuclear ruthenium(II) complexes that catalyze water oxidation. Inorganic Chemistry 47(24):11763-11773.
Wada et al., (2000) Electrochemical oxidation of water to dioxygen catalyzed by the oxidized form of the bis(ruthenium—hydroxo) complex in H2O. Angewandte Chem., International Edition 39(8): 1479-1482.
Wada et al., (2001) Syntheses and redox properties of bis(hydroxoruthenium) complexes with quinone and bipyridine ligands. Water-oxidation catalysis. Inorganic Chemistry 40(2): 329-337.
Wasylenko et al., (2010) Examination of water oxidation by catalysts containing cofacial metal sites. European Journal of Inorganic Chemistry 2010(20): 3135-3142.
Wasylenko et al., (2010) Insight into water oxidation by mononuclear polypyridyl Ru catalysts. Inorganic Chemistry 49(5): 2202-2209.
Weizhong Chen et al., (2009) Homogeneous photocatalytic oxidation of alcohols by a chromophore-catalyst dyad of ruthenium complexes. Angewandte Chemie, International Edition 48(51): 9672-9675.
Yamaguchi et al., (1998) Syntheses of mixed-ligand ruthenium(II) complexes with a terpyridine or a tris (pyrazolyl) methane and a bidentate ligand: their application for catalytic hydroxylation of alkanes. Inorganic Chemistry Communications 1(8): 299-301.
Yu et al., (1994) Synthesis, redox properties and reactivities of ruthenium(II) complexes of 1,1'-biisoquinoline (BIQN) and X-ray crystal structure of [RuII(terpy)(BIQN)(Cl)]ClO4 (terpy=2,2':6', 2"-terpyridine). Polyhedron 13(21): 2963-9.
Zhang et al. (2009) Ru-TsDPEN with formic acid/hünig's base for asymmetric transfer hydrogenation, a practical synthesis of optically enriched N-propyl pantolactam. The Journal of Organic Chemistry 74(3): 1411-4.
Zhang et al. (2011) Efficient conversion of d-glucose into d-sorbitol over MCM-41 supported Ru catalyst prepared by a formaldehyde reduction process. Carbohydrate Research 346(11) 1327-32.
Zhang et al., (1996) Homogeneous catalytic synthesis of formic acid (salts) by hydrogenation of CO2 with H2 in the presence of ruthenium species. J Mol Catal A: Chem 112(1): 9-14.
Zhang et al., (2008) Theoretical studies on the electronic structures and spectroscopic properties for a series of Osmium(II)-2,2',6',2"-terpyridine complexes. Theoretical Chemistry Account 121(3-4): 123-134.

(56) References Cited

OTHER PUBLICATIONS

Zhang et al., (2011) Structures and spectroscopic properties of (Ru(iph(L)2)2+ (L=cpy, mpy, npy) complexes containing tetradentate ligands. Wuli Huaxue Xuebao 27(5): 1089-1094. Translated abstract.

Zhao et al., (2008) Monolithic Ru-based catalyst for selective hydrogenation of benzene to cyclohexene. Catalysis Communications 9(3): 459-464.

Zhao et al., (2008) Selective hydrogenation of benzene to cyclohexene on a Ru/Al2O3/Cordierite monolithic catalyst: effect of mass transfer on the catalytic performance. Industrial and Engineering Chemistry Research 47(14):4641-4647.

Zhao et al., (2008) Selective hydrogenation of benzene to cyclohexene by a circulating method on monolithic catalyst Ru/Al2o3/Cordierite. Ranliao Huaxue Xuebao/Journal of Fuel Chemistry and Technology 36(4): 499-502. Translated abstract.

Zhao et al., (2009) Liquid-phase selective hydrogenation of benzene to cyclohexene on Ru/Al2O3—ZrO2/cordierite monolithic catalysts. Journal of Molecular Catalysis A: Chemical 309(1/2): 35-39.

Zhao et al., (2009) Preparation and characterization of Ru/Al2O3/Cordierite monolithic catalysts for selective hydrogenation of benzene to cyclohexene . Catalysis Letters 131(3-4): 597-605.

Zhou et al., (2009) Ruthenium(II) terpyridyl complexes exhibiting DNA photocleavage: the role of the substituent on monodentate ligand. Journal of Physical Chemistry B 113(33): 11521-11526.

Zhou et al., (2012) Synthesis of an ionic paramagnetic ruthenium(III) complex and its application as an efficient and recyclable catalyst for the transfer hydrogenation of ketones. European Journal of Inorganic Chemistry 2012(21):3435-3440.

Hirosawa et al., (1996) Hydrogenation of amides by the use of bimetallic catalysts consisting of group 8 to 10, and group 6 or 7 metals. Tetrahedron Letters 37(37): 6749-6752.

Masaoka et al., (2009) Clear evidence showing the robustness of a highly active oxygen-evolving mononuclear ruthenium complex with an Aqua Ligand. Chemistry Letters 38 (2): 182-183.

Hino et al., (2004) Redox behavior of Ru-dioxolene-ammine complexes and catalytic activity toward electrochemical oxidation of alcohol under mild conditions. Chemistry Letters 33(12): 1596-1597.

\* cited by examiner

RUTHENIUM COMPLEXES AND THEIR USES IN PROCESSES FOR FORMATION AND/OR HYDROGENATION OF ESTERS, AMIDES AND DERIVATIVES THEREOF

FIELD OF THE INVENTION

The present invention relates to novel Ruthenium complexes and related borohydride complexes, and their use, inter alia, for (1) hydrogenation of amides (including polyamides) to alcohols and amines; (2) preparing amides from alcohols with amines (including the preparation of polyamides (e.g., polypeptides) by reacting dialcohols and diamines and/or by polymerization of amino alcohols); (3) hydrogenation of esters to alcohols (including hydrogenation of cyclic esters (lactones) or cyclic di-esters (di-lactones), or polyesters); (4) hydrogenation of organic carbonates (including polycarbonates) to alcohols and hydrogenation of carbamates (including polycarbamates) or urea derivatives to alcohols and amines; (5) dehydrogenative coupling of alcohols to esters; (6) dehydrogenation of secondary alcohols to ketones; (7) amidation of esters (i.e., synthesis of amides from esters and amines); (8) acylation of alcohols using esters; (9) coupling of alcohols with water and a base to form carboxylic acids; and (10) dehydrogenation of beta-amino alcohols to form pyrazines. The present invention further relates to the novel uses of certain pyridine Ruthenium complexes.

BACKGROUND OF THE INVENTION

Reduction of carboxylic acids and their derivatives plays an important role in organic synthesis, both in laboratory and industrial processes. Traditionally, the reduction is performed using stoichiometric amounts of hydride reagents, generating stoichiometric amounts of waste (Seyden-Penne). A much more attractive, atom-economical approach is a catalytic reaction using $H_2$; however, hydrogenation of carboxylic acid derivatives under mild conditions is a very challenging task (Rylander; Hartwig), with amides presenting the one of the highest challenges among all classes of carbonyl compounds. A few examples of the important hydrogenation of amides to amines, in which the C—O bond is cleaved with the liberation of water (Scheme 1), were reported (Hirosawa et al., Núñez Magro et al., Beamson et al.). This reaction can also be affected with silanes as reducing agents (Fernandes et al., Das et al.). In addition, the interesting hydrogenation of cyclic N-acylcarbamates and N-acylsolfonamides, which involves cleavage of the C—N bond, but does not form amines, was recently reported (Ito et al., 2009).

On the other hand, selective, direct hydrogenation of amides to form amines and alcohols has not been reported. Hydrogenation of amides to amines (via C—O cleavage, generating water) can have C—N cleavage as a side reaction, requiring the presence of water, and resulting from catalytic hydrolysis of the amides to acids and amines, followed by hydrogenation of the acids to alcohols: see Núñez Magro et al. and Beamson et al) However, no amide C—N hydrogenolysis to form alcohols and amines was reported in absence of water.

Amines and alcohols are used extensively in the chemical, pharmaceutical and agrichemical industries (Lawrence; Ricci; Kumara et al.). Design of such a reaction is conceptually challenging, since the first mechanistic step in amide hydrogenation is expected to be $H_2$ addition to the carbonyl group to form a very unstable hemiaminal which, in the case of primary or secondary amides, spontaneously liberates water to form an imine; further hydrogenation of the imine then leads to amine formation (Scheme 1). For amine and alcohol formation, cleavage of the C—N bond in preference to the C—O bond is required.

Scheme 1. General scheme for hydrogenation of amides.

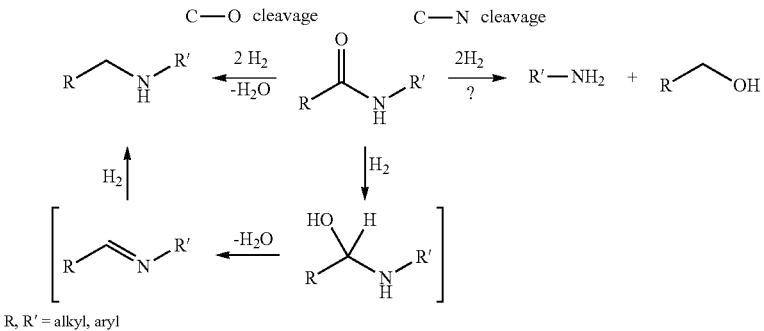

R, R' = alkyl, aryl

The reverse reaction, i.e., amide formation from alcohols and amines with liberation of $H_2$, was previously reported by inventors of the present invention, and later, by others (Nordstrom; Ghosh; Shimizu) Formation of amides from alcohols and amines by use of hydrogen acceptors was also reported recently (Zweifel; Watson). The importance of amides in chemistry and biology is well recognized and has been studied extensively (Sewald et al.; Greenberg et al.; Smith and March; Bray). Although several methods are known for the synthesis of amides, preparation under neutral conditions and without generation of waste is a challenging goal (Larock; Smith). Synthesis of amides is mostly based on activated acid derivatives (acid chlorides, anhydrides) or rearrangement reactions induced by acid or base which often involve toxic chemical waste and tedious work-up (Smith). Transition-metal catalyzed conversion of nitriles into amides was reported (Cobley et al.; Murahashi et al. 1986 and 1992). Catalytic acylation of amines by aldehydes in the presence of a stoichiometric amount of oxidant and a base is known (Tamaru et al., Tillack et al.). Recently, oxidative amide synthesis was achieved from terminal alkynes (Chan et al.). Cu(I) catalyzed reaction of sulfonyl azides with terminal alkynes is a facile method for the synthesis of sulfonyl amides (Cho et al.; Cassidy et al.).

Polyamides are one of the most important polymer classes, extensively used in fiber products, plastics and their derivatives, with many applications, including in biomedical studies. Recently, the synthesis of functional polyamides has received considerable attention. Generally, polyamides are synthesized by condensation of diamines and activated dicarboxylic acid derivatives and/or in the presence of coupling reagents. In some cases, ring opening of small-ring lactams at high temperatures leads to polyamides. To avoid the use of activators, waste generation, or harsh conditions, the development of economical, efficient and environmentally benign protocols are desirable.

Transition metal borohydride complexes display extensive reactivity with organic substrates and are useful starting materials for the preparation of transition metal hydrides and borides (Dick et al; White et al). They have found uses in catalytic hydroboration (Burgess et al., Isagawa et al., Lee et al); polymerization of olefins (Barbier-Baudry et al., Bonnet et al, and Marks et al.) and cyclic esters (Palard et al.). Ruthenium hydrido borohydride complexes based on bidentate phosphorus ligands and diamines, reported by Ohkuma et al, Sandoval et al. and Guo et al. are effective catalysts in asymmetric transfer hydrogenation of ketones (Ohkuma et al., Sandoval et al., Guo et al) and enantioselective Michael addition (Guo et al.). In addition, borohydride complexes may represent plausible models for $CH_4$ coordination in the transition state for C—H activation (Jensen et al. 1986 and 1988).

Transition metal complexes of bulky, electron-rich tridentate ligands have found useful applications in synthesis, bond activation, and catalysis (see recent reviews: Van der Boom et al., Albrecht et al., Vigalok et al., Jensen 1999 and Rybtchinski et al.). The highly electron-donating $^t$Bu-PNP (2,6-bis(di-tert-butylphosphinomethyl)pyridine) and its group 8 metal complexes have been explored by several groups (Kawatsura et al., Stambuli et al., Gibson et al., and Kloek et al) as well as by some of the inventors of the present invention (Hermann et al., Ben-Ari et al. 2003 and 2006, Zhang et al. 2004, 2005 and 2006, and Feller et al).

Dehydrogenation of alcohols to carbonyl compounds without a hydrogen acceptor or oxidant, with the evolution of molecular hydrogen, is attractive economically and environmentally (Scheme 2), but homogeneous systems capable of thermally catalyzing dehydrogenation of alcohols are relatively rare (Zhang et al. 2004 and 2005, Murahashi et al. 1987, Charman et al., Morton et al., Dobson et al., Jung et al., Ligthart et al., Shinoda et al., Matsubara et al., Adair et al., Lin et al. 1997 and 1992, Blum et al., and Zhao et al.).

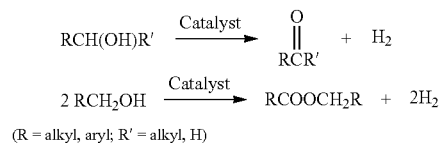

Scheme 2

(R = alkyl, aryl; R' = alkyl, H)

Catalytic hydrogenation of polar carbonyl bonds is a simple, convenient, and sustainable method which plays a pivotal role in both industrial processes and academic research. The hydrogenation of esters to alcohols is an important transformation and remains a challenging task in the perspective of "green and sustainable chemistry (GSC)" where the transformation is atom-economic without generating any large amount of metal waste. Despite well-documented homogeneously catalyzed reductions of ketones and aldehydes, the catalytic hydrogenation of esters to alcohols under mild and homogeneous conditions is relatively under-developed, owing to the poor hydridophilicity (electrophilicity) of the ester carbonyl functionality. The common trend in the reactivity of carbonyl groups towards hydrogenation reactions is RC(O)H>RC(O) R'>>RC(O)OR'>RC(O)NR'.

Simple 1,2-diols, e.g., propylene glycol (PG) and ethylene glycol (EG), are utilized as high value-added specialty chemical intermediates, in the manufacture of biodegradable polyester fibers, unsaturated polyester resins, antifreeze, pharmaceuticals and other important products. Currently, these two vicinal diols are industrially produced from petroleum-derived propylene and ethylene via hydration of their corresponding epoxy alkanes. However, as crude oil resources become limited, substitutes for petroleum feedstocks are increasingly sought after, and as such the synthesis 1,2-diols, indirectly from biomass derived resources is of great interest. Alternative methods which proceed under mild reaction conditions with stable and easy-to-handle homogeneous catalysts and environmentally benign are desirable.

Glycolide and lactide are important classes of cyclic di-esters (di-lactones) utilized as starting materials for Lewis-acid catalyzed polymerization reactions to synthesize biodegradable polymers. Since these compounds are produced from biomass derived resources such as glycolic acid (derived from sugar cane) and lactic acid (from fermentation of glucose) respectively via self-esterification, their efficient hydrogenation can provide alternative, mild approaches to the indirect transformation of biomass to important synthetic building blocks. Although few catalytic hydrogenations of (mono lactones) to diols are known in the literature, the complete hydrogenation of cyclic di-esters to the corresponding 1,2-diols (e.g. ethylene glycol and propylene glycol) is extremely difficult due to presence of two ester moieties and the chelating ability of the final product, 1,2-diol, which may retard the catalytic activity of the catalyst. Indeed, to the applicant's best knowledge, catalytic hydrogenation of these important families of cyclic di-esters has never been reported, be it under heterogeneous or homogeneous catalysis.

The applicants of the present invention have recently reported on new catalytic reactions of alcohols, such as dehydrogenative coupling of primary alcohols to esters and dehydrogenation of secondary alcohols to ketones using pyridine-based pincer complexes (Zhang et al. 2004, 2005, 2006 and 2007; Gunanathan 2007; Gnanaprakasam and Milstein) and acridine (Gunanathan 2008 and 2009). The catalytic efficiency of the reaction of the conversion of primary alcohols to ester was enhanced with Ru(II) complexes of an analogous ligand having a potentially "hemilabile" amine "arm", PNN (2-(di-tert-butylphosphinomethyl)-6-(diethylaminomethyl) pyridine). (PNN)Ru(II) complexes effectively catalyze the acceptorless dehydrogenation of primary alcohols to the corresponding esters and molecular hydrogen in high yields and turnover numbers, in the presence of a catalytic amount of base. Mechanistic studies of this reaction have led to the discovery of a PNN Ru hydrido carbonyl complex, which does not require the presence of base, the catalytic reaction proceeding very effectively under neutral, mild conditions (Zhang et al. 2005).

The pyridine-based PNN Ru complex 1 (FIG. 1A) efficiently catalyzes the dehydrogenative coupling of alcohols to form esters (Zhang 2005, Zhang 2007 and Milstein), the hydrogenation of esters to alcohols under mild conditions (Zhang 2006 and Milstein) and the coupling of alcohols and amines to form amides and $H_2$ (Gunanathan 2007 and Milstein). The PNP complex 2 (FIG. 1A) is an efficient catalyst for the dehydrogenative coupling of alcohols and amines to form imines (Gnanaprakasam 2010 and Milstein). Complex 1 is also effective in N—H activation (Khaskin et al.) and in the unique light induced splitting of water to $H_2$ and $O_2$ (Kohl et al.).

US patent publication no. US 2009/0112005, to some of the inventors of the present invention, describes methods for preparing amides, by reacting a primary amine and a primary alcohol in the presence of Ruthenium complexes, to generate the amide compound and molecular hydrogen.

PCT patent publication no. WO 2010/018570, to some of the inventors of the present invention, describes methods for preparing primary amines from alcohols and ammonia in the presence of Ruthenium complexes, to generate the amine and water.

Zeng et al., published after the priority date of the present application, describes a process for preparation of polyamides via catalytic dehydrogenation of diols and diamines using PNN pincer ruthenium complexes.

Given the widespread importance of amines, alcohols, amides and esters in biochemical and chemical systems, efficient syntheses that avoid the shortcomings of prior art processes are highly desirable.

SUMMARY OF THE INVENTION

The present invention relates to novel Ruthenium complexes and related borohydride complexes, and the use of such complexes (e.g., catalysts), inter alia, for (1) hydrogenation of amides (including polyamides) to alcohols and amines; (2) preparing amides from alcohols with amines (including the preparation of polyamides (e.g., polypeptides) by reacting dialcohols and diamines and/or by polymerization of amino alcohols); (3) hydrogenation of esters to alcohols (including hydrogenation of cyclic esters (lactones) or cyclic di-esters (di-lactones) or polyesters); (4) hydrogenation of organic carbonates (including polycarbonates) to alcohols and hydrogenation of carbamates (including polycarbamates) or urea derivatives to alcohols and amines; (5) dehydrogenative coupling of alcohols to esters; (6) dehydrogenation of secondary alcohols to ketones; (7) amidation of esters (i.e., synthesis of amides from esters and amines); (8) acylation of alcohols using esters; (9) coupling of alcohols with water to form carboxylic acids; and (10) dehydrogenation of beta-amino alcohols to form pyrazines. The present invention further relates to the novel uses of certain pyridine Ruthenium complexes.

The inventors have unexpectedly discovered new, bipyridine-based pincer complexes of general formulae A1, A2 and A3 as described herein. Examples of such complexes include, but are not limited to, compounds of general formulae B1, C1, B2 and C2, and compounds represented by the structures 3, 4, 7 and 9. Also unexpectedly discovered are borohydride complexes of said bipyridine-based pincer complexes, represented by the structure of general formulae D and E, as well as pyridine-based borohydride complexes of general formulae F, G or H and some borohydride complexes such as 2', 4', 6' and 8'. These compounds efficiently catalyze various processes as described and exemplified herein. In one embodiment, the complex is a pincer complex represented by the structure of formula 3 (FIG. 1B). It has unexpectedly been discovered that complex 3 efficiently catalyzes the unprecedented selective hydrogenation of amides to form amines and alcohols (Scheme 3). The reaction proceeds under mild pressure and neutral conditions, with no additives being required. Since the reaction proceeds well under anhydrous conditions, hydrolysis of the amide is not involved in this process.

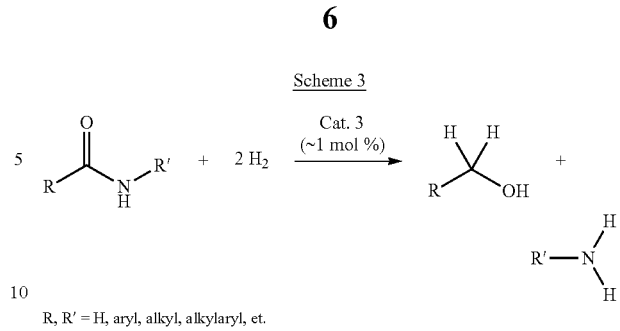

Scheme 3

R, R' = H, aryl, alkyl, alkylaryl, et.

Other reactions catalyzed by pincer complex 3 and the other pincer complexes described herein, and their borohydride derivatives, are described in more detail hereinbelow. The simplicity, generality and excellent atom-economy of these processes make them attractive for use both in small and large scale applications.

In one embodiment, the Ruthenium complex is represented by any one of formulae A1, A2 or A3:

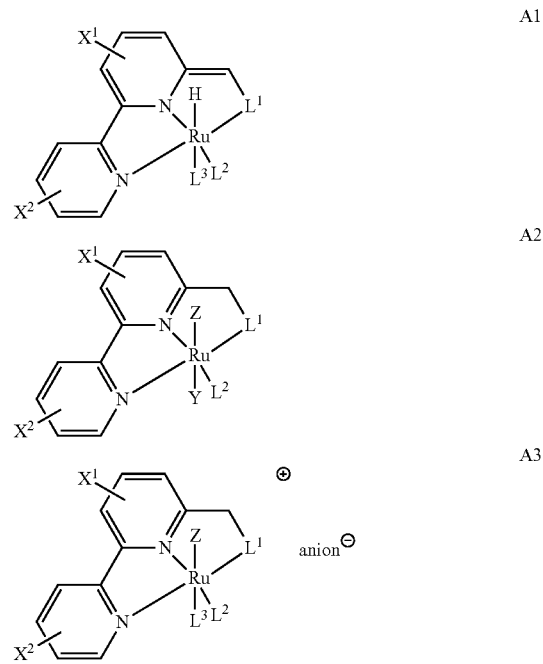

wherein $L^1$ is selected from the group consisting of phosphine ($PR^aR^b$), phosphite $P(OR^a)(OR^b)$, phosphinite $P(OR^a)(R^b)$, amine ($NR^aR^b$), imine, oxazoline, sulfide ($SR^a$), sulfoxide ($S(=O)R^a$), heteroaryl containing at least one heteroatom selected from nitrogen and sulfur; arsine ($AsR^aR^b$), stibine ($SbR^aR^b$) and a N-heterocyclic carbene represented by the structures:

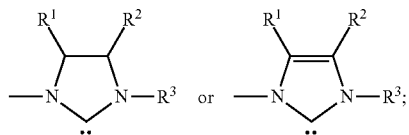

$L^2$ is a mono-dentate two-electron donor selected from the group consisting of CO, $PR^aR^bR^c$, $P(OR^a)(OR^b)(OR^c)$, NO$^+$, AsR$^a$R$^b$R$^c$, SbR$^a$R$^b$R$^c$, SR$^a$R$^b$, nitrile (RCN), isonitrile (RNC), N$_2$, PF$_3$, CS, heteroaryl, tetrahydrothiophene, alkene and alkyne;

L$^3$ is absent or is L$^2$;

Y and Z are each independently H or an anionic ligand selected from the group consisting of H, halogen, OCOR, OCOCF$_3$, OSO$_2$R, OSO$_2$CF$_3$, CN, OR, N(R)$_2$ and RS;

R$^a$, R$^b$ and R$^c$ are each independently alkyl, cycloalkyl, aryl, heterocyclyl, heteroaryl, alkylcycloalkyl, alkylaryl, alkylheterocyclyl or alkylheteroaryl;

R, R$^1$, R$^2$ and R$^3$ are each independently H, alkyl, cycloalkyl, aryl, heterocyclyl, heteroaryl, alkylcycloalkyl, alkylaryl, alkylheterocyclyl or alkylheteroaryl;

X$^1$ represents zero one, two or three substituents and X$^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; and anion represents a group bearing a single negative charge; or a borane derivative of said complex.

In one embodiment, X$^1$ and X$^2$ are each absent (i.e., the bipyridine moiety is unsubstituted). In another embodiment, L$^1$ is phosphine (PR$^a$R$^b$). In another embodiment, L$^1$ is amine (NR$^a$R$^b$). In another embodiment, L$^2$ is CO. Each possibility represents a separate embodiment of the present invention.

In some embodiments, the Ruthenium complex acts as a catalyst (and is thus designated "Ruthenium catalyst").

In one embodiment, the Ruthenium complex is represented by the structure of formula A1. In a particular embodiment of formula A1, the Ruthenium complex is represented by the structure of formula B1. In another particular embodiment of formula A1, the Ruthenium complex is represented by the structure of formula C1. In one embodiment, the Ruthenium complex is represented by the structure of formula 3 (also shown in FIG. 1B).

In another embodiment of the present invention, the Ruthenium complex is represented by the structure of formula A2. In one embodiment of formula A2, the Ruthenium complex is represented by the structure of formula B2. In another particular embodiment of formula A2, the Ruthenium complex is represented by the structure of formula C2.

In one embodiment, Y is halogen, such as chloro. For example, the Ruthenium complex is represented by the structure of formulae 4, 7 or 9.

In another embodiment of the present invention, the Ruthenium complex is represented by the structure of formula A3.

The structures of Ruthenium complexes of Formulae A1, B1, C1, A2, B2, C2, A3, 3, 4, 7 and 9 are described in detail hereinbelow.

In another embodiment, the present invention provides a borane derivative of a Ruthenium complex, the borane derivative represented by the structure of formula F:

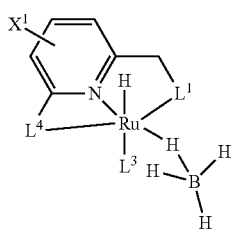

F wherein
each L$^1$ is independently selected from the group consisting of phosphine (PR$^a$R$^b$), phosphite P(OR$^a$)(OR$^b$), phosphinite P(OR$^a$)(R$^b$), amine (NR$^a$R$^b$), imine, oxazoline, sulfide (SR$^a$), sulfoxide (S(=O)R$^a$), heteroaryl containing at least one heteroatom selected from nitrogen and sulfur; arsine (AsR$^a$R$^b$), stibine (SbR$^a$R$^b$) and a N-heterocyclic carbene represented by the structures:

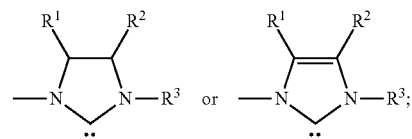

L$^3$ is absent or is a mono-dentate two-electron donor selected from the group consisting of CO, PR$^a$R$^b$R$^c$, P(OR$^a$)(OR$^b$)(OR$^c$), NO$^+$, AsR$^a$R$^b$R$^c$, SbR$^a$R$^b$R$^c$, SR$^a$R$^b$, nitrile (RCN), isonitrile (RNC), N$_2$, PF$_3$, CS, heteroaryl, tetrahydrothiophene, alkene and alkyne;

L$^4$ is —CH$_2$-L$^1$- or a group of the formula:

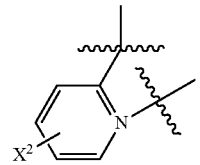

R$^a$, R$^b$ and R$^c$ are each independently alkyl, cycloalkyl, aryl, heterocyclyl, heteroaryl, alkylcycloalkyl, alkylaryl, alkylheterocyclyl or alkylheteroaryl;

R, R$^1$, R$^2$ and R$^3$ are each independently H, alkyl, cycloalkyl, aryl, heterocyclyl, heteroaryl, alkylcycloalkyl, alkylaryl, alkylheterocyclyl or alkylheteroaryl;

X$^1$ represents zero, one, two or three substituents and X$^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety.

In some embodiments, the borane derivative is represented by the structure of any of formulae D, E, G and H. It is noted that compounds D and E are borane derivatives of the Ruthenium complex of formula A1 as described hereinabove.

In other embodiments, the borane derivative is represented by the structure of any of formulae 2', 4', 6' and 8'.

The structures of borohydride-Ruthenium complexes of D, E, G, H, 2', 4', 6' and 8' are described in detail hereinbelow.

The present invention further provides various processes which utilize the Ruthenium complexes of the present invention as catalysts.

Thus, in some embodiments, the present invention provides a process for hydrogenating amides (including polyamides and polypeptides) by reacting the amide with molecular hydrogen (H$_2$) in the presence of the Ruthenium complexes of the present invention to generate the corresponding alcohol and amine. As contemplated herein, the inventors have discovered a novel process for converting amides to alcohols and amines in high yields and high turnover numbers. This reaction is catalyzed by a Ruthenium complex, which is represented by anyone of formulae A1, A2, A3, B1, B2, C1, C2, 3, 4, 7 and 9, or any other Ruthenium complex covered by such formulae, optionally in the presence of a base. In addition, this reaction is catalyzed by the Ruthenium complexes described in US Patent publication US 2009/0112005, in particular Ruthenium complexes of formula A1', A2' and A3' wherein $L_1$ is $N(R)_2$. The contents of US 2009/0112005 are incorporated by reference herein and the structures of the Ruthenium complexes of formula A1', A2' and A3' are provided hereinbelow. One embodiment of such compounds is a pincer complex represented by the structure of formula 1 (FIG. 1A). Each possibility represents a separate embodiment of the present invention.

In a similar manner, lactams (cyclic amides) can be hydrogenated to the corresponding amino alcohols. In addition, polyamides and/or polypeptides can be hydrogenated to the corresponding alcohols and amines.

Depending on the complex being used, the reaction permits the optional use of one or more equivalents of a base.

Similar to the hydrogenation of amides, the novel Ruthenium complexes of the present invention can also catalyze the hydrogenation of esters and organic carbonates to alcohols, or the hydrogenation of carbamates to the corresponding amines and alcohols, or the hydrogenation of urea derivatives to the corresponding amines and methanol. Thus, in other embodiments, the present invention further provides a process for hydrogenating an ester, organic carbonate, carbamate or urea derivative, with molecular hydrogen ($H_2$) in the presence of the Ruthenium complex, as described herein. As contemplated herein, the inventors have further discovered a novel process for converting esters (e.g., formate esters), organic carbonates, carbamates or urea derivatives to alcohols and/or amines in high yields and high turnover numbers. Polyesters, polycarbonates, polycarbamates and/or polyureas can be hydrogenated in a similar manner. These reactions are catalyzed by a Ruthenium complex, which is represented by anyone of formulae A1, A2, A3, B1, B2, C1, C2, 3, 4, 7 and 9 or any other Ruthenium complex covered by such formulae. These reactions are also catalyzed by the borohydride complexes described herein, such as complexes D, E, F, G and H, and compounds 2', 4', 6' and 8'. Currently preferred catalysts (complexes) for hydrogenation of organic carbonates, carbamates and urea derivatives are Ruthenium complexes which are represented by anyone of formulae A1, A2, A3, B1, B2, C1, C2, 3, 4, 7 and 9, In some preferred embodiments, hydrogenation of esters is catalyzed by the borohydride complexes described herein, such as complexes D, E, F, G and H, and compounds 2', 4', 6' and 8' Depending on the complex being used, the reaction permits the optional use of one or more equivalents of a base.

In another embodiment, the hydrogenation of organic carbonates, carbamates and urea derivatives to amines and alcohols (including hydrogenation of polycarbonates, polycarbamates and polyurea derivatives) can be catalyzed by any of the Ruthenium complexes described in US Patent publication US 2009/0112005, in particular Ruthenium complexes of formula A1', A2' and A3' wherein $L_1$ is $N(R)_2$. One embodiment of such compounds is a pincer complex represented by the structure of formula 1 (FIG. 1A). Each possibility represents a separate embodiment of the present invention.

In a similar manner, lactones (e.g., cyclic esters) can be hydrogenated to alcohols. For example, cyclic di-esters (di-lactones) can be hydrogenated to the corresponding (vicinal) diols. In one particular embodiment, the present invention is directed to a process comprising hydrogenation of cyclic di-esters (di-lactones), which may be biomass-derived. e.g., glycolide and lactide to the corresponding 1,2-diols (vicinal diols). The process of lactone hydrogenation can be catalyzed by the same complexes described above with respect to hydrogenation of esters to alcohols. In other embodiments, the present invention includes process for hydrogenating polyesters to the corresponding alcohols. Each possibility represents a separate embodiment of the present invention.

The present invention further provides a process for preparing amides (including polyamides and polypeptides), by reacting an amine and an alcohol in the presence of a Ruthenium complex, to generate the amide compound and molecular hydrogen ($H_2$). As contemplated herein, the inventors have further discovered a novel process for preparing amides in which primary and secondary amines are directly acylated by equimolar amounts of alcohols to produce amides and molecular hydrogen in high yields and high turnover numbers. This reaction is catalyzed by a Ruthenium complex or a boronated complex thereof, which is represented by anyone of formulae A1, A2, A3, B1, C1, B2, C2, D, E, F (for complex F preferably $L_4$ is $CH_2NR^aR^b$), H, 3, 4, 7, 9, 4' and 8', or any other Ruthenium complex or their boronated complexes covered by such formulae. Depending on the complex being used, the reaction permits the optional use of one or more equivalents of a base. Use of diamines or dialcohols in the reaction leads to diamides, whereas when diamines and dialcohols are used together, the process results in a polyamide. Similarly, beta-amino alcohols can be dehydrogenated in the presence of the Ruthenium complexes of the present invention to form polypeptides. Also, the process of the invention covers inter or intramolecular coupling of amino alcohols to form lactams, including cyclic peptides (in the case of coupling of beta-amino alcohols).

The amidation or polyamidation reactions (including the coupling of beta-amino alcohols to form polypeptides), can also be catalyzed by the Ruthenium complexes described in US Patent publication US 2009/0112005, in particular Ruthenium complexes in which $L_1$ is $N(R)_2$. One embodiment of such compounds is a pincer complex represented by the structure of formula 1 (FIG. 1A). Other compounds are represented by any of formulae A1', A2' or A3' wherein $L_1$ is $N(R)_2$ as described herein. Polypeptide (or cyclic peptide) preparation from beta-amino alcohols, catalyzed by the Ruthenium complexes described in US Patent publication US 2009/0112005, namely compounds A1', A2' or A3' wherein $L_1$ is $N(R)_2$ has not previously been described, and constitutes another embodiment of the present invention.

In some embodiments, beta-amino alcohols can be dehydrogenated in the presence of Ruthenium complexes to form cyclic dipeptides. Such reactions are catalyzed by a Ruthenium complex or a boronated complex thereof, which is represented by anyone of formulae A1, A2, A3, B1, C1, B2, C2, D, E, F (for complex F preferably $L_4$ is $CH_2NR^aR^b$), H, 3, 4, 7, 9, 4' and 8', or any other Ruthenium complex or their boronated complexes covered by such formulae. Alternatively, such reactions can also be catalyzed by the Ruthenium complexes described in US Patent publication US 2009/0112005, in particular Ruthenium complexes in which $L_1$ is $N(R)_2$.

In other embodiments, beta-amino alcohols can be dehydrogenated in the presence of Ruthenium complexes to form pyrazines. Ruthenium complexes which catalyze such reactions are those which contain two phosphnine ligands or N-heterocyclic carbene ligands. Examples of such complexes include borohydride complexes represented by formula F (wherein each one of $L^1$ and $L^4$ contain a phosphine and/or N-heterocyclic carbene), G, 2' and 6'. Other Ruthenium complexes which catalyze such reactions are described in US Patent publication US 2009/0112005, in particular Ruthenium complexes of formula A1', A2' and A3' which contain two phosphnine ligands or N-heterocyclic carbene ligands.

The present invention further provides a process for preparing esters by coupling of alcohols in the presence of a Ruthenium complex, to generate the ester compound and molecular hydrogen. In one embodiment, the process involves coupling of primary alcohols. In another embodiment, the process involves coupling of a primary and secondary alcohol. These reactions are catalyzed by a Ruthenium complex or a boronated complex thereof, which is represented by anyone of formulae A1, A2, A3, B1, C1, B2, C2, D, E, F, G, H, 3, 4, 7, 9, 2', 4', 6' and 8' or any other Ruthenium complex or their boronated complexes covered by such formulae. Depending on the complex being used, the reaction permits the optional use of one or more equivalents of a base. Use of dialcohols in the reaction leads to polyesters or to lactones.

The present invention further relates to a process for preparing a ketone by dehydrogenation of a secondary alcohol, by reacting the secondary alcohol in the presence of the Ruthenium complex which is represented by anyone of formulae A1, A2, A3, B1, C1, B2, C2, D, E, F, G, H, 3, 4, 7, 9, 2', 4', 6' and 8' or any other Ruthenium complex or their boronated complexes covered by such formulae, thereby generating the ester and molecular hydrogen.

The present invention further relates to a process for the coupling of alcohols with water and a base to form carboxylic acid salts, by contacting the alcohol and a base with water in the presence of the Ruthenium complex which is represented by anyone of formulae A1, A2, A3, B1, C1, B2, C2, D, E, F, G, H, 3, 4, 7, 9, 2', 4', 6' and 8' or any other Ruthenium complex or their boronated complexes covered by such formulae, thereby generating the carboxylic acid salt and molecular hydrogen. Optionally, the salt can be converted to the carboxylic acid upon reaction with an acid. This reaction can also be catalyzed by the Ruthenium complexes described in US Patent publication US 2009/0112005, such as, but not limited to the compounds of formula A1', A2' and A3', and Pincer complex of Formula 1.

The present invention further provides a process for preparing amides, by reacting an amine and an ester in the presence of a Ruthenium complex, to generate the amide compound and molecular hydrogen ($H_2$). As contemplated herein, the inventors have further discovered a novel process for preparing amides in which primary and secondary amines are directly reacted with esters to produce amides and molecular hydrogen in high yields and high turnover numbers. This reaction is catalyzed by a Ruthenium complex or a boronated complex thereof, which is represented by anyone of formulae A1, A2, A3, B1, C1, B2, C2, D, E, F (when complex F is used and $L^4$ is —$CH_2$-$L^1$, $L^1$ is preferably $NR^aR^b$), H, 3, 4, 7, 9, 4' and 8', or any other Ruthenium complex or their boronated complexes covered by such formulae. Depending on the complex being used, the reaction permits the optional use of one or more equivalents of a base. Reactions of esters with diamines leads to diamides.

The present invention further provides a process for preparing esters by acylation of alcohols using esters in the presence of a Ruthenium complex, to generate the ester compound and molecular hydrogen. In one embodiment, the process involves reaction of primary alcohols and esters. In another embodiment, the process involves reaction of a secondary alcohols and esters. These reactions are catalyzed by a Ruthenium complex or a boronated complex thereof, which is represented by anyone of formulae A1, A2, A3, B1, C1, B2, C2, D, E, F, G, H, 3, 4, 7, 9, 2', 4', 6' and 8' or any other Ruthenium complex or their boronated complexes covered by such formulae. Depending on the complex being used, the reaction permits the optional use of one or more equivalents of a base.

In some embodiments, the process of any of the embodiments of the present invention as described herein is conducted under neat conditions in the absence of a solvent. In other embodiments, however, the process is conducted in the presence of an organic solvent such as, but not limited to benzene, toluene, o-, m- or p-xylene, mesitylene (1,3,5-trimethyl benzene), dioxane, THF, DME, anisole and cyclohexane.

In some embodiments the process is conducted under heat. In other embodiments, the process is conducted under inert gas. In other embodiments, the process is conducted under heat and under inert gas. However, the reactions of the invention can, when appropriate, also be conducted in the open air.

In one embodiment, the Ruthenium complex of the present invention is represented by the structure of formula A1, and the reactions described herein do not require the presence of a base. In another embodiment, Ruthenium complex is represented by the structure of formula A2. When Z is H and Y is other than H, the process further comprises adding at least one equivalent of a base relative to the Ruthenium complex. When Z and Y are other than H, the process further comprises adding at least two equivalents of a base relative to the Ruthenium complex. When Z and Y are both H, the process is conducted in the absence of a base. In another embodiment, Ruthenium complex is represented by the structure of formula A3. When Z is H, the process further comprises adding at least one equivalent of a base relative to the Ruthenium complex. When Z is other than H, the process further comprises adding at least two equivalents of a base relative to the Ruthenium complex.

Also encompassed by the present invention are certain intermediate compounds and their use in the preparation of the Ruthenium complexes of the present invention. Thus, in one embodiment, the present invention relates to a compound represented by the structure of formula Z:

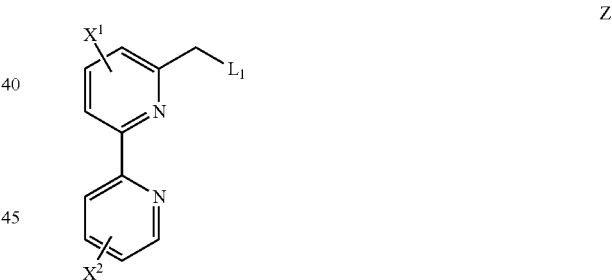

Z wherein
$L^1$ is selected from the group consisting of phosphine (PR$^a$R$^b$), phosphite P(OR$^a$)(OR$^b$), phosphinite P(OR$^a$)(R$^b$), amine (NR$^a$R$^b$), imine, oxazoline, sulfide (SR$^a$), sulfoxide (S(=O)R$^a$), heteroaryl containing at least one heteroatom selected from nitrogen and sulfur; arsine (AsR$^a$R$^b$), stibine (SbR$^a$R$^b$) and a N-heterocyclic carbene represented by the structures:

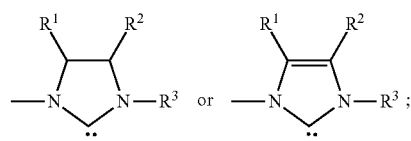

$X^1$ represents zero, one, two or three substituents and $X^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; and $R^a$ and $R^b$ are each independently alkyl, cycloalkyl, aryl, heterocyclyl, heteroaryl, alkylcycloalkyl, alkylaryl, alkylheterocyclyl or alkylheteroaryl.

In some embodiments, the compound selected from the group consisting of

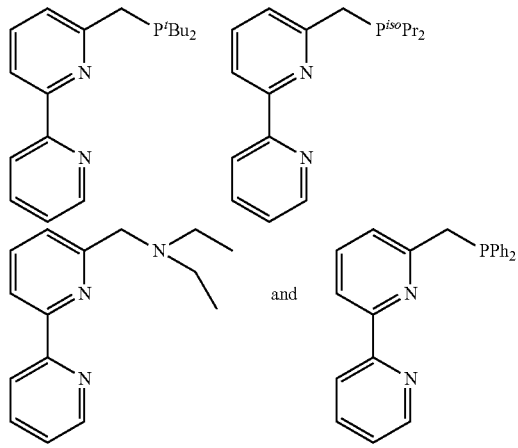

and

BRIEF DESCRIPTION OF THE DRAWINGS

The present invention will be understood and appreciated more fully from the following detailed description taken in conjunction with the appended figures:

FIG. 5: shows MALDI-TOF mass spectra of polyamides synthesized by the processes of the present invention.

DETAILED DESCRIPTION OF THE PRESENT INVENTION

Figure 1A:
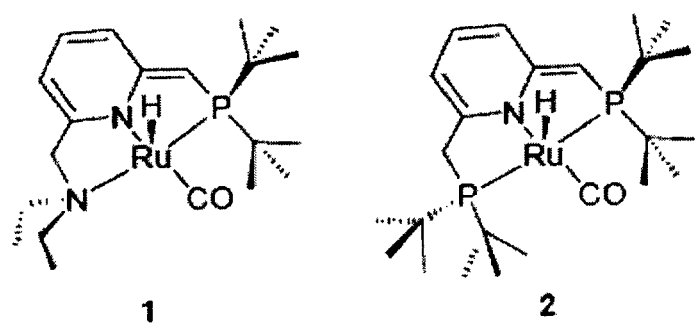
FIG. 1: shows the structure of dearomatized PNN pincer complexes 1 and 2 (FIG. 1A) and complex 3 (FIG. 1B).

The present invention provides novel Ruthenium based complexes and catalysts and borohydride complexes thereof, and the use of such complexes for, inter alia, (1) hydrogenation of amides (including polyamides) to alcohols and amines; (2) preparing amides from alcohols with amines (including the preparation of polyamides (e.g., polypeptides) by reacting dialcohols and diamines and/or by polymerization of amino alcohols); (3) hydrogenation of esters to alcohols (including hydrogenation of cyclic esters (lactones) or cyclic di-esters (lactones) or polyesters); (4) hydrogenation of organic carbonates (including polycarbonates) to alcohols and hydrogenation of carbamates (including polycarbamates) or urea derivatives to alcohols and amines; (5) dehydrogenative coupling of alcohols to esters; (6) dehydrogenation of secondary alcohols to ketones; (7) amidation of esters (i.e., synthesis of amides from esters and amines); (8) acylation of alcohols using esters; (9) coupling of alcohols with water to form carboxylic acids; and (10) dehydrogenation of beta-amino alcohols to form pyrazines. The present invention further relates to the novel uses of certain pyridine Ruthenium complexes.

Ruthenium Complexes

In one embodiment, the Ruthenium complex is represented by any one of formulae A1, A2 or A3:

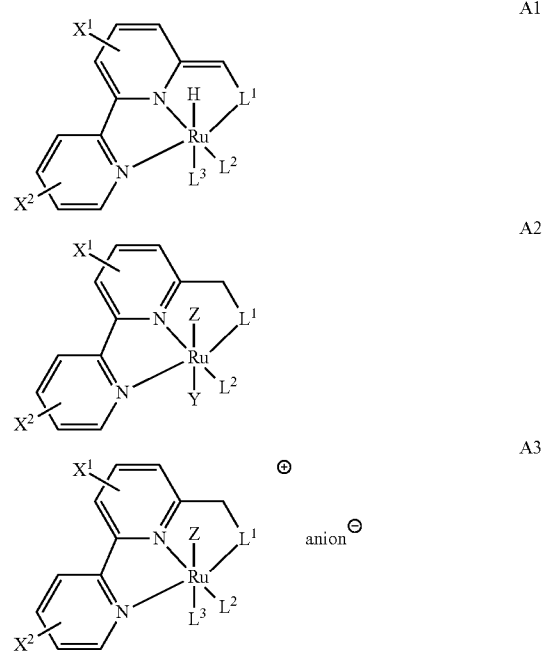

wherein $L^1$ is selected from the group consisting of phosphine ($PR^aR^b$), phosphite $P(OR^a)(OR^b)$, phosphinite $P(OR^a)(R^b)$, amine ($NR^aR^b$), imine, oxazoline, sulfide ($SR^a$), sulfoxide ($S(=O)R^a$), heteroaryl containing at least one heteroatom selected from nitrogen and sulfur; arsine ($AsR^aR^b$), stibine ($SbR^aR^b$) and a N-heterocyclic carbene represented by the structures:

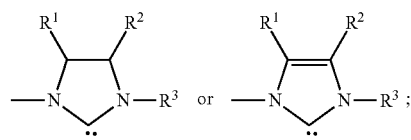

$L^2$ is a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene and alkyne;

L³ is absent or is L²;

Y and Z are each independently H or an anionic ligand selected from the group consisting of H, halogen, OCOR, OCOCF₃, OSO₂R, OSO₂CF₃, CN, OR, N(R)₂ and RS;

$R^a$, $R^b$ and $R^c$ are each independently alkyl, cycloalkyl, aryl, heterocyclyl, heteroaryl, alkylcycloalkyl, alkylaryl, alkylheterocyclyl or alkylheteroaryl;

R, $R^1$, $R^2$ and $R^3$ are each independently H, alkyl, cycloalkyl, aryl, heterocyclyl, heteroaryl, alkylcycloalkyl, alkylaryl, alkylheterocyclyl or alkylheteroaryl;

$X^1$ represents zero, one, two or three substituents and $X^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; and anion represents a group bearing a single negative charge; or a borane derivative of said complex.

In one embodiment, $X^1$ and $X^2$ are absent (i.e, the bipyridine moiety is unsubstituted). In another embodiment, $L^1$ is phosphine ($PR^aR^b$). In another embodiment, $L^2$ is CO.

In one embodiment, the Ruthenium complex is represented by the structure of formula A1:

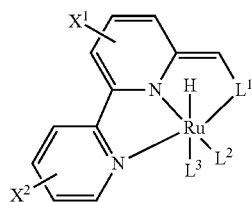

A1

In a particular embodiment of formula A1, the Ruthenium complex is represented by the structure of formula B1. In another particular embodiment of formula A1, the Ruthenium complex is represented by the structure of formula C1.

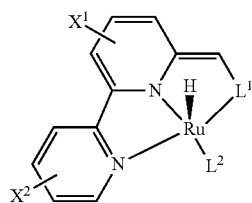

B1

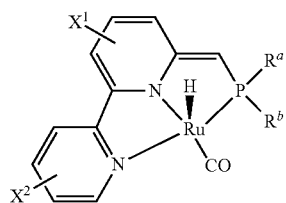

C1

Each of $L^1$, $L^2$, $X^2$, $R^a$ and $R^b$ in Formulae B1 and C1 are as defined for formula A1. Each possibility represents a separate embodiment of the present invention.

In one embodiment, each of $R^a$ and $R^b$ is tert-butyl. In another currently, each of $R^c$ and $R^d$ are isopropyl. Each possibility represents a separate embodiment of the present invention.

Figure 1B:
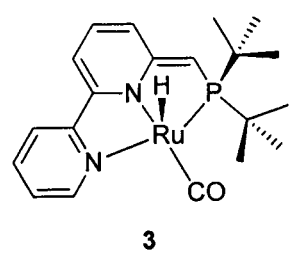

In one embodiment, the Ruthenium complex is represented by the structure of formula 3 (also shown in FIG. 1B).

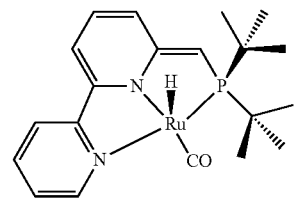

3

In another embodiment of the present invention, the Ruthenium complex is represented by the structure of formula A2:

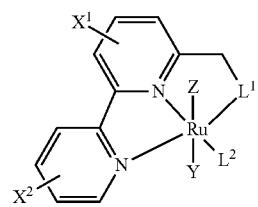

A2

In one embodiment of Formula A2, Z and Y are either each H, each a halogen (e.g., F, Cl, Br, I) or one of Z and Y is H and the other a halogen. Each possibility represents a separate embodiment of the present invention.

In one particular embodiment, Z is H and Y is other than H in formula A2. When such a complex is used, the processes of the invention as described hereinbelow are typically conducted in the presence of at least one equivalent of a base relative to the Ruthenium complex. In another particular embodiment, each of Z and Y is other than H in formula A2. When such a complex is used, the processes of the invention as described hereinbelow are typically conducted in the presence of at least two equivalents of a base relative to the Ruthenium complex. In another particular embodiment, Z and Y are both H in formula A2. When such a complex is used, no base is required for the processes of the invention.

In one embodiment of formula A2, the Ruthenium complex is represented by the structure of formula B2:

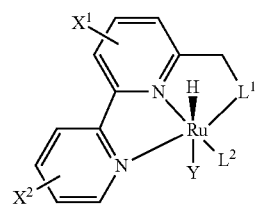

B2

In another particular embodiment of formula A2, the Ruthenium complex is represented by the following structure of formula C2:

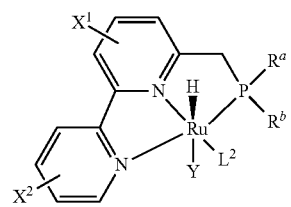

C2

Each of $L^1$, $L^2$, $X^1$, $X^2$, Y, $R^a$ and $R^b$ in formulae B2 and C2 are as defined in formula A2. Each possibility represents a separate embodiment of the present invention.

In one embodiment, Y is halogen, such as chloro. For example, the Ruthenium complex may be represented by the structure of any of formulae 4, 7 or 9:

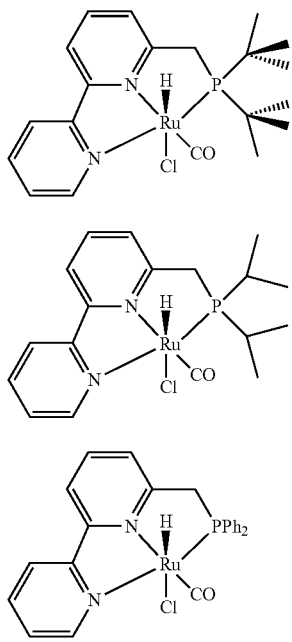

In another embodiment of the present invention, the Ruthenium complex is represented by the structure of formula A3:

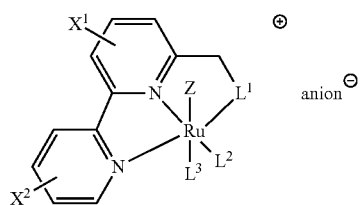

In one particular embodiment, Z is H in formula A3. When such a complex is used, the processes of the invention as described hereinbelow are typically conducted in the presence of at least one equivalent of a base relative to the Ruthenium complex. In another particular embodiment, Z is other than H in formula A3. When such a complex is used, the processes of the invention as described hereinbelow are typically conducted in the presence of at least two equivalents of a base relative to the Ruthenium complex.

Compounds of formula A2 and formula A3 are precursors of compounds of formula A1. Additionally some precursors of the complexes of formula A1 include, but are not limited to, compounds of general formulae (i), (ii) and (iii):

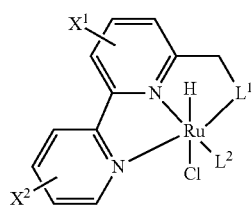

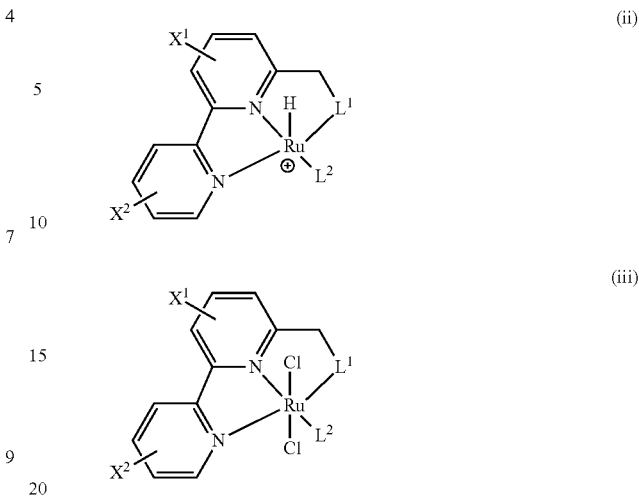

It is understood that any one or more of the precursors can themselves function as complexes in the process of the present invention. For example, when structures (i) and (ii) and their equivalents are used, at least one equivalent of base relative to the Ruthenium complex can be used (e.g., alkoxide, hydroxide). Alternatively, when structure (iii) or its equivalents are used, at least two equivalents of base relative to the Ruthenium complex can be used. Non-limiting examples of bases are alkoxide (e.g., t-butoxide, methoxide, ethoxide), or hydroxide.

Borohydride Complexes:

It has been unexpectedly discovered that certain reactions such conversion of primary alcohols to esters, as well as the dehydrogenation of secondary alcohols to ketones, as well as other reactions contemplated herein, can be effectively accomplished with stable, readily synthesized PNN- and PNP Ru borohydride complexes, in the absence of a base, under mild and neutral conditions, optionally in the absence of hydrogen acceptor.

Thus, in one embodiment, the present invention provides a borane derivative of a Ruthenium complex, the borane derivative represented by the structure of formula F:

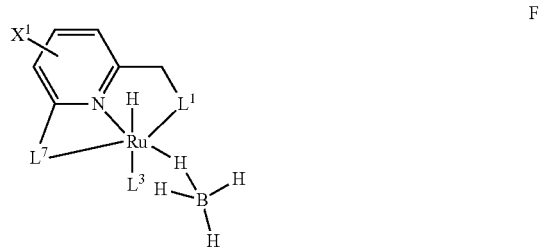

wherein each $L^1$ is independently selected from the group consisting of phosphine ($PR^aR^b$), phosphite $P(OR^a)(OR^b)$ phosphinite $P(OR^a)(R^b)$, amine ($NR^aR^b$), imine, oxazoline, sulfide ($SR^a$), sulfoxide ($S(=O)R^a$), heteroaryl containing at least one heteroatom selected from nitrogen and sulfur; arsine ($AsR^aR^b$), stibine ($SbR^aR^b$) and a N-heterocyclic carbene represented by the structures:

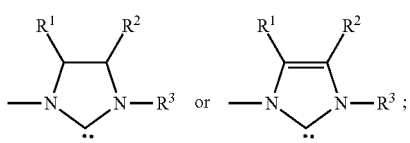

L³ is absent or is a mono-dentate two-electron donor selected from the group consisting of CO, PR$^a$R$^b$R$^c$, P(OR$^a$)(OR$^b$)(OR$^c$), NO$^+$, AsR$^a$R$^b$R$^c$, SbR$^a$R$^b$R$^c$, SR$^a$R$^b$, nitrile (RCN), isonitrile (RNC), N$_2$, PF$_3$, CS, heteroaryl and tetrahydrothiophene;

L⁴ is —CH$_2$-L¹- or a group of the formula:

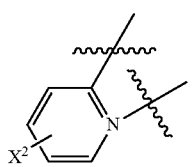

R$^a$, R$^b$ and R$^c$ are each independently alkyl, cycloalkyl, aryl, heterocyclyl, heteroaryl, alkylcycloalkyl, alkylaryl, alkylheterocyclyl or alkylheteroaryl;

R, R¹, R² and R³ are each independently H, alkyl, cycloalkyl, aryl, heterocyclyl, heteroaryl, alkylcycloalkyl, alkylaryl, alkylheterocyclyl or alkylheteroaryl;

X¹ represents zero, one, two or three substituents and X² represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety.

In some embodiments, the borane derivative is represented by the structure of any of formulae D, E, G and H. Each possibility represents a separate embodiment of the present invention. It is noted that compounds D and E are borane derivatives of the Ruthenium complex of formula A1 as described hereinabove.

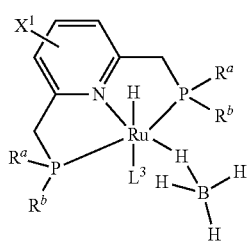

G

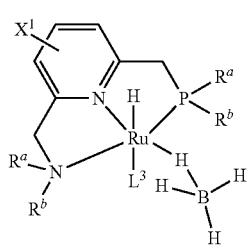

H

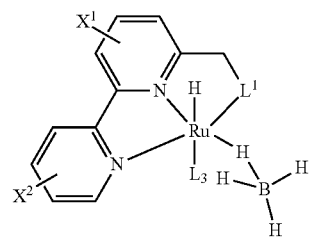

D

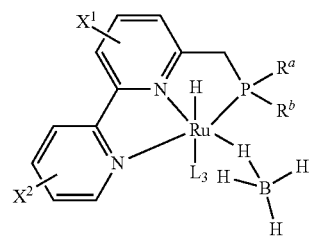

E

In some other embodiments, the borane derivative is represented by the structure of any of formulae 2', 4', 6' and 8'. Each possibility represents a separate embodiment of the present invention.

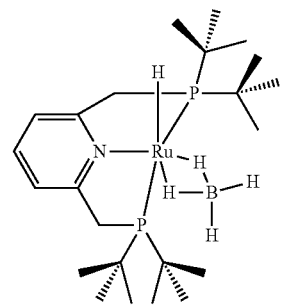

2'

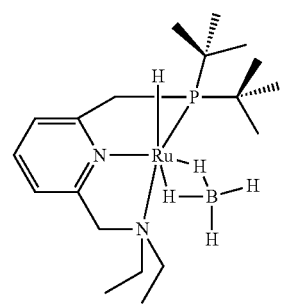

4'

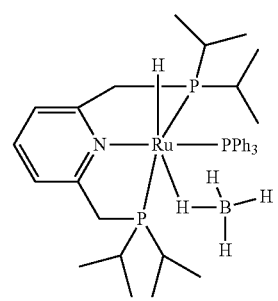

6'

-continued

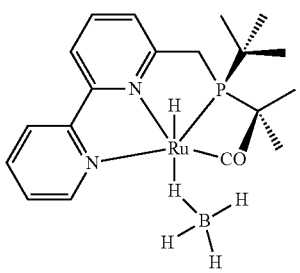

8'

The present invention further provides processes for preparing the novel boronated derivatives of Ruthenium based catalytic complexes. Thus, in one embodiment, the present invention provides a process for preparing a Ruthenium complex represented by the structure of formula D

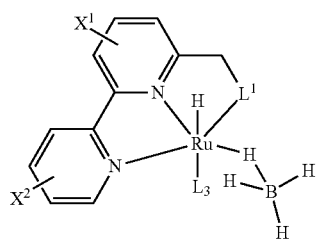

D by reacting sodium borohydride ($NaBH_4$) with a precursor of formula A2

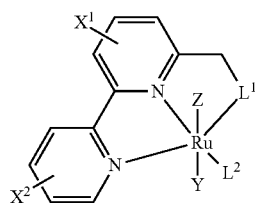

A2 wherein $L^1$ is selected from the group consisting of phosphine ($PR^aR^b$), phosphite $P(OR^a)(OR^b)$, phosphinite $P(OR^a)(R^b)$, amine ($NR^aR^b$), imine, oxazoline, sulfide ($SR^a$), sulfoxide ($S(=O)R^a$), heteroaryl containing at least one heteroatom selected from nitrogen and sulfur; arsine ($AsR^aR^b$), stibine ($SbR^aR^b$) and a N-heterocyclic carbene represented by the structures:

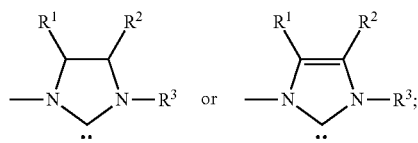

$L^2$ is a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene and alkyne;

$L^3$ is absent or is $L^2$;

Y and Z are each independently halogen, $OCOCF_3$, $OSO_2R$ or $OSO_2CF_3$, $R^a$, $R^b$ and $R^c$ are each independently alkyl, cycloalkyl, aryl, heterocyclyl, heteroaryl, alkylcycloalkyl, alkylaryl, alkylheterocyclyl or alkylheteroaryl;

R, $R^1$, $R^2$ and $R^3$ are each independently H, alkyl, cycloalkyl, aryl, heterocyclyl, heteroaryl, alkylcycloalkyl, alkylaryl, alkylheterocyclyl or alkylheteroaryl;

$X^1$ represents zero, one, two or three substituents and $X^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety.

In another embodiment, the present invention provides a process for preparing a borane derivative of a Ruthenium complex represented by the structure of formula F

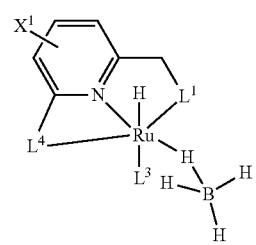

F the process comprising the step of reacting sodium borohydride ($NaBH_4$) with a precursor of formula

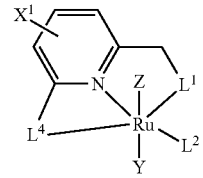

wherein $L^1$ is selected from the group consisting of phosphine ($PR^aR^b$), phosphite $P(OR^a)(OR^b)$, phosphinite $P(OR^a)(R^b)$, amine ($NR^aR^b$), imine, oxazoline, sulfide ($SR^a$), sulfoxide ($S(=O)R^a$), heteroaryl containing at least one heteroatom selected from nitrogen and sulfur; arsine ($AsR^aR^b$), stibine ($SbR^aR^b$) and a N-heterocyclic carbene represented by the structures:

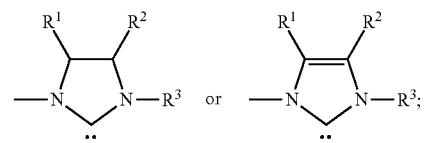

$L^2$ is a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene and alkyne;

$L^3$ is absent or is $L^2$;
$L^4$ is —CH$_2$-$L^1$- or a group of the formula:

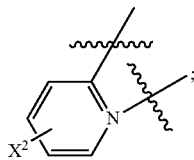

Y and Z are each independently halogen, OCOCF$_3$, OSO$_2$R or OSO$_2$CF$_3$, R$^b$ and R$^c$ are each independently alkyl, cycloalkyl, aryl, heterocyclyl, heteroaryl, alkylcycloalkyl, alkylaryl, alkylheterocyclyl or alkylheteroaryl;

R, R$^1$, R$^2$ and R$^3$ are each independently H, alkyl, cycloalkyl, aryl, heterocyclyl, heteroaryl, alkylcycloalkyl, alkylaryl, alkylheterocyclyl or alkylheteroaryl;

X$^1$ represents zero, one, two or three substituents and X$^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety.

Chemical Definitions

As used herein, the term alkyl, used alone or as part of another group, refers, in one embodiment, to a "C$_1$ to C$_{12}$ alkyl" and denotes linear and branched, saturated or unsaturated (e.g., alkenyl, alkynyl) groups, the latter only when the number of carbon atoms in the alkyl chain is greater than or equal to two, and can contain mixed structures. Non-limiting examples are alkyl groups containing from 1 to 6 carbon atoms (C$_1$ to C$_6$ alkyls), or alkyl groups containing from 1 to 4 carbon atoms (C$_1$ to C$_4$ alkyls). Examples of saturated alkyl groups include, but are not limited to, methyl, ethyl, n-propyl, isopropyl, n-butyl, iso-butyl, sec-butyl, tert-butyl, amyl, tert-amyl, hexyl. Examples of alkenyl groups include, but are not limited to, vinyl, allyl, butenyl and the like. Examples of alkynyl groups include, but are not limited to, ethynyl, propynyl and the like. Similarly, the term "C$_1$ to C$_{12}$ alkylene" denotes a bivalent radical of 1 to 12 carbons.

The alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylaryl amino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents. By way of illustration, an "alkoxyalkyl" is an alkyl that is substituted with an alkoxy group.

The term "cycloalkyl" used herein alone or as part of another group, refers to a "C$_3$ to C$_8$ cycloalkyl" and denotes any unsaturated or unsaturated (e.g., cycloalkenyl, cycloalkynyl) monocyclic or polycyclic group. Nonlimiting examples of cycloalkyl groups are cyclopropyl, cyclobutyl, cyclopentyl, cyclohexyl or cycloheptyl. Examples or cycloalkenyl groups include cyclopentenyl, cyclohexenyl and the like. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl. An alkylaryl group denotes an alkyl group bonded to an aryl group (e.g., benzyl).

The term "heteroaryl" used herein alone or as part of another group denotes a heteroaromatic system containing at least one heteroatom ring atom selected from nitrogen, sulfur and oxygen. The heteroaryl contains 5 or more ring atoms. The heteroaryl group can be monocyclic, bicyclic, tricyclic and the like. Also included in this expression are the benzo-heterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "heterocyclic ring" or "heterocyclyl" used herein alone or as part of another group denotes a five-membered to eight-membered rings that have 1 to 4 heteroatoms, such as oxygen, sulfur and/or nitrogen. These five-membered to eight-membered rings can be saturated, fully unsaturated or partially unsaturated. Non-limiting examples of heterocyclic rings include piperidinyl, piperidinyl, pyrrolidinyl pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The inorganic support which is attached to the bipyridine ring can be, for example, silica, silica gel, glass, glass fibers, titania, zirconia, alumina and nickel oxide.

The polymer which is attached to the bipyridine pyridine ring can be, for example, selected from polyolefins, polyamides, polyethylene terephthalate, polyvinylchloride, polyvinylidenechloride, polystyrene, polymethracrylate, natural rubber, polyisoprene, butadiene-styrene random copolymers, butadiene acrylonitrile copolymers, polycarbonate, polyacetal, polyphenylenesulfide, cyclo-olefin copolymers, styrene-acrylonitrile copolymers, ABS, styrene-maleic anhydride copolymers, chloroprene polymers, isobutylene copolymers, polystyrene, polyethylene, polypropylene, and the like.

The term "anion" as used herein refers to any moiety or group bearing a negative charge. Examples of anionic moieties include, but are not limited to halogen (e.g., F, Cl, Br, I), OCOR', OCOCF$_3$, OSO$_2$R', OSO$_2$CF$_3$, BF$_4$, PF$_6$, SbF$_6$, BR$_4$, ClO$_4$, AlCl$_4$, CN, OH, OR' or NR'$_2$ wherein R' is selected from alkyl, cycloalkyl, aryl, alkylaryl, heterocyclyl and heteroaryl, wherein each of the alkyl, cycloalkyl, aryl, alkylaryl, heterocyclyl and heteroaryl is as defined above.

Novel Processes

The present invention further provides various processes which utilize the Ruthenium complexes of the present invention as catalysts.

In general, the processes of the present invention can be conducted in the absence or in the presence of a solvent. When a solvent is present, it can be an organic solvent, including but not limited to benzene, toluene, o-, m- or p-xylene mesitylene (1,3,5-trimethyl benzene), dioxane, THF, DME, anisole and cyclohexane.

The stoichiometric ratios of reagents can vary, and depend on the particular alcohol, amine, amide, ester etc., being used, as well as solvent used for the reaction. The reactions of the present invention can be performed for as long as needed so as to effect desired transformation, for example 1 hr to 24 hr or longer than 24 hr. The temperature range can vary from room temperature to heated conditions, for example up to 200° C.

1. Hydrogenation of Amides to Alcohols and Amines

The present invention provides a process for hydrogenating amides (including polyamides and polypeptides) by reacting the amide with molecular hydrogen ($H_2$) in the presence of the Ruthenium complexes of the present invention to generate the corresponding alcohol and amine. As contemplated herein, the inventors have discovered a novel process for converting amides to alcohols and amines in high yields and high turnover numbers. This reaction is catalyzed by a Ruthenium complex, which is represented by anyone of formulae A1, A2, A3, B1, B2, C1, C2, 3, 4, 7 and 9 or any other Ruthenium complex covered by such formulae. In addition, this reaction is catalyzed by any of the Ruthenium complexes described in US Patent publication US 2009/0112005, the contents of which are incorporated by reference herein. The compounds of US 2009/0112005 are pyridine based derivatives represented by the structure of formula A1', A2' and A3'. Compounds which catalyze hydrogenation of amides to alcohols and amines are those wherein $L_1$ is $N(R)_2$:

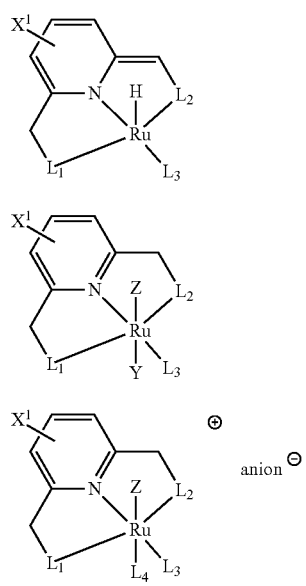

wherein
$L_1$ is $N(R)_2$,
$L_2$ is selected from the group consisting of nucleophilic carbene (:C(R)$_2$), P(R)$_2$, P(OR)$_2$, N(R)$_2$, imine, SR, SH, S(=O)R, heteroaryl wherein the heteroatom is selected from nitrogen and sulfur, As(R)$_2$, Sb(R)$_2$ and an N-heterocyclic carbene represented by the structure:

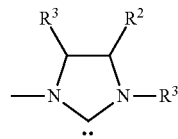

each of R, $R^2$ and $R^3$ are independently selected from the group consisting of alkyl, cycloalkyl, aryl, alkylaryl, heterocyclyl and heteroaryl;

$L_3$ is a mono-dentate two-electron donor selected from the group consisting of CO, P(R)$_3$, P(OR)$_3$, NO$^+$, As(R)$_3$, Sb(R)$_3$, S(R)$_2$, nitrile (RCN) and isonitrile (RNC) wherein R is as defined above;

$L_4$ is absent or is $L_3$;

Y and Z are each independently H or an anionic ligand selected from the group consisting of halogen, OCOR, OCOCF$_3$, OSO$_2$R, OSO$_2$CF$_3$, CN, OH, OR, N(R)$_2$, RS and SH; wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and anion represents a group bearing a single negative charge.

One embodiment of such compounds is a pincer complex represented by the structure of formula 1 (FIG. 1A).

Depending on the complex being used, the reaction permits the optional use of one or more equivalents of a base.

The process of the invention, i.e., the direct catalytic conversion of amides to alcohols and amides is illustrated in Scheme 4. This novel, environmentally benign reaction can be used to prepare alcohols and amines from any type of amide, with high atom economy and in some embodiments no stoichiometric activating agents, thus generating no waste. Thus, in one embodiment, the present invention provides a process for hydrogenating an amide represented by the formula $R^4C(=O)-N-R^5R^{5'}$ to an alcohol of formula $R^4CH_2OH$ and amine of formula $R^5R^{5'}NH$:

Scheme 4

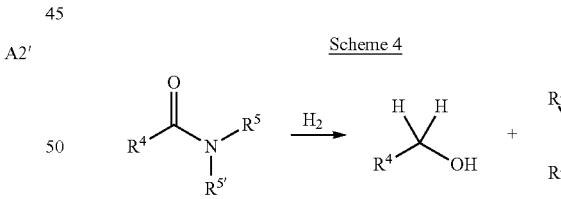

wherein $R^4$, $R^5$ and $R^{5'}$ are each independently selected from the group consisting of H, an unsubstituted or substituted alkyl, alkoxyalkyl, cycloalkyl, aryl, alkylaryl, heterocyclyl and heteroaryl.

A variety of amides can be used in the process of the invention. In some embodiments, the amide is selected from the group consisting of N-benzyl-2-methoxyacetamide, N-hexyl-2-methoxyacetamide, N-hexyl-3-methyloxetane-3-carboxamide, N-hexyl-2-furanylcarboxamide, N-benzylbenzamide, N-ethylacetamide, N-methylpropionamide, N-cyclohexyl-2-methoxyacetamide, N-phenylacetamide, N-phenylhexylamide, 2-methoxy-N-phenylacetamide, N-phenylbenzamide, Ethylenediamine-N,N'-(2-methoxyacetamide), N-hexanoylmorpholine, N-butanoylmorpholine, N-2-metoxyacetylpyrrolidine, N-formylmorpholine, N,N-dimethylformamide, N,N-diethylbenzamide, benzamide, 4-methylbenzamide, cyclohexanecarboxamide, hexanamide, acetamide, acrylamide and pivalamide. Each possibility represents a separate embodiment of the present invention.

In a similar manner, cyclic amides (lactams) can be hydrogenated to the corresponding amino alcohols. In one embodiment, the lactam is a cyclic peptide, which can be hydrogenated with the Ruthenium complex of the present invention to the respective amino alcohol. In a similar manner, polyamides can be hydrogenated to amines and alcohols, and polypeptides can be hydrogenated to amino alcohols.

2. Hydrogenation of Esters, Organic Carbonates, Carbamates and Urea Derivatives

Similar to the hydrogenation of amides, the novel Ruthenium complexes of the present invention can also catalyze the hydrogenation of esters, hydrogenation of organic carbonates, hydrogenation of carbamates, or hydrogenation of urea derivatives to the corresponding amines and/or alcohols. Thus, in some embodiments, the present invention further provides a process for hydrogenating an ester, organic carbonate, carbamate or urea derivative with molecular hydrogen ($H_2$) in the presence of the Ruthenium complex of the present invention. As contemplated herein, the inventors have discovered a novel process for converting esters (e.g., formate esters), organic carbonates, carbamates and/or urea derivatives to alcohols and/or amines in high yields and high turnover numbers. This reaction is catalyzed by a Ruthenium complex, which is represented by anyone of formulae A1, A2, A3, B1, B2, C1, C2, 3, 4, 7 and 9 or any other Ruthenium complex covered by such formulae. These reactions are also catalyzed by the borohydride complexes described herein, such as complexes D, E, F, G and H, and compounds 2', 4', 6' and 8'. Currently preferred complexes for hydrogenation of organic carbonates, carbamates and urea derivatives are Ruthenium complexes which are represented by anyone of formulae A1, A2, A3, B1, B2, C1, C2, 3, 4, 7 and 9. In some preferred embodiments, hydrogenation of esters is catalyzed by the borohydride complexes described herein, such as complexes D, E, F, G and H, and compounds 2', 4', 6' and 8'. Again, depending on the complex being used, the reaction permits the optional use of one or more equivalents of a base.

In other embodiments, the hydrogenation of organic carbonates, carbamates and urea derivatives can be catalyzed by any of the Ruthenium complexes described in US Patent publication US 2009/0112005, the contents of which are incorporated by reference herein. Examples of such compounds are compounds of formula A1', A2' and A3' wherein $L_1$ is $N(R)_2$, as described above with respect to processes for hydrogenation of amides to amines and alcohols.

One embodiment of such compounds is a pincer complex represented by the structure of formula 1 (FIG. 1A).

One embodiment of the process of the invention, i.e., the direct catalytic conversion of esters to alcohols, is illustrated in Scheme 5A, whereby an ester represented by the formula $R^6C(=O)$—$OR^7$ is hydrogenated to the corresponding alcohol or alcohols:

Scheme 5A

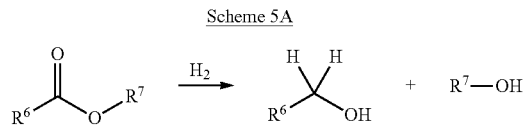

wherein $R^6$ is selected from the group consisting of H, an unsubstituted or substituted alkyl, alkoxyalkyl, cycloalkyl, aryl, alkylaryl, heterocyclyl and heteroaryl; and $R^7$ is selected from the group consisting of an unsubstituted or substituted alkyl, alkoxyalkyl, cycloalkyl, aryl, alkylaryl, heterocyclyl and heteroaryl.

It is apparent to a person of skill in the art that when the ester is symmetric (i.e., $R^6=R^7$), the reaction yields two equivalents of the same alcohol. However, when the ester is asymmetric (i.e., $R^6$ is different from $R^7$), the reaction yields a mixture of two alcohols.

In one embodiment, $R^6$ is H and the process comprises hydrogenating a formate ester of formula H—C(=O)—$OR^7$ to methanol and an alcohol of formula $R^7$—OH.

A variety of esters can be used in the process of the invention. In some embodiments, the ester is selected from the group consisting of hexyl hexanoate, butyl butyrate, methyl formate, ethyl formate, propyl formate and butyl formate. In other embodiments, the ester is a cyclic ester (a lactone). In yet other embodiments, the ester is a cyclic di-ester (di-lactone).

In yet other embodiments, the ester is a biomass-derived cyclic di-ester (di-lactone) such as, but not limited to glycolide or lactide. In yet another embodiment, the ester is polyester. Each possibility represents a separate embodiment of the present invention.

Catalytic homogeneous hydrogenation of cyclic di-esters (di-lactone), specifically glycolide and lactide to the corresponding 1,2-diols (vicinal diols) is of significant interest conceptually and practically, since these compounds are produced from biomass sources such as glycolic acid and lactic acid respectively via self-esterification, and their efficient hydrogenation can provide an alternative, mild approach to the indirect transformation of biomass resources to important synthetic building blocks. As contemplated herein, the unprecedented, environmentally benign, atom-economical route for the synthesis of propylene glycol and ethylene glycol are efficiently catalyzed by bipyridine based PNN—Ru (II) dearomatized pincer complex of formula (1), as well as other Ruthenium complexes as described herein. These catalytic reactions proceed under neutral, homogeneous conditions, at mild temperatures and mild hydrogen pressures. The optical purity of a chiral diol is unaffected during the hydrogenation reactions.

The process of lactone or di-lactone hydrogenation can be catalyzed by the same complexes described above with respect to hydrogenation of esters to alcohols.

Scheme 5B

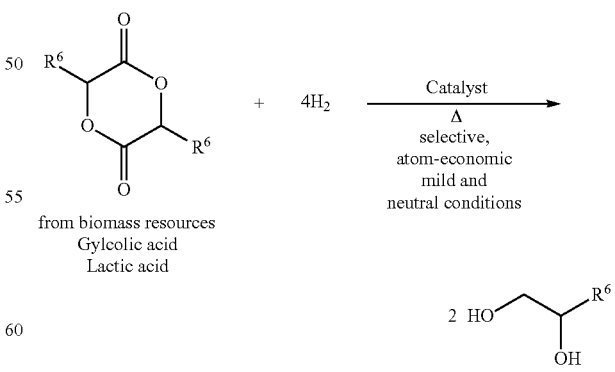

from biomass resources
Gylcolic acid
Lactic acid $R^6$ =, e.g., H, Me (racemic or chiral), etc.

wherein $R^6$ is as described above.

A variety of cyclic di-esters (di-lactones) can be used in the process of the invention. In some embodiments, the ester is a biomass-derived cyclic di-ester (di-lactone) such as, but not limited to glycolide or lactide. Each possibility represents a separate embodiment of the present invention.

Another embodiment of the process of the invention, i.e., the direct catalytic hydrogenation of organic carbonates, is illustrated in Scheme 6, whereby a carbonate represented by the formula $R^8O-C(=O)-OR^{8'}$ is hydrogenated to the corresponding alcohols(s) and methanol:

Scheme 6

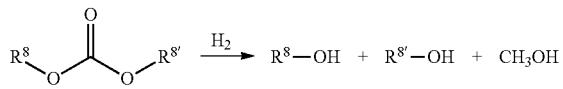

wherein $R^8$ and $R^{8'}$ are the same or different and are selected from the group consisting of an unsubstituted or substituted alkyl, alkoxyalkyl, cycloalkyl, aryl, alkylaryl, heterocyclyl and heteroaryl.

It is apparent to a person of skill in the art that when the organic carbonate is symmetric (i.e., $R^8=R^{8'}$) the reaction yields two equivalents of the same alcohol, and one equivalent of methanol. However, when the organic carbonate is asymmetric (i.e., $R^8$ is different from $R^{8'}$), the reaction yields a mixture of two alcohols, and methanol.

A variety of organic carbonates can be used in the process of the invention. In some embodiments, the carbonate is dimethyl carbonate, diethyl carbonate, dipropyl carbonate or dibutyl carbonate. In another embodiment, the carbonate is a polycarbonate, such as polyethylene carbonate or polypropylene carbonate. Each possibility represents a separate embodiment of the present invention.

Another embodiment of the process of the present invention, i.e., the direct catalytic hydrogenation of carbamates, is illustrated in Scheme 7A, whereby a carbamate represented by the formula $R^{9O}-C(=O)-NHR^{10}$ is hydrogenated to the corresponding amine, alcohol and methanol:

Scheme 7A

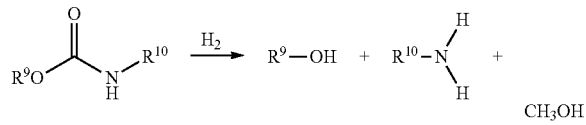

wherein $R^9$ is selected from the group consisting of an unsubstituted or substituted alkyl, alkoxyalkyl, cycloalkyl, aryl, alkylaryl, heterocyclyl and heteroaryl; and $R^{10}$ is selected from the group consisting of H or an unsubstituted or substituted alkyl, alkoxyalkyl, cycloalkyl, aryl, alkylaryl, heterocyclyl and heteroaryl.

A variety of organic carbamates can be used in the process of the invention. In some embodiments, the carbamate is methyl benzylcarbamate or methyl 4-methoxybenzylcarbamate. In another embodiment, the carbamate is a polycarbamate. Each possibility represents a separate embodiment of the present invention.

Another embodiment of the process of the present invention, i.e., the direct catalytic hydrogenation of urea derivatives, is illustrated in Scheme 7B, whereby a urea derivative is hydrogenated to the corresponding amine(s) and methanol:

Scheme 7B

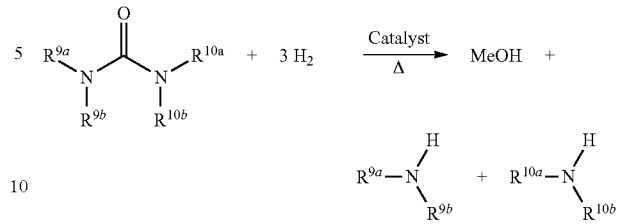

wherein each of $R^{9a}$ and $R^{10a}$, which may be the same or different, is selected from the group consisting of an unsubstituted or substituted alkyl, alkoxyalkyl, cycloalkyl, aryl, alkylaryl, and heterocyclyl, and each of $R^{9b}$ and $R^{10b}$, which may be the same or different, is selected from the group consisting of H, an unsubstituted or substituted alkyl, alkoxyalkyl, cycloalkyl, aryl, alkylaryl, and heterocyclyl. Alternatively, at least one of $R^{9a}$ and $R^{10a}$, and/or $R^{9b}$ and $R^{10b}$ together with the nitrogen to which they are attached form a heterocyclic ring.

A variety of symmetrical ($R^{9a}=R^{10a}$, $R^{9b}=R^{10b}$) and asymmetrical ($R^{9a}\neq R10^a$, $R^{9b}\neq R^{10b}$) urea derivatives can be used in the process of the invention, with each possibility representing a separate embodiment of the present invention. In some embodiments, the urea derivative is 1,3-dimethylurea, and the product of the reaction is methanol and two molecules of methylamine. In another embodiment, the urea derivative is selected from the group consisting of 1,3-dipropylurea, 1,3-dihexylurea, 1,3-bis(2-methoxyethyl)urea, 1,3-dicyclohexylurea, 1,3-dibenzylurea, 1,3-bis(4-methylbenzyl)urea, 1,3-bis(4-methylbenzyl)urea, 1,3-diphenylurea, 1,3-bis(4-(tert-butyl)phenyl)urea, 1,1,3,3-tetramethylurea, and di(piperidin-1-yl)methanone. Polyurea derivatives can also be hydrogenated in a similar manner. Each possibility represents a separate embodiment of the present invention.

3. Dehydrogenative Coupling of Alcohols and Amines with Liberation of $H_2$ to Form Amides or of Beta-Amino Alcohols to Form Pyrazines:

The present invention further provides a process for preparing amides, by reacting an amine and an alcohol in the presence of a Ruthenium complex, to generate the amide compound and molecular hydrogen ($H_2$). As contemplated herein, the inventors have further discovered a novel process for preparing amides in which primary and secondary amines are directly acylated by equimolar amounts of alcohols to produce amides and molecular hydrogen in high yields and high turnover numbers. This reaction is catalyzed by a Ruthenium complex or a boronated complex thereof, which is represented by anyone of formulae A1, A2, A3, B1, C1, B2, C2, D, E, F (when complex F is used and $L^4$ is $-CH_2-L^1$, $L^1$ is preferably $NR^aR^b$), H, 3, 4, 7, 9, 4' and 8', or any other Ruthenium complex or their boronated complexes covered by such formulae. Depending on the complex being used, the reaction permits the optional use of one or more equivalents of a base.

Use of diamines or dialcohols in the reaction leads to diamides, whereas when diamines and dialcohols are used together, the process results in a polyamide. Furthermore, reactions of amino-alcohols results in cyclic amides (lactams). For example, reaction of $H_2N(CR^1R^2)_nCH_2OH$ results in lactams for n=4, 5 or 6, such as caprolactam for n=6 and $R^1=R^2=H$. For n>6, the reaction typically results in polymers. In another embodiment, when amino alcohols such as $R-CH(NH_2)CH_2OH$ are used, peptides or polypeptides are formed (e.g., dehydrogenation of alaninol with the Ruthenium complexes of the present invention results in polyalanine).

The process of the invention, i.e., the direct catalytic conversion of alcohols and amines into amides and dihydrogen is illustrated in Scheme 8A. In accordance with this process, an amine represented by formula $R^{11}R^{11'}NH$ is reacted with an alcohol represented by the formula $R^{12}CH_2OH$ to generate an amide represented by the structure $R^{12}$—C(=O)—$NR^{11}R^{11'}$. This novel, environmentally benign reaction can be used to produce various amides from very simple substrates, with high atom economy and in some embodiments no stoichiometric activating agents, thus generating no waste.

Scheme 8A

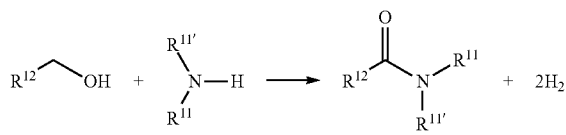

wherein $R^{10}$, $R^{11}$ and $R^{12}$ are each independently selected from the group consisting of H an unsubstituted or substituted alkyl, alkoxyalkyl, cycloalkyl, aryl, alkylaryl, heterocyclyl and heteroaryl, wherein $R^{10}$, $R^{11}$ and $R^{12}$ can be the same or different from each other.

A variety of alcohols can be used in the process of the invention. In some embodiments, the alcohol is selected from the group consisting of methanol, ethanol, propanol, butanol, pentanol, hexanol, 2-methoxyethanol, and 2-methyl-1-butanol. Each possibility represents a separate embodiment of the present invention.

A variety of primary and secondary amines (as well as ammonia) may be used in the process of the invention. In some embodiments, the amine is selected from the group consisting of benzylamine, 1-hexylamine, 1-pentylamine, 1-(2-furyl)methylamine, aniline, morpholine, pyrrolidine, 2-methylhexylamine, and cyclohexylamine. Each possibility represents a separate embodiment of the present invention.

In another embodiment, the process of the invention can also be applied to bis-acylation reactions with diamines. Upon reacting alcohols and diamines, the corresponding bis-amides are produced in high yields. In some embodiments, the diamine is ethylenediamine, diethylenetriamine or 1,6-diaminohexane.

Similarly, when diamines and dialcohols are used, polyamides or peptides are obtained. The applicants have surprisingly discovered that Ruthenium complexes catalyze the synthesis of polyamides directly from diols and diamines. This polyamidation reaction is general, environmentally benign and atom economical. It proceeds under neutral reaction conditions without the use of activators, condensing agents or other additives. A preferable solvent for use in this reaction is 1,4-dioxane, however other solvents can be used as apparent to a person of skill in the art. Moreover, these methods produce $H_2$ as the only byproduct (Scheme 8B):

Scheme 8B

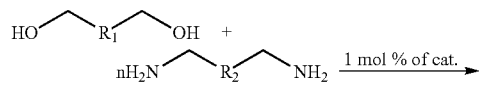

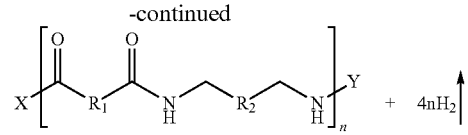

A variety of dialcohols can be used for this reaction, non-limiting examples of which include hexane-1,2-diol, octane-1,8-diol, 1,3-phenylenedimethanol, (5-methoxy-1,3-phenylene)dimethanol, 1,4-phenylenedimethanol, pyridine-2,6-diyldimethanol, pentane-1,5-diol, cyclohexane-1,4-diyldimethanol, and (5-(hexyloxy)-1,3-phenylene)dimethanol.

A variety of diamines can be used for this reaction, non-limiting examples of which include hexane-1,6-diamine, ethane-1,2-diamine, 1,3-phenylenedimethanamine, and 1,4-phenylenedimethanamine. The reaction between the amine and alcohol can be inter-molecular (i.e., the amine and the alcohol are present in separate molecules). Alternatively, the reaction between the amine and alcohol can be intra-molecular, i.e., the amine and alcohol functionalities can be present in the same molecule, resulting in intra-molecular cyclization to generate a lactam.

In addition, the aforementioned amidation and polyamidation reactions are also catalyzed by the Ruthenium complexes described in US Patent publication US 2009/0112005, in particular Ruthenium complexes in which $L_1$ is $N(R)_2$, as described above for the reciprocal hydrogenation reactions of amides to alcohols and amines. One embodiment of such compounds is a pincer complex represented by the structure of formula 1 (FIG. 1A).

In some embodiments, beta-amino alcohols can be dehydrogenated in the presence of Ruthenium complexes to form cyclic dipeptides. Such reactions are catalyzed by a Ruthenium complex or a boronated complex thereof, which is represented by anyone of formulae A1, A2, A3, B1, C1, B2, C2, D, E, F (for complex F preferably $L_4$ is $CH_2NR^aR^b$), H, 3, 4, 7, 9, 4' and 8', or any other Ruthenium complex or their boronated complexes covered by such formulae. Alternatively, such reactions can also be catalyzed by the Ruthenium complexes described in US Patent publication US 2009/0112005, in particular Ruthenium complexes in which $L_1$ is $N(R)_2$, as described above for the reciprocal hydrogenation reactions of amides to alcohols and amines.

Preparation of polypeptides or cyclic peptides by dehydrogenation of beta-amino alcohols, catalyzed by the Ruthenium complexes described in US Patent publication US 2009/0112005, namely compounds A1', A2' or A3' in which $L_1$ is $N(R)_2$, has not previously been described, and constitutes another embodiment of the present invention.

In another embodiment, beta-amino alcohols can be dehydrogenated to form pyrazines in the presence of Ruthenium complexes. Ruthenium complexes which catalyze the dehydrogenation of beta-amino alcohols to pyrazines are those which contain two phosphnine ligands or N-heterocyclic carbene ligands. Examples of such complexes are described in US Patent publication US 2009/0112005, in particular Ruthenium complexes of Formulae A1', A2' and A3', and any Ruthenium complexes covered by such Formulae, wherein the Ruthenium complex comprises two phosphine $(P(R)_2)$ ligands or two N-heterocyclic carbene ligands:

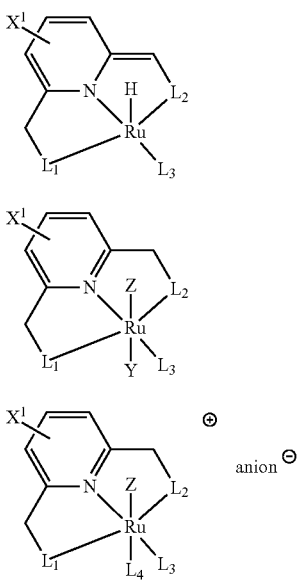

wherein
L₁ and L₂ are each independently selected from the group consisting of phosphine (P(R)₂), and an N-heretocyclic carbene represented by the structure:

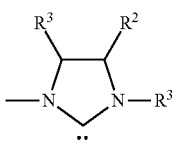

wherein each of R, $R^2$ and $R^3$ are independently selected from the group consisting of alkyl, cycloalkyl, aryl, alkylaryl, heterocyclyl and heteroaryl;

$L_3$ is a mono-dentate two-electron donor selected from the group consisting of CO, P(R)₃, P(OR)₃, NO⁺, As(R)₃, Sb(R)₃, S(R)₂, nitrile (RCN) and isonitrile (RNC) wherein R is as defined above;

$L_4$ is absent or is $L_3$;

Y and Z are each independently H or an anionic ligand selected from the group consisting of halogen, OCOR, OCOCF₃, OSO₂R, OSO₂CF₃, CN, OH, OR, N(R)₂, RS and SH; wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety;

and anion represents a group bearing a single negative charge.

Preferably the Ruthenium complex is represented by the structure of formula 2.

Other examples of such complexes include borohydride complexes represented by formula F (wherein each one of $L^1$ and $L^4$ contain a phosphine (PR$^a$R$^b$), and/or N-heterocyclic carbene), or complexes G, 2' and 6', with each possibility representing a separate embodiment of the present invention. A non-limiting example of a process for pyrazine formation is illustrated in Scheme 46 hereinbelow.

4. Dehydrogenative Coupling of Alcohols:

The present invention further provides a process for preparing esters by coupling of alcohols in the presence of a Ruthenium complex, to generate the ester compound and molecular hydrogen. In one embodiment, the process involves coupling of primary alcohols. In another embodiment, the process involves coupling of a primary and secondary alcohol. These reactions are catalyzed by a Ruthenium complex or a boronated complex thereof, which is represented by anyone of formulae A1, A2, A3, B1, C1, B2, C2, D, E, F, G, H, 3, 4, 7, 9, 2', 4', 6' and 8' or any other Ruthenium complex or their boronated complexes covered by such formulae. Depending on the complex being used, the reaction permits the optional use of one or more equivalents of a base. Use of dialcohols in the reaction leads to polyesters or to lactones.

In one embodiment, the process of the invention, i.e., the direct catalytic coupling of primary alcohols into esters and dihydrogen is illustrated in Scheme 9A. In accordance with this process, two equivalents of a primary alcohol represented by formula $R^{13}CH_2OH$ are converted to an ester by the structure $R^{13}$—C(=O)—OCH₂R¹³. This novel, environmentally benign reaction, can be used to produce various esters from very simple substrates, with high atom economy and in some embodiments no stoichiometric activating agents, thus generating no waste.

Scheme 9A

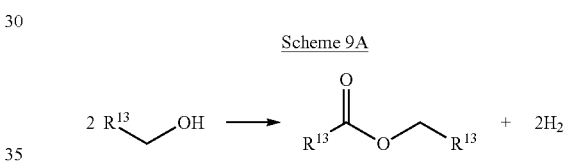

In another embodiment, the process of the invention involves the catalytic coupling of a primary alcohol and a secondary alcohol, as illustrated in Scheme 9B.

Scheme 9B

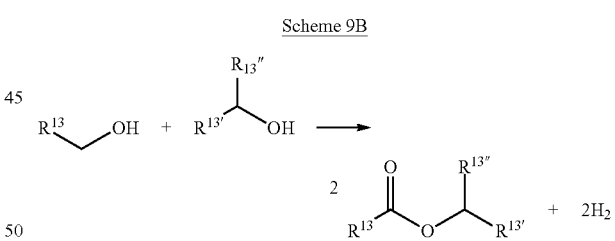

wherein $R^{13}$, $R^{13'}$ and $R^{13''}$ are each independently selected from the group consisting of H, an unsubstituted or substituted alkyl, alkoxyalkyl, cycloalkyl, aryl, alkylaryl, heterocyclyl and heteroaryl.

When primary alcohols are used, the process of the invention contemplates symmetric coupling of alcohols to yield symmetric esters (i.e., 2 equivalents of the same alcohol are coupled). However, the present invention further contemplates the generation of asymmetric esters by coupling of different alcohols. In accordance with this embodiment, a first primary alcohol represented by formula $R^{13}CH_2OH$ is reacted with a second alcohol represented by formula $R^{13'}CH_2OH$ so as to generate an ester by the structure $R^{13}$—C(=O)—OCH₂R¹³' or an ester of formula $R^{13'}$—C(=O)—OCH₂R¹³, as illustrated in Scheme 10:

Scheme 10

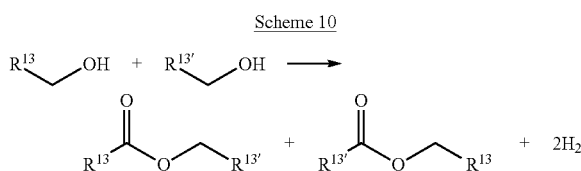

wherein $R^{13}$ and $R^{13'}$ are the same or different from each other and are each independently selected is from the group consisting of H, an unsubstituted or substituted alkyl, alkoxyalkyl, cycloalkyl, aryl, alkylaryl, heterocyclyl and heteroaryl.

A variety of alcohols can be used in the process of the invention. In some embodiments, the alcohol is selected from the group consisting of methanol, ethanol, propanol, butanol, pentanol, hexanol, 2-methoxyethanol, 2-methyl-1-butanol, benzyl alcohol, 1-phenylethanol and cyclohexane methanol. Each possibility represents a separate embodiment of the present invention.

In another embodiment, the process of the invention can also be applied to bis-acylation reactions with dialcohols to yield polyesters.

The reaction between the alcohols can be inter-molecular (i.e., the two alcohols are separate molecules). Alternatively, the reaction between the alcohols can be intra-molecular, i.e., the alcohol functionalities can be present in the same molecule, resulting in intra-molecular cyclization to generate a lactone. In some embodiments, the intra-molecular dehydrogenation of diols to generate a lactone is catalyzed by borohydride Ruthenium complexes as described herein, for example compounds D, E, F, G, H, 2', 4', 6' and 8'. In some embodiments, the complex is a Ruthenium complex of formula 2'. In other embodiment, the complex is a Ruthenium complex of formula 4'. Each possibility represents a separate embodiment of the present invention.

5. Dehydrogenation of Secondary Alcohols:

The present invention further relates to a process for preparing a ketone by dehydrogenation of a secondary alcohol, comprising the step of reacting the secondary alcohol in the presence of the Ruthenium complex which is represented by anyone of formulae A1, A2, A3, B1, C1, B2, C2, D, E, F, G, H, 3, 4, 7, 9, 2', 4', 6' and 8' or any other Ruthenium complex or their boronated complexes covered by such formulae, thereby generating the ketone and molecular hydrogen.

The process of the invention, i.e., the direct catalytic conversion of secondary alcohols into ketones and dihydrogen is illustrated in Scheme 11A. In accordance with this process, a secondary alcohol represented by formula $R^{14}CH(OH)R^{14'}$ is converted to a ketone represented by the structure $R^{14}$—C(=O)—$R^{14'}$:

Scheme 11A

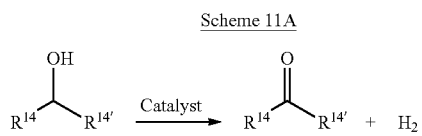

A variety of alcohols can be used in the process of the invention. In some embodiments, the alcohol is selected from the group consisting of 1-phenyl-1-ethanol, 2-hexanol, cyclohexanol and 2-propanol. Each possibility represents a separate embodiment of the present invention.

6. Synthesis of Amides from Esters and Alcohols

The present invention further provides a process for preparing amides, by reacting an amine and an ester in the presence of a Ruthenium complex, to generate the amide compound and molecular hydrogen ($H_2$). As contemplated herein, the inventors have further discovered a novel process for preparing amides in which primary and secondary amines are directly reacted with esters to produce amides and molecular hydrogen in high yields and high turnover numbers. This reaction is catalyzed by a Ruthenium complex or a boronated complex thereof, which is represented by anyone of formulae A1, A2, A3, B1, C1, B2, C2, D, E, F (when complex F is used and $L^4$ is —$CH_2$-$L^1$, $L^1$ is preferably $NR^aR^b$), H, 3, 4, 7, 9, 4' and 8', or any other Ruthenium complex or their boronated complexes covered by such formulae. Depending on the complex being used, the reaction permits the optional use of one or more equivalents of a base. Reactions of esters with diamines leads to diamides.

The process of the invention, i.e., the direct catalytic reaction of esters and amines into amides and dihydrogen is illustrated in Scheme 11B. In accordance with this process, an amine represented by formula $R^{15}R^{15'}NH$ is reacted with an ester represented by the formula $R^{16}$—C(=O)—$OCH_2R^{16'}$ to generate an amide represented by the structure $R^{16}$—C(=O)—$NR^{15}R^{15'}$. This novel, environmentally benign reaction can be used to produce various amides from very simple substrates, with high atom economy and in some embodiments no stoichiometric activating agents, thus generating no waste.

Scheme 11B

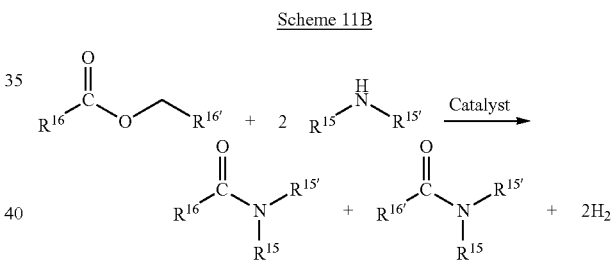

wherein $R^{15}$, $R^{15'}$, $R^{16}$ and $R^{16'}$ are each independently selected from the group consisting of H, an unsubstituted or substituted alkyl, alkoxyalkyl, cycloalkyl, aryl, alkylaryl, heterocyclyl and heteroaryl, wherein $R^{15}$, $R^{15'}$ and $R^{16}$ can be the same or different from each other.

A variety of esters can be used in the process of the invention. In some embodiments, the ester is selected from the group consisting of ethyl acetate, butyl butyrate, pentyl pentanoate and hexyl hexanoate. Each possibility represents a separate embodiment of the present invention.

A variety of primary and secondary amines (as well as ammonia) may be used in the process of the invention. In some embodiments, the amine is selected from the group consisting of pyrrolidine, morpholine, 1-methyl piperazine, piperidine, piperazine, 1-hexylamine and p-tolylmethanamine.

In another embodiment, the process of the invention can also be applied to bis-acylation reactions with diamines. Upon reacting alcohols and diamines, the corresponding bis-amides are produced in high yields.

7. Acylation of Alcohols Using Esters with Liberation of $H_2$

The present invention further provides a process for preparing esters by acylation of alcohols using esters in the presence of a Ruthenium complex, to generate the ester compound and molecular hydrogen. In one embodiment, the process involves reaction of primary alcohols and esters. In another embodiment, the process involves reaction of a secondary alcohols and esters. These reactions are catalyzed by a Ruthenium complex or a boronated complex thereof, which is represented by anyone of formulae A1, A2, A3, B1, C1, B2, C2, D, E, F, G, H, 3, 4, 7, 9, 2', 4', 6' and 8' or any other Ruthenium complex or their boronated complexes covered by such formulae. Depending on the complex being used, the reaction permits the optional use of one or more equivalents of a base.

In one embodiment, the process of the invention, i.e., the direct catalytic acylation of alcohols using esters to yield an ester and dihydrogen is illustrated in Scheme 12A. In accordance with this process, two equivalents of a primary or secondary alcohol represented by formula $R^{17}R^{17'}CHOH$ reacts with one equivalent an ester by the structure $R^{18}$—C (=O)—OCH$_2$R$^{18'}$ as shown in Scheme 12A. This novel, environmentally benign reaction, can be used to produce various esters from very simple substrates, with high atom economy and in some embodiments no stoichiometric activating agents, thus generating no waste.

Scheme 12A

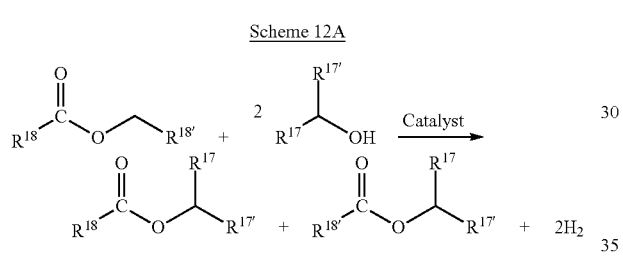

wherein $R^{17}$, $R^{17'}$, $R^{18}$ and $R^{18'}$ are each independently selected from the group consisting of H, an unsubstituted or substituted alkyl, alkoxyalkyl, cycloalkyl, aryl, alkylaryl, heterocyclyl and heteroaryl.

A variety of alcohols can be used in the process of the invention. In some embodiments, the alcohol is selected from the group consisting of cyclohexanol, cyclopentanol, 1-phenylethanol, isopropanol and 3-pentanol. Each possibility represents a separate embodiment of the present invention.

A variety of esters can be used as the starting materials. In some embodiments, the ester is selected from the group consisting of ethyl acetate, hexyl hexanoate, pentyl pentanoate, butyl butyrate, ethyl butyrate and methyl hexanoate.

8. Coupling of Alcohols with Water to Form Carboxylic Acid with Liberation of H$_2$ The present invention further provides a process for preparing carboxylic acids by contacting primary alcohols with water in the presence of a Ruthenium complex and a base, to generate the carboxylic acid salt and molecular hydrogen and, if desired, followed by conversion of the carboxylic acid salt to the corresponding carboxylic acid. These reactions are catalyzed by a Ruthenium complex or a boronated complex thereof, which is represented by anyone of formulae A1, A2, A3, B1, C1, B2, C2, D, E, F, G, H, 3, 4, 7, 9, 2', 4', 6' and 8' or any other Ruthenium complex or their boronated complexes covered by such formulae. Depending on the complex being used, the reaction permits the optional use of one or more equivalents of a base. This reaction can also be catalyzed by the Ruthenium complexes described in US Patent publication US 2009/0112005, such as, but not limited to compounds of formulae A 1', A2' and A3':

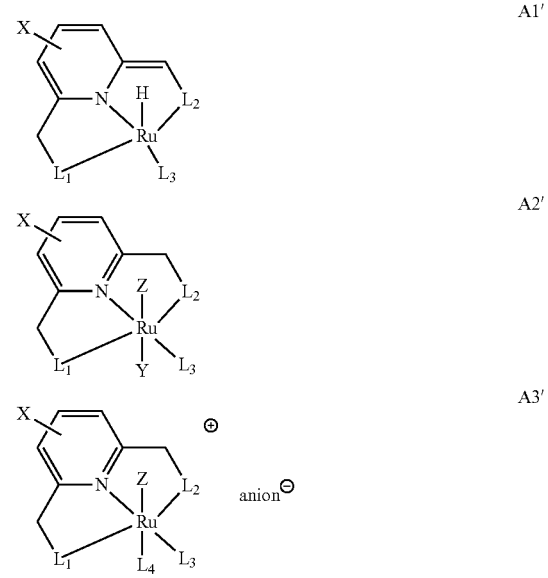

wherein
$L_1$ and $L_2$ are each independently selected from the group consisting of nucleophilic carbene (:C(R)$_2$), P(R)$_2$, P(OR)$_2$, N(R)$_2$, imine, SR, SH, S(=O)R, heteroaryl wherein the heteroatom is selected from nitrogen and sulfur, As(R)$_2$, Sb(R)$_2$ and an N-heretocyclic carbene represented by the structure:

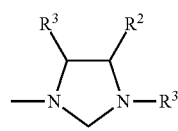

each of R, R$^2$ and R$^3$ are independently selected from the group consisting of alkyl, cycloalkyl, aryl, alkylaryl, heterocyclyl and heteroaryl;
$L_3$ is a mono-dentate two-electron donor selected from the group consisting of CO, P(R)$_3$, P(OR)$_3$, NO$^+$, As(R)$_3$, Sb(R)$_3$, S(R)$_2$, nitrite (RCN) and isonitrile (RNC) wherein R is as defined above;
$L_4$ is absent or is $L_3$;
Y and Z are each independently H or an anionic ligand selected from the group consisting of halogen, OCOR, OCOCF$_3$, OSO$_2$R, OSO$_2$CF$_3$, CN, OH, OR, N(R)$_2$, RS and SH; wherein R is as defined above;
X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and
anion represents a group bearing a single negative charge.

Preferred complexes for this reaction are Pincer complexes represented by the structure of Formula 1.

In one embodiment, the process of the invention, i.e., the direct catalytic conversion of primary alcohols to carboxylic acids and dihydrogen is illustrated in Scheme 12B. In accordance with this process, a primary alcohol represented by formula $R^{17}CH_2OH$ is contacted with water and a base (e.g., NaOH) as shown in Scheme 12B. This novel, environmentally benign reaction, can be used to produce various carboxylic acids and their salts from very simple substrates, with high atom economy and in some embodiments no stoichiometric activating agents, thus generating no waste. If desired, the salt is neutralized with the appropriate acid to provide the corresponding carboxylic acid.

Scheme 12B

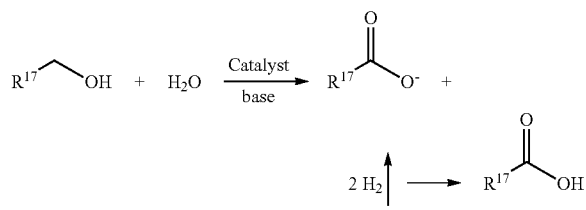

wherein $R^{17}$ is selected from the group consisting of H, an unsubstituted or substituted alkyl, alkoxyalkyl, cycloalkyl, aryl, alkylaryl, heterocyclyl and heteroaryl.

A variety of bases can be used for this reaction, non-limiting examples of which include an inorganic or organic base selected from sodium carbonate, potassium carbonate, sodium hydroxide, potassium hydroxide, sodium ethoxide, potassium tert-butoxide, sodium methoxide. The acid used to neutralize the salt can be, e.g. a mineral acid such as hydrochloric acid, hydrobromic acid, and the like. Each possibility represents a separate embodiment of the invention.

A variety of alcohols can be used in the process of the invention. In some embodiments, the alcohol is selected from the group consisting of butanol, pentanol, decanol, 2-methoxyethanol, 2-phenylethanol, cyclohexylmethanol, 3-phenylbutan-1-ol, but-3-en-1-ol, (4-methoxyphenyl)methanol, and (2,4-dimethoxyphenyl)methanol. Each possibility represents a separate embodiment of the present invention.

The disclosures of all cited references are incorporated by reference as if fully set forth herein.

The principles of the present invention are demonstrated by means of the following non-limiting processes.

EXAMPLES

Example 1

Hydrogenation of Amides to the Corresponding Alcohols and Amines

Examples of processes involving the hydrogenation of amides to alcohol and amines are shown in Scheme 13:

Scheme 13

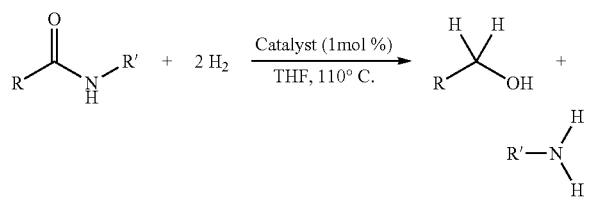

R, R' = H, Aryl, alkyl, Aryalkyl, etc.

(a) Using Catalyst 3:

A 100 mL Fischer-Porter tube was charged under nitrogen with the catalyst 3 (0.01 mmol), an amide (1.0 mmol), and THF (2 mL). The nitrogen present in the Fischer-Porter (100 mL) was replaced by $H_2$ (twice with 30 psi) at room temperature, then it was filled with $H_2$ (10 atm). The solution was heated at 110° C. (bath temperature) with stirring for 48 hrs. After cooling to room temperature, the $H_2$ was vented carefully and the products were determined by GC with m-xylene as internal standard, using a Carboxen 1000 column on a HP 690 series GC system.

(b) Using Complex 4+Base (Generation of Catalyst 3 In Situ):

In an open air, a solution of amide (1.0 mmol) in THF (1.0 mL) was transferred via syringe into a Fischer-Porter tube (100 mL) contains 0.01 mmol of catalyst 4. Then, KO$^t$Bu (0.01 mmol) in THF (1.0 mL) was added and the air present in the Fischer-Porter tube was flushed with hydrogen (thrice with 30 psi) and filled with $H_2$ (10 atm). The solution was heated at 110° C. (bath temperature) with stirring for 48 hrs. After cooling to room temperature, the $H_2$ was vented carefully and the products were determined by GC with m-xylene as internal standard, using a Carboxen 1000 column on a HP 690 series GC system.

Results of some typical processes are shown in Tables 1A, 1B and 2.

A. Selective Hydrogenation of Amides to Alcohols and Amines Using $H_2$ catalyzed by BPy-PNN—Ru(II) Pincer Complexes 1, 4 and 7

TABLE 1A

Hydrogenation of amides catalyzed by complex 1, 4 and 7

Reaction condition[a]

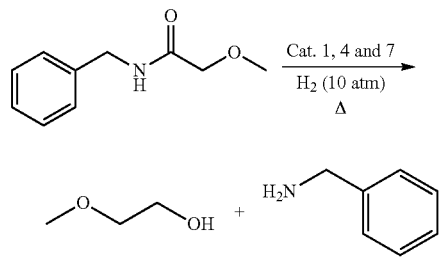

| | | Scheme 13 Yield (%)[b] | |
|---|---|---|---|
| Entry | Catalyst | Alcohol | Amine |
| 1 | 1 | 62.7 | 62.0 |
| 2 | 1 | 66.3 | 66.8[c] |
| 3 | 4 | — | — |
| 4 | 4 + KO$^t$Bu | 80.2 | 81.8[d] |
| 5 | 7 + KO$^t$Bu | 76.8 | 78.0[d] |

[a]Complex 1, 4 and 7 (0.01 mol), amide (1 mmol), $H_2$ (10 atm), and dry THF (2 ml) were heated in a Fischer-Porter tube at 100° C. (bath temperature) for 48 h.

[b]Yields of products were analyzed by GC (m-xylene as internal standard).

[c]1,4-dioxane (2 mL) at 140° C. after 48 h.

[d]one equivalent (relative to Ru) of base was used.

TABLE 1B

Hydrogenation of amides to alcohols and amines selectively catalyzed by pincer complex 3[a]

| Entry | Amide | Products (yield [%])[b] | |
|---|---|---|---|
| | | Alcohol | Amine |
| 1 | PhCH₂-NH-C(O)-CH₂-O-Me | MeO-CH₂CH₂-OH (89.2) | PhCH₂-NH₂ (89.6) |
| 2 | n-C₅H₁₁-NH-C(O)-CH₂-O-Me | MeO-CH₂CH₂-OH (90.7) | H₂N-(CH₂)₅-Me (90.3) |
| 3 | n-C₄H₉-NH-C(O)-(3-methyloxetan-3-yl) | (3-methyloxetan-3-yl)-CH₂OH (73.6) | H₂N-(CH₂)₅-Me (73.9) |
| 4 | n-C₅H₁₁-NH-C(O)-(2-furyl) | (2-furyl)-CH₂OH (68.8) | H₂N-(CH₂)₅-Me (68.1) |
| 5 | PhCH₂-NH-C(O)-Ph | PhCH₂OH (56.8) | PhCH₂-NH₂ (57.3) |
| 6 | Et-NH-C(O)-Me | EtOH (71.0) | EtNH₂[c] |
| 7 | Me-NH-C(O)-Et | n-PrOH (68.4) | MeNH₂[c] |
| 8 | Cyclohexyl-NH-C(O)-CH₂-O-Me | MeO-CH₂CH₂-OH (88.0) | Cyclohexyl-NH₂ (87.3) |
| 9 | Ph-NH-C(O)-Me | EtOH (94.1) | Ph-NH₂ (94.9)[d] |
| 10 | Ph-NH-C(O)-(CH₂)₃-Me | Me-(CH₂)₃-OH (92.1) | Ph-NH₂ (92.0) |

TABLE 1B-continued

Hydrogenation of amides to alcohols and amines selectively catalyzed by pincer complex 3[a]

| Entry | Amide | Products (yield [%])[b] | |
|---|---|---|---|
| | | Alcohol | Amine |
| 11 | PhNHC(O)CH₂OMe | MeOCH₂CH₂OH (95.3) | PhNH₂ (94.6) |
| 12 | PhNHC(O)Ph | PhCH₂OH (91.6) | PhNH₂ (91.0) |
| 13 | MeOCH₂C(O)NHCH₂CH₂NHC(O)CH₂OMe | MeOCH₂CH₂OH (78.0) | H₂NCH₂CH₂NH₂ (76.9)[e] |
| 14 | 4-acetylmorpholine | EtOH (97.1) | morpholine (98.0) |
| 15 | 4-pentanoylmorpholine | HO(CH₂)₃CH₃ (95.8) | morpholine (95.7) |
| 16 | 1-(methoxyacetyl)pyrrolidine | MeOCH₂CH₂OH (97.0) | pyrrolidine (97.4) |
| 17 | 4-formylmorpholine | MeOH (97.1) | morpholine (98.3)[f] |
| 18 | Me₂NCHO | MeOH (96.3) (32.1)[g] | Me₂NH |

TABLE 1B-continued

Hydrogenation of amides to alcohols and amines selectively catalyzed by pincer complex 3[a]

| Entry | Amide | Products (yield [%])[b] | |
|---|---|---|---|
| | | Alcohol | Amine |
| 19 | PhC(O)NEt₂ | benzyl alcohol (OH) | EtNH₂[c] |

[a]Complex 3 (0.01 mol), amide (1 mmol), $H_2$ (10 atm), and dry THF (2 ml) were heated in a Fischer-Porter tube at 110° C. (bath temperature) for 48 h.
[b]Yields of products were analyzed by GC (m-xylene as internal standard).
[c]The amines (EtNH₂ (entry 6 and 18) and MeNH₂ (entry 7)) were analyzed in the gas phase by GC-MS.
[d]In the reactions involving anilide derivatives (entries 9-12), trace amounts of the corresponding secondary amines were detected by GC-MS.
[e]0.5 mmol of bis-amide was used.
[f]Yield after 32 h.
[g]Complex 1 was used.

B. Selective Hydrogenation of Primary Amides to Alcohols and Ammonia Using $H_2$ Catalyzed by Ruthenium Pincer Complex 3

Scheme 14

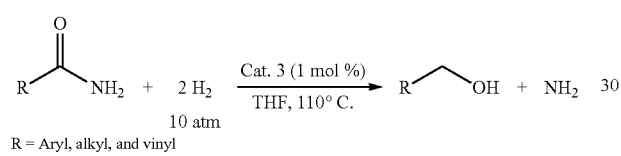

R = Aryl, alkyl, and vinyl

TABLE 2

Hydrogenation of primary amides to alcohols and ammonia selectively catalyzed by complex 3

| Entry | Amides | Alcohols | Yield (%)[b] |
|---|---|---|---|
| 1 | benzamide (PhC(O)NH₂) | benzyl alcohol | 86.8 (63.7)[c,d] |
| 2 | 4-methylbenzamide | 4-methylbenzyl alcohol | 88.1[d] |
| 3 | cyclohexanecarboxamide | cyclohexylmethanol | 90.7[d] |
| 4 | hexanamide | hexanol | 89.1 (91.7)[d,e] |

TABLE 2-continued

Hydrogenation of primary amides to alcohols and ammonia selectively catalyzed by complex 3

| Entry | Amides | Alcohols | Yield (%)[b] |
|---|---|---|---|
| 5 | CH₃C(O)NH₂ (acetamide) | ethanol (CH₃CH₂OH) | 92.5[d] |
| 6 | CH₂=CHC(O)NH₂ (acrylamide) | n-propanol | 95.7 |
| 7 | (CH₃)₃CC(O)NH₂ (pivalamide) | neopentyl-type alcohol ((CH₃)₃CCH₂OH) | 42.4 |

[a]Complex 3 (0.01 mol), amide (1 mmol), H₂ (10 atm), and dry THF (2 ml) were heated in a Fischer-Porter tube at 110° C. (bath temperature) for 72 h.
[b]Yields of products were analyzed by GC (m-xylene as internal standard) and ammonia was analyzed in the gas phase by GC-MS.
[c]Yield in the parenthesis after 48 h.
[d]Traces of corresponding esters were also observed in GC.
[e]1,4-dioxane (2 mL) at 140° C. after 60 h.

Discussion:

The applicants have previously reported the dehydrogenative coupling of alcohols with amines to form amides, catalyzed by complex 1, with liberation of hydrogen gas (Gunanathan 2007). To explore whether it might be possible to reverse this reaction by the application of hydrogen pressure, complexes 1-4 were tested as catalysts for the hydrogenation of amides. Thus, upon treatment of N-benzyl-2-methoxyacetamide with dihydrogen (10 atm) at 110° C. (bath temperature) in dry THF for 48 h with a catalytic amount of 1 (1 mol %), 62.7% of 2-methoxyethanol and 62.0% of benzyl amine were obtained. Performing the reaction at 140° C. using 1,4-dioxane as solvent did not significantly improve the yield (alcohol yield 66.3%). It was significant that the reaction was selective and the corresponding secondary amine was not observed. Under the same conditions complex 2 was inactive. Remarkably, employing complex 3 (1 mol %) as catalyst, hydrogenation of N-benzyl-2-methoxyacetamide under identical conditions (THF, 110° C.) resulted in the selective formation of 89.2% 2-methoxyethanol and 89.6% benzyl amine (Table 1B, entry 1). Thus, the normally observed C—O hydrogenolysis did not take place at all. Of practical significance, the air-stable complex 4 (which is stable in air for at least two days in solution) in the presence of one equivalent (relative to Ru) of base also efficiently catalyzes the hydrogenation of amides to alcohols and amines, by generation of the catalyst 3 in situ. Thus, upon heating a THF solution of 4 (1 mol %) with KO′Bu (1 mol %) and N-benzyl-2-methoxyacetamide (1 mmol) at 110° C. under H₂ (10 atm) for 48 h, 80.2% of alcohol and 81.8% of amine were formed. No reaction took place in the absence of base. Hydrogenation of N-hexyl-2-methoxyacetamide catalyzed by 3 yielded 2-methoxy ethanol and hexyl amine in 90.7% and 90.3% yields, respectively (Table 1B, entry 2). N-hexyl-3-methyloxetane-3-carboxamide undergoes hydrogenation to the alcohol and amine without hydrogenolysis of the strained oxetane ring (Table 1B, entry 3). The heterocyclic amide, N-hexylfuran-2-carboxamide was hydrogenated to yield 68.8% of furfuryl alcohol and 68.1% of hexylamine (Table 1B, entry 4). The aromatic non-activated amide, N-benzylbenzamide is also hydrogenated to benzyl alcohol and benzyl amine (Table 1B, entry 5), but the yield is lower, probably because of steric reasons. Significantly, the aliphatic non-activated amides, N-ethylacetamide and N-methylpropionamide also underwent hydrogenation to yield the corresponding alcohols and amines (71% of ethanol and ethylamine for entry 6 and 68.4% of n-propanol and methylamine for entry 7). The product gaseous amines were analyzed by GC-MS spectrometry of the gas phase and not quantified. As expected, the activated amides, anilide derivatives, were converted into their corresponding alcohols and aniline in excellent yields (91-95%; Table 1B, entries 9-12) along with trace amounts of the secondary amines (detected by GC-MS) under similar conditions. The reaction is also effective for bis-amides. Thus, N,N′-(ethane-1,2-diyl)bis(2-methoxyacetamide) (0.5 mmol) was also hydrogenated using catalyst 3 under mild conditions (Table 1B, entry 13). Noteworthy, tent-amides also underwent hydrogenation almost quantitatively to yield alcohols and secondary amines in equivalent amounts (Table 1B, entries 14-16). Gratifyingly, heating a solution of N-formylmorpholine (1 mmol) and complex 3 in THF at 110° C. yielded after 32 h 97.1% of methanol and 98.3% of morpholine; no decarbonylation of the formyl group took place (Table 1B, entry 17). These results highlight the substantial scope of the unprecedented, selective hydrogenation of amides catalyzed by 3, or by the air-stable 4 with an equivalent of base (which generates 3 in situ).

In conclusion, amides can be selectively hydrogenated to alcohols and amines for the first time. The reaction proceeds under mild pressure, neutral, homogeneous conditions using Ruthenium complexes as catalysts according to the invention and dihydrogen by metal-ligand cooperation. This new catalytic protocol exhibits a broad substrate scope providing a variety of amines and alcohols in good to excellent yield.

C. Hydrogenation of Cyclic Di-Peptides

The process of the present invention can also be used for catalytic hydrogenation of di-peptides. For example, cyclic di-peptides can be hydrogenated to amino alcohols. In a general procedure, a 100 mL Fischer-Porter tube was charged with the catalyst 1 (0.02 mmol), the cyclic di-peptides (1.0 mmol) and THF (2 mL) under an atmosphere of purified nitrogen in a Vacuum Atmospheres glove box. The pressure tube was taken out of the glove box, and subjected to three successive cycles of pressurization/venting with $H_2$ (3 atm), then pressurized with $H_2$ (12 atm) and closed. The tube was placed behind a protective shield and the reaction mixture was heated in an oil bath at 110° C. with constant stirring for 60 h. After cooling to room temperature, excess $H_2$ was vented off carefully and the product was determined by GC and GC-MS. Some representative results are presented in Table 3 hereinbelow.

Scheme 15

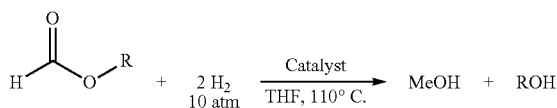

TABLE 3

Hydrogenation of cyclic di-peptides to amino alcohols selectively catalyzed by complex 1

| Entry | Cyclic di-peptides | Conditions | Amino alcohols (Yield (%)) |
|---|---|---|---|
| 1 | (cyclic dipeptide with two benzyl groups) | Solvent = THF (2 mL)<br>$PH_2$ = 10 atm<br>Temperature = 110° C. (bath)<br>Time = 60 h | (phenylalaninol) (58%) |
| 2 | (bicyclic diketopiperazine from proline) | | (prolinol) (67%) |

Example 2

Hydrogenation of Formate Esters to Methanol and Alcohols; Dimethyl Carbonate to Methanol; Esters and Lactones to Alcohols, and Hydrogenation of Polycarbonates A. Hydrogenation of Formates/Carbonate:

A 100 mL Fischer-Porter tube was charged under nitrogen with catalyst 3 (0.01 mmol), formate ester (15.0 mmol) or dimethyl carbonate (10.0 mmol) and THF (2 mL). After the nitrogen present in the Fischer-Porter tube was replaced by $H_2$ (twice with 30 psi) at room temperature, the tube was filled with $H_2$ (10 atm). The solution was heated at 110° C. (bath temperature) with stirring for 36 hrs. After cooling to room temperature, excess $H_2$ was vented carefully and the products were analyzed by GC with m-xylene as internal standard, using a Carboxen 1000 column on a HP 690 series GC system.

B. Hydrogenation of Methyl Formate and Dimethyl Carbonate Under 50 Atmospheres and Very Low Catalyst Loading (Entries 6 and 10, Respectively, Table 4):

A 30 mL Teflon coated Iron-Fischer-Porter (Autoclave) was charged under nitrogen with catalyst 3 (0.005 mmol), Methyl Formate (25.0 mmol) and THF (5 mL). After the nitrogen present in the autoclave was replaced by $H_2$ (twice with 50 psi) at room temperature, it was filled with $H_2$ (40 atm). The solution was heated at 110° C. (bath temperature) with stirring for 14 hrs. After cooling to room temperature, the $H_2$ was vented carefully at 0° C. and the products were determined by GC with m-xylene as internal standard, using a Carboxen 1000 column on a HP 690 series GC system. The same procedure was used for hydrogenation of dimethyl carbonate.

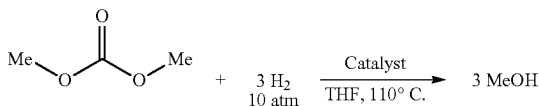

TABLE 4

Hydrogenation of Formates[a] and Dimethyl Carbonate[b]

| Entry | Catalyst | Substrate | Conv. (%) | Products (%)[c] | TON |
|---|---|---|---|---|---|
| 1 | 1 | HCOOMe (MF) | 71.7 | 71.0[d] | 710 |
| 2 | 1 | HCOOMe | >99 | ~99[e] | 990 |
| 3 | 1 | HCOOMe | 78.3 | 2 MeOH (77.0)[a] | 1155 |
| 4 | 3 | HCOOMe | 96.0 | 2 MeOH (95.8) | 1440 |
| 5 | 7 + KO[t]Bu | HCOOMe | 92.8 | 2 MeOH (91.2)[f] | 1370 |
| 6 | 3 | HCOOMe | 94.0 | 2 MeOH (93.7)[g] | 4685 |
| 7 | 3 | HCOOEt | 92.0 | MeOH (92.0) and EtOH (91.7) | 1380 |
| 8 | 3 | HCOO[n]Bu | 86.3 | MeOH (86.3) and n-BuOH (86.0) | 1295 |
| 9 | 3 | DMC | 96.2 | 3 MeOH (96.2) | 962 |
| 10 | 3 | DMC | 89.0 | 3 MeOH (87.6)[g] | 4380 |

[a]Complex 1 or 3 (0.01 mmol), formate (15 mmol), $H_2$ (10 atm), and dry THF (2 ml) were heated in a Fischer-Porter tube at 110° C. (bath temperature) for 48 h.
[b]10 mmol of DMC was used.
[c]Yields of products and conversion of starting material were analyzed by GC (m-xylene as internal standard).
[d]100 psi $H_2$, 1,4-dioxane (2 mL) at 145° C. after 30 h.
[e]130 psi $H_2$, 1,4-dioxane (2 mL) at 145° C. after 36 h.
[f]one equivalent (relative to Ru) of base was used.
[g]Complex 3 (0.005 mmol), MF/DMC (25 mmol), $H_2$ (50 atm), and dry THF (5 ml) were heated in a autoclave at 110° C. (bath temperature) for 14 h.

C. Hydrogenation of Methyl Formate and Dimethyl Carbonate Under Neat Conditions

A 100 mL Fischer-Porter tube was charged under nitrogen with catalyst 3 (0.01 mmol), and methyl formate or dimethyl carbonate (10.0 mmol). After the nitrogen in the Fischer-Porter tube was replaced by $H_2$ (twice with 30 psi) at 0° C., the tube was filled with $H_2$ (10 atm). The solution was heated at 80° C. (for MF) and 100° C. (for DMC) (bath temperature) with stirring for 8 hrs. After cooling to room temperature, excess $H_2$ was vented carefully and the products were analyzed by GC with m-xylene as internal standard, using a Carboxen 1000 column on a HP 690 series GC system.

Scheme 16

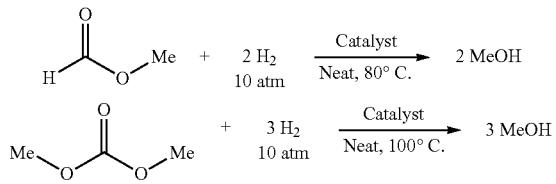

TABLE 5

Hydrogenation of methyl formate and dimethyl carbonate

| Entry | Catalyst | Substrate | Conv. (%) | Products (%)[a] |
|---|---|---|---|---|
| 1 | 1 | HCOOMe | 15.6 | 2 MeOH (15.2)[b] |
| 2 | 3 | HCOOMe | >99 | 2 MeOH (>99)[c] |
| 3 | 3 | DMC | >99 | 3 MeOH (>99)[d] (89.1)[e] |

[a]Yields of product and conversion of starting material were analyzed by GC (m-xylene as internal standard).
[b]Complex 3 or 1 (0.01 mol), formate (10 mmol), and $H_2$ (10 atm) were heated in a Fischer-Porter tube at 80° C. (bath temperature) for 18 h.
[c]10 mmol of DMC was used.
[d]Yields after 8 h.
[d]at 100° C. after 8 h.
[e]at 100° C. after 2 h.

D. Hydrogenation of Carbamates:[a]

TABLE 6 hydrogenation of carbamates to amines and alcohols

| Entry | Carbamate | Alcohol | Amine | Yield[b] |
|---|---|---|---|---|
| 1 | PhCH2-NH-C(O)-O-Me | 2 MeOH | PhCH2NH2 | 97.8 |
| 2 | MeO-C6H4-CH2-NH-C(O)-O-Me | 2 MeOH | MeO-C6H4-CH2NH2 | 98.0 |

[a]Complex 3 (0.01 mol), carbamate (1 mmol), and $H_2$ (10 atm) were heated in a Fischer-Porter tube a 110° C. (bath temperature) for 48 h.
[b]Yields of product (based on MeOH) were analyzed by GC (m-xylene as internal standard).

E. Hydrogenation of Unactivated Esters (Hexyl Hexanoate):

A 30 mL Teflon coated Iron-Fischer-Porter (Autoclave) was charged under nitrogen with catalyst 3 (0.01 mmol for entry 1 and 0.005 mmol for entry 2 respectively), hexyl hexanoate (20.0 mmol) and THF (5 mL). After the nitrogen present in the autoclave was replaced by $H_2$ (twice with 50 psi) at room temperature, it was filled with $H_2$ (50 atm). The solution was heated at 110° C. (bath temperature) with stirring for 16 hrs. After cooling to room temperature, the $H_2$ was vented carefully and the yields of product and conversion of starting material were analyzed by GC (m-xylene as internal standard, using a Carboxen 1000 column on a HP 690 series GC system. Very high turnover numbers (TON) were obtained.

Scheme 17

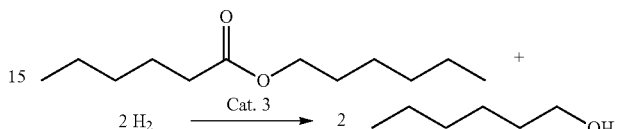

TABLE 7

Hydrogenation of esters to alcohols

| Entry | Cat. | Ester | Alcohol (20 mmol) | Yield (%) | TON |
|---|---|---|---|---|---|
| 1 | 3 (0.01 mmol) | Hexyl hexanoate | 1-Hexanol | >99 | 2000 |
| 2 | 3 (0.005 mmol) | Hexyl hexanoate | 1-Hexanol | 82.1 | 3284 |

F. Hydrogenation of Biomass-Derived Cyclic Di-Esters to 1,2-Diols

The cyclic di-ester of glycolic acid (derived from sugar cane), glycolide was chosen as a model substrate for catalytic hydrogenation by Ruthenium complex 3. A 1,4-dioxane solution containing glycolide (1 mmol) and 1 mol % of complex 3 was heated under hydrogen pressure (6 atm) at 135° C. for 36 h using a pressure vessel. The reaction mixture was cooled and excess $H_2$ was vented carefully and the products were determined by GC and GC-MS showing formation of ethylene glycol (EG) as the only product in 61% yield (Table 8, entry 1) with 67% conversion of the glycolide. After removal of the solvent, the obtained crude viscous liquid was further analyzed by ESI, illustrating that there was no formation of polymeric material.

Performing the same reaction under similar conditions using 10 atm of $H_2$ resulted in 88% of ethylene glycol after 36 h (Table 8, entry 2). Optimization studies revealed that the reaction could be performed at lower temperature using THF as solvent. Thus, heating complex 3 (0.01 mmol) with glycolide (1 mmol) and dihydrogen (10 atm) at 110° C. in 3 mL of dry THF for 48 h using a Fisher-Porter tube, yielded 93% of ethylene glycol (Table 8, entry 3). A high turnover number (425) was achieved at higher pressure. Thus, heating a THF solution of glycolide (10 mmol) and a catalytic amount of complex 3 (0.02 mmol) at 110° C. under $H_2$ (50 atm) using a high pressure reactor resulted in 85% yield of ethylene glycol selectively after 12 h (Table 8, entry 4).

Scheme 18

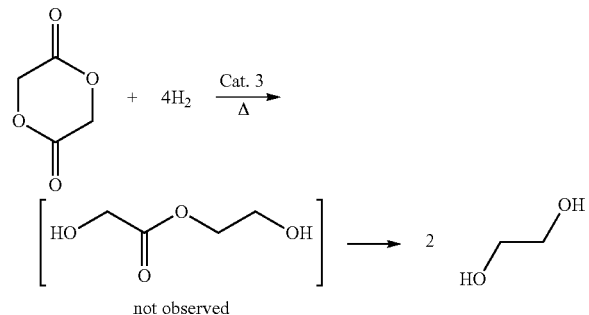

not observed

TABLE 8

Catalytic hydrogenation of glycolide to ethylene glycol

| entry | solvent | temp. (° C.) | P($H_2$) (atm) | time (h) | yield (%)[b] |
|---|---|---|---|---|---|
| 1 | 1,4-dioxane | 135 | 6 | 36 | 61 |
| 2 | 1,4-dioxane | 135 | 10 | 36 | 88 |
| 3 | THF | 110 | 10 | 48 | 93 |
| 4[c] | THF | 110 | 50 | 12 | 85 |

[a]Complex 3 (0.01 mmol), glycolide (1 mmol), $H_2$ and dry solvent (3 mL) were heated in a Fischer-Porter bute at the specified (oil bath) temperature.
[b]Yields of ethylene glycol were analyzed by GC using m-xylene as an internal standard.
[c]Complex 3 (0.02 mmol), glycolide (10 mmol), and THF (5 mL) were heated under $H_2$ pressure in a high-pressure reactor.

To expand the scope of this efficient hydrogenation reaction, optimized catalytic conditions were further tested with lactide, which is derived from the glucose fermentation product lactic acid. Thus, meso-lactide was heated with $H_2$ (10 atm) at 110° C. in THF for 48 h with a catalytic amount of 3 (1 mol %), 87% of 1,2-propanediol was obtained selectively (Table 9, entry 1). Remarkably, the hydrogenation of chiral lactide, L-lactide catalyzed by complex 3 under the optimized conditions yielded optically pure (S)-(+)-1,2-propanediol as sole product without racemization even under high pressure. Hence, upon treatment of L-lactide (10 mmol) with dihydrogen (50 atm) at 135° C. for 12 h with a catalytic amount of 3 (0.02 mmol) using 5 mL of THF as a solvent, selectively yielded 91% to propylene glycol (Table 9, entry 3). After careful removal of the solvent under reduced pressure, the reaction mixture was passed through short silica gel bed and the diol was eluted with $CH_2Cl_2$:MeOH (10:1) and concentrated under vacuum to yield 73% of the optically pure 1,2-propanediol. The optical rotation of the pure product was essentially the same as reported in the literature. Thus, under these experimental condition, no racemization took place.

Scheme 19

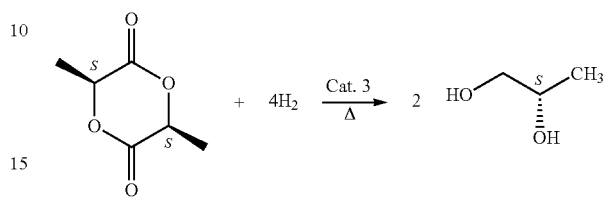

TABLE 9

Catalytic hydrogenation of lactide to propylene glycol

| Entry | di-ester (lactide) | solvent | temp (° C.) | P($H_2$) (atm) | time (h) | yield (%)[b] |
|---|---|---|---|---|---|---|
| 1 | meso | THF | 110 | 10 | 48 | 87 |
| 2 | chiral (S,S) | THF | 110 | 10 | 48 | 82 |
| 3[c] | chiral (S,S) | THF | 110 | 50 | 12 | 91(73)[d] |

[a] Complex 3 (0.01 mmol), meso or chiral lactide (1 mmol), $H_2$, and dry THF (3 mL) were heated in a Fischer-Porter tube at 110° C. (oil bath) temperature.
[b]Yields of propylene glycol were analyzed by GC using m-xylene as an internal standard.
[c]Complex 3 (0.02 mmol), L-lactide (10 mmol), and THF (5 mL) were heated under $H_2$ pressure in a high-pressure reactor.
[d]Isolated yield.

In conclusion, cyclic di-esters such as glycolide and lactide are selectively hydrogenated to the corresponding 1,2-diols for the first time. This offers an environmentally benign, atom economic and an alternative approach to the indirect transformation of biomass to important synthetic building blocks, propylene and ethylene glycol. The reactions proceed under mild, neutral and homogeneous conditions with minimal pressure of molecular hydrogen. Importantly, the chirality is unaffected during the hydrogenation.

General Experimental:

All experiments with metal complexes and phosphine ligands were carried out under an atmosphere of purified nitrogen in a Vacuum Atmospheres glove box equipped with a MO 40-2 inert gas purifier or using standard Schlenk techniques. All solvents were reagent grade or better. All non-deuterated solvents were refluxed over sodium/benzophenone ketyl and distilled under argon atmosphere. Deuterated solvents were used as received. All solvents were degassed with argon and kept in the glove box over 4 Å molecular sieves. Most of the chemicals used in the catalytic reactions (cyclic di-esters) are commercially available and were used as received.

Thin layer chromatography (TLC) was performed using Merck 1.05554 aluminum sheets precoated with silica gel 60 F254 and the spots were visualized with UV light at 254 nm or under iodine vapor. Column chromatography purifications were performed by flash chromatography using Merck silica gel 60 (0.063-0.200 mm).

1H, 13C and 31P NMR spectra were recorded using a Bruker AMX-300 NMR spectrometer. NMR chemical shifts are reported in ppm downfield from tetramethylsilane (for CDCl3). $^1H$ NMR chemical shift is referenced to the residual hydrogen signal of the deuterated solvent (7.15 ppm for benzene). $^{31}P$ NMR chemical shift is reported in ppm downfield from $H_3PO_4$ and referenced to an external 85% solution of phosphoric acid in D2O. Abbreviations used in the NMR follow-up experiments: br, broad; s, singlet; d, doublet; t, triplet; q, quartet; m, multiplet. IR spectra were recorded on a Nicolet FT-IR spectrophotometer. Mass spectra were recorded on Micromass Platform LCZ 4000, using Electro Spray Ionization (ESI) mode. GC-MS was carried out on HP 6890 (flame ionization detector and thermal conductivity detector) and HP 5973 (MS detector) instruments equipped with a 30 m column (Restek 5MS, 0.32 mm internal diameter) with a 5% phenylmethylsilicone coating (0.25 mm) and helium as carrier gas. GC analysis were carried out using a Carboxen 1000 column on a HP 690 series GC system or HP-5 cross linked 5% phenylmethylsilicone column (30 m×0.32 mm×0.25 μm film thickness, FID) on a HP 6890 series GC system using m-xylene (1 mmol) as an internal standard.

General Procedure for Catalytic Hydrogenation:

(a) Catalytic Hydrogenation of Glycolide to Ethylene Glycol:

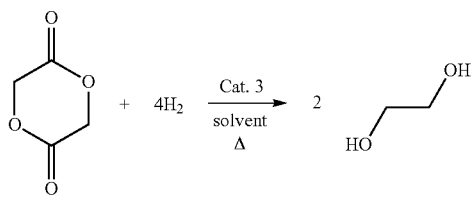

(i) Substrate/catalyst 100/1: A solution of catalyst 3 (4.5 mg, 0.01 mmol) in THF or 1,4-dioxane (1.0 mL) was transferred into a 100 mL Fischer-Porter tube followed by addition of the glycolide (116 mg, 1.0 mmol) in THF or 1,4-dioxane (2.0 mL) under an atmosphere of purified nitrogen in a Vacuum Atmospheres glove box. The pressure tube was taken out of the glove box, followed by three successive cycles of pressurization/venting with $H_2$ (2 atm), then pressurized with $H_2$ (10 atm) and well-closed. The tube was covered by a protective shield and the reaction mixture was heated in an oil bath at 110° C. with constant stirring for 48 h. After cooling to room temperature, excess $H_2$ gas was vented carefully and the products were determined by GC with m-xylene (1.0 mmol) as an internal standard, using a HP-5 cross linked 5% phenylmethylsilicone column (30 m×0.32 mm×0.25 μm film thickness) on a HP 6890 series GC system.

(ii) Substrate/catalyst 500/1: in a nitrogen glove box, a solution of catalyst 3 (9 mg, 0.02 mmol) in THF (5 mL) was added to a stainless-steel high pressure reactor (30 mL) equipped with a magnetic stirring bar containing 10.0 mmol (1.16 g) of the solid glycolide. The high pressure reactor was taken out of the glove box and the nitrogen present in the pressure reactor was flushed with hydrogen by two successive cycles of pressurization/venting with $H_2$ (5 atm), then pressurized with $H_2$ (50 atm) and well-closed. The tube was covered by a protective shield and the reaction mixture was heated in an oil bath at 110° C. with constant stirring for 12 h. After cooling to room temperature, excess $H_2$ gas was vented carefully and the products were determined by GC with m-xylene (1.0 mmol) as an internal standard. (After 3 hrs, the conversion of the glycolide was only 39%).

(Note: Complex 3 also catalyzed the dehydrogenation of ethylene glycol to glycolide and other polymeric material (poly glycolide) with liberation of $H_2$ after 24 hrs in 1,4-dioxane (conversion of ethylene glycol 16%) or under solvent free (neat) condition with less conversion (21%)).

(b) Catalytic Hydrogenation of Meso-Lactide to Propylene Glycol:

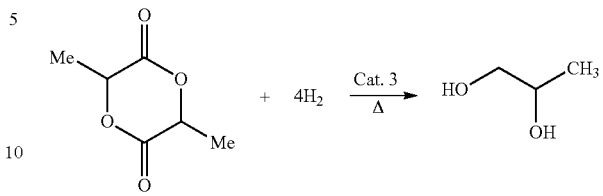

A solution of catalyst 3 (4.5 mg, 0.01 mmol) in THF (1.0 mL) was transferred into a 100 mL Fischer-Porter tube followed by addition of the meso-lactide (144 mg, 1.0 mmol) in THF (2.0 mL) under an atmosphere of purified nitrogen in a Vacuum Atmospheres glove box. The pressure tube was taken out of the glove box, followed by three successive cycles of pressurization/venting with $H_2$ (2 atm), then pressurized with $H_2$ (10 atm) and well-closed. The tube was covered by a protective shield and the reaction mixture was heated in an oil bath at 110° C. with constant stirring for 48 h. After cooling to room temperature, excess $H_2$ gas was vented carefully and the products were determined by GC with m-xylene (1.0 mmol) as an internal standard.

(c) Catalytic hydrogenation of L-lactide to S-(+)-1,2-propanediol:

Scheme 19

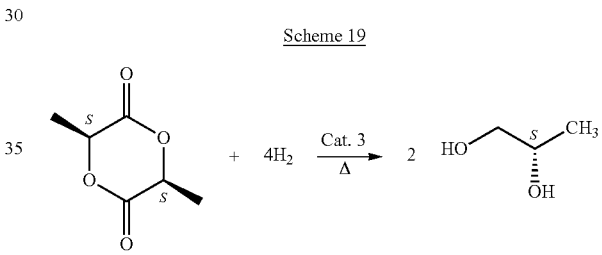

(i) Substrate/catalyst 100/1: A solution of catalyst 3 (4.5 mg, 0.01 mmol) in THF (1.0 mL) was transferred into a 100 mL Fischer-Porter tube followed by addition of L-lactide (144 mg, 1.0 mmol) in THF (2.0 mL) under an atmosphere of purified nitrogen in a glove box. The pressure tube was taken out of the glove box, followed by three successive cycles of pressurization/venting with $H_2$ (2 atm), then pressurized with $H_2$ (10 atm) and closed. The tube was covered by a protective shield and the reaction mixture was heated in an oil bath at 110° C. with constant stirring for 48 h. After cooling to ~5° C. (with a cold water bath), excess $H_2$ gas was vented carefully and the products were determined by GC with m-xylene (1.0 mmol) as an internal standard. After careful removal of the solvent under reduced pressure, the reaction mixture was passed through short silica gel bed and the diol was eluted with $CH_2Cl_2$:MeOH (10:1) and concentrated under vacuum to yield 67% of the optically pure 1,2-propanediol. The optical rotation of the pure product was essentially the same as reported in the literature.

(ii) Substrate/catalyst 500/1: in a nitrogen glove box, a solution of catalyst 3 (9 mg, 0.02 mmol) in THF (5 mL) was added to a stainless-steel high pressure reactor (30 mL) equipped with a magnetic stirring bar containing 10.0 mmol (1.44 g) of the L-lactide. The high pressure reactor was taken out of the glove box and the nitrogen present in the pressure reactor was flushed with hydrogen by two successive cycles of pressurization/venting with $H_2$ (5 atm), then pressurized with H$_2$ (50 atm) and well-closed. The tube was covered by a protective shield and the reaction mixture was heated in an oil bath at 110° C. with constant stirring for 12 h. After cooling to ~5° C. (with a cold water bath), excess H$_2$ gas was vented carefully and the products were determined by GC with m-xylene as an internal standard. After careful removal of the solvent under reduced pressure, the reaction mixture was passed through short silica gel bed and the diol was eluted with CH$_2$Cl$_2$:MeOH (10:1) and concentrated under vacuum to yield 67% of the optically pure 1,2-propanediol. The optical rotation of the pure product was essentially the same as reported in the literature.

Hydrogenation of L-Lactide to S-(+)-1,2-Propanediol Catalyzed by NHC—Ru(II) Catalyst

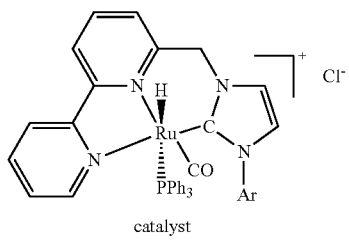

catalyst

The NHC Ru(II) pincer catalyst was prepared according to: E. Fogler, E. Balaraman, Y. Ben-David, G. Leitus, L. J. W. Shimon and D. Milstein, *Organometallics*, 2011, 30, 3826

A 100 mL Fischer-Porter tube was charged under nitrogen with the catalyst (4.5 mg, 0.01 mmol), L-lactide (144 mg, 1.0 mmol) and THF (3 mL). The Fischer-Porter tube was purged by three successive cycles of pressurization/venting with H$_2$ (2 atm), then pressurized with H$_2$ (10 atm). The solution was heated at 110° C. (bath temperature) with stirring for 48 h. After cooling to ~5° C. excess H$_2$ gas was vented and the products were determined by GC. The solvent was removed under reduced pressure and the reaction mixture was passed through short silica gel bed. The 1,2-diol was eluted with CH$_2$Cl$_2$:MeOH (10:1) and concentrated under vacuum to yield 57% of the optically pure (S)-(+)-1,2-propanediol ($[\alpha]_D^{22}$=+27° (c=1, CHCl$_3$)

G. Hydrogenation of Urea Derivatives to Amines and Methanol

Scheme 20

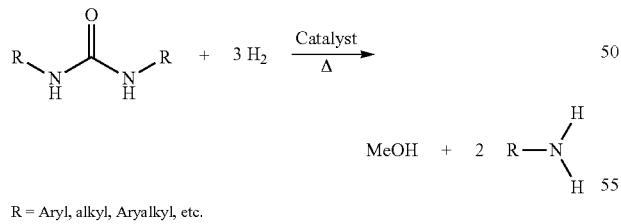

R = Aryl, alkyl, Aryalkyl, etc.

1,3-Dimethylurea was selected as a benchmark substrate for the unprecedented hydrogenation of urea derivatives catalyzed by complex 3. Upon treatment of 1,3-dimethylurea (1 mmol) and a catalytic amount of complex 3 (1 mol %) with H$_2$ (10 atm) at 110° C. (bath temperature) in dry THF resulted in 41% conversion of dimethylurea to methanol and methylamine after 48 h (Table 10, entry 1). The formed methanol was quantified as 35% by GC and the gaseous amine was characterized by GC-MS of the gas phase of the reaction mixture and not quantified. The yield of methanol increased at longer reaction time (Table 10, entry 2). Performing the same reaction under using 13.6 atm of H$_2$ and 2 mol % of catalyst resulted in 93% of methanol after 72 h (Table 10, entry 3).

TABLE 10

Novel hydrogenation of 1,3-dimethylurea to methanol and methylamine catalyzed by 3

$$H_3C\underset{H}{N}\overset{O}{\underset{\|}{C}}\underset{H}{N}CH_3 + 3\,H_2 \xrightarrow{\text{Cat. 3}}{\Delta}$$

$$MeOH + 2\,H_3C-NH_2$$

| | | Reaction conditions[a] | | | |
|---|---|---|---|---|---|
| Entry | Cat. 3 (mol %) | PH$_2$ (atm) | hrs (atm) | Conv. (%)[b] | Yield of MeOH (%)[b],[c] |
| 1 | 1 | 10 | 48 | 41 | 35 |
| 2 | 1 | 10 | 60 | 53 | 52 |
| 3 | 2 | 13.6 | 72 | 96 | 93 |

[a]Complex 3, 1,3-dimethylurea (1 mmol), H$_2$, and dry THF (2 mL) were heated in a Fischer-Porter tube (100 mL) at 110° C. (bath temperature) for specified time.

[b]Conversion of dimethylurea and yields of methanol were analyzed by GC using m-xylene as an internal standard.

[c]The MeNH$_2$ was analyzed in the gas phase (as well as in the liquid phase) by GC-MS and not quantified.

Various urea derivatives were subjected to hydrogenation (Table 11). Hydrogenation of 1,3-dihexylurea under the same conditions (cat/urea derivative=2:100 (mmol), 13.6 atm of H$_2$, 2 mL of dry THF, at 110° C.) yielded methanol and 1-hexylamine in 83% and 87% respectively after 72 h (Table 11, entry 2). As expected, the activated urea derivative, 1,3-bis(2-methoxyethyl)urea gave almost quantitative conversion to methanol and 2-methoxyethylamine upon hydrogenation (Table 11, entry 3). Aromatic and substituted aromatic urea derivatives also underwent hydrogenation very efficiently in moderate yields (Table 11, entries 5-7) along with trace amounts of the corresponding formamides (detected by GC-MS). The hydrogenation of diphenylurea derivatives proceeds very smoothly to yield methanol and anilines. Thus, upon heating a THF solution of 3 (0.02 mmol) and 1,3-diphenylurea (1 mmol) at 110° C. under H$_2$ (12 atm), complete conversion to selectively form 90% of methanol and 95% of aniline took place (Table 11, entry 8). Remarkably, tetra-substituted urea derivatives were also selectively hydrogenated to yield methanol and the corresponding amines, with cleavage of the C—N bond. Thus, heating a THF solution containing 1,1',3,3'-tetramethylurea (1 mmol) and a catalytic amount of the complex 3 (2 mol %) under hydrogen pressure (13.6 atm) using pressure vessel at 110° C. for 72 h resulted in 53% conversion of tetramethylurea (TMU) to methanol (51%) and N,N'-dimethylamine (Table 11, entry 11).

TABLE 11

Hydrogenation of urea derivatives to amines and methanol catalyzed by BPy-PNN-Ru(II) pincer complex 3.[a]

$$\underset{R'}{\overset{R}{N}}-\underset{H}{\overset{O}{\parallel}}-\underset{R'}{\overset{R}{N}} + 3\ H_2\ (13.6\ \text{atm}) \xrightarrow[\text{THF, 110° C., 72 h}]{\text{Cat. 3 (2 mol \%)}} \text{MeOH} + 2\ \underset{R'}{\overset{R}{N}}-H$$

| Entry | Amide | Products (yield {%})[b] | |
|---|---|---|---|
| | | MeOH | Amine |
| 1[c] | N,N'-dipropylurea | 89 | propylamine |
| 2 | N,N'-dihexylurea | 83 | hexylamine (87) |
| 3 | N,N'-bis(2-methoxyethyl)urea | 94 | 2-methoxyethylamine (97) |
| 4 | N,N'-dicyclohexylurea | 73 | cyclohexylamine (79) |
| 5[c] | N,N'-dibenzylurea | 61 | benzylamine (60) |
| 6[c] | N,N'-bis(4-methylbenzyl)urea | 67 | 4-methylbenzylamine 71 |
| 7 | N,N'-bis(4-fluorobenzyl)urea | 58 | 4-fluorobenzylamine 59 |
| 8 | N,N'-diphenylurea | 90 | aniline 95 |
| 9 | N,N'-bis(4-tert-butylphenyl)urea | 93 | 4-tert-butylaniline 87 |

TABLE 11-continued

Hydrogenation of urea derivatives to amines and methanol catalyzed by BPy-PNN-Ru(II) pincer complex 3.[a]

$$R-N(R')-C(=O)-N(R')-R + 3 H_2 \xrightarrow[THF, 110°C., 72 h]{Cat. 3 (2 mol \%)} MeOH + 2\ R(R')N-H$$

(13.6 atm)

| | | Products (yield {%})[b] | |
|---|---|---|---|
| Entry | Amide | MeOH | Amine |
| 10[c],[d] | 1,3-dimethylurea | 51 | (CH₃)₂NH |
| 11[c] | 1,1'-carbonyldipiperidine | 63 | morpholine 57 |

R = H; R = Aryl, alkyl, and Aryalkyl
R = R' = Me and —(CH₂(CH₂)₃CH₂)—
[a]Complex 3 (0.02 mmol), urea derivative (1 mmol), H₂ (13.6 atm), and dry THF (2 mL) were heated in a Fischer-Porter tube (100 mL) at 110° C. (bath temperature) for 72 hrs (most of the reactions were repeated twice).
[b]Yields of products were analyzed by GC (1 mmol of m-xylene as an internal standard).
[c]The amines n-propylamine and Me₂NH for (entries 1 and 10 respectively) were analyzed in the gas phase (as well as in liquid phase) by GC-MS and not quantified.
[d]The corresponding formamides (entries 5-6 and 10-11) were observed on GC-MS and not quantified.

General Procedure for the Catalytic Hydrogenation of Urea Derivatives:

A 100 mL Fischer-Porter tube was charged with catalyst 3 (0.02 mmol), urea derivative (1.0 mmol) and THF (2 mL) under an atmosphere of purified nitrogen in a Vacuum Atmospheres glove box.

The pressure tube was taken out of the glove box, followed by three successive cycles of pressurization/venting with H₂ (3 atm), then pressurized with H₂ (10 atm) and well-closed. The tube was covered by a protective shield and the reaction mixture was heated in an oil bath at 110° C. with constant stirring for 48 h. After cooling to room temperature, excess H₂ gas was vented carefully and the products were determined by gas chromatography (GC).

G. Hydrogenation of Polypropylene Carbonate

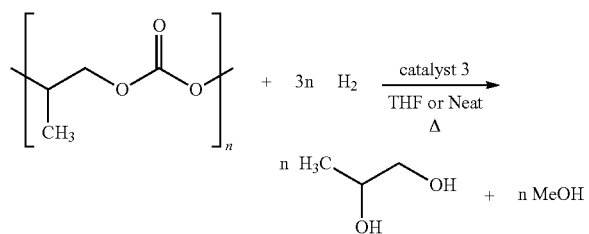

(1) A 100 mL Fischer-Porter tube was charged under nitrogen with catalyst 3 (9 mg, 0.02 mmol), polypropylene carbonate (M_n=50,000 by GPC; 0.255 g) and THF (2 mL). The Fischer-Porter tube was purged by three successive cycles of pressurizing/venting with H₂ (3 atm) and pressurized with 10 atm of H₂. The solution was heated at 110° C. (bath temperature) with stirring for 8 h. After cooling (~5° C.; ice/water), excess H₂ was vented carefully and the products were analyzed by GC-MS. The solvent was removed under vacuum to give pure 1,2-propanediol (isolated yield=0.180 g corresponds to 94.8%) and methanol (97% yield).

(2) Hydrogenation Under Solvent-Free (Neat) Conditions:

A 100 mL Fischer-Porter tube was charged with catalyst 3 (0.01 mmol) and polypropylene carbonate (M_n=50,000 by GPC; 0.510 g) under an atmosphere of purified nitrogen in a glovebox. The pressure tube was taken out of the glove box and purged by three successive cycles of pressurization/venting with H₂ (2 atm), then pressurized with H₂ (12.2 atm). The tube was placed behind a protective shield and heated in an oil bath at 130° C. with constant stirring for 14 h. After cooling to ~5° C., excess H₂ gas was vented carefully and the products (methanol and 1,2-propanediol) were analyzed by gas chromatography (GC and GC-MS) and quantified by ¹H NMR using toluene as internal standard. Quantitative conversion of the polymer took place, to yield 4.96 mmol of 1,2-propanediol and methanol. Isolated yield of 1,2-propanediol was 0.368 g (4.83 mmol).

Example 3

Dehydrogenative Coupling of Primary Alcohols to Esters

Some processes involving the coupling of alcohols to esters are shown in Scheme 21:

Scheme 21

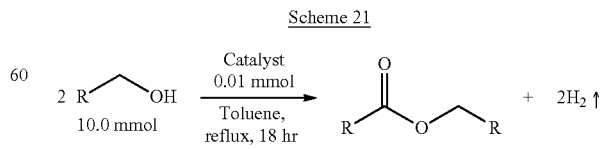

A. Typical Procedures for the Catalytic Dehydrogenative Coupling of Primary Alcohols (Table 12)
(a) Complex 3 (0.01 mmol), an alcohol (10 mmol), and toluene (2 mL) were taken in a Schlenk flask under an atmosphere of purified nitrogen in a glove box. The flask was equipped with a condenser and the solution was refluxed with stirring in an open system under argon for 24 hrs. After cooling to room temperature, the consumption of starting material and the formation of ester were determined by GC with m-xylene as an internal standard using a Carboxen 1000 column on a HP 690 series GC system.

(b) Complex 4 (0.01 mmol), an alcohol (10 mmol), KO$^t$Bu (0.01 mmol) and toluene (2 mL) were taken in a Schlenk flask under an atmosphere of purified nitrogen in a glove box. The flask was equipped with a condenser and the solution was refluxed with stirring in an open system under argon for 18 hrs. After cooling to room temperature, the consumption of starting material and the formation of ester were determined by GC with m-xylene as an internal standard using a Carboxen 1000 column on a HP 690 series GC system.

TABLE 12

Coupling of primary alcohols to form esters

| Entry | Cat. | Alcohol | Ester | Conv. (%) | Yield (%) |
|---|---|---|---|---|---|
| 1 | 4 | 1-Hexanol | Hexyl hexanoate | — | — |
| 2 | 4 + t-BuOK | 1-Hexanol | Hexyl hexanoate | 95.3 | 95.0 + traces of aldehyde |
| 3 | 7 + t-BuOK | 1-Hexanol | Hexyl hexanoate | 90.0 | 89.3 + traces of aldehyde |
| 4 | 3 | 1-Hexanol | Hexyl hexanoate | 98.6 | 98.2 |
| 5 | 3 | 1-Pentanol | Pentyl pentanoate | 98.3 | 98.0 |
| 6 | 3 | Benzyl alcohol | Benzyl benzoate | 94.1 | 92.9 + 0.9% aldehyde |
| 7 | 3 | 1-Butanol | Butyl butyrate | 90.1 | 89.7 + 0.3% aldehyde |
| 8 | 3 | Cyclohexane methanol | Cyclohexyl- methyl cyclohexane carboxylate | 98 | 96.2 + 1.6% aldehyde |

B. Catalytic Dehydrogenation of Primary Alcohols Under Neat Condition (Absence of Solvent) (Table 13):

Complex 3 (0.01 mmol) was heated under an argon flow in different alcohols (10 mmol) at the specified temperatures and times (Table 13). After cooling to room temperature, the consumption of starting material and the formation of ester were determined by GC with m-xylene as an internal standard using a Carboxen 1000 column on a HP 690 series GC.

TABLE 13

Coupling of primary alcohols to form esters under neat conditions

| Entry | Cat. | Alcohol | Temp. (° C.) | Time (hrs) | Ester | Conv. (%) | Yield (%) |
|---|---|---|---|---|---|---|---|
| 1 | 3 | 1-Pentanol | 138 | 12 | Pentyl penta-noate | 97.7 | 97.5 + traces of aldehyde |
| 2 | 3 | 1-Butanol | 117 | 12 | Butyl butyrate | 89.0 | 87.7 + 1.2% aldehyde |
| 3 | 3 | Ethanol (20 mmol) | 79 | 72 | Ethyl acetate | 52.0 | 51.7 |

C. Catalytic Dehydrogenative Coupling of Alcohols Under Open Air (Table 14):

To an oven dried Schlenk flask cooled to room temperature under open air were added complex 4 (0.01 mmol), an alcohol (5 mmol) in toluene (2 mL), followed by KO$^t$Bu (0.01 mmol) in toluene (1 mL) and the flask was equipped with a condenser and the solution was refluxed with stirring in an open system under air for 18 hrs. After cooling to room temperature, the consumption of starting materials was determined by GC with m-xylene as an internal standard, using a Carboxen 1000 column on a HP 690 series GC system.

TABLE 14

Coupling of primary alcohols to form esters under open air

| Entry | Alcohol | Ester | Conv. (%) | Yield (%) |
|---|---|---|---|---|
| 1 | 1-Hexanol | Hexyl hexanoate | 89.8 | 86.3 + 2.8% aldehyde |
| 2 | Benzyl alcohol | Benzyl benzoate | 90.4 | 84.8 + 5.3% aldehyde |

Example 4

Dehydrogenative Coupling of Alcohols and Amines with Liberation of H$_2$ to Form Amides Some processes involving the coupling of alcohols and amines to generate amides are shown in Scheme 22:

Scheme 22

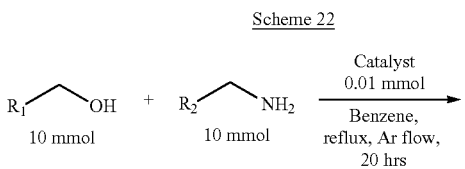

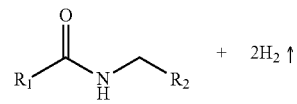

A. Typical Procedure for the Catalytic Dehydrogenative Mono-Acylation of Amines with Alcohols (Table 15):

(a) Complex 3 (0.01 mmol), an alcohol (10 mmol), an amine (10 mmol), and benzene (3 mL) were taken in a Schlenk flask under an atmosphere of purified nitrogen in a Vacuum Atmospheres glove box. The flask was equipped with a condenser and the solution was refluxed with stirring in an open system under argon for 20 hrs. After cooling to room temperature, the consumption of starting materials was checked by GC using a Carboxen 1000 column on a HP 690 series GC system. (b) Complex 4 (0.01 mmol), an alcohol (10 mmol), an amine (10 mmol), KO$^t$Bu (0.01 mmol), and benzene (3 mL) were taken in a Schlenk flask under an atmosphere of purified nitrogen in a Vacuum Atmospheres glove box. The flask was equipped with a condenser and the solution was refluxed with stirring in an open system under argon for 20 hrs. After cooling to room temperature, the consumption of starting materials was checked by GC using a Carboxen 1000 column on a HP 690 series GC system.

TABLE 15

Coupling of amines and alcohols to generate amides

| Entry | Alcohol | Amine | Amide | Yield (isolated) |
|---|---|---|---|---|
| 1 | HO−(−)₄−CH₃ | PhCH₂NH₂ | PhCH₂NH−C(O)−(−)₄−CH₃ | 95.0 |
| 2 | HO−(−)₂−CH₃ | PhCH₂NH₂ | PhCH₂NH−C(O)−(−)₂−CH₃ | 96.3 |
| 3 | HO−CH₂CH₂−OCH₃ | PhCH₂NH₂ | PhCH₂NH−C(O)−CH₂−OCH₃ | 97.8 (94.0)[a] |
| 4 | HO−CH₂CH₂−OCH₃ | H₂N−(−)₄−CH₃ | CH₃−(−)₄−NH−C(O)−CH₂−OCH₃ | 93.0 |
| 5 | HO−(−)₄−CH₃ | H₂N−(−)₄−CH₃ | CH₃−(−)₄−NH−C(O)−(−)₄−CH₃ | 85.8 |
| 6 | HO−(−)₃−CH₃ | H₂N−(−)₃−CH₃ | CH₃−(−)₃−NH−C(O)−(−)₃−CH₃ | 86.7 |
| 7 | HO−CH₂CH₂−OCH₃ | Ph−NH₂ | Ph−NH−C(O)−CH₂−OCH₃ | 62.0 |
| 8 | HO−(−)₄−CH₃ | Ph−NH₂ | Ph−NH−C(O)−(−)₄−CH₃ | 56.0 |
| 9 | HO−(−)₄−CH₃ | furfurylamine | furfuryl-NH−C(O)−(−)₄−CH₃ | 72.2 |
| 10 | HO−CH₂CH₂−OCH₃ | cyclohexyl-NH₂ | cyclohexyl-NH−C(O)−CH₂−OCH₃ | 96.1 |
| 11 | HO−(−)₄−CH₃ | morpholine | morpholine-C(O)−(−)₄−CH₃ | 84.3 |

TABLE 15-continued

Coupling of amines and alcohols to generate amides

| Entry | Alcohol | Amine | Amide | Yield (isolated) |
|---|---|---|---|---|
| 12 | HO-CH2CH2-O-CH3 | pyrrolidine | N-(methoxyacetyl)pyrrolidine | 87.0 |
| 13 | HO-CH2CH2-O-CH3 | H2N-CH2CH2-NH2 | CH3O-CH2-C(O)-NH-CH2CH2-NH-C(O)-CH2-OCH3 | 90.0 |
| 14 | (S)-2-methylbutan-1-ol | BnNH2 | (S)-2-methyl-N-benzylbutanamide | 68[b] |
| 15 | HO-(CH2)5-CH3 | H2N-(CH2)6-NH2 | CH3-(CH2)4-C(O)-NH-(CH2)6-NH-C(O)-(CH2)4-CH3 | 88.4 |

[a]Complex 3 (0.0033 mmol), an alcohol (5.0 mmol), an amine (5.0 mmol), and benzene (3 mL) were refluxed for about 38 hrs (maximum turnover number = 1500).
[b]No racemisation was observed.

B. Catalytic Dehydrogenative Bis-Acylation of Diamines with Alcohols (Table 15; Entries 13 and 15):

Complex 3 (0.01 mmol), an alcohol (10.5 mmol), a diamine (5 mmol), and benzene (5 mL) were placed in a Schlenk flask under an atmosphere of purified nitrogen in a Vacuum Atmospheres glove box. The flask was equipped with a condenser and the solution was refluxed with stirring in an open system under argon flow. The reaction mixture was cooled to room temperature and the consumption of starting materials was checked by GC using a Carboxen 1000 column on a HP 690 series GC system.

C. Amidation Reaction Under Open Air (Table 16):

To an oven dried Schlenk flask cooled to room temperature under open air were added complex 4 (0.01 mmol), an alcohol (5 mmol), an amine (5 mmol) in benzene (2 mL), followed by KO$^t$Bu (0.01 mmol) in benzene (1 mL) and the flask was equipped with a condenser and the solution was refluxed with stirring in an open system under air for 24 hrs. After cooling to room temperature, the consumption of starting materials was determined by GC with m-xylene as an internal standard, using a Carboxen 1000 column on a HP 690 series GC system.

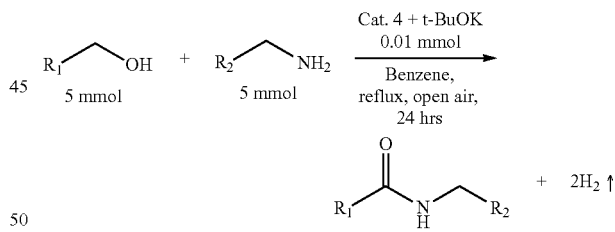

Scheme 23

TABLE 16

Coupling of amines and alcohols to generate amides under open air

| Entry | Alcohol | Amine | Amide | Conv. of alcohol (%) | Yield (isolated) |
|---|---|---|---|---|---|
| 1 | HO-(CH2)5-CH3 | BnNH2 | Bn-NH-C(O)-(CH2)4-CH3 | 77 | 71 |

TABLE 16-continued

Coupling of amines and alcohols to generate amides under open air

| Entry | Alcohol | Amine | Amide | Conv. of alcohol (%) | Yield (isolated) |
|---|---|---|---|---|---|
| 2 | HO-CH₂CH₂-O-CH₃ | BnNH₂ | PhCH₂-NH-C(O)-CH₂-O-CH₃ | 88 | 80 |
| 3 | HO-CH₂CH₂-O-CH₃ | H₂N-(CH₂)₄-CH₃ | CH₃(CH₂)₄-NH-C(O)-CH₂-O-CH₃ | 81 | 74 |
| 4 | HO-(CH₂)₄-CH₃ | morpholine | morpholine-C(O)-(CH₂)₄-CH₃ | 66 | 61 |

D. Amidation Reaction Under Neat Condition (Table 17):

Complex 3 (0.01 mmol), an alcohol (5 mmol), an amine (5 mmol) were taken in a Schlenk flask under an atmosphere of purified nitrogen in a Vacuum Atmospheres glove box. The flask was equipped with a condenser and the solution was heated at 130° C. (bath temperature) with stirring in an open system under argon for 24 hrs. After cooling to room temperature, the consumption of starting materials was determined by GC with m-xylene as an internal standard, using a Carboxen 1000 column on a HP 690 series GC system.

Scheme 24

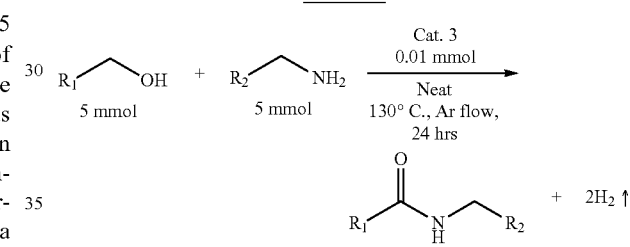

TABLE 17

Coupling of amines and alcohols to generate amides under neat conditions

| Entry | Alcohol | Amine | Amide | Conv. of alcohol (%) | Yield (isolated) |
|---|---|---|---|---|---|
| 1 | HO-CH₂CH₂-O-CH₃ | BnNH₂ | PhCH₂-NH-C(O)-CH₂-O-CH₃ | 97 | 87.6 |
| 2 | HO-(CH₂)₂-CH₃ | H₂N-(CH₂)₃-CH₃ | CH₃(CH₂)₃-NH-C(O)-(CH₂)₂-CH₃ | 85.2 | 76.0 |
| 3 | HO-CH₂CH₂-O-CH₃ | H₂N-(CH₂)₄-CH₃ | CH₃(CH₂)₄-NH-C(O)-CH₂-O-CH₃ | 92.3 | 82.0 |
| 4 | HO-(CH₂)₃-CH₃ | H₂N-(CH₂)₃-CH₃ | CH₃(CH₂)₃-NH-C(O)-(CH₂)₃-CH₃ | 87.0 | 79.6 |

TABLE 17-continued

Coupling of amines and alcohols to generate amides under neat conditions

| Entry | Alcohol | Amine | Amide | Conv. of alcohol (%) | Yield (isolated) |
|---|---|---|---|---|---|
| 5 | HO-CH2CH2-O-CH3 | morpholine | morpholine-N-C(=O)-CH2-O-CH3 | 82.7 | 73.0 |

E. Amidation Reaction by In-Situ Generation of the Catalyst from the Precursor Ligand (Table 18):

To a Schlenk flask cooled under argon were added ligand, BPy-$^t$PNN (5) (0.01 mmol) and Ru-Precursor RuHCl(CO)(PPh$_3$)$_3$ (0.01 mmol), followed by benzene (1 mL) and the solution was heated (~80° C.) with stirring for about 1 hr. After cooling to room temperature, were added an alcohol (5 mmol), an amine (5 mmol), and t-BuOK (0.01 mmol) in benzene (2 mL) and the solution was refluxed with stirring in an open system under air for 24 hrs. After cooling to room temperature, the consumption of starting materials was determined by GC with m-xylene as an internal standard, using a Carboxen 1000 column on a HP 690 series GC system.

Purification of Amides:

After completion of the reaction, the solvent was removed (Table 15-16, and 18) under vacuum and the resulting residue was purified by the column chromatography on silica gel using EtOAc/n-hexane.

Example 5

Polyamides Synthesis from Diols and Diamines

The applicants have unexpectedly discovered that the catalysts of the present invention also catalyze the synthesis of polyamides directly from diols and diamines. In some preferred embodiments, 1,4-dioxane is used as a solvent. This polyamidation reaction is general, environmentally benign and atom economical. It proceeds under neutral reaction conditions without the use of activators, condensing agents or other additives. Moreover, these methods produce H$_2$ as the only byproduct (Scheme 26).

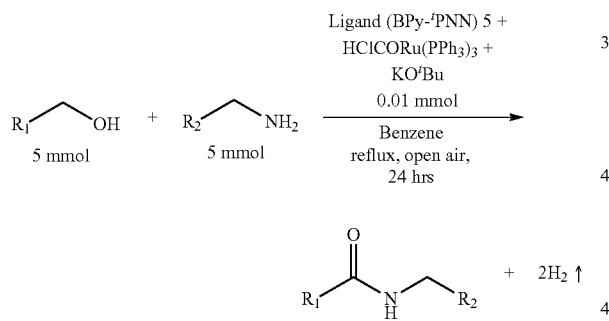

Scheme 25

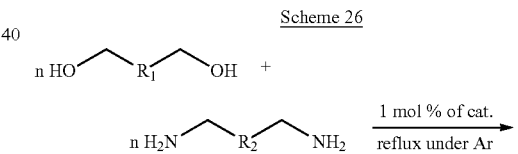

Scheme 26

TABLE 18

Coupling of amines and alcohols to generate amides with in-situ generation of catalyst

| Entry | Alcohol | Amine | Amide | Yield (isolated) |
|---|---|---|---|---|
| 1 | HO-CH2CH2-O-CH3 | PhCH2NH2 | PhCH2-NH-C(=O)-CH2-O-CH3 | 72.0 |
| 2 | HO-(CH2)4-CH3 | PhCH2NH2 | PhCH2-NH-C(=O)-(CH2)4-CH3 | 67.6 |

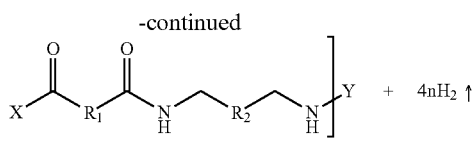

Figure 5A:
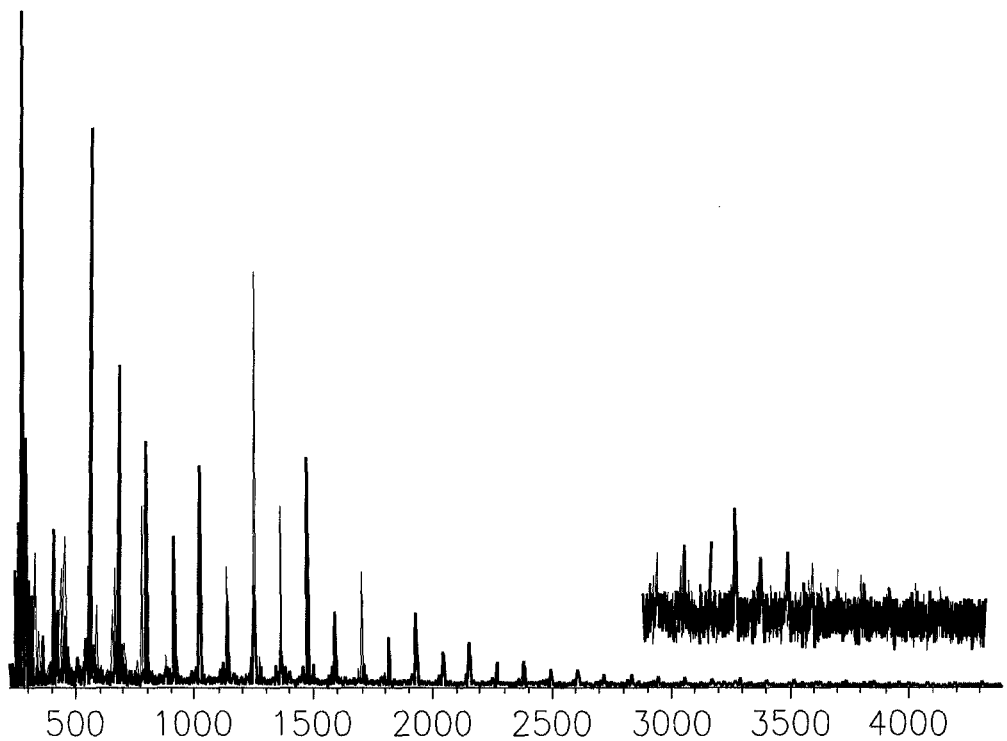
FIG. 5A: polyamide 3a in TFA using HBA matrix.

Upon refluxing a 1,4-dioxane solution containing equimolar amounts of 1,6-hexanediol and 1,6-hexanediamine in the presence of 1 mol % of complex 1 under an argon atmosphere for 3 days, a white solid separated out in the reaction mixture. The solid was filtered off and successively washed with THF:EtOAc (1:1), dichloromethane and 20% methanol in water. The resultant white solid was dried under high vacuum at 80° C. for 12 hrs to afford polymer 3a in 82% yield (Table 19, entry 1). The solid was insoluble in MeOH, THF, 1,4-dioxane and chlorinated solvents, partially soluble in dimethylsulfoxide and dimethylformamide upon warming. The polyamide obtained was dissolved in deuterated trifluoroacetic acid (TFA) or trifluoroethanol (TFE) and characterized by NMR. The presence of $CH_2$ attached to the carbonyl group was confirmed by $^1H$ NMR, showing a broad singlet at 2.39 ppm for the four hydrogen atoms. A peak at 180.4 ppm in the $^{13}C\{^1H\}$ NMR spectrum and an IR band at 1633 $cm^{-1}$ confirm the presence of the amide C=O group. The average molecular weight $M_n$ of the polyamide 3a was 16.6 kDa as measured by $^1H$ NMR using trifluoroethanol (TFE) as a solvent. The obtained solid was dissolved in TFA:$CH_3CN$ (1:1) and MALDI-TOF mass spectrum was recorded using DHB (2,5-dihydroxybenzoic acid) as the matrix (FIG. 5A). The polyamide has three possible types of end groups (amine-amine, amine-alcohol or alcohol-alcohol, compounds 3aa, 3ab and 3ac, respectively) and it also might result in a cyclic form. The spectrum revealed the highest molecular weight of 4195 Da, which corresponds to a polyamide having 18 monomers with OH/OH end groups. Due to insolubility of the polymer in DMF, GPC (gel permeation chromatography) was not performed.

Different Types of End Groups in Polyamide 3a:

plexes 1 and 3 exhibit similar catalytic activity in the polyamidation reaction. However, using complex 3 it is possible to perform the polyamidation reaction in the absence of solvent, and using a lower catalyst loading. Thus, heating equivalent amounts of 1,6-hexanediol and 1,6-hexanediamine with the thermally stable complex 3 (0.2 mol %) in the absence of solvent at 130° C. for 14 hrs, followed by heating to 190° C. for an hour under Argon flow and cooling to room temperature resulted in a solid (Table 19, entry 16). The solid was washed with THF, water, ethanol and hexane and dried under vacuum for 12 hrs and isolated in 84% yield. The MALDI-TOF mass spectrum of this solid exhibited a highest molecular weight of 4951 Da. The higher molecular weight obtained under these conditions is likely due to the higher temperatures employed and absence of solvent, allowing polymerization in the melt.

Refluxing of 1,10-decanediol and 1,6-hexanediamine in 1,4-dioxane in the presence of 1 mol % of complex 1 resulted in 88% yield of the polyamide 3b (Table 19, entry 2). The presence of the amide functional group of 3b was confirmed by IR, showing an absorption frequency at 1637 $cm^{-1}$ and a signal at 181.6 ppm in the $^{13}C\{^1H\}$ NMR spectrum. The number average molecular weight of 3b was found to be 10.3 kDa based on $^1H$ NMR spectra using trifluoroethanol (TFE) as a solvent. A MALDI-TOF mass spectrum indicated a molecular weight up to 4965 Da, which corresponds to a polyamide comprised of 18 monomers. Due to insolubility in DMF, GPC was not performed.

To further investigate the polyamidation reaction, various combinations of diols and diamines were studied. Thus, polyamidation reaction of 1,3-phenylenedimethanol and 1,6-hexanediamine with 1 mol % of complex 1 under argon atmosphere for 3 days resulted in a solid which was isolated by filtration. The solid was washed successively with THF:EtOAC (1:1), dichloromethane and 20% MeOH in water, and finally dried under high vacuum at 80° C. to afford 82% of compound 3c (Table 19, entry 3). The IR spectrum of the polyamide 3c showed the presence of the NH group as broad

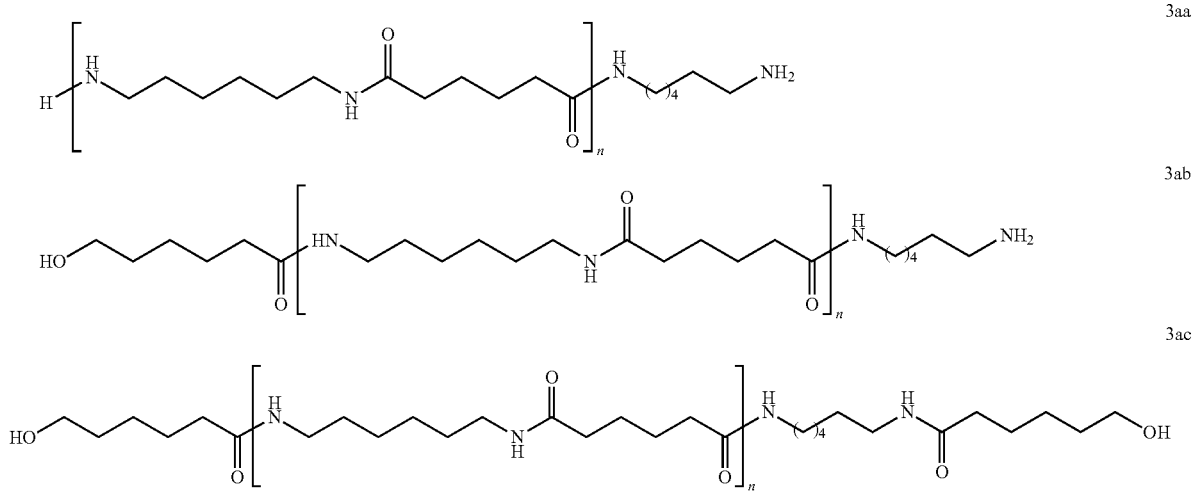

Figure 5B:
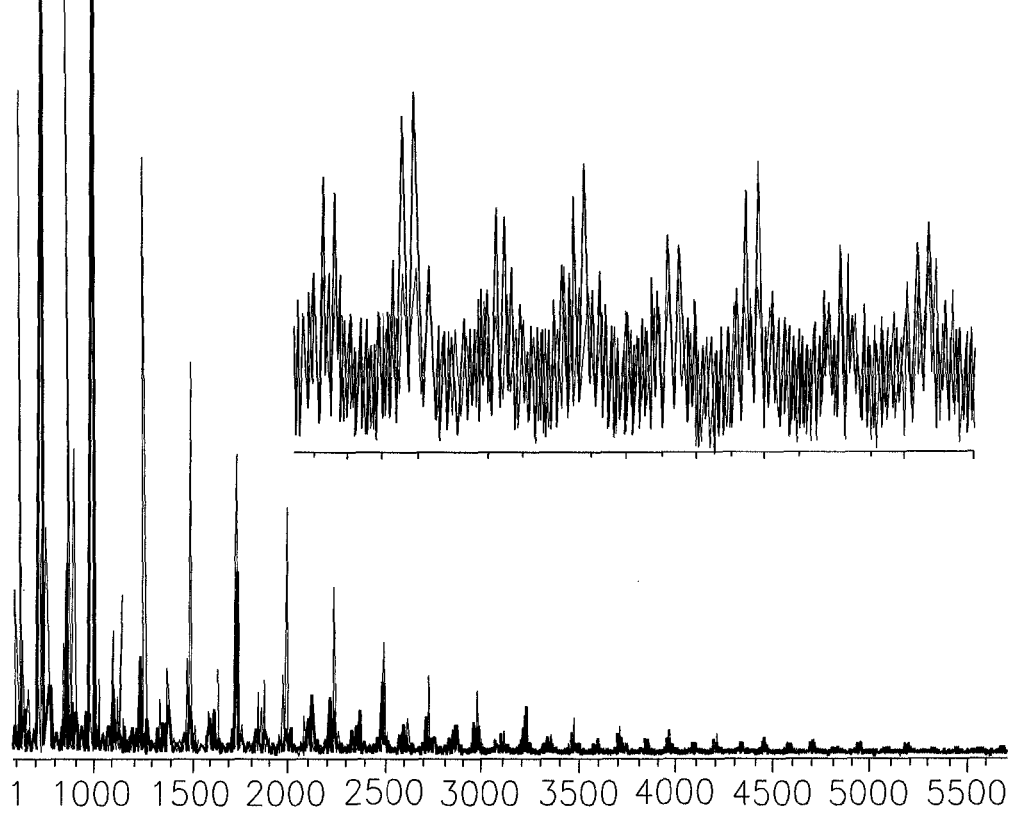
FIG. 5B: polyamide 3c in TFA using HBA matrix.

The same reaction was performed using the bipyridine based complex 3 as catalyst. After 3 days in refluxing dioxane polymer 3a was formed as a white solid and isolated after work-up in 78% yield. Analysis of the obtained solid exhibited a similar MALDI-TOF pattern and $^1HNMR$ spectrum as observed with catalyst 1. Thus, under these conditions compeak at 3297 $cm^{-1}$ and the amide C=O peak at 1631 $cm^{-1}$. The $^{13}C\{^1H\}$ NMR spectrum exhibited the C=O carbon at 165.8 ppm. Polyamide 3c was further analyzed by MALDI-TOF by dissolving it in 80% TFA in acetonitrile using DHB as matrix (FIG. 5B). It gave a series of peaks in the range of 700-5932 Da. In an attempt to get a higher molecular weight, polyamide 3c was refluxed with- or without 1,3-phenylenedimethanol in the presence of the complex 1. However, a higher molecular weight was not observed. This might be due to the insolubility of 3c in 1,4-dioxane. Due to insolubility in DMF, GPC analysis was not performed.)

pyridine-2,6-diyldimethanol and 1,6-hexanediamine catalyzed by 1 mol % 1, furnished after 3 days of reflux in 1,4-dioxane the polyamide 3g (Table 19, entry 7) as a gummy insoluble solid which separated out from the reaction mixture and after work up gave a yield of 74%. The NMR and IR

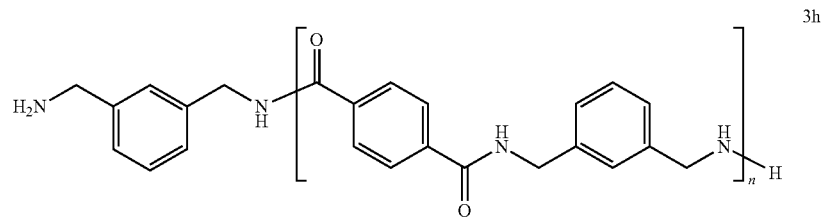

3c

Figure 5C:
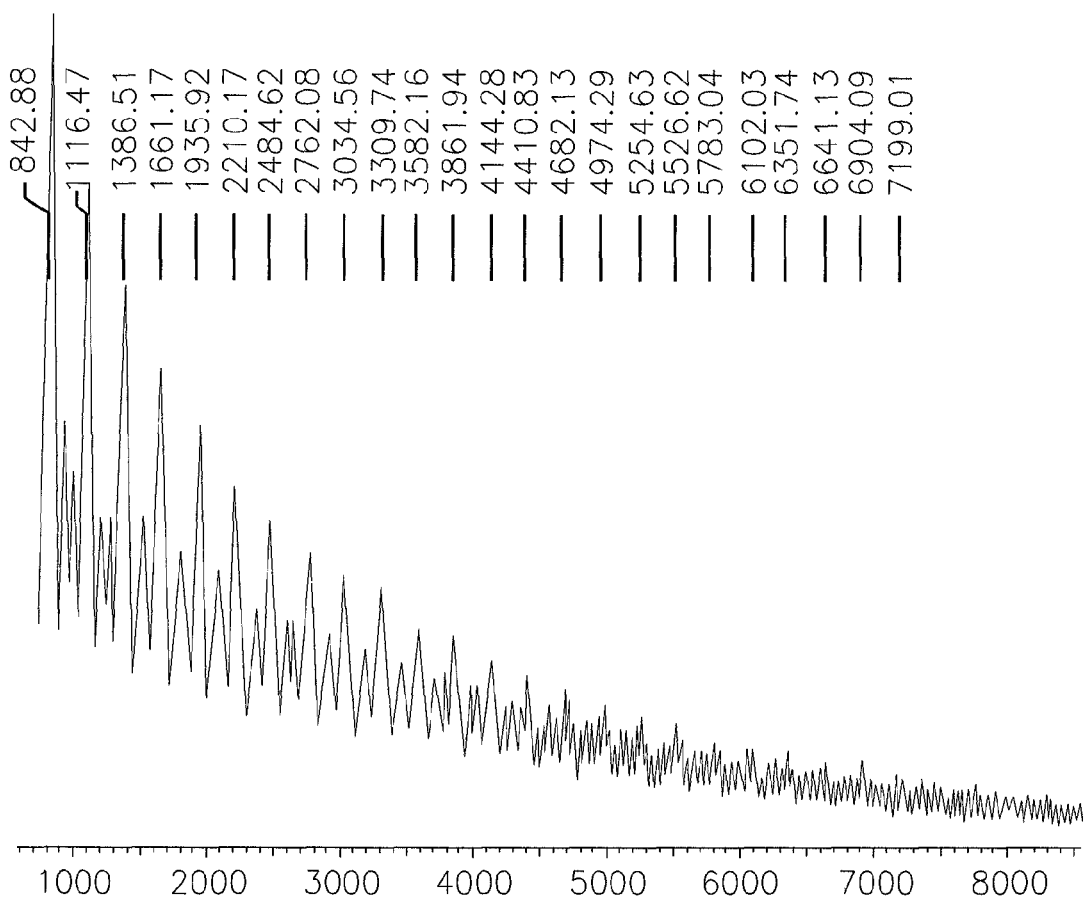
FIG. 5C: polyamide 3d in 50% TFA/DCM using HBA-NaI.

In order to increase the solubility of the polyamides, ether substituted aromatic diols were employed for the polymerization reactions. Thus, the reaction of (5-methoxy-1,3-phenylene)dimethanol and 1,6-hexanediamine gave 86% of compound 3d (Table 19, entry 4) as a gummy solid and exhibited a mass peak at 7199 Da in the MALDI-TOF spectrum using HBA+NaI as a matrix and a solution of the polyamide 3d in TFA:dichloromethane 1:1 (FIG. 5C). The polyamide 3d was dissolved completely in warm DMF and the molecular weight was measured using gel-permeation chromatography (GPC) using DMF with 0.1% LiBr (wt/v) as the eluent at a flow rate of 1.0 mL/min with column temperature at 50° C., yielding Mn=18.7 kDa with PDI of 2.08. The significantly lower molecular weight in MALDI-TOF when compared with GPC is likely to be a result of the high PDI. As previously reported, in case of polydispersities higher than PDI=1.2, MALDI-TOF leads to under-represented high-mass components with respect to the lower mass components, resulting in significantly lower average molecular weight values.

Figure 5D:
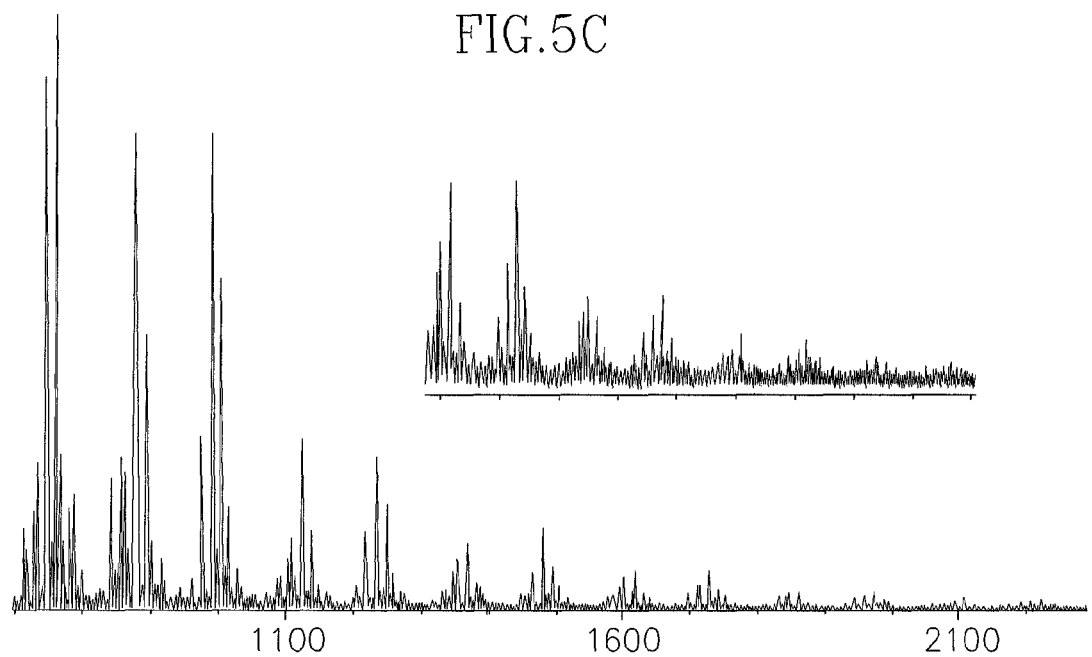
FIG. 5D: polyamide 3e in TFA using HBA matrix.

Exploring the scope of the polyamidation reaction, equivalent amounts of 1,4-phenylenedimethanol and 1,6-hexanediamine were refluxed with 1 mol % of complex 1 for 3 days, leading to 88% yield of the crude compound 3e (Table 19, entry 6). Successive washings with THF:EtOAC (1:1), dichloromethane, and 20% MeOH in water resulted in 80% yield of the solid after drying under vacuum. IR (peak at 1626 cm$^{-1}$) and NMR spectra confirm the presence of amide functionality. MALDI-TOF spectrum of the compound 3e in TFA:CH$_3$CN (1:1) revealed only oligomeric mixtures in the range of 700-2500 Da (FIG. 5D). The mass unit of 2322 Da corresponds to only 9 monomer units. Reaction of the shorter diamine 1,2-ethylenediamine with 1,4-phenylenedimethanol did not result in significant progress of the polyamidation reaction, giving the polyamide 3f in 63% yield (Table 19, entry 6), comprised of low molecular weight oligomeric mixtures in the range of 600-1900.

Next, the polyamidation reaction was examined using heteroaromatic diols. Thus, reaction of equivalent amounts of spectra confirm the presence of the amide carbonyl group. GPC analysis was performed for polyamide 3g using DMF as a solvent upon heating at 80° C. The Mn calculated from the GPC was 26.9 kDa with PDI of 1.98. The polyamide 3g was also analyzed by MALDI-TOF. The MALDI-TOF mass spectrum shows a series of peaks in the range of 600-4700 Da and the highest mass peak at 4583 appeared with low intensity and corresponds to 18 monomer units.

Figure 5E:
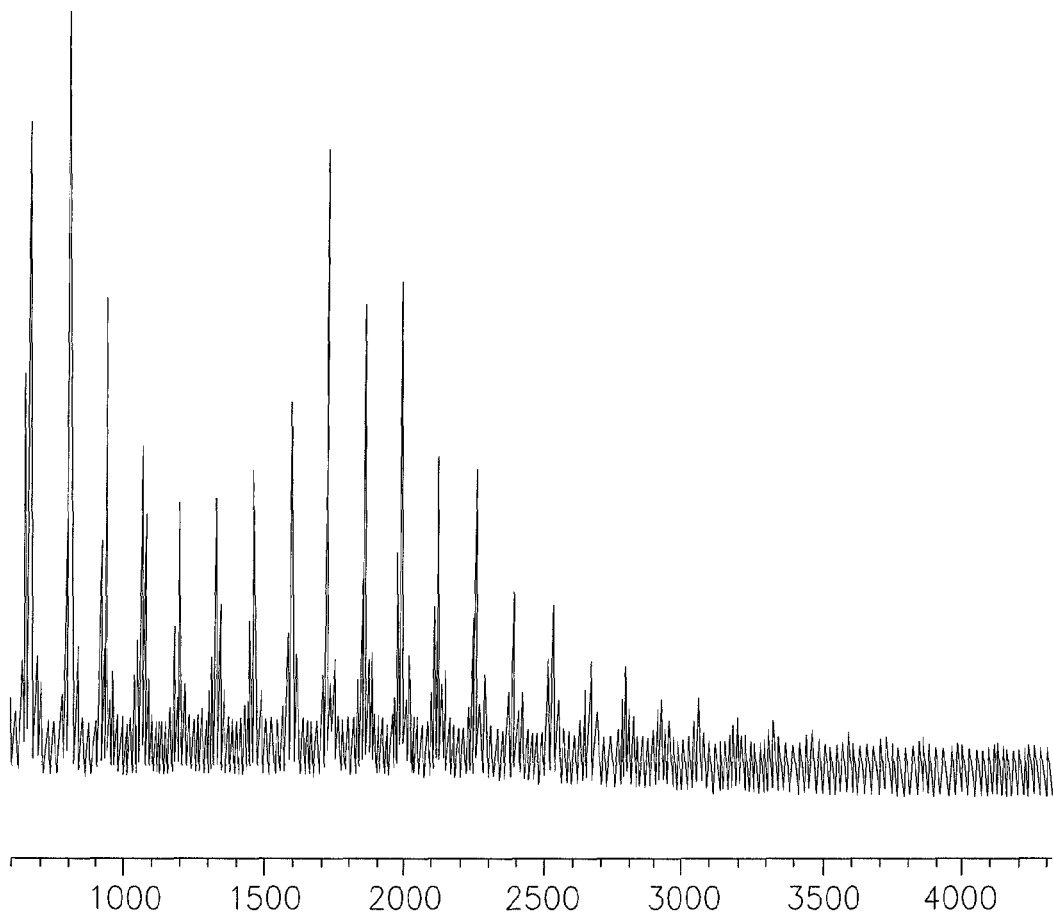
FIG. 5E: polyamide 3h in TFA using HBA matrix.

Next, aromatic diamines were studied for polyamidation reactions. Upon refluxing 1,4-phenylenedimethanol and 1,3-phenylenedimethanamine, a white solid was obtained after 3 days and was filtered off and dried under vacuum to provide 86% of polyamide 3h (Table 19, entry 8). The NMR and MALDI-TOF of 3h (FIG. 5E) reveal high molecular weight oligomeric mixtures. The highest mass unit obtained for the polyamide 3h was 3861 Da, having amine end groups and corresponding to 14 monomer units in the chain. The other oligomer peaks appear at 3594, 3328, 3062, 2796, 2530, 2264, 1732, 1466, 1200, 668 mass units. Further, heating the compound 3h in refluxing 1,4-dioxane in the presence of 1 mol % of the catalyst 1 did not result in progress of the polymer chain (due to insolubility in DMF, GPC analysis was not performed).

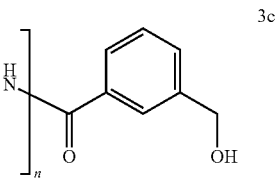

3h

The polyamidation reaction of 1,4-phenylenedimethanol and 1,4-phenylenedimethanamine afforded a mixture of oligomers 3i in 84% isolated yield (Table 19, entry 9). The MALDI-TOF spectrum showed the highest mass unit of 3747 Da, indicating the presence of 14 monomer units. The reaction of 1,3-phenylenedimethanol and 1,3-phenylenedimethanamine led to 3j (Table 19, entry 10) in 78% yield after workup, with a maximum mass unit of 1467, corresponding to 5.5 monomer units. The reaction of 1,5-pentanediol and 1,4-phenylenedimethanamine gave 80% of compound 3k (Table 19, entry 11). Interestingly, 3k showed a series of mass peaks in the range of 500-5200 Da corresponding to 22 monomer units. Reaction of cyclohexane-1,4-diyldimethanol and 1,4-phenylenedimethanamine gave 66% of compound 31 (Table 15, entry 12), with peaks at 1912 Da corresponding to only 7 monomeric units in MALDI-TOF spectrum. (Due to insolubility in DMF, GPC analysis was not performed.)

Polyamidation of (5-methoxy-1,3-phenylene)dimethanol, 1,4-phenylenedimethanamine using 1 mol % catalyst 1 afforded compound 3m (Table 19, entry 13) in 76% yield, with the mass obtained at 4450 Da by MALDI-TOF, corresponding to 15 monomer units. The GPC analysis of 3m showed a molecular weight Mn=5.3 kDa. Similarly, the reaction of (5-(hexyloxy)-1,3-phenylene)dimethanol and 1,3-phenylenedimethanamine gave 88% of the polyamide 3n (Table 19, entry 14). The number average molecular weight Mn of 3n was 11.3 kDa based on GPC analysis. Reaction of (5-(hexyloxy)-1,3-phenylene)dimethanol and 1,4-phenylenedimethanamine gave 77% of the polyamide 3o (Table 15, entry 15) with a mass of 3052 Da corresponding to 8 monomers based on the MALDI-TOF spectrum.

Thus, a variety of polyamides have been synthesized having different spacers in good yield. The synthesis of polyamides using non-activated/non-ether linked substrates was demonstrated. The synthesized polyamides were characterized by spectroscopic techniques. The molecular weight was determined by $^1$H NMR and GPC analysis. The heteroaromatic polyamide 3g gave the highest number average molecular weight compared to the corresponding aliphatic and aromatic derived polyamides (3a and 3d respectively). MALDI-TOF spectra of insoluble polyamides was also obtained. The results are summarized in Table 19.

TABLE 19

Catalytic polyamidation using diols and diamines.[a]

| Entry | Diols | Diamines | Polyamides | Isolated Yield (%) | Highest molecular weight by MALDI-TOF (Da) | Mn (10$^3$) | PDI |
|---|---|---|---|---|---|---|---|
| 1 | HO-(CH$_2$)$_4$-OH | H$_2$N-(CH$_2$)$_4$-NH$_2$ | 3a | 82 | 4195 | 16.6[b] | — |
| 2 | HO-(CH$_2$)$_8$-OH | H$_2$N-(CH$_2$)$_4$-NH$_2$ | 3b | 88 | 5000 | 10.3[b] | — |
| 3 | 1,3-bis(hydroxymethyl)benzene | H$_2$N-(CH$_2$)$_4$-NH$_2$ | 3c | 82 | 5932 | — | — |
| 4 | 5-methoxy-1,3-bis(hydroxymethyl)benzene | H$_2$N-(CH$_2$)$_4$-NH$_2$ | 3d | 86 | 7199 | 18.7[c] | 2.08 |
| 5 | 1,4-bis(hydroxymethyl)benzene | H$_2$N-(CH$_2$)$_4$-NH$_2$ | 3e | 80 | 2322 | — | — |

TABLE 19-continued
Catalytic polyamidation using diols and diamines.[a]
| Entry | Diols | Diamines | Polyamides | Isolated Yield (%) | Highest molecular weight by MALDI-TOF (Da) | Mn (10³) | PDI |
|---|---|---|---|---|---|---|---|
| 6 | 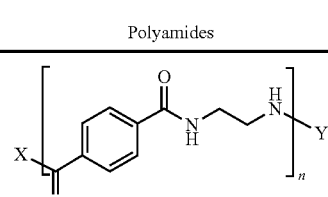 | 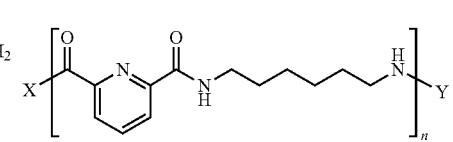 | 3f | 63 | 1849 | — | — |
| 7 | | | 3g | 74 | 4583 | 26.9[c] | 1.98 |
| 8 | | | 3h | 86 | 3861 | — | — |
| 9 | | | 3i | 84 | 3734 | — | — |
| 10 | | | 3j | 78 | 1467 | — | — |
| 11 | | | 3k | 80 | 5200 | — | — |
| 12 | | | 3l | 66 | 1912 | — | — |
| 13 | | | 3m | 76 | 4450 | 5.3[c] | 3.20 |

TABLE 19-continued

Catalytic polyamidation using diols and diamines.[a]

| Entry | Diols | Diamines | Polyamides | Isolated Yield (%) | Highest molecular weight by MALDI-TOF (Da) | Mn (10³) | PDI |
|---|---|---|---|---|---|---|---|
| 14 | HO–⟨⟩–OH, OCH₃ | H₂N–⟨⟩–NH₂ | 3n | 88 | — | 11.3[c] | 2.18 |
| 15 | HO–⟨⟩–OH, Ohexyl | H₂N–⟨⟩–NH₂ | 3o | 77 | 3052 | 5.4[c] | 2.51 |
| 16[d] | HO–(CH₂)₄–OH | H₂N–(CH₂)₄–NH₂ | 3a | 84 | 4951 | — | — |

[a]Complex 1 (0.01 mmol), diol (1 mmol), diamine (1 mmol) and 1,4-dioxane (2 mL) were refluxed at an oil bath temperature of 135° C. in a Schlenk tube under Argon for 3 days.
[b]Mn was calculated from ¹H NMR
[c]Mn was obtained from GPC analysis
[d]No solvent was used. Catalyzed by complex 3.

Figure 6:
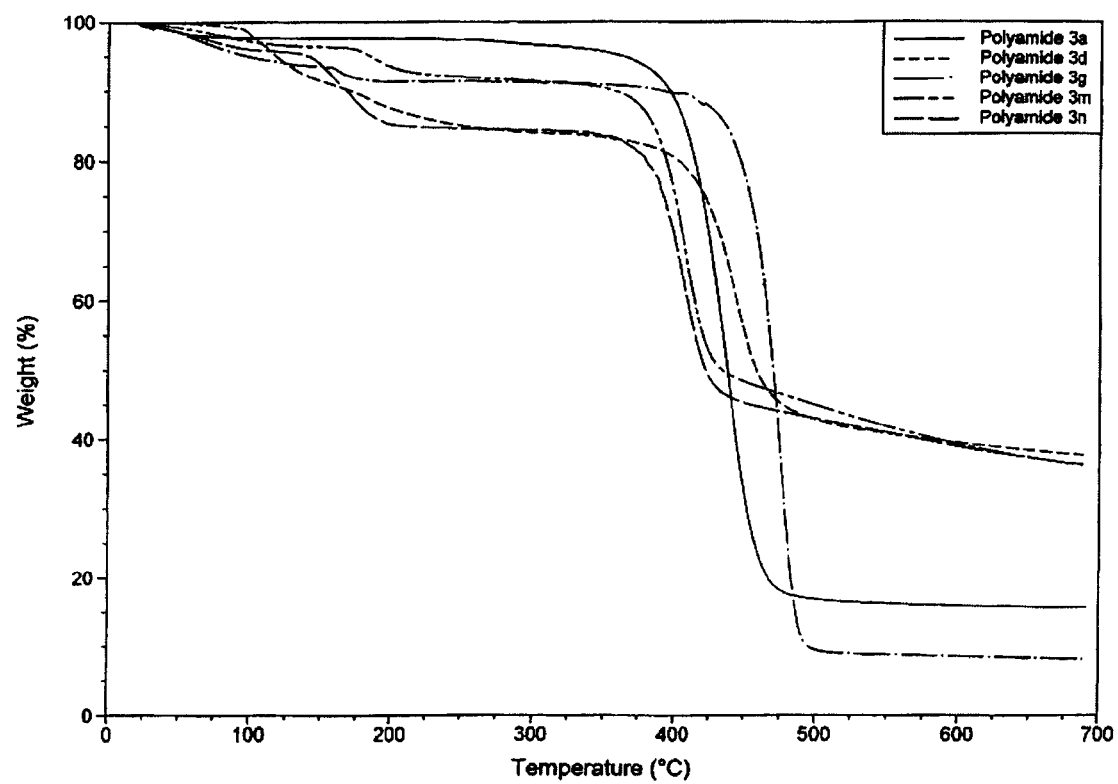
FIG. 6: TGA of polyamides 3.

Thermogravimetric analyses (TGA) of the synthesized polyamides were performed. Weight losses of 30% and 50% occurred at similar temperatures and were not significantly dependent on polymer structure (FIG. 6, Table 20). However, the aliphatic polyamide 3a was less thermally stable and exhibited 83% weight loss at 495° C., while the arene-based polyamides 3d, m, n (except 3g) exhibited 62-70% weight loss at 680° C. (Table 20). The pyridine-based polyamide 3g was less stable, and exhibited 92% weight loss at 520° C.

TABLE 20

Thermal studies of polyamides 3 at various temperatures by TGA.

| Polyamides | Mn (10³¹) | T (° C. at 5% weight loss) | T (° C. at 10% weight loss) | T (° C. at 30% weight loss) | T (° C. at 50% weight loss) | T (° C. at 70% weight loss) |
|---|---|---|---|---|---|---|
| 3a | 16.6 | 360 | 395 | 425 | 437 | 451 (70%) 495 (83%) |

TABLE 20-continued

Thermal studies of polyamides 3 at various temperatures by TGA.

| Polyamides | Mn (10³¹)) | T (° C. at 5% weight loss) | T (° C. at 10% weight loss) | T (° C. at 30% weight loss) | T (° C. at 50% weight loss) | T (° C. at 70% weight loss) |
|---|---|---|---|---|---|---|
| 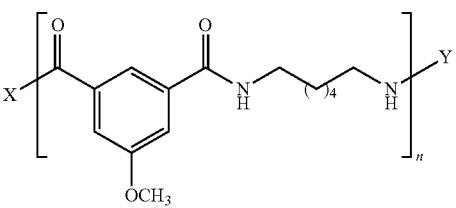 3d | 18.7 | 120 | 170 | 430 | 458 | 680 (62%) |
| 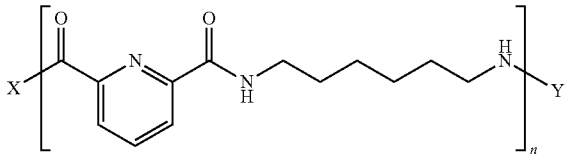 3g | 26.9 | 100 | 380 | 458 | 470 | 478 (70%) 520 (92%) |
| 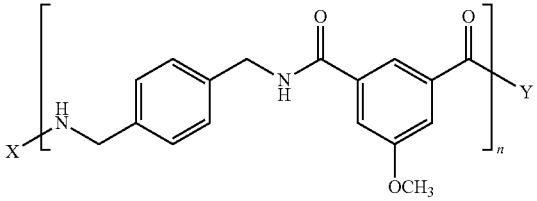 3m | 5.3 | 180 | 350 | 402 | 430 | 680 (64%) |
| 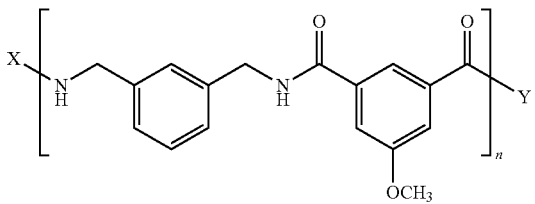 3n | 11.3 | 140 | 170 | 400 | 420 | 680 (64%) |

Polymerization with Catalyst 3:

Synthesis of Nylon-6,6 by Catalytic Method Under Neat Condition:

Complex 3 (0.01 mmol), 1,6-hexanediol (5 mmol), and 1,6-hexanediamine (5 mmol) were taken in a Schlenk flask under an atmosphere of purified nitrogen in a glove box. The flask was equipped with a condenser and gradually heated up to 135° C. (bath temperature) and continued the heating at the same temperature with stirring in an open system under argon for 14 hrs. During the heating effervescence was observed and the viscous liquid became solid. After cooling to room temperature, the solid thus obtained (low molecular weight oligomer; m.p=215.9° C. (by TGA)) was again heated up to 190° C. using sand bath for about an hour in an open system under argon. The resulting solid was washed with THF, water, ethanol and finally with hexane (in order to remove other impurities) and dried under vacuum for overnight.

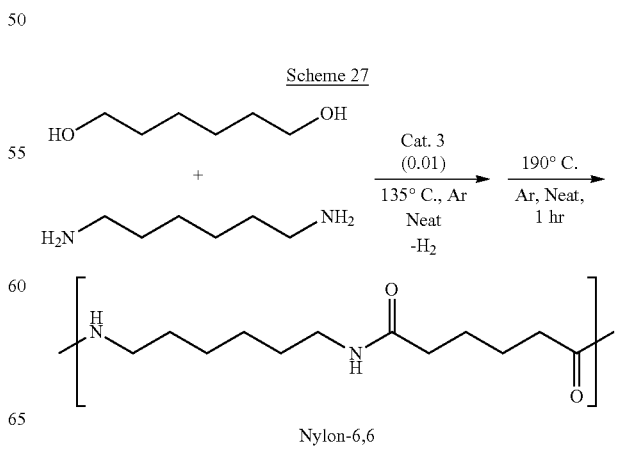

Scheme 27

DSC:

| Temperature (° C.) | Weight loss (in %) |
|---|---|
| 100 | 2.70 |
| 200 | 3.5 |
| 300 | 5.7 |
| 350 | 8.47 |
| 400 | 22.2 |
| 450 | 62.2 |
| 500 | 64.7 |
| 550 | 65.5 |
| 600 | 66.0 |

TGA: m.p 251.9° C. (regenerated with the same melting point after 4 cycles with freezing point of 216.1° C.).

MOLDI-TOF: (matrix=DHB (2,5-dihydroxybenzoicacid), solvent=trifluoroethanol:$CH_2Cl_2$) up to 4800 Da.

In conclusion, polyamidation based on coupling of non-activated diols and diamines, with extrusion of $H_2$, catalyzed by complexes 1 and 3 was developed. Guan et al have also reported the utilization of the amidation reaction catalyzed by complex 1 for the preparation of other polyamides, bearing ether-functionalized spacers. The polyamidation reaction proceeds under neutral conditions, with liberation of molecular hydrogen and with no preactivation of the substrate being required. The reaction can be applied to a variety of diols and diamines for the synthesis of functional polyamides. The number average molecular weight of the polymers obtained in our work was measured by $^1$H NMR, MALDI-TOF and, in case of the DMF-soluble polymers, by GPC analysis. Mean molecular weights up to 26.9 kDa were obtained, with polydispersities in the range of PDI=1.98-3.2. The variation in chain lengths for different substrate combinations is probably influenced by the different solubilities of the polymers. The insoluble polyamides were characterised spectroscpoically and by MALDI-TOF. It was observed that molecular weights determined by GPC were significantly higher than those obtained by MALDI-TOF. This is another example of the MALDI-TOF method favoring lower molecular weights in case of PDI>1.2 The thermal properties of the polyamides with different spacers were studied and it was found that aliphatic/pyridinic spacer-based polyamides are less stable at high temperature as compared with aromatic derived polyamides. Polyamidation in absence of solvent was also demonstrated. This simple, environmentally benign and general polymerization reaction provides a new approach to the important area of polyamide synthesis.

General Procedure for the Catalytic Direct Polyamidation of Diols with Diamines Catalyzed by Complex 1:

Complex 1 (0.01 mmol), diol (1 mmol), amine (1 mmol), and 1,4-dioxane (2 mL) were added to schlenk flask under an atmosphere of purified nitrogen in a glove box. The flask was equipped with a condenser and the solution was refluxed with stirring in an open system under argon flow for 3 days. During the course of the reaction, a white colored solid separated out for 24 hrs. The reflux was continued for 3 days. After cooling to room temperature, the solid obtained was filtered and washed successively with methanol and dichloromethane, or with THF:ethylacetate (1:1), dichloromethane and 20% methanol in water to give the product polyamide. T. The solid obtained was dried under vacuum at 80° C. for 8-12 hrs. The products were analyzed by NMR, IR and MALDI TOF.

Spectral Data for Polyamides:
Polyamide 3a:

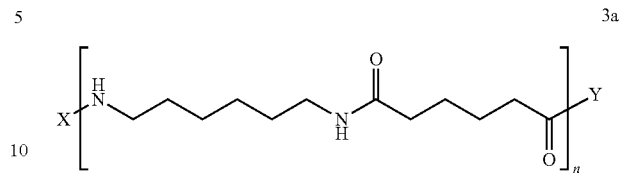

3a

IR (KBr pellet): 3304, 2935, 2859, 1633, 1536, 1474, 1276 $cm^{-1}$; $^1$H NMR (TFA-d): 1.08 (broad s, 4H), 1.34 (broad s, 4H), 1.52 (broad s, 4H), 2.39 (broad s, 4H), 3.17 (broad s, 4H); $^{13}C\{^1H\}$NMR (TFA-d): 26.8, 27.8, 29.5, 35.0, 44.5, 180.4.

MALDI-TOF (matrix: HBA (2,5-dihydroxybenzoic acid), solvent acetonitrile: TFA): m/z=569 to 4195 Da. The spectrum of polyamide 3a shows a series of peaks at 569 (3aa+$H^+$ (n=2)), 795 (3aa+$H^+$ (n=3)), 909 (3ab+$H^+$(n=3)), 1022 (3c (n=4)), 1135 (3ab+$H^+$ (n=4)), 1247 (3aa+$H^+$ (n=5)), 1361 (3ab+$H^+$ (n=5)), 1474 (3ac(n=6)), 1588 (3ab+2$H^+$ (n=6)), 1700 (3ac (n=7)), 1814 (3ab+2$H^+$ (n=7)), 1926 (3ac (n=8)), 2041 (3ab+3$H^+$ (n=8)), 2153 (3ac+$H^+$ (n=9)), 2266 (3ab+2$H^+$ (n=9)), 2379 (3ac+$H^+$ (n=10)), 2494 (3ab+4$H^+$ (n=10)), 2606 (3ac+2$H^+$ (n=11)), 2720 (3ab+4$H^+$ (n=11)), 2832 (3ac+2$H^+$ (n=12)), 2947 (3ab+5$H^+$ (n=12)), 3058 (3ac+2$H^+$ (n=13)), 3170 (3ab+$H^+$ (n=13)), 3288 (3ac+6$H^+$ (n=14)), 3402 (3ab+8$H^+$ (n=14)), 3515 (3ac+7$H^+$ (n=15)), 3625, 3739 (3ac+5$H^+$ (n=16)), 3840, 3853, 3966 (3ac+5$H^+$ (n=17)), 4079 (3ab+6$H^+$ (n=13)), 4195 (3ac+9$H^+$ (n=18))).

Polyamide 3b:

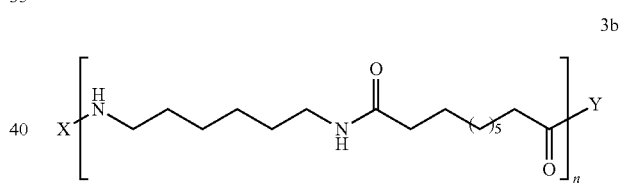

3b

IR (KBr pellet): 3306, 2933, 2854, 1637, 1540, 1437, 1383, 1239 $cm^{-1}$; $^1$H NMR (TFA-d): 1.28 (broad s, 12H), 1.63 (broad s, 8H), 2.61 (broad s, 4H), 3.46 (broad s, 4H); $^{13}C\{^1H\}$NMR (TFA-d): 27.6, 29.3, 30.4, 35.5, 44.7, 181.6. MALDI-TOF (matrix: HBA (2,5-dihydroxybenzoic acid)+NaI, solvent dichloromethane: TFA): m/z=1258 to 4965 Da.

Polyamide 3c:

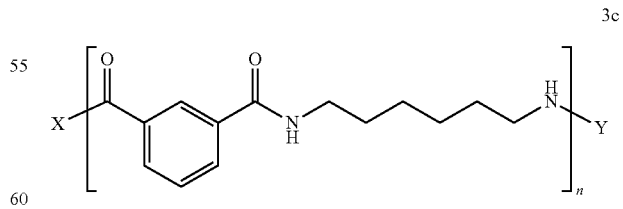

3c

IR (KBr pellet): 3297, 2935, 2857, 1631, 1532, 1274 $cm^{-1}$; $^1$H NMR (DMSO-$d_6$): 1.32 (broad s, 4H, $CH_2$), 1.51 (broad s, 4H, $CH_2$), 3.23-3.32 (m, 4H, $NCH_2$), 7.50 (t, 1H, =CH), 7.91 (d, 2H, =CH), 8.26 (s, 1H, =CH), 8.54 (broad s, 2H, NH). $^{13}C\{^1H\}$NMR (DMSO-$d_6$): 26.2, 29.1, 39.2, 126.1, 128.2, 129.5, 134.9, 165.8. MALDI-TOF (matrix: 2,5-dihydroxybenzoic acid, solvent acetonitrile:TFA): m/z=700 to 5932 Da. The following peaks were observed: 5932 (3c (n=23)+24), 5918 (3c (n=23)+10), 5685 (3c (n=22)+23), 5671 (3c (n=22)+9), 5439 (3c (n=21)+23), 5425 (3c (n=21)+9), 5192 (3c (n=20)+22), 5178 (3c (n=20)+8), 4946 (3c (n=19)+22), 4932 (3c (n=19)+8), 4699 (3c (n=18)+21), 4685 (3c (n=18)+7), 4453 (3c (n=17)+21), 4439 (3c (n=17)+7), 4207 (3c (n=16)+21), 4193 (3c (n=16)+7), 3961 (3c (n=15)+21), 3947 (3c (n=15)+7), 3714 (3c (n=14)+20), 3700 (3c (n=14)+6), 3468 (3c (n=13)+20), 3454 (3c (n=13)+6), 3219 (3c (n=12)+17), 3205 (3c (n=12)+3), 2973 (3c (n=11)+17), 2959 (3c (n=11)+3), 2727 (3c (n=10)+17), 2713 (3c (n=10)+3), 2481 (3c (n=9)+17), 2467 (3c (n=9)+3), 2234 (3c (n=8)+16), 2220 (3c (n=8)+2), 1988 (3c (n=7)+16), 1974 (3c (n=7)+2), 1742 (3c (n=6)+16), 1728 (3c (n=6)+2), 1496 (3c (n=5)+16), 1482 (3c (n=5)+2). The excess mass units are due to the protonation of the amine functionality in TFA.

Polyamide 3d:

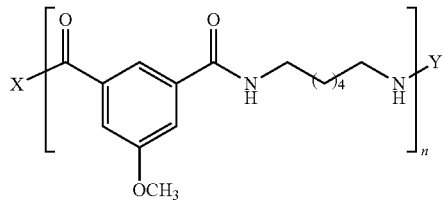

$^1$H NMR (DMSO-d$_6$): 1.32 (broad s, 4H, CH$_2$), 1.51 (broad s, 4H, CH$_2$), 3.15 (s, 2H, NCH$_2$), 3.38 (broad s, 2H, NCH$_2$), 3.82 (s, 3H, OCH$_3$), 7.48 (s, 2H, =CH), 7.88 (s, 1H, =CH), 8.53 (broad s, 2H, NH); $^{13}$C{$^1$H}NMR (DMSO-d$_6$): 26.3, 29.1, 48.6, 55.6, 66.4, 115.0, 119.1, 136.3, 159.1, 165.6;

GPC (0.1% LiBr in DMF): Mn=18.7×10$^3$ g/mol, Mw=39.1×10$^3$ g/mol

MALDI-TOF (matrix: 2,5-dihydroxybenzoic acid+NaI, solvent dichloromethane:TFA): m/z=1116 to 7199 Da. The MALDI-TOF exhibited a series of oligomeric peaks at 1116 (3d (n=4)+8H$^+$, NH$_2$/OH), 1386 (3d (n=5)+2H$^+$, NH$_2$/OH), 1661 (3d (n=6)+H$^+$, NH$_2$/OH), 1935 (3c (n=7)+3H$^+$, cyclic), 2210 (3d (n=8)+2H$^+$, cyclic), 2484 (3d (n=9), cyclic), 2762 (3d (n=10)+2H$^+$, cyclic), 3034, 3309, 3582, 3861, 4144 (3d (n=15), NH$_2$/OH), 4410, 4682, 4974 (3d (n=18)+2H$^+$, NH$_2$/OH), 5254 (3d (n=19)+6H$^+$, NH$_2$/OH), 5526 (3d (n=20)+2H$^+$, NH$_2$/OH), 6102 (3d (n=22)+Na+3H$^+$, NH$_2$/OH), 6351 (3d (n=23)+3, cyclic), 6641 (3d (n=24)+13, NH$_2$/OH), 6904 (3d (n=25), NH$_2$/OH) and 7199 (3d (n=26)+23, cyclic).

Polyamide 3e:

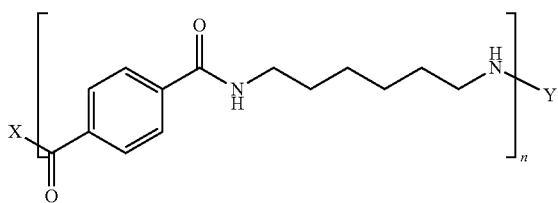

IR (KBr pellet): 3312, 2936, 2857, 1626, 1540, 1498, 1287 cm$^{-1}$. $^1$H NMR (DMSO-d$_6$): 1.29-1.51 (m, 8H), 3.23 (broad s, 4H), 4.52 (s), 5.32 (broad s), 7.36 (d), 7.78 (d), 7.87 (s), 8.38 (t), 8.54 (broad s).

MALDI-TOF (matrix=DHB, solvent acetonitrile: TFA): m/z=743 to 2322 Da. The oligomeric peaks are 743 (3e (n=3)+H$^+$), 989 (3e (n=4)+H$^+$), 1235 (3e (n=5)+H$^+$), 1482 (3e (n=6)+2H$^+$), 1728 (3e (n=7)+H$^+$), 1973 (3e (n=8)+H$^+$), 2221 (3e (n=9)+3H$^+$), 2464 (3e (n=10)+3H$^+$).

Polyamide 3f:

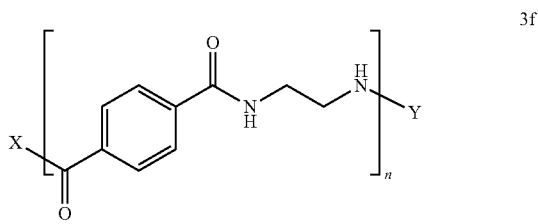

$^1$H NMR (DMSO-d$_6$): 2.67 (t), 3.44 (broad s), 4.53 (s), 7.37 (d), 7.80 (d), 7.90 (s), 8.56 (broad s), 8.71 (broad s). MALDI-TOF (matrix: 2,5-dihydroxybenzoic acid, solvent: acetonitrile: TFA): m/z=765 to 1835 Da. Oligomeric peaks were observed at 765 (3f(n=4)+H$^+$), 955 (3f(n=5)+H$^+$), 1145 (3f (n=6)+H$^+$), 1335 (3f (n=7)+H$^+$), 1525 (3f (n=8)+H$^+$), 1715 (3f(n=9)+H$^+$), 1849 (3f(n=9)+H$^+$, ending with OH/OH groups).

Polyamide 3g:

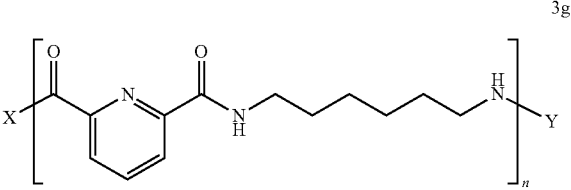

IR (KBr pellet): 3325, 2932, 2859, 1662, 1538, 1445, 1243 cm$^{-1}$; $^1$H NMR (DMSO-d$_6$): 1.27 (broad m, 4H, CH$_2$), 1.50 (broad m, 4H, CH$_2$), 3.29 (broad s, 4H, NCH$_2$), 8.13 (m, 3H, =CH), 9.28 (broad s); $^{13}$C NMR (DMSO-d$_6$): 13.9, 22.1, 26.1, 29.4, 30.9, 40.1, 124.1, 139.3, 148.8, 163;

GPC (0.1% LiBr in DMF): Mn=26.9×10$^3$ g/mol, Mw=53.3×10$^3$ g/mol

MALDI-TOF (matrix: 2,5-dihydroxybenzoic acid, solvent acetonitrile: TFA): m/z=610 to 4583 Da. The spectrum exhibits a series of oligomeric peaks at 610 (3g (n=2), NH$_2$/NH$_2$), 742 (3g (n=3)+H$^+$, cyclic), 907 (3g (n=3)+Na$^+$+3H$^+$, OH/OH), 989 (3g (n=4)+H$^+$, cyclic), 1203, 1236 (3g (n=5)+H$^+$, cyclic), 1484 (3g (n=6)+2H$^+$, cyclic), 1500, 1732 (3g (n=7)+3H$^+$, cyclic), 1781, 1796, 1914, 1978 (3g (n=8)+2H$^+$, cyclic), 2063, 2079, 2092, 2210, 2226 (3g (n=9)+3H$^+$, cyclic), 2242, 2360, 2374, 2389, 2473 (3g (n=10)+3H$^+$, cyclic), 2492, 2507, 2657, 2671, 2685, 2789, 2803, 2836, 2953, 2968, 2981, 3085, 3100, 3132, 3250, 3264, 3278, 3396 (3g (n=13)+3Na$^+$, NH$_2$/NH$_2$), 3427 (3g (n=13)+KK, OK/OH), 3561, 3576 (3g (n=14)+2H$^+$, NH$_2$/NH$_2$), 3679, 3709 (3g (n=15)+3H$^+$, cyclic), 3726, 3844 (3g (n=15)+Na$^+$, NH$_2$/NH$_2$), 3975 (3g (n=16)+Na$^+$, cyclic), 4449 (3g (n=18)+3H$^+$, cyclic), 4569 (3g (n=18)+7H$^+$, NH$_2$/NH$_2$).

Polyamide 3h:

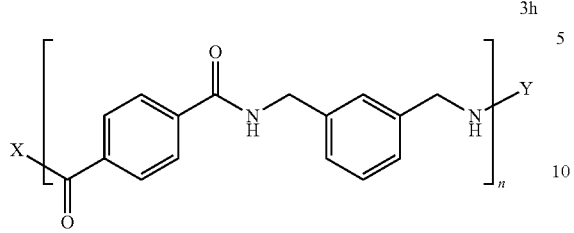

IR (KBr pellet): 3285, 2921, 1638, 1540, 1439, 1318 cm$^{-1}$. $^1$H NMR (DMSO-d$_6$): 3.68 (s), 4.47 (broad s), 7.21-7.37 (broad m), 7.92-7.94 (m), 9.15 (broad s); $^{13}$C{$^1$H}NMR (DMSO-d$_6$): 42.7, 45.5, 62.6, 125.2, 125.8, 126.1, 127.2, 136.6, 139.6, 165.6; MALDI-TOF (matrix: 2,5-dihydroxybenzoic acid, solvent acetonitrile: TFA): m/z=668 to 3861 Da.

Polyamide 3i:

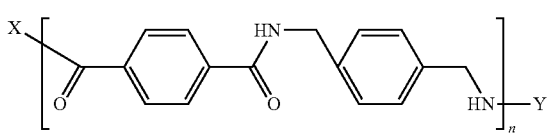

IR (KBr pellet): 3346, 3056, 2923, 1640, 1540, 1496, 1317 cm$^{-1}$; $^1$H NMR (DMSO-d$_6$): 3.59 (s), 4.43 (broad m), 7.23-7.27 (broad m), 7.37 (d), 7.83 (d), 7.94 (m), 9.13 (broad s); $^{13}$C{$^1$H}NMR (DMSO-d$_6$): 42.4, 45.1, 62.4, 126.0, 127.1, 132.7, 137.5, 137.9, 138.0, 138.3, 142.1, 145.9, 165.5, 166.1; MALDI-TOF (matrix: 2,5-dihydroxybenzoic acid, solvent ACETONITRILE: TFA): m/z=400 to 3734 Da Polyamide 3j:

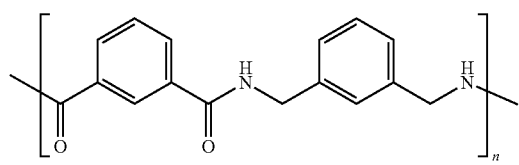

IR (KBr pellet): 3290, 3061, 2920, 1640, 1533, 1478, 1272 cm$^{-1}$; $^1$H NMR (DMSO-d$_6$): 4.45-4.47 (m, 4H), 7.17-7.28 (m, 4H), 7.50 (t, 1H), 7.97 (d, 2H), 8.36 (s, 1H), 9.13 (broad m, 2H); $^{13}$C{$^1$H}NMR (DMSO-d$_6$): 42.8, 66.4, 125.6, 126.5, 126.7, 128.5, 128.7, 129.9, 134.6, 139.7, 165.9.

GPC (0.1% LiBr in DMF): Mn=1.4×10$^3$ g/mol, Mw=5.01×10$^3$ g/mol

MALDI-TOF (matrix: 2,5-dihydroxybenzoic acid, solvent acetonitrile: TFA): m/z=500 to 1467 Da

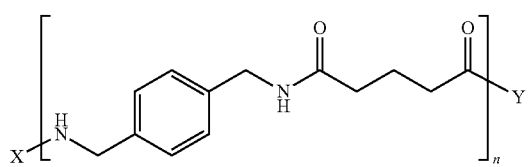

Polyamide 3k:
IR (KBr pellet): 3245, 3069, 2964, 2944, 1629, 1556, 1424, 1262 cm$^{-1}$; $^1$H NMR (DMSO-d$_6$): 1.35-1.79 (m, 2H), 2.07-2.15 (m, 4H), 4.19-4.21 (broad m, 4H), 7.16 (broad s, 4H), 8.27 (broad m); $^{13}$C{$^1$H}NMR (DMSO-d$_6$): 21.3, 21.9, 32.9, 35.0, 41.7, 46.8, 61.1, 127.0, 127.3, 138.1, 171.6. MALDI-TOF (matrix=DHB, solvent acetonitrile: TFA): m/z=500 to 5200 Da Polyamide 3l:

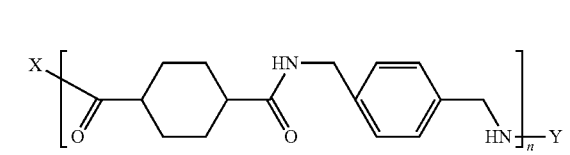

IR (KBr pellet): 3282, 3060, 2934, 2860, 1633, 1551, 1443, 1386 cm$^{-1}$; $^1$H NMR (TFA-d): 7.26 (d), 7.19 (d), 7.11 (broad s), 4.44 (broad s), 4.18 (s), 3.83 (s), 2.56 (broad s), 2.00 (broad s), 0.92-1.82 (m); $^{13}$C{$^1$H}NMR (TFA-d): 29.3, 45.2, 46.9, 130.6, 131.0, 131.9, 139.2, 182.7.

MALDI-TOF (matrix=DHB, solvent acetonitrile: TFA): m/z=400 to 1912 Da

Polyamide 3m:

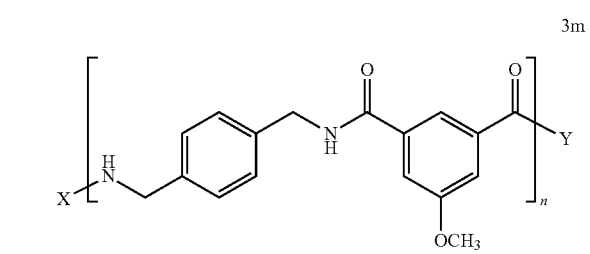

IR (KBr pellet): 3294, 3063, 2935, 1642, 1593, 1536, 1423, 1283, 1061 cm$^{-1}$. $^1$H NMR (DMSO-d$_6$): 3.56 (s), 3.81 (s), 4.42 (broad s), 7.24 (broad s), 7.54 (s), 7.96 (s), 9.11 (broad s); $^{13}$C{$^1$H}NMR (DMSO-d$_6$): 42.5, 55.6, 66.3, 115.3, 118.7, 127.3, 135.9, 138.0, 159.1, 165.5, 165.8;

GPC (0.1% LiBr in DMF): Mn=5.39×10$^3$ g/mol, Mw=17.3737×10$^3$ g/mol

MALDI-TOF (matrix: 2,5-dihydroxybenzoic acid, solvent acetonitrile: TFA): m/z=600 to 4450 Da Polyamide 3n:

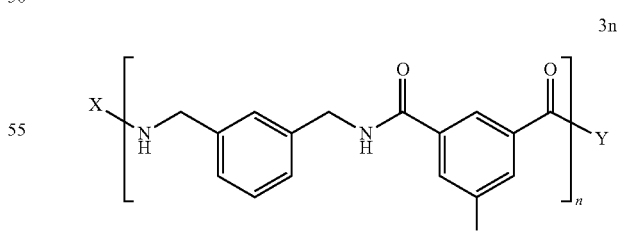

$^1$H NMR (TFA-D): 3.74 (s, 2H, NCH$_2$), 3.88 (s, 2H, NCH$_2$), 4.60 (s, 3H, OCH$_3$), 7.19-7.23 (m, 4H, Arom-H), 7.44 (s, 2H, Arom-H), 7.77 (s, 1H, Arom-H); $^{13}$C{$^1$H}NMR (TFA-D): 47.2, 57.6, 68.7, 119.7, 121.1, 129.0, 129.8, 131.9, 136.3, 138.5, 162.3, 173.0; GPC (0.1% LiBr in DMF): Mn=11.3×10$^3$ g/mol, Mw=24.71×10$^3$ g/mol Polyamide 3o:

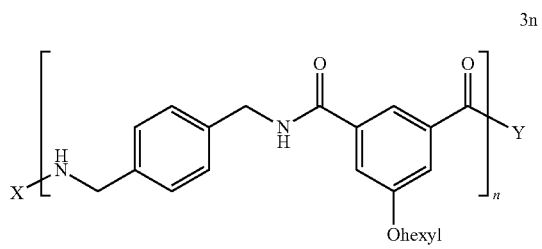

IR (KBr pellet): 3325, 3079, 2929, 2869, 1644, 1592, 1532, 1434, 1333, 1062 cm$^{-1}$; $^1$H NMR (TFA-d): 7.78 (s, 1H), 7.46 (s, 2H), 7.21 (s, 4H), 4.56 (broad s, 4H), 3.94 (broad s, 2H), 1.65 (broad s, 2H), 1.26 (broad s, 2H), 1.15 (broad s, 4H), 0.70 (broad s, 3H); $^{13}$C{$^1$H}NMR (TFA-d): 14.5, 24.1, 27.1, 30.5, 33.2, 47.0, 72.1, 120.4, 121.0, 130.5, 136.0, 137.8, 162.1, 173.0.

GPC (0.1% LiBr in DMF): Mn=5.4×10$^3$ g/mol, Mw=13.76×10$^3$ g/mol

MALDI-TOF (matrix=DHB, solvent acetonitrile: TFA): up to m/z=3052 Da

Example 6

Dehydrogenation of L-Alaminol to Form Poly(Alanine) Catalyzed by Ruthenium Complexes 1 or 3

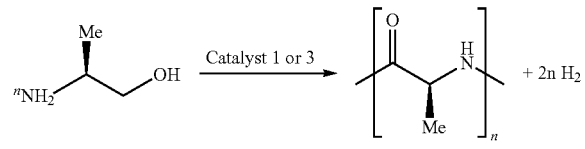

Scheme 28

Complex 3 (0.01 mmol), L-alaninol (1 mmol), and 1,4-dioxane (2 mL) were taken in a Schlenk flask under an atmosphere of purified nitrogen in a glove box. The flask was taken out the glove box, and equipped with a condenser. The solution was refluxed with stirring in an open system under argon for 48 h. After cooling to room temperature, the solvent was concentrated (~0.5 mL) under reduced vacuum followed by addition of CH$_2$Cl$_2$ (in order to remove the unreacted starting material). The white solid precipitated out from the solution at ~5° C. (after 30 min) and was collected by simple filtration and washed with toluene and dried under vacuum at 80° C. for about 14 h to yield 77% of polypeptide.

Using Complex 1 under the same procedure, 72% yield was obtained.

Poly(alanine):

mp: 190-194° C. (decompose) $^1$H NMR (400 MHz, DMSO-d$_6$): 0.93 (broad s, 3H, CH$_3$), 4.22-4.26 (m, 1H, NCH), 8.00 (1H, CONH). $^{13}$C{$^1$H}NMR (300 MHz, TFA-d$_4$): 20.0 (CH$_3$), 21.7 (CH$_3$), 53.1 (NCH), 53.4 (NCH), 174.9 (C=O).

MS (ES): 165.3 (100%, cycloala-ala+Na, $^+$), 240 (18%, M (n=1)+Na), 311 (65%, M (n=2)+Na), 382 (32%, M (n=3)+Na)), 453 (10%, M (n=4)+Na)), 524 (6%, M (n=5)+Na)).

Maldi-T of: 754 ((M (n=8)+K$^+$H)), 903 ((M (n=10)+2Na+H)), 1001 ((M (n=12)+3H)), 1150 ((M (n=14)+10H)), 1248, 1396 ((M (n=17)+K+3H)), 1494 ((M (cyclic, n=21)+3H), 1644 ((M (n=23)+7H)). [α]=−105° (50 mg/5 mL, Acetic Acid)

Example 7

Coupling of Alcohols with water to form Acids with Liberation of H$_2$

Scheme 29

TABLE 21

Direct Transformation of Alcohols to Acids Using Water

| Entry | Alcohols | Acids | Yield (%) isolated |
|---|---|---|---|
| 1 |  |  | 84 |
| 2 |  |  | 88 |
| 3 | 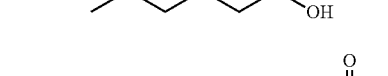 |  | 78 |
| 4 |  | | 73 |

TABLE 21-continued

Direct Transformation of Alcohols to Acids Using Water

| Entry | Alcohols | Acids | Yield (%) isolated |
|---|---|---|---|
| 5 | PhCH₂CH₂OH | PhCH₂COOH | 78 |
| 6 | cyclohexyl-CH₂OH | cyclohexyl-COOH | 80 |
| 7 | Ph-CH(CH₃)-CH₂-CH₂OH | Ph-CH(CH₃)-CH₂-COOH | 74 |
| 8 | CH₂=CH-CH₂-CH₂OH | CH₃CH₂CH₂COOH | 63 |
| 9 | PhCH₂OH | PhCOOH | 91 |
| 10 | 4-MeO-C₆H₄-CH₂OH | 4-MeO-C₆H₄-COOH | 89 |
| 11 | 2,4-(MeO)₂-C₆H₃-CH₂OH | 2,4-(MeO)₂-C₆H₃-COOH | 83 |

General Procedure for the Dehydrogenation of Alcohols to Acids Catalyzed by 3:

A mixture of an alcohol (10 mmol), degassed double distilled water (2 mL) and sodium hydroxide (11 mmol) were combined in a Schlenk-flask under argon atmosphere. The biphasic mixture was degassed by purging with argon for 10 min. Complex 3 (0.02 mmol) was added and the reaction mixture was refluxed under a stream of argon. After 18 h water was added (10 mL), and the mixture was extracted with diethyl ether (2×10 mL). The aqueous phase was acidified with 5N HCl and extracted with ethyl acetate (5×20 mL). The combined extracts were washed with brine (25 mL), dried over Na₂SO₄, and evaporated under reduced pressure, affording the pure acid.

Example 8

General Experimental (Ruthenium Complex)

All experiments with metal complexes and phosphine ligands were carried out under an atmosphere of purified nitrogen in a Vacuum Atmospheres glove box equipped with a MO 40-2 inert gas purifier or using standard Schlenk techniques. All solvents were reagent grade or better. All non-deuterated solvents were refluxed over sodium/benzophenone ketyl and distilled under argon atmosphere. Deuterated solvents were used as received. All solvents were degassed with argon and kept in the glove box over 4 Å molecular sieves. Most of the chemicals used in catalysis reactions were purified according to standard procedure (or by vacuum distillation/sublimation). The 6-methyl-2,2'-bipyridine (BPy-Me) and 6-chloromethyl-2,2'-bipyridine (BPy-CH₂Cl) precursors (Schubert et al.; Smith et al.), and RuHCl(PPh₃)₃(CO) (Ahmad et al.) were prepared according to literature procedures. Thin layer chromatography (TLC) was performed on Merck 1.05554 aluminum sheets precoated with silica gel 60 F254 and the spots visualized with UV light at 254 nm or under iodine. Column chromatography purifications were performed by flash chromatography using Merck silica gel 60 (0.063-0.200 mm). $^1$H, $^{13}$C and $^{31}$P NMR spectra were recorded at 300, 75, and 122 MHz, respectively, using Bruker AMX-300 NMR spectrometers. $^1$H and $^{13}$C{$^1$H} NMR chemical shifts are reported in ppm downfield from tetramethylsilane. $^{31}$P NMR chemical shifts are reported in parts per million downfield from $H_3PO_4$ and referenced to an external 85% solution of phosphoric acid in $D_2O$. Abbreviations used in the NMR follow-up experiments: br, broad; s, singlet; d, doublet; t, triplet; q, quartet; m, multiplet. IR spectra were recorded on a Nicolet FT-IR spectrophotometer. Mass spectra were recorded on Micromass Platform LCZ 4000, using Electro Spray Ionization (ESI) mode. Elemental analysis were performed on Thermo Finnigan Italia S.p.A-FlashEA 1112 CHN Elemental Analyzer (manufactured by Thermo Finnigam Italia S.p.A).

Synthesis of Ligand 5:

6-methyl-2,2'-bipyridine (BPy-Me):

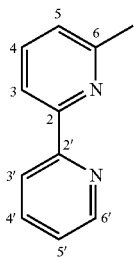

Prepared according to procedure described in *Org. Lett.* 2000, 3373 (Schubert et al.). NMR ($CDCl_3$): 2.61 (s, 3H, $CH_3$), 7.13 (d, 1H, $J_{HH}$=7.80 Hz, H-5), 7.26-7.27 (m, 1H, H-5'), 7.57 (t, 1H, $J_{HH}$=7.80 Hz, H-4), 7.74-7.79 (m, 1H, H-4'), 8.17 (d, 1H, $J_{HH}$=7.50 Hz, H-3), 8.40 (d, 1H, $J_{HH}$=8.10 Hz, H-3'), 8.64-8.67 (m, 1H, H-6').

6-chloromethyl-2,2'-bipyridine (BPy-$CH_2Cl$):

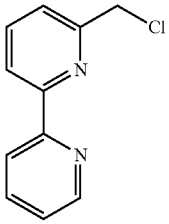

Prepared according to procedure described in *Org. Synth.* 2002, 78, 82 (Smith et al.). $^1$H NMR ($CDCl_3$): 4.75 (s, 2H, $CH_2$), 7.27-7.32 (m, 1H), 7.49 (d, 1H, $J_{HH}$=7.50 Hz), 7.77-7.86 (m, 2H), 8.33 (d, 1H, $J_{HH}$=7.80 Hz), 8.43 (d, 1H, $J_{HH}$=8.10 Hz), 8.66-8.68 (m, 1H).

6-di-tert-butylphosphinomethyl-2,2'-bipyridine (BPy-$^t$PNN) 5:

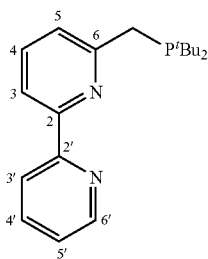

To an oven dried 50 mL pressure vessel equipped with magnetic stirring bar was added 6-chloromethyl-2,2'-bipyridine (BPy-$CH_2Cl$) (2.05 g, 10.00 mmol), di-tert-butyl phosphine (1.75 g, 12.00 mmol), and 30 mL MeOH in a nitrogen glove box. The flask was sealed and heated at 50° C. for 48 hrs with stirring outside the glove box. After cooling, it was reintroduced to the glove box, triethylamine (1.82 g, 18.00 mmol) was added and the reaction mixture was stirred at room temperature for 1 hr. The solvents were removed under reduced pressure to obtain a white solid. The residue was washed with ether (3×20 mL) and the ether filtered and was removed under reduced pressure to yield a white solid. It was recrystallized from MeOH at ca. −30° C. to yield 2.67 g (85%) of 6-di-tert-butylphosphinomethyl-2,2'-bipyridine (BPy-$^t$PNN).

Alternative method for the Preparation of BPy-$^t$PNN (5):

An oven-dried 500 mL three-necked round bottom flask equipped with an argon inlet, a stirring bar, dropping funnel and one rubber septum was cooled under a stream of argon. The flask was then charged with 6-methyl-2,2'-bipyridine (3.40 g, 20 mmol) in 80 mL dry ether. The solution was cooled to 0° C. and 13.4 mL of a 1.8 M solution of commercial lithium diisopropylamide (LDA) in heptane/THF/ethylbenzene (24 mmol) was added dropwise via syringe during 15 minutes. The resulting brown colored mixture was stirred for 1 hr at 0° C. and then cooled to −78° C. and a solution of di-tert-butylchlorophosphine (4.34 g, 24 mmol) in 30 mL dry ether was added dropwise (~30 min) to it. The stirring was continued for a further 1 hr at −78° C. and the mixture was allowed to slowly warm up to room temperature and stirred overnight. To this reaction mixture was added 40 mL of degassed water and the ether phase was separated under $N_2$ atmosphere. The aqueous phase was extracted with ether (2×50 mL). The combined ether solutions were dried over anhydrous $Na_2SO_4$, filtered under $N_2$ pressure, and the solvent was removed under vacuum to get brownish-white solid. This was purified by column chromatography in the nitrogen glove box (basic alumina; hexane:ether (10:1) as eluent) to yield 4.46 g (71%) of 6-di-tert-butylphosphinomethyl-2,2'-bipyridine (BPy-$^t$PNN) as a white solid.

$^{31}P\{^1\}$NMR ($CD_2Cl_2$): 37.57 (s). $^1$H NMR ($CD_2Cl_2$): 1.17 (d, $J_{PH}$=11.0 Hz, 18H, $P(C(CH_3)_3)_2$), 3.12 (d, $J_{PH}$=3.3 Hz, 2H, P—$CH_2$), 7.24 (ddd, $J_{HH}$=7.5 Hz, $J_{HH}$=4.8H, $J_{PH}$=1.2 Hz, 1H, H-5'), 7.40 (td, $J_{HH}$=7.8 Hz, $J_{PH}$=1.0H, 1H, H-5), 7.67 (t, $J_{HH}$=7.8 Hz, 1H, H-4), 7.76 (dt, $J_{HH}$=7.8 Hz, $J_{HH}$=1.8H, 1H, H-4'), 8.14 (br d, $J_{HH}$=7.8 Hz, 1H, H-3), 8.40 (td, $J_{HH}$=8.0 Hz, $J_{HH}$=1.0 Hz, 1H, H-3'), 8.62-8.64 (m, 1H, H-6'). $^{13}C\{^1H\}$NMR ($CDCl_3$): 29.61 (s, $P(C(C_aH_3)_3)$, 29.74 (s, $P(C(C_bH_3)_3)$), 31.77 (d, $J_{PC}$=24.0 Hz, $PCH_2$), 31.93 (d, $J_{PC}$=21.8, $P(C(CH_3)_3)_2$), 117.72 (s, C-3), 121.04 (s, C-3'), 123.38 (s, C-5'), 123.85 (d, $J_{PC}$=8.4 Hz, C-5), 136.75, (s, C-4'), 136.91 (s, C-4), 148.98 (s, C-6'), 154.97 (s, C-2), 156.49 (s, C-2'), 161.43 (d, $J_{PC}$=13.8, C-6). Assignment of signals was confirmed by DEPT 135, COSY, and HSQC. Anal. Calcd. for $C_{19}H_{27}N_2P$: C, 72.58; H, 8.66. Found: C, 72.75; H, 8.83.

Synthesis of Complexes 4 and 3:

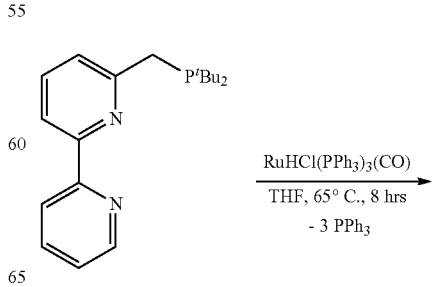

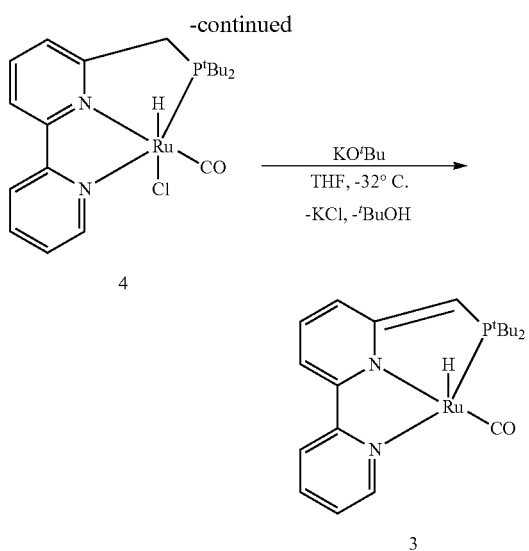

X-Ray Crystal Structure Determination of 4:

A crystal was mounted in a MiTeGen loop and flash frozen in a nitrogen stream at 120K. Data were collected on a Nonius Kappa CCD diffractometer mounted on a FR590 generator equipped with a sealed tube with MoKa radiation (λ=0.71073 Å) and a graphite monochromator. The structure was solved using direct methods with SHELXS-97 based on $F^2$.

Complex 4:

$C_{20}H_{28}N_2OPClRu$, Orange, prism, 0.16×0.16×0.12 mm$^3$, monoclinic, P2$_1$/c, a=8.1380 (2) Å, h=14.3161 (2) Å, c=17.5802 (3) Å, β=92.253 (1) deg., V=2046.59 (7) Å$^3$, Z=4, fw=479.93, $D_c$=1.558 Mg/m$^3$, μ=0.986 mm$^{-1}$. Full matrix least-squares of refinement based on $F^2$ gave an agreement factor R=0.0326 for data with I>2σ(I) and R=0.0435 for all data (4691 reflections) with a goodness-of-fit of 0.994. Idealized hydrogen atoms were placed and refined in the riding mode, with the exception of the hydride ligand H1-Ru, which was located in the difference map and refined independently.

Synthesis of [RuH(CO)(BPy-$^t$PNN*)] 3.

Synthesis of RuHCl(CO)(BPy-$^t$PNN) 4:

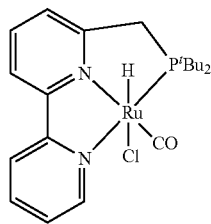

To an oven dried 25 mL pressure vessel equipped with magnetic stirring bar was added ligand, BPy-$^t$PNN (5) (157 mg, 0.52 mmol), RuHCl(CO)(PPh$_3$)$_3$ (476 mg, 0.5 mmol), and 12 mL dry THF in a nitrogen glove box. The flask was sealed and heated at 65° C. for 8 hrs with stirring outside the glove box, then cooled to room temperature to lead to reddish-brown solid. It was reintroduced to the glove box, and the solvent was decanted and the solid thus obtained was washed with ether (3×3 mL), then dried under vacuum to give pure complex 4 (212 mg, 88%).

$^{31}$P {$^1$H}NMR (CD$_2$Cl$_2$): 107.01 (s). $^1$H NMR (CD$_2$Cl$_2$): −15.26 (d, $^2J_{PH}$=24.6 Hz, 1H, Ru—H), 1.27 (d, $J_{PH}$=13.2 Hz, 9H, P(C(CH$_{a3}$)$_3$), 1.49 (d, $J_{PH}$=13.8 Hz, 9H, P(C(CH$_{b3}$)$_3$), AB system centered at 3.06 and 3.75 (ABq, $J_{HH}$=16.8 Hz and $J_{PH}$=10.2 Hz, 2H, PCH$_a$H$_h$), 7.44-7.46 (m, 1H, H-5'), 7.57 (d, $J_{HH}$=7.8 Hz, 1H, H-5), 7.83-7.90 (m, 2H, H-4 and H-4'), 7.97 (d, $J_{HH}$=8.1 Hz, 1H, H-3), 8.05 (d, $J_{HH}$=7.8 Hz, 1H, H-3'), 9.12-9.15 (br m, 1H, H-6'). $^{13}$C {$^1$H}NMR (CD$_2$Cl$_2$): 28.63 (d, $J_{PC}$=3.8 Hz, P(C(C$_a$H$_3$)$_3$), 29.79 (d, $J_{PC}$=4.5 Hz, P(C(C$_b$H$_3$)$_3$), 36.20 (d, $J_{PC}$=24.0 Hz, PGH$_2$), 37.21 (d, $J_{PC}$=15.0 Hz, P(C$_a$(CH$_3$)$_3$), 37.27 (d, $J_{PC}$=15.8 Hz, P(C$_h$(CH$_3$)$_3$), 119.39 (s, C-3), 121.31 (s, C-3'), 122.82 (d, $J_{PC}$=9.0 Hz, C-5), 126.11 (s, C-5'), 136.30, (s, C-4'), 137.26 (s, C-4), 153.19 (s, C-6'), 154.80 (s, C-2), 155.89 (s, C-2'), 161.72 (br d, $J_{PH}$=14 Hz, C-6), 207.37 (d, $J_{PC}$=15.0 Hz, Ru—CO). IR (KBr, pellet): 1990 (vRu—H), 1906 (vCO) cm$^{-1}$. Anal. Calcd. for $C_{20}H_{28}N_2OPClRu$: C, 50.05; H, 5.88. Found: C, 50.28; H, 6.01. MS (ESI, MeOH): 446 (100%, (M-Cl)$^+$). The crystal suitable for a single-crystal X-ray diffraction was obtained from CD$_2$Cl$_2$ (20 mg in 0.3 mL) at −32° C. after several days.

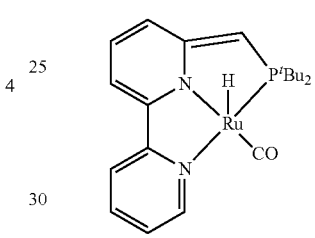

(a) To a suspension of complex 4 (48 mg, 0.1 mmol) in dry THF (5 ml) in a nitrogen glove box was added KO$^t$Bu (11.2 mg, 0.1 mmol) at ca.−32° C. and the mixture was stirred at −32° C. for 3 hrs and the solvent was removed under vacuum. The product was extracted using a benzene:pentane (3:7) mixture (3×5 mL) and passed through celite. The resulting solution was concentrated under vacuum to ca. 0.5 mL and 5 mL pentane was added to cause precipitation of a greenish-block solid, which was filtered and washed with pentane (3×2 mL), then dried under vacuum (42 mg, 94%).

(b) 9.6 mg. of RuHCl(CO)(BPy$^2$-$^t$PNN) 4 (0.02 mmol) were placed in to a J. Young NMR tube, dissolved in ~0.4 mL of $C_6D_6$ and 1 eq. of potassium bis(trimethylsilyl)amide (KHMDS, 4.0 mg) was added to generate dark-green/black complex 3. The resulting complex 3 exhibits a broad singlet at 92.70 in $^{31}$P{$^1$H}NMR, and the hydride ligand appears as broad doublet at −25.73 ppm ($^2J_{PH}$=23 Hz) in the $^1$HNMR spectrum.

$^{31}$P{$^1$H}NMR (THF-d; 202 MHz): 95.64 (s). $^1$H NMR (THF-d; 500 MHz): −20.93 (d, $^2J_{PH}$=25.0 Hz, 1H, Ru—H), 1.25 (d, $J_{PH}$=13.0 Hz, 9H, P(C(CH$_{a3}$)$_3$), 1.28 (d, $J_{PH}$ 12.5 Hz, 9H, P(C(CH$_{b3}$)$_3$), 3.36 (s, 1H, =CHP), 6.00 (d, 1H, H-3), 6.12 (d, $J_{HH}$=9.0 Hz, 1H, H-5), 6.37 (d, $J_{HH}$=8.0 Hz, 1H, H-4), 7.19 (t, $J_{HH}$=6.0 Hz, 1H, H-5'), 7.65-7.71 (m, 2H, H-3' and H-4'), 8.89-8.90 (br m, 1H, H-6'). $^{13}$C{$^1$H}NMR (THF-d; 125 MHz): 30.09 (d, $J_{PC}$=5.0 Hz, P(C(C$_a$H$_3$)$_3$), 30.19 (d, $J_{PC}$=3.8 Hz, P(C(C$_b$H$_3$)$_3$), 36.20 (d, $J_{PC}$=22.5 Hz, P(C$_a$(CH$_3$)$_3$), 37.45 (d, $J_{PC}$=27.5 Hz, P(C$_b$(CH$_3$)$_3$), 66.56 (d, $J_{PC}$=48.8 Hz, =CHP), 99.87 (s, C-3), 117.64 (d, $J_{PC}$=17.5 Hz, C-5), 121.47 (s, C-3'), 124.60, (s, C-5'), 131.81 (s, C-4), 136.92 (s, C-4'), 153.21 (s, C-6'), 155.06 (s, C-2), 161.55 (s, C-2'), 168.97 (d, $J_{PC}$=16.3 Hz, C-6), 208.1 (d, $J_{PC}$=13.8 Hz, Ru—CO). Assignment of signals was confirmed by DEPT 135, COSY, and HSQC. IR (KBr, pellet): 2017 (vRu—H), 1907 (vCO) cm$^{-1}$. Anal. Calcd. for $C_{20}H_{27}N_2OPRu$: C, 54.17; H, 6.14. Found: C, 54.32; H, 6.37. MS (ESI, $CH_3CN$): 445 (100%, (M+1)$^+$).

Synthesis of 6-di-iso-propylphosphinomethyl-2,2'-bipyridine (BPy-$^{iso}$(Pr)PNN) 6:

To an oven dried 50 mL pressure vessel equipped with magnetic

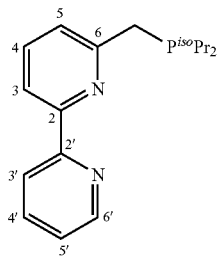

6 stirring bar was added 6-chloromethyl-2,2'-bipyridine (BPy-$CH_2Cl$) (1.03 g, 5.00 mmol), di-iso-propyl phosphine (710 mg, 6.00 mmol), and 15 mL MeOH in nitrogen glove box. The flask was sealed and heated at 50° C. for 48 hrs with stirring outside the glove box. After cooling, it was reintroduced to the glove box, triethylamine (910 mg, 9.00 mmol) was added and the reaction mixture was stirred at room temperature for 1 hr. The solvents were removed under reduced pressure to obtain a white solid. The residue was washed with ether (2×10 mL), filtered and was removed under reduced pressure to yield a pale yellow liquid. It was further purified by basic alumina chromatography under the glove box using hexane as an eluent to yield pure 6.

Yield=874 mg (61%). $^{31}P\{^1H\}$NMR ($CD_2Cl_2$): 15.84 (s). $^1H$ NMR ($CD_2Cl_2$): 1.11 (dd, $J_{PH}$=13.8 Hz, $J_{HH}$=7.2 Hz, 6H, P(CH(CH)$_2$), 1.17 (dd, $J_{PH}$=14.4 Hz, $J_{HH}$=7.2 Hz, 6H, P(CH(CH$_{b3}$)$_2$), 1.89 (sep d, $J_{HH}$=7.2 Hz, $J_{PH}$=2.1 Hz, 2H, P(CH(CH$_{a/b3}$)$_2$), 3.12 (d, $J_{PH}$=1.8 Hz, 2H, P—$CH_2$), 7.28-7.34 (m, 1H, H-5'), 7.33 (d merged with m, $J_{HH}$=7.8 Hz, H-5), 7.73 (t, $J_{HH}$=7.8 Hz, 1H, H-4), 7.82 (dt, $J_{HH}$=7.8 Hz, $J_{HH}$=1.8H, 1H, H-4'), 8.21 (d, $J_{HH}$=7.8 Hz, 1H, H-3), 8.46 (br d, $J_{HH}$=8.1 Hz, 1H, H-3'), 8.67-8.69 (m, 1H, H-6'). $^{13}C\{^1H\}$NMR ($CD_2Cl_2$): 18.89 (d, $J_{PC}$=10.5 Hz, P(C(C$_a$H$_3$)$_2$), 19.62 (d, $J_{PC}$=15.0 Hz, P(C(C$_b$H$_3$)$_2$), 23.62 (d, $J_{PC}$=15.0 Hz, PCH$_2$), 32.45 (d, $J_{PC}$=22.5, P(C(C$_{a/b}$H$_3$)$_2$), 117.63 (s, C-3), 120.77 (s, C-3'), 123.50 (s, C-5'), 123.60 (s, C-5), 136.68, (s, C-4'), 136.90 (s, C-4), 149.06 (s, C-6'), 155.18 (s. C-2), 156.38 (s, C-2'), 161.34 (d, $J_{PC}$=9.0, C-6). Assignment of signals was confirmed by DEPT 135. Anal. Calcd. for $C_{17}H_{23}N_2P$: C, 71.30; H, 8.10. Found: C, 71.52; H, 8.34.

Synthesis of RuHCl(CO)(BPy-$^{iso}$(Pr)PNN) 7:

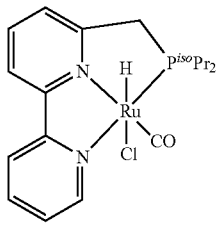

7

To a suspension of RuHCl(CO)(PPh$_3$)$_3$ (476 mg, 0.5 mmol) in dry THF (12 ml) in a nitrogen glove box was added ligand, BPy-$^{iso}$(Pr)PNN (6) (143 mg, 0.5 mmol), and the mixture was stirred for overnight at room temperature to obtain reddish-brown solid. The solvent was decanted and the solid thus obtained was washed with pentane (3×5 mL), then dried under vacuum to give pure complex 7 (206 mg, 91%). $^{31}P\{^1H\}$ NMR (see below) of complex shows a singlet at 95.38 ppm. The $^1H$ NMR spectrum of the complex exhibits a doublet resonance at −15.26 ppm ($^2J_{PH}$=24.6 Hz) for Ru—H. The "arm" methylene protons give rise ABq system centered at 3.65 and 3.77 ppm with $J_{HH}$=17.4 Hz and $J_{PH}$=10.2 Hz. The BPy-C6'H appears as multiplet at 9.18-9.26 ppm, representing an upfield shift of ca. 0.53 ppm relative to the corresponding proton of the ligand (8.67-8.69 ppm), upon complexation with ruthenium.

$^{31}P\{^1H\}$NMR ($CD_2Cl_2$): 95.38 (s). $^1H$ NMR ($CD_2Cl_2$): −14.75 (d, $J_{PH}$=23.7 Hz, 1H, Ru—H), 0.95 (dd, $J_{PH}$=15.3 Hz, $J_{HH}$=6.9 Hz, 3H, P(CH(CH)$_2$), 1.12 (dd, $J_{PH}$=17.1 Hz, $J_{HH}$=6.9 Hz, 3H, P(CH(CH$_{a3}$)$_2$), 1.38 (dd, $J_{PH}$=13.2 Hz, $J_{HH}$=7.2 Hz, 3H, P(CH(CH$_{b3}$)$_2$), 1.49 (dd, $J_{PH}$=16.8 Hz, $J_{HH}$=7.2 Hz, 3H, P(CH(CH$_{b3}$)$_2$), 2.16-2.33 (m, 1H, P(CH(CH$_{a,a3}$)$_2$), 2.66-2.82 (m, 1H, P(CH(CH$_{b,b3}$)$_2$), AB system centered at 3.65 and 3.77 (ABq, $J_{HH}$=17.4 Hz and $J_{PH}$=10.2 Hz, 2H, PCH$_a$H$_b$), 7.44-7.48 (m, 1H, H-5'), 7.53 (d, $J_{HH}$=7.8 Hz, 1H, H-5), 7.83-7.94 (m, 2H, H-4 and H-4'), 7.97 (d merged with m, $J_{HH}$=8.1 Hz, 1H, H-3), 8.06 (d, $J_{HH}$=8.1 Hz, 1H, H-3'), 9.18-9.26 (br m, 1H, H-6'). $^{13}C\{^1H\}$NMR ($CD_2Cl_2$): 17.35 (d, $J_{PC}$=4.5 Hz, P(C(C$_a$H$_3$)$_2$), 18.21 (s, P(C(C$_a$H$_3$)$_2$), 19.24 (d, $J_{PC}$=5.3 Hz, P(C(C$_b$H$_3$)$_2$), 20.15 (d, $J_{PC}$=4.5 Hz, P(C(C$_b$H$_3$)$_2$), 24.58 (d, $J_{PC}$=29.3 Hz, P(C$_a$(CH$_3$)$_2$), 28.12 (d, $J_{PC}$=24.0 Hz, P(C$_b$(CH$_3$)$_2$), 40.94 (d, $J_{PC}$=21.8 Hz, PGH$_2$), 119.63 (s, C-3), 122.59 (s, C-3'), 122.80 (d, $J_{PC}$=9.8 Hz, C-5), 126.00 (s, C-5'), 136.25, (s, C-4'), 137.02 (s, C-4), 153.06 (s, C-6'), 154.47 (s, C-2), 155.99 (s, C-2'), 161.11 (d, $J_{PC}$=4.5, C-6). 207.31 (d, $J_{PC}$=15.0 Hz, Ru—CO). IR (KBr, pellet): 1962 (vRu—H), 1915 (vCO) cm$^{-1}$. Anal. Calcd. for $C_{18}H_{24}N_2OPClRu$: C, 47.84; H, 5.35. Found: C, 48.01; H, 5.54.

Synthesis of 6-(N,N-diethyl)aminomethyl-2,2'-bipyridine (BPy-NNN) 8:

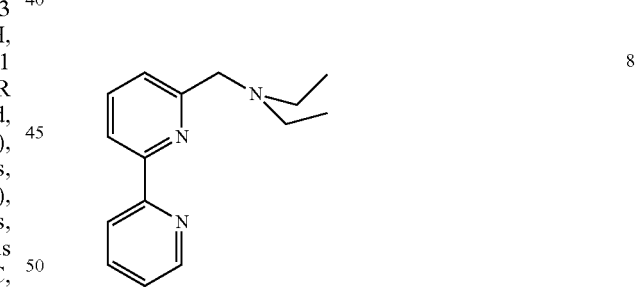

8

A solution of 6-chloromethyl-2,2'-bipyridine (BPy-$CH_2Cl$) in 20 mL of dry THF was cooled to 0° C. and a solution diethylamine (5 mL) in THF (10 mL) was added to it dropwise over 10 min. The mixture was allowed to slowly warm up to room temperature and refluxed under N$_2$ for 6 hrs. The solvent was removed under vacuum and the residue was dissolved in 50 mL of diethyl ether and washed with 2×10 mL of a 10% aqueous KOH solution. The organic phase was separated and dried over Na$_2$SO$_4$ and the ether was removed under vacuum. The residue was purified by flash chromatography (silica gel; EtOAc:Hexane as eluent), yielding (78% yield) 6-(N,N-diethyl)aminomethyl-2,2'-bipyridine (BPy-NNN) 8 as a yellow-brown oil.

$^1H$ NMR (CDCl$_3$): 1.15 (t, $J_{HH}$=7.2 Hz, 6H, N(CH$_2$CH$_3$)$_2$), 2.70 (q, $J_{HH}$=7.2 Hz, 4H, N(CH$_2$CH$_3$)$_2$), 7.28-7.32 (m, 1H,

H-5'), 7.54 (d, $J_{HH}$=7.8 Hz, 1H, H-5), 7.77-7.84 (m, 2H, H-4 and H-4'), 8.26 (d, $J_{HH}$=8.1 Hz, 1H, H-3), 8.41 (br d, $J_{HH}$=8.1 Hz, 1H, H-3'), 8.67-8.69 (m, 1H, H-6'). $^{13}C\{^1H\}$NMR (CDCl$_3$): 11.69 (s, N(CH$_2$CH$_3$)$_2$), 47.36 (s, N(CH$_2$CH$_3$)$_2$), 58.81 (s, Arm-CH$_2$), 119.33 (s, C-3), 121.17 (s, C-3'), 123.26 (s, C-5'), 123.58 (s, C-5), 136.87, (s, C-4'), 137.33 (s, C-4), 149.14 (s, C-6'), 155.34 (s, C-2), 156.33 (s, C-2'), 158.68 (br s, C-6). Assignment of signals was confirmed by DEPT 135. Anal. Calcd. for C$_{15}$H$_{19}$N$_3$: C, 74.65; H, 7.94. Found: C, 74.81; H, 8.08.

Example 9

Borohydride Complexes

As contemplated herein, certain reactions described herein, such as novel ester synthesis, novel amide synthesis, as well as the dehydrogenation of secondary alcohols to ketones, and hydrogenation of esters to alcohols, can be effectively accomplished also with stable, readily synthesized PNN- and PNP Ru borohydride complexes, in absence of base, under neutral conditions, and in absence of hydrogen acceptor.

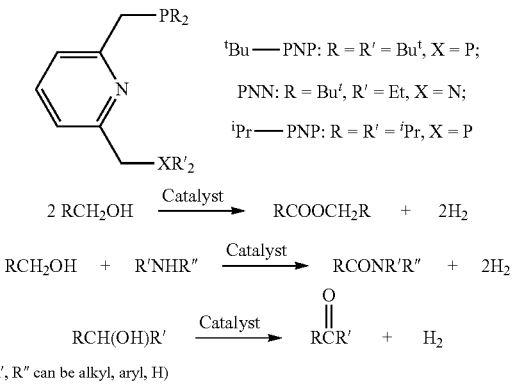

Scheme 30

R, R', R'' can be alkyl, aryl, H)

Synthesis and Characterization of [RuH($\eta^2$-BH$_4$)($^t$Bu-PNP] 2'

The N$_2$-bridged binuclear Ru(II) complex [($^t$Bu-PNP) RuCl$_2$]$_2$($\mu$-N$_2$) 1' was prepared by the reaction of RuCl$_2$ (PPh$_3$)$_3$ with one equivalent of $^t$Bu-PNP (Zhang et al. 2004). Treatment of with an excess (5 equiv) of NaBH$_4$ in 2-propanol for 12 hrs resulted in formation of the Ru(II) hydrido borohydride complex 2' in almost quantitative yield (by NMR) (Scheme 25). The $^{31}P\{^1H\}$ NMR spectrum of 2' exhibits a singlet peak at 86.3 ppm, representing a downfield shift of 21 ppm relative to 1' (65.0 ppm). In the NMR spectrum, the hydride ligand gives rise to a triplet peak at −16.09 ppm with $J_{PH}$=18.0 Hz. In addition, two broad signals are observed for the two bridging hydrides at −16.01 and −4.48 ppm and another broad feature at 5.49 ppm belonging to the terminal boron hydrides. The IR spectrum of 2' indicates two strong bands in the terminal B—H region at 2395 and 2327 cm$^{-1}$ and two bands in the bridging M–H—B region at 2104 and 2024 cm,$^{-1}$ consistent with the bidentate $\eta^2$-BH$_4$ binding mode (Marks et al.).

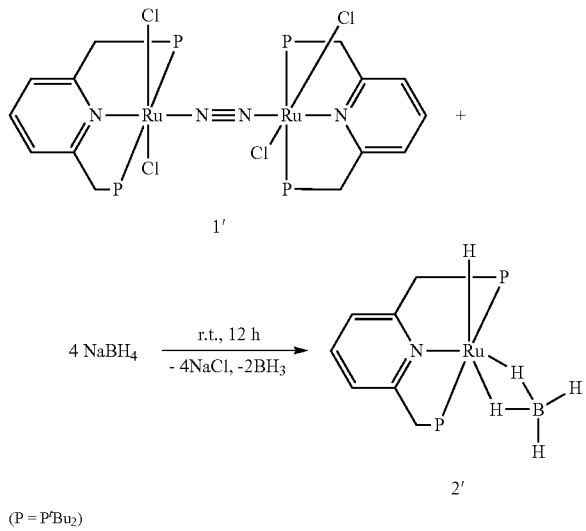

Scheme 31

(P = P$^t$Bu$_2$)

Figure 3:
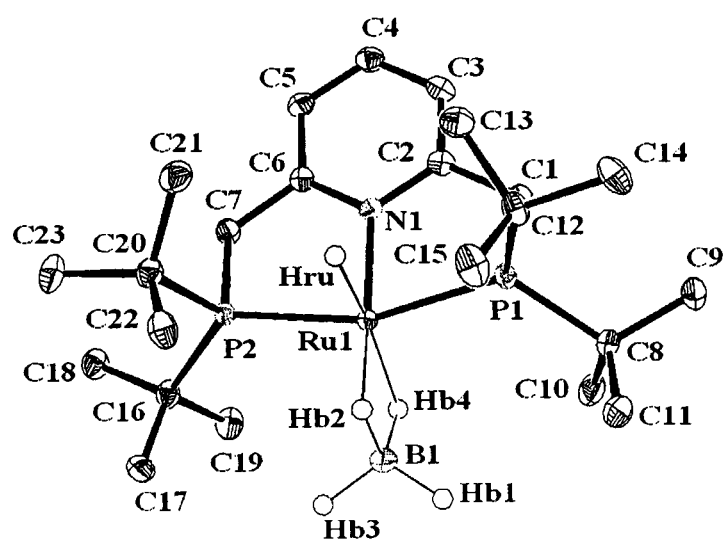
FIG. 3: shows the X-ray structure of Ruthenium borohyride complex 2' with the thermal ellipsoids at 50% probability level. All C—H hydrogen atoms are omitted for clarity.
Figure 4:
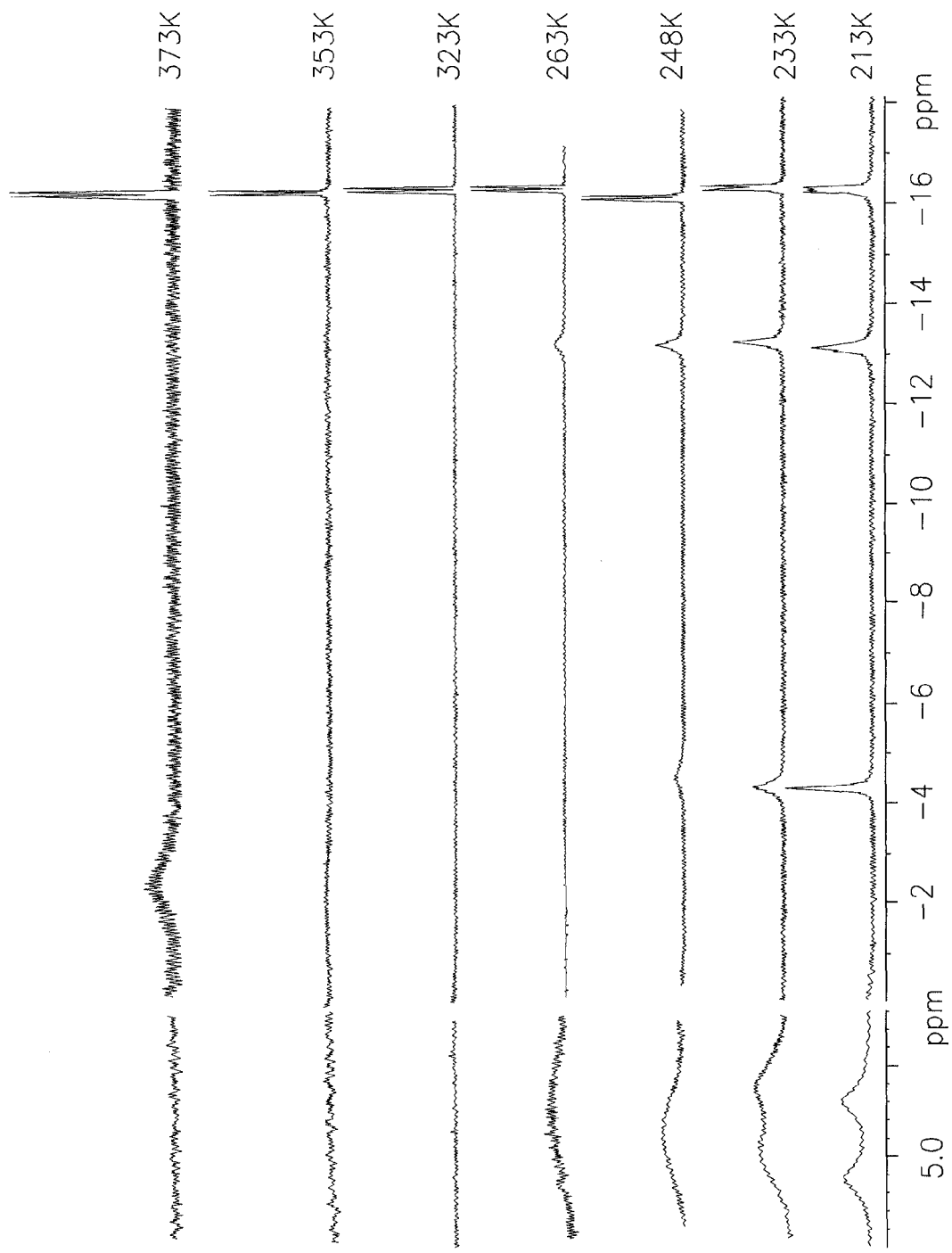
FIG. 4: shows the variable-temperature (213K-373K) $^1$H NMR of Ruthenium borohydride complex 4' in the region of Ru—H and $BH_4^-$ ligands (toluene-$d_8$ as solvent).

Single crystals suitable for an X-ray diffraction study were obtained by slow evaporation of a pentane solution of 2' at −32'° C. The crystal structure of 2' (FIG. 3) displays a distorted octahedral geometry around the ruthenium center, including the $^t$Bu-PNP, hydride and BH$_4$ units. The hydride ligand is bound to the Ru center cis to the pyridine nitrogen (N1-Ru1-Hru, 81 (2)°, while the BH$_4$ unit is coordinated to Ru(II) center in a $\eta^{2'}$ mode. The two Ru—H bonds to the chelating BH$_4$ unit are not equal (1.67(5) and 1.85(6) Å, respectively), while the corresponding Ru—H bonds in the structure of RuH(BH$_4$)(PMe$_3$)$_3$ (Statler et al.) are of equal length. The difference in the case of 2' is a result of the larger trans effect of hydride relative to that of the pyridinic nitrogen atom. Because of the meridional coordination geometry of the $^t$Bu-PNP framework and lack of a plane of symmetry involving the P, N, P atoms, the protons of the four tert-butyl and two methylene groups are magnetically inequivalent.

TABLE 22

| Selected Bond Distances (Å) and Angles (deg) of Complex 2' | | | |
|---|---|---|---|
| Ru1-N1 | 2.123 (3) | Ru1-P1 | 2.311 (1) |
| Ru1-P2 | 2.322 (1) | Ru1-HRu | 1.57 (5) |
| Ru1-HB2 | 1.67 (5) | Ru1-HB4 | 1.85 (6) |
| N1-Ru1-HRu | 81 (2) | HRu-Ru1-HB4 | 166 (2) |
| P1-Ru1-P2 | 159.6 (1) | HB2-Ru1-N1 | 177 (2) |
| N1-Ru1-P2 | 83.0 (1) | P1-Ru1-N1 | 82.5 (1) |
| P2-Ru1-HRU | 79 (2) | HRU-Ru1-P1 | 85 (2) |
| HB2-Ru1-HB4 | 70 (2) | HB3-B1-HB1 | 113 (3) |
| HB2-B1-HB4 | 104 (3) | | |

Synthesis and Characterization of [RuH($\eta^2$-BH$_4$)(PNN)]4'

The N$_2$-bridged binuclear Ru(II) complex [(RuCl$_2$ (PNN))$_2$]($\mu$-N$_2$) 3' was prepared by the reaction of RuCl$_2$ (PPh$_3$)$_3$ with one equivalent of PNN, employing a similar method to the one used for the preparation of 1. Treatment of 3' with an excess (5 equiv) of NaBH$_4$ in 2-propanol for 12 hrs resulted in the formation of the ruthenium(II) hydrido borohydride complex 4' in excellent yield as indicated by $^{31}P\{^1H\}$ NMR spectroscopy (Scheme 26). The $^{31}P\{^1H\}$ NMR spectrum of 4' shows a singlet peak at 116.7 ppm, representing a downfield shift of 29 ppm relative to 3'. The hydride ligand gives rise to a doublet at −16.24 ppm with $J_{PH}$=28.0 Hz in the $^1$H NMR spectrum. The IR spectrum of 4' exhibits two strong bands in the terminal B—H region at 2378 and 2311 cm$^{-1}$ and two bands in the bridging M-H—B region at 2096 and 1956 cm$^{-1}$ similar to the IR spectrum of complex 2', consistent with the bidentate $\eta^2$-BH$_4$ binding mode (Marks et al.).

Scheme 32

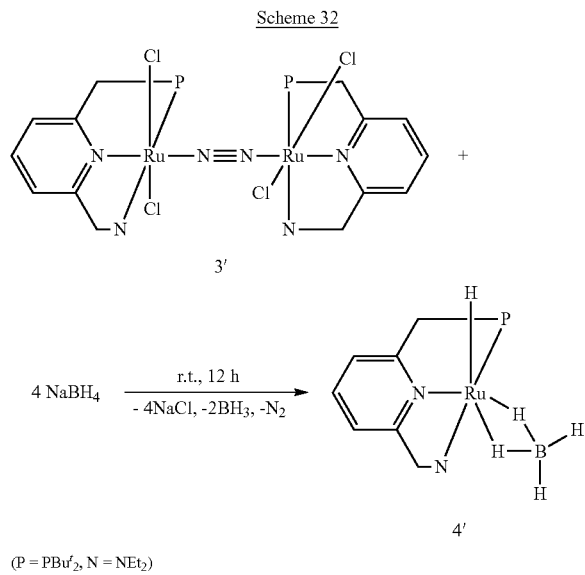

(P = PBu$^t_2$, N = NEt$_2$)

Figure 2:
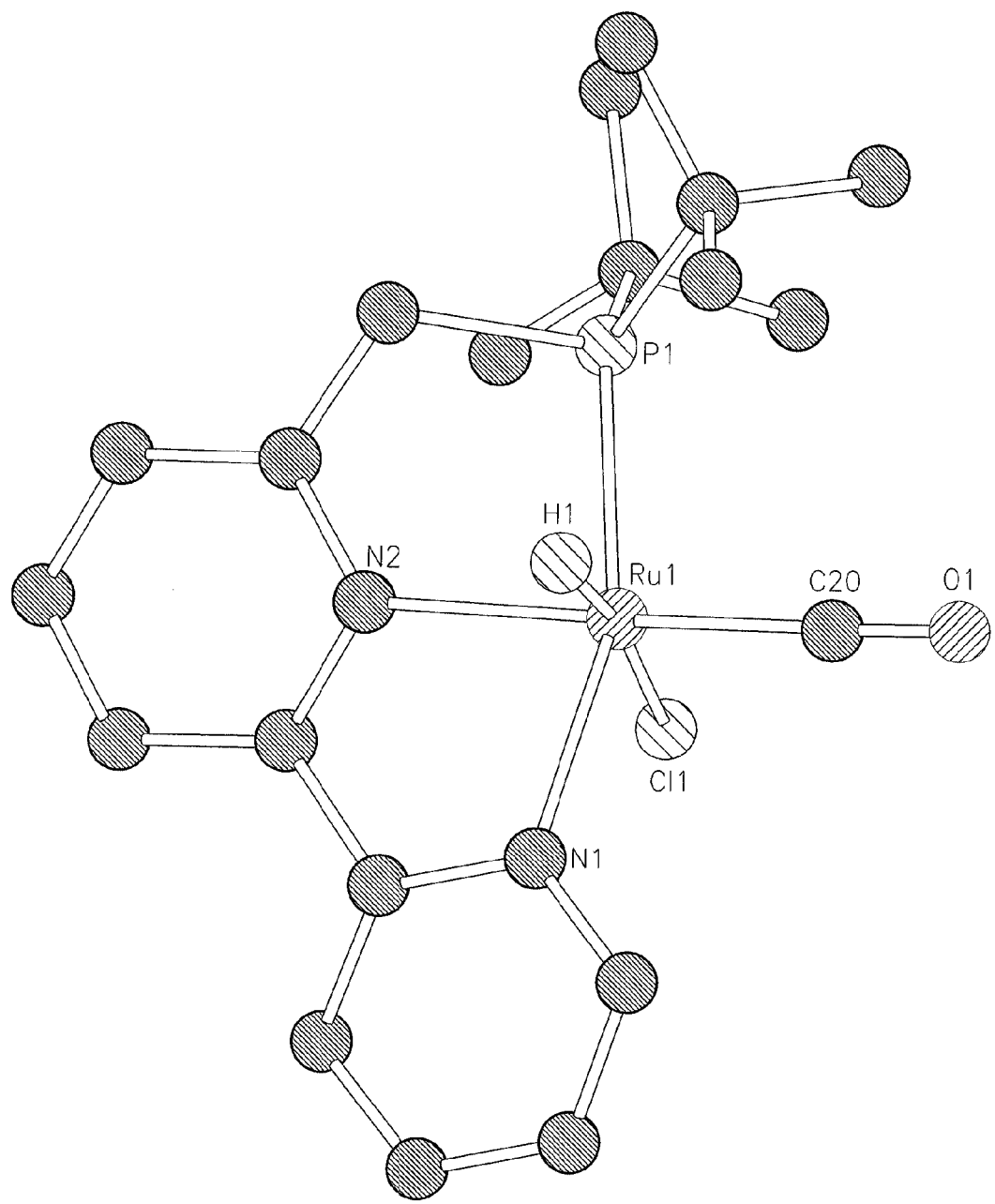
FIG. 2: shows the X-ray structure of Ruthenium complex 4 with the thermal ellipsoids at 50% probability level. All C—H hydrogen atoms are omitted for clarity.

At room temperature, one broad singlet peak at –13.01 ppm is observed in the $^1$H NMR spectrum of 4' for one proton of BH$_4^-$. A variable-temperature $^1$H NMR study of 4' in toluene-d$_8$ is shown in FIG. 2, revealing interesting fluxional behavior of the BH$_4^-$ ligand. At 213K, two singlets are observed at –13.21 and –4.33 ppm for the bridging hydrides and two broad singlets at 4.70 and 5.13 ppm for the two terminal hydrides of the BH$_4^-$ ligand, respectively. Upon raising the temperature to 248K, the signals for the two terminal hydrides coalesce while the signal at –4.33 ppm collapses. At 263K, the signals (~5 ppm) for the two terminal hydrides and the signal at –4.33 ppm for one bridging hydride disappear in the baseline and the signal (–13.21 ppm) of another bridging hydride also collapses. Upon temperature increase to 323K, the resonance at –13.21 ppm also disappears into the baseline. Upon raising the temperature to 353K, a very broad singlet peak appears at –2 ppm, indicating that the four hydrides of BH$_4^-$ start to coalesce. The signal of the terminal Ru—H ligand appears as a doublet peak throughout the 213-373K temperature range, indicating that it does not participate in the fluxional process of the BH$_4^-$ ligand. These variable-temperature $^1$H NMR spectra of complex 4' are similar to those reported for the complexes RuH(BH$_4$)(PMe)$_3$ (Statler et al.) and RuH(BH$_4$)(ttp) (ttp=PhP(CH$_2$CH$_2$CH$_2$PPh$_2$)$_2$) (Letts et al.). The bridging hydride (–4.33 ppm) trans to the terminal Ru—H exchanges positions with the two terminal hydrides on the boron at 263K. These hydrogen atoms further exchange with the bridging hydride (–13.21 ppm) trans to pyridinic nitrogen above 323K and the calculated coalescence frequency at –2.0 ppm was observed at 353K.

Synthesis and Characterization of [RuCl$_2$(PPh$_3$)($^i$Pr-PNP)] 5 and [RuH($\eta^1$-BH$_4$)(PPh$_3$)($^i$Pr-PNP)]6'.

Heating of RuCl$_2$(PPh$_3$)$_3$ with one equivalent of $^i$Pr-PNP ($^i$Pr-PNP=2,6-bis(di-iso-propylphosphinomethyl)pyridine) in THF at 65° C. for 6 hrs resulted in formation of the PPh$_3$ complex 5' in 75% yield (Scheme 27). The $^{31}$P {$^1$H} NMR spectrum of 5' exhibits one doublet at 46.4 ppm and one triplet peak at 43.2 ppm, indicating that triphenylphosphine is coordinated to the Ru(II) center, as observed also with the reported Ph-PNP—Ru(II) dichloride complex (Ph-PNP=2,6-bis(diphenylphosphinomethyl)pyridine) (Jia et al.). In contrast, the $^t$Bu complexes 1' and 3' do not contain coordinated PPh$_3$, under similar preparation conditions, probably because of the steric bulk of the tert-butyl group of $^t$Bu-PNP and PNN ligands. The two methylene groups of $^i$Pr-PNP give rise to one triplet peak at 3.92 ppm with J$_{PH}$=4.0 Hz, indicating the existence of a symmetric plane involving the P, N, P atoms. The PPh$_3$ ligand is coordinated to the Ru(II) center trans to the nitrogen atom of $^i$Pr-PNP and the chloride ligands are coordinated to metal center trans to each other.

In analogy to the preparation of complexes 2' and 4', treatment of complex 5' with excess (2.5 equiv) of NaBH$_4$ in isopropanol at room temperature resulted in precipitation of the Ru(II) hydrido borohydride complex 6' as a yellow solid in 85% yield (Scheme 27). The $^{31}$P{$^1$H} NMR spectrum of 6' exhibits a doublet signal at 61.6 ppm and a triplet signal at 67.9 ppm, corresponding to the two phosphorus atoms of $^i$Pr-PNP and one phosphorus atom of PPh$_3$, respectively. It is noted that the signal of the PPh$_3$ ligand of 6' is downfield shifted relative to that of $^i$Pr-PNP, unlike the corresponding signals of complex 5. The Ru—H gives rise in the $^1$H NMR of 6' to a quartet signal at –14.00 ppm with J$_{PH}$=J$_{P'H}$=28.0 Hz. A broad peak at –0.84 ppm is assigned to the four protons of the BH$_4$ ligand, which is probably coordinated to the Ru(II) center in a $\eta^1$ mode, similar to the reported bonding of ruthenium borohydride complexes by Ohkuma et al. and Guo et al. The IR spectrum of 6' exhibits strong absorptions at 2361, 2292 and a strong broad peak at 1884 cm,$^{-1}$ consistent with the monodentate $\eta^1$-BH$_4$ bonding mode (Marks et al.).

Scheme 33

RuCl$_2$(PPh$_3$)$_3$ + $^i$Pr—PNP $\xrightarrow[\text{-2 PPh}_3]{\text{THF, 65° C., 6 hrs}}$

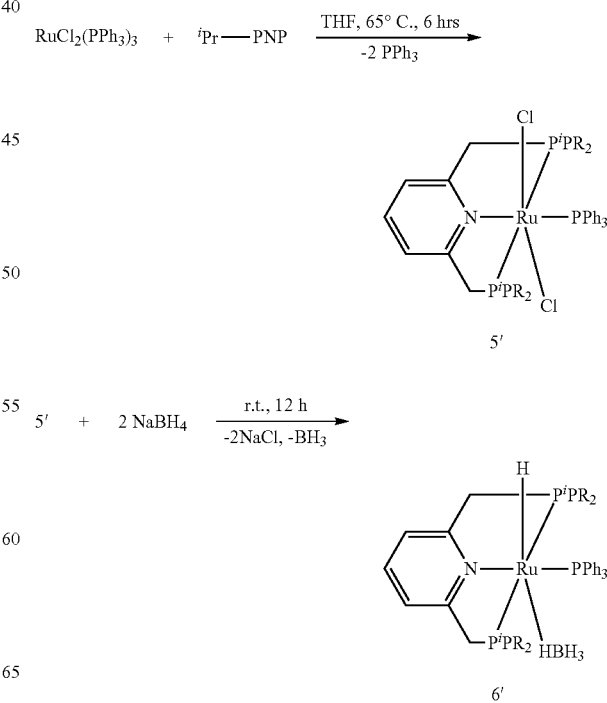

5' + 2 NaBH$_4$ $\xrightarrow[\text{-2NaCl, -BH}_3]{\text{r.t., 12 h}}$

Synthesis of Borohydride Complex 8'

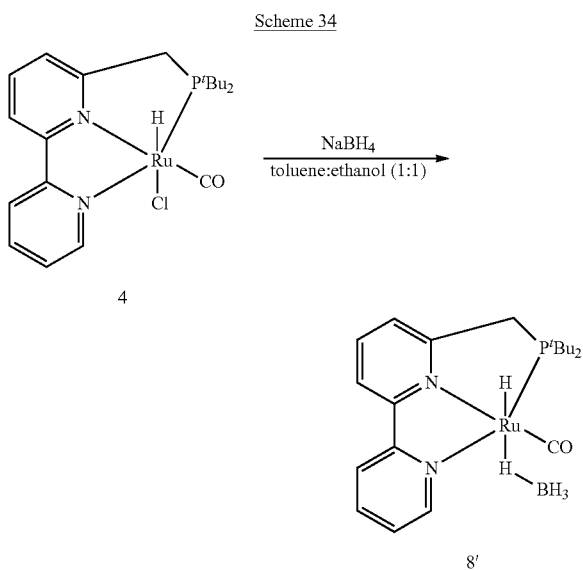

Scheme 34

RuHCl(CO)(BPy-$^t$PNN) complex 4 (82 mg, 0.17 mmol) and NaBH$_4$ (32 mg, 0.85 mmol) were placed in a 20 mL Schlenk flask equipped with a Teflon-coated magnetic stirring bar. A 1:1 mixture of toluene and ethanol (4 mL) was added to the flask. It was then stirred at 65° C. for 5 min (to get homogeneous solution) then at room temperature for 2 hr to give a reddish yellow solution. The solvent was removed in vacuo. The resulting residue was dissolved in CH$_2$Cl$_2$ (6 mL) and the remaining insoluble materials were removed by filtration through a Celite pad (0.5 g). The filtrate was concentrated to ca. 0.5 mL and 5 mL of pentane was added to cause precipitation of a orange-yellow solid, which was filtered and dried under vacuum to give 72 mg (92%) of analytically pure RuH(CO)($\eta^1$BH4)BPy-$^t$PNN) complex 8'. $^{31}$P {$^1$H}NMR (202 MHz, CD$_2$Cl$_2$): 110.67 (s). $^1$H NMR (500 MHz, CD$_2$Cl$_2$): −12.27 (d, $^2J_{PH}$=21.5 Hz, 1H, Ru—H), −2.34--1.90 (br d, 4H, Ru—HBH$_3$), 1.31 (d, J$_{PH}$=13.0 Hz, 9H, P(C(CH$_{a3}$)$_3$), 1.43 (d, J$_{PH}$=13.5 Hz, 9H, P(C(CH$_{b3}$)$_3$), ABX system centred at 3.62 and 3.69 (2H, PCH$_a$H$_b$), 7.41-7.43 (m, 1H, H-5'), 7.56 (d, J$_{HH}$=8.0 Hz, 1H, H-5), 7.85-7.89 (m, 2H, H-4 and H-4'), 7.96 (d, J$_{HH}$=7.5 Hz, 1H, H-3), 8.04 (d, J$_{HH}$=8.0 Hz, 1H, H-3'), 9.12-9.13 (br m, 1H, H-6'). $^{13}$C{$^1$H}NMR (125 MHz, CD$_2$Cl$_2$): 28.43 (d, J$_{PC}$=3.8 Hz, P(C(C$_a$H$_3$)$_3$), 29.63 (d, J$_{PC}$=3.8 Hz, P(C(C$_b$H$_3$)$_3$), 35.87 (d, J$_{PC}$=16.3 Hz, P(C$_{a/b}$(CH$_3$)$_3$), 37.34 (d, J$_{PC}$=16.3 Hz, PCH$_2$), 119.26 (s, C-3), 121.16 (s, C-3'), 122.53 (d, J$_{PC}$=8.8 Hz, C-5), 125.71 (s, C-5'), 135.97, (s, C-4'), 137.07 (s, C-4), 153.69 (s, C-6'), 154.79 (br s, C-2), 155.91 (s, C-2'), 163.95 (d, J$_{PC}$=3.78 Hz, C-6), 206.90 (br d, J$_{PC}$=15 Hz, Ru—CO). IR (KBr disc, CH$_2$Cl$_2$): 2313 (B—H stretching), 1988 (Ru—H stretching), 1046 (BH$_3$ deformation), 1019 (BH$_3$ deformation). Assignment of signals was confirmed by DEPT 135, COSY, and HSQC.

Dehydrogenation of Alcohols Using Complexes 2', 4', 6' and 8' as Catalysts.

As some of the inventors of the present invention have demonstrated (Zhang 2004, Zhang 2005), PNP and PNN Ru(II) complexes catalyze the dehydrogenation of secondary alcohols to ketones and primary alcohols to esters. It has now been discovered that the ruthenium hydrido borohydride complexes of 2', 4', and 6' and 8' catalyze the dehydrogenation of alcohols under base-free conditions and in absence of hydrogen acceptors. Indeed, when complex 2' was heated with 1000 equivalents of 1-phenyl-1-ethanol in toluene for 24 hrs, 28.6% of the alcohol were converted to acetophenone, accompanied by the evolution of hydrogen gas (Table 23, entry 1). Similarly, upon heating of 1-phenyl-1-ethanol with 0.1% 4' or 6' in toluene for 24 hrs, acetophenone was formed in 86.5% and 76.5% yield, respectively (Table 23, entry 2 and 3), indicating that the catalytic activity of 4' was significantly higher than that of complexes 2' and 6', probably as a result of the potentially "hemilabile" amine arm of 4', which can play an important role in the catalytic cycle (Zhang 2005). A longer reaction time resulted in a higher yield of the ketone (Table 23, entry 4). Other secondary alcohols can also be dehydrogenated to the corresponding ketones using 4' as catalyst in good yields (Table 23, entries 5-8). The catalysis by 4' was quite sensitive to the reaction temperature, and when 2-propanol was heated at 83° C. with 0.1% 4', acetone was formed in only 12.6% yield after 48 hrs (TON=126), while when heated in toluene at 105° C., 89.9% of acetone were formed during the same reaction period (TON=899).

TABLE 23

Dehydrogenation of secondary alcohols to the corresponding ketones with complexes 2', 4', 6' as catalysts

| entry | Cat. | Alcohol | Temp. (° C.) | Time (h) | Conversion (%) | Yield of ketone (%)$^a$ |
|---|---|---|---|---|---|---|
| 1 | 2' | 1-phenyl-1-ethanol | 115 | 24 | 28.6 | 28.6 |
| 2 | 4' | 1-phenyl-1-ethanol | 115 | 24 | 86.5 | 86.5 |
| 3 | 6' | 1-phenyl-1-ethanol | 115 | 24 | 77 | 76.5 |
| 4 | 4' | 1-phenyl-1-ethanol | 115 | 48 | 93 | 93 |
| 5 | 4' | 2-hexanol | 115 | 48 | 83.2 | 83 |
| 6 | 4' | 2-butanol | 110 | 48 | 88.8 | 88.7 |
| 7 | 4' | cyclohexanol | 115 | 48 | 56.5 | 56.5 |
| 8 | 4' | 2-propanol | 105 | 48 | 90 | 89.9 |
| 9 | 4' | 2-propanol | 83$^b$ | 48 | 12.6 | 12.6 |

$^a$reaction conditions: catalyst 0.01 mmol, alcohol 10 mmol, toluene 2 mL, reflux under argon flow
$^b$reflux in neat 2-propanol under argon.

In comparison to the dehydrogenation of secondary alcohols to the corresponding ketones, homogeneous systems capable of dehydrogenation of primary alcohols to the corresponding aldehydes or esters are very rare (Zhang 2005, Murahashi et al., Blum et al., Lin et al. and Zhao et al), probably because of decarbonylation of the product (or intermediate) aldehyde to form an inactive carbonyl complex.

When a toluene solution of benzyl alcohol and 0.1% complex 2' was refluxed for 24 hrs in an open system, benzyl benzoate was formed in 70% yield, accompanied by a small amount of benzaldehyde (4%) (Table 24, entry 1). Refluxing 1-hexanol with 0.1% 2 in toluene (115° C.) or neat (157° C.) for 24 hrs resulted in formation of 60-70% of hexyl hexanoate, accompanied by 2.5-10% hexanal (Table 24, entries 2 and 3). Complex 6' was slightly less catalytically active than 2 (Table 24, entry 7). The PNN complex 4' exhibited significantly higher catalytic activity than that of the PNP complexes 2' and 6'; benzyl alcohol, 1-hexanol and 1-butanol were dehydrogenated to the corresponding esters in over 90% yield after heating with 0.1% 4' in toluene (Table 24, entry 4-6).

TABLE 24

Dehydrogenation of primary alcohols to esters and aldehydes with complexes 2', 4', 6' as catalysts

| entry | Cat. | Alcohol | Temp. (°C.) | Conversion (%) | Yield of Aldehyde (%) | Yield of ester (%)[a] |
|---|---|---|---|---|---|---|
| 1 | 2' | benzyl alcohol | 115 | 75 | 4 | 70 |
| 2 | 2' | 1-hexanol | 115 | 72 | 2.5 | 69 |
| 3 | 2' | 1-hexanol | 157[a] | 70 | 10 | 59.4 |
| 4 | 4' | benzyl alcohol | 115 | 99 | 0 | 99 |
| 5 | 4' | 1-hexanol | 115 | 94 | 0 | 94 |
| 6 | 4' | 1-butanol | 110 | 96 | 0.2 | 95.5 |
| 7 | 6' | benzyl alcohol | 115 | 62 | 3.4 | 58.6 |
| 8 | 6' | 1-hexanol | 157[b] | 57.5 | 9.5 | 47.4 |

[a]reaction conditions: catalyst 0.01 mmol, alcohol 10 mmol, toluene 2 mL heated under reflux for 24 hrs under argon flow
[b]reflux in neat 1-hexanol under argon flow Dehydrogenation of Alcohols to Esters Using Complex 8' as Catalyst Scheme 35

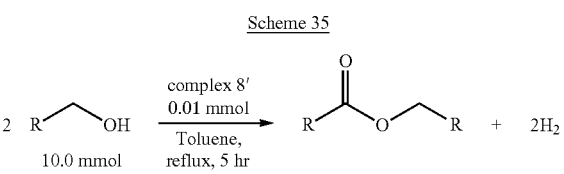

TABLE 25

Dehydrogenation of alcohols to esters using complex 8' as catalyst

| Entry | Alcohols | Esters | Conv. (%) | Yield (%)[a] |
|---|---|---|---|---|
| 1 | 1-Hexanol | Hexyl hexanoate | 99.8 | 99.0 |
| 2 | Benzyl alcohol | Benzyl benzoate | ~100 | 99.3 |

[a]Complete conversion of alcohol was observed and no formation of aldehyde (by GC).

Amidation Using Complex 4' as a Catalyst

Scheme 36

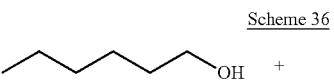

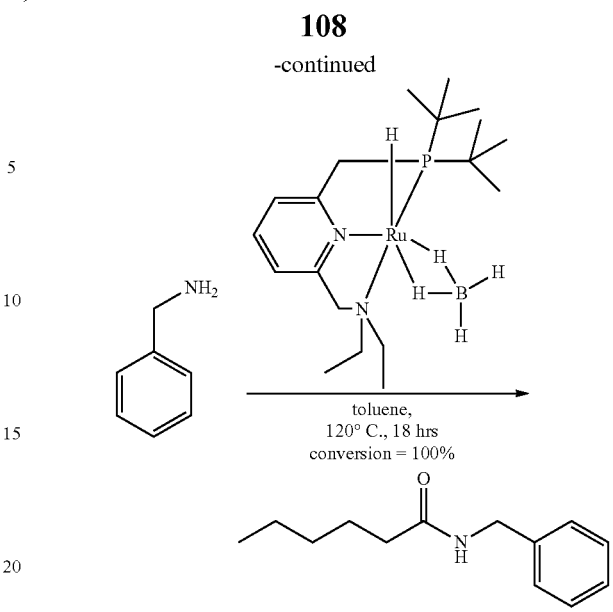

isolated yield: 98%

Complex 4' (4.4 mg, 0.01 mmol), 1-hexanol (1.02 g, 10 mmol), benzyl amine (1.07 g, 10 mmol) and toluene (3 mL) were taken in a Schlenk flask under an atmosphere of purified nitrogen in a glove box. The flask was equipped with a condenser and the solution was refluxed with stirring in an open system under argon for 18 h. After cooling to room temperature, the consumption of starting materials was checked by GC using a Carboxen 1000 column on a HP 690 series GC system and shows that 100% conversion of the 1-hexanol. To the reaction mixture, hexane (30 mL) was added to precipitate out the N-benzylhexanamide as white coloured solid and filtered off the solid to get the pure product in 98% yield.

Amidation Using Complex 8' as Catalyst

Scheme 37

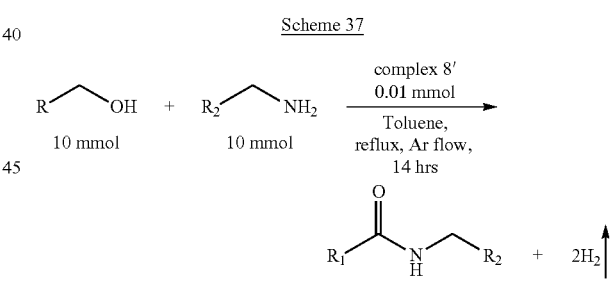

TABLE 26

Amidation using complex 8' as a catalyst

| Entry | Alcohols | Amines | Amides | Yield (isolated) |
|---|---|---|---|---|
| 1 | HO–(–)₄– | PhCH₂NH₂ | PhCH₂NHC(O)(–)₄ | 59[a] |

TABLE 26-continued

Amidation using complex 8' as a catalyst

| Entry | Alcohols | Amines | Amides | Yield (isolated) |
|---|---|---|---|---|
| 3 | HO‾‾‾O‾ | BnNH$_2$ | MeOCH$_2$C(O)NHBn | 71[b] |

[a]Conversion of alcohol is 87.8%. Other products are Ester (5.2%) and Imine (17%) also formed (by GC).
[b]Conversion of alcohol is 91.1%. Other products are Ester (3.5%) and Imine (12%) also formed (by GC).

Ester Hydrogenation Using Complexes as Catalysts

Scheme 38

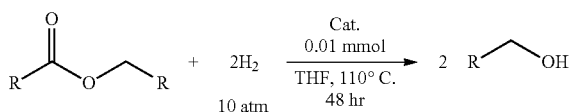

TABLE 27

Ester hydrogenation

| Entry | Cat. | Esters | Alcohols | Conv. (%) | Yield (%) |
|---|---|---|---|---|---|
| 1 | 8' | Hexyl hexanoate (2 mmol) | 1-Hexanol | 99.8 | 98.9 |
| 2 | 8' | Methyl formate (15 mmol) | MeOH | 96.5 | 94.7 |
| 3 | 4' | Hexyl hexanoate (2 mmol) | 1-Hexanol | ~100 | 99.4 |
| 4 | 4' | Butyl butyrate (2 mmol) | 1-Butanol | ~100 | 98.0 |
| 5 | 6' | Butyl butyrate (2 mmol) | 1-Butanol | 9.8 | 9.0 |

Dehydrogenation of diols to the corresponding lactones catalyzed by complexes 2' and 4'[a]

TABLE 28

Dehydrogenation of esters to lactones

| entry | cat. | diol | Lactone yield (%)[b] |
|---|---|---|---|
| 1 | 2' | 6-hydroxyhexan-2-ol | 6-methyltetrahydro-2H-pyran-2-one (33) |
| 2 | 4' | 6-hydroxyhexan-2-ol | 6-methyltetrahydro-2H-pyran-2-one (72) |
| 3 | 4' | 1,5-pentanediol | tetrahydro-2H-pyran-2-one (81) |
| 4 | 4' | 1,4-butanediol | γ-butyrolactone (86) |
| 5 | 4' | 1,2-benzenedimethanol | isobenzofuran-1(3H)-one (90) and 76[c] |

[a]Reaction conditions: catalyst (0.01 mmol), diol (3 mmol) and 2 mL of toluene were refluxed in an open system under argon for 48 hrs.
[b]Yields of the lactones were analyzed by $^1$H NMR of the reaction mixture.
[c]Isolated yield.

General procedure for the catalytic dehydrogenation of diols to lactones. Complexes 2' or 4' (0.01 mmol), diol (3 mmol), and toluene (2 mL) were taken in a Schlenk flask under an atmosphere of purified nitrogen in a Vacuum Atmospheres glove box. The flask was equipped with a condenser and the solution was refluxed with stirring in an open system under argon for 48 hrs. After cooling to room temperature, the yield of the lactones was determined by $^1$H NMR spectroscopy from the reaction mixture. The resulting mixture was concentrated in vacuo for about 3-4 h. The purification was performed on silica gel column using hexane-ethylacetate mixture as eluent. The products were analyzed by $^1$H NMR and the spectra were identical with the authentic samples.

Example 10

Experimental Section—Borohydride Complexes

General Procedures

All experiments with metal complexes and phosphine ligands were carried out under an atmosphere of purified nitrogen in a Vacuum Atmospheres glove box equipped with a MO 40-2 inert gas purifier or using standard Schlenk techniques. All solvents were reagent grade or better. All non-deuterated solvents were refluxed over sodium/benzophenone ketyl and distilled under argon atmosphere. Deuterated solvents were used as received. All solvents were degassed with argon and kept in the glove box over 4 Å molecular sieves. Complexes 1' and 3' were prepared as reported previously (Zhang 2004, Milstein). $^i$Pr-PNP (2,-6-bis-(di-iso-propylphosphinomethyl)pyridine) (Jansen et al.), $RuCl_2(PPh_3)_3$, (Holm et al.) were prepared according to literature procedures.

$^1H$, $^{13}C$ and $^{31}P$ NMR spectra were recorded at 400 or 500, 100 or 126, and 162 or 202 MHz, respectively, using a Bruker AMX-400 and AMX-500 NMR spectrometers. $^1H$ and $^{13}C\{^1H\}$ NMR chemical shifts are reported in ppm downfield from tetramethylsilane. $^{31}P$ NMR chemical shifts are reported in parts per million downfield from $H_3PO_4$ and referenced to an external 85% solution of phosphoric acid in $D_2O$. Abbreviations used in the NMR follow-up experiments: b, broad; s, singlet; d, doublet; t, triplet; q, quartet; m, multiplet, v, virtual. Elemental analyses were performed at Kolbe Laboratorium, Mulheim, Germany.

Synthesis of $[RuH(BH_4)(^tBu-PNP)]$ 2'.

To a suspension of complex 1' (58 mg, 0.05 mmol) in 2-propanol (10 ml) was added a very fine powder of $NaBH_4$ (9.5 mg, 0.25 mmol), and the mixture was stirred at room temperature for 12 hrs. The mixture was filtered and the orange filtrate was taken to dryness under vacuum. The residue was extracted with diethyl ether (3×5 mL). The ether solution was evaporated under vacuum to yield complex 2' as an orange solid. The complex was dried under vacuum overnight. Yield: 50 mg (98%).

$^{31}P\{^1H\}$ NMR ($C_6D_6$): 86.3 (s); $^1H$ NMR ($C_6D_6$): −16.09 (t, 1H, $J_{PH}$=18.0 Hz, Ru—H), −16.01 (br s, 1H, $BH_4$), −4.48 (br s, 1H, $BH_4$), 1.45 (t, 18H, $J_{PH}$=6.0 Hz, $P(C(CH_3)_3)$), 1.56 (t, 18H, $J_{PH}$=6.0 Hz, $P(C(CH_3)_3)_2$), 3.08 (dt, 2H, $J_{HH}$=16.0 Hz, $J_{PH}$=4.0 Hz, —CHHP), 3.19 (dt, 2H, $J_{HH}$=16.0 Hz, $J_{PH}$=4.0 Hz, —CHHP), 5.49 (br s, 2H, $BH_4$), 6.52 (d, 2H, $J_{HH}$=8.0 Hz, pyridine-H3, H5), 6.76 (t, 1H, $J_{HH}$=8.0 Hz, pyridine-H4). $^{13}C\{^1H\}$ NMR($C_6D_6$): 29.7 (s, $P(CH(CH_3)_2)_2$), 30.2 (s, $P(C(CH_3)_3)_2$), 35.0 (t, $J_{PC}$=6.5 Hz, $P(C(CH_3)_3)_2$), 35.6 (t, $J_{PC}$=5.0 Hz, $P(C(CH_3)_3)_2$), 39.0 (t, $J_{PC}$=7.0 Hz, $CH_2P$), 118.2 (t, $J_{PC}$=4.0 Hz, pyridine-C3, C5), 131.0 (s, Pyridine-C4), 165.1 (t, $J_{PC}$=4.5 Hz, Pyridine-C2, C6).

IR (KBr pellets): 2395, 2327, 2104, 2024, 1461, 1184 $cm^{-1}$.

Anal. Calcd. for $C_{23}H_{48}BNP_2Ru$: C, 53.90; H, 9.45. Found: C, 53.86; H, 9.49.

Synthesis of $[RuH(BH_4)(PNN)]$ 4'.

To a suspension of complex 3' (51 mg, 0.05 mmol) in 2-propanol (10 ml) was added a very fine powder of $NaBH_4$ (9.5 mg, 0.25 mmol), and the mixture was stirred at room temperature for 12 hrs. The mixture was filtered and the orange filtrate was taken to dryness under vacuum. The orange solid residue was extracted with diethyl ether (3×5 mL). The ether solution was evaporated under vacuum yielding complex 4' as a red-orange solid, which was dried under vacuum overnight. Yield: 40 mg (91%).

$^{31}P\{^1H\}$ NMR ($C_6D_6$): 116.7 (s); $^1H$ NMR ($C_6D_6$, 298 K): −16.24 (t, 1H, $J_{PH}$=28.0 Hz, Ru—H), −13.10 (Br s, 1H, $BH_4$), 0.84 (t, 3H, $J_{HH}$=6.0 Hz, $N(CH_2CH_3)_2$), 0.99 (t, 3H, $J_{HH}$=6.0 Hz, $N(CH_2CH_3)_2$), 1.28 (d, 9H, $J_{PH}$=12.0 Hz, $P(C(CH_3)_3)$), 1.43 (d, 9H, $J_{PH}$=12.0 Hz, $P(C(CH_3)_3)_2$), 2.31 (m, 1H, $N(CH_2CH_3)_2$), 2.49 (m, 1H, $N(CH_2CH_3)_2$), 2.71 (dd, 1H, $J_{HH}$=16.0 Hz, $J_{PH}$=8.0 Hz, —CHHP), 2.98 (dd, 1H, $J_{HH}$=16.0 Hz, $J_{PH}$=12.0 Hz, —CHHP), 3.05 (m, 1H, $N(CH_2CH_3)_2$), 3.41 (d, 1H, $J_{HH}$=14.0 Hz, NCHH-py), 3.54 (d, 1H, $J_{HH}$=14.0 Hz, NCHH-py), 3.73 (m, 1H, $N(CH_2CH_3)_2$), 6.30 (d, 1H, $J_{HH}$=8.0 Hz, pyridine-H5), 6.51 (d, 1H, $J_{HH}$=8.0 Hz, pyridine-H3), 6.71 (t, 1H, $J_{HH}$=8.0 Hz, pyridine-H4). $^1H$ NMR (Toluene-$d_8$, 243 K): −16.30 (t, 1H, $J_{PH}$=28.0 Hz, Ru—H), −13.21 (Br s, 1H, $BH_4$), −4.33 (br s, 1H, $BH_4$), 0.71 (br s, 3H, $N(CH_2CH_3)_2$), 0.92 (br s, 3H, $N(CH_2CH_3)_2$), 1.18 (d, 9H, $J_{PH}$=12.0 Hz, $P(C(CH_3)_3)$), 1.35 (d, 9H, $J_{PH}$=12.0 Hz, $P(C(CH_3)_3)_2$), 2.10 (m, 1H, $N(CH_2CH_3)_2$), 2.31 (m, 1H, $N(CH_2CH_3)_2$), 2.53 (dd, 1H, $J_{HH}$=16.0 Hz, $J_{PH}$=8.0 Hz, —CHHP), 2.82 (dd, 1H, $J_{HH}$=16.0 Hz, $J_{PH}$=8.0 Hz, —CHHP), 2.93 (br m, 1H, $N(CH_2CH_3)_2$), 3.15 (d, 1H, $J_{HH}$=16.0 Hz, NCHH-py), 3.33 (d, 1H, $J_{HH}$=16.0 Hz, NCHH-py), 3.37 (m, 1H, $N(CH_2CH_3)_2$), 4.69 (br s, 1H, $BH_4$), 5.00 (br s, 1H, $BH_4$), 6.16 (d, 1H, $J_{HH}$=8.0 Hz, pyridine-H5), 6.38 (d, 1H, $J_{HH}$=8.0 Hz, pyridine-H3), 6.62 (t, 1H, $J_{HH}$=8.0 Hz, pyridine-H4). $^{13}C\{^1H\}$ NMR ($C_6D_6$): 8.8 (s, $N(CH_2CH_3)_2$), 11.0 (s, $N(CH_2CH_3)_2$), 29.0 (d, $J_{PC}$=4.0 Hz, $P(C(CH_3)_3)_2$), 34.2 (d, $J_{PC}$=15.1 Hz, $P(C(CH_3)_3)_2$), 37.0 (d, $J_{PC}$=10.0 Hz, $P(C(CH_3)_3)_2$), 38.9 (d, $J_{PC}$=19.1 Hz, $PCH_2$—), 51.1 (s, $N(CH_2Me)_2$), 51.2 (s, $N(CH_2Me)_2$), 63.7 (s, py-$CH_2N$), 117.5 (s, Py-C3), 118.5 (s, Py-05), 128.8 (s, Py-C4), 159.9 (s, Py-C6), 163.7 (d, $J_{PC}$=4.0 Hz, py-C2).

IR (KBr pellets): 2378, 2311, 2096, 1956, 1469, 1177 $cm^{-1}$.

Anal. Calcd. for $C_{19}H_4OBN_2PRu$: C, 51.93; H, 9.18. Found: C, 51.86; H, 9.24.

Synthesis of $[RuCl_2(PPh_3)(^iPr-PNP)]$ 5'.

To a suspension of $Ru(PPh_3)_3Cl_2$ (480 mg, 0.5 mmol) in dry THF (20 ml) was added $^iPr$-PNP (170 mg, 0.5 mmol) and the mixture was stirred and heated at 65° C. for 6 hrs. The yellow solution was concentrated to 4 mL under vacuum and 20 mL of pentane were added to precipitate a yellow solid. The solid was isolated by filtration, washed with pentane (3×2 mL) and dried under vacuum to give 290 mg (75% yield) of 5 as a yellow solid.

$^{31}P$ NMR ($CD_2Cl_2$): 46.4 (d, $J_{PP}$=27.5 Hz), 43.2 (t, $J_{PP}$=27.5 Hz). $^1H$ NMR ($CD_2Cl_2$): 0.87 (q, 12H, $J_{PH}=J_{HH}$=8.0 Hz, $P(CH(CH_3)_2)_2$), 1.13 (q, 12H, $J_{PH}=J_{HH}$=8.0 Hz, $P(CH(CH_3)_2)_2$), 2.43 (m, 4H, $P(CH(CH_3)_2)_2$), 3.92 (t, 4H, $J_{PH}$=4.0 Hz, —$CH_2P$), 7.26 (m, 9H, $P(C_6H_5)_3$), 7.30 (d, 2H, $J_{HH}$=8.0 Hz, pyridine-H3, 5), 7.53 (t, 1H, $J_{HH}$=8.0 Hz, pyridine-H4), 7.91 (m, 6H, $P(C_6H_5)_3$). $^{13}C\{^1H\}$ NMR ($CD_2Cl_2$): 19.6 (s, $P(CH(CH_3)_2)_2$), 20.7 (s, $P(CH(CH_3)_2)_2$), 25.1 (t, $J_{PC}$=8.0 Hz, $P(CH(CH_3)_2)_2$), 38.9 (t, $J_{PC}$=10.1 Hz, $CH_2P$), 119.9 (s, Py-C3,5), 127.2 (d, $J_{PC}$=9.0 Hz, m-$C_6H_5$—P), 128.8 (s, p-$C_6H_5$—P), 135.0 (d, $J_{PC}$=9.0 Hz, o-$C_6H_5$—P), 136.7 (s, Py-C4), 140.4 (d, $J_{PC}$=36.2 Hz, ipso-$C_6H_5$—P), 164.8 (t, $J_{PP}$=4.0 Hz, py-C2,6).

Anal. Calcd. for $C_{37}H_{50}NP_3Cl_2Ru$: C, 57.44; H, 6.52. Found: C, 57.28; H, 6.53.

Synthesis of $[RuH(BH_4)(PPh_3)(^iPr-PNP)]$ 6'.

To a suspension of complex 5 (77 mg, 0.1 mmol) in 2-propanol (10 ml) was added a fine powder of $NaBH_4$ (9.5 mg, 0.25 mmol). The mixture was stirred at room temperature for 12 hrs and then filtered. The resulting yellow solid was washed with 2-propanol (3×1.5 mL) and then dissolved in benzene (10 mL) and the solution was filtered. The yellow filtrate was evaporated to dryness under vacuum, yielding complex 6' as a yellow solid which was dried under vacuum overnight to give 61 mg (85% yield). $^{31}P\{^1H\}$ NMR ($C_6D_6$): 61.6 (d, $J_{PP}$=29.2 Hz), 67.9 (t, $J_{PP}$=29.2 Hz). $^1H$ NMR ($C_6D_6$): −14.0 (q, 1H, $J_{PH}$=28.0 Hz, Ru—H), −0.84 (br s, 4H, $BH_4$), 0.91 (q, 6H, $J_{PH}=J_{HH}$=8.0 Hz, $P(CH(CH_3)_2)_2$), 0.87 (m, 12H, $J_{PH}=J_{HH}$=8.0 Hz, $P(CH(CH_3)_2)_2$), 1.18 (q, $J_{PH}=J_{HH}$=8.0 Hz, 6H, $P(CH(CH_3)_2)_2$), 1.44 (m, 2H, $P(CH(CH_3)_2)_2$), 1.77 (m, 2H, $P(CH(CH_3)_2)_2$), 2.85 (dt, 2H, $J_{HH}$=16.0 Hz, $J_{PH}$=4.0 Hz, -CHHP), 3.92 (dt, 2H, $J_{HH}$=16.0 Hz, $J_{PH}$=4.0 Hz, —CHHP), 6.56 (d, 2H, $J_{HH}$=8.0 Hz, pyridine-H3, 5), 6.79 (t, 1H, $J_{HH}$=8.0 Hz, pyridine-H4), 7.01 (d, 3H, $J_{HH}$=8.0 Hz, $P(C_6H_5)_3$), 7.12 (t, 6H, $J_{HH}$=8.0 Hz, $P(C_6H_5)_3$), 8.18 (t, 6H, $J_{HH}$=8.0 Hz, $P(C_6H_5)_3$). $^{13}C\{^1H\}$ NMR ($C_6D_6$): 18.0 (s, P(CH($CH_3$)$_2$)$_2$), 18.5 (s, P(CH($CH_3$)$_2$)$_2$), 19.6 (s, P(CH($CH_3$)$_2$)$_2$), 20.8 (s, P(CH($CH_3$)$_2$)$_2$), 25.6 (t, $J_{PC}$=8.0 Hz, P(CH($CH_3$)$_2$)$_2$), 26.4 (t, $J_{PC}$=11.6 Hz, $CH_2$P), 39.2 (t, $J_{PC}$=6.0 Hz, P(CH($CH_3$)$_2$)$_2$), 118.4 (t, $J_{PC}$=2.5 Hz, Py-C3,5), 127.1 (d, $J_{PC}$=9.0 Hz, m-$C_6H_5$—P), 128.8 (s, p-$C_6H_5$—P), 134.2 (s, Py-C4), 135.7 (d, $J_{PC}$=10.1 Hz, o-$C_6H_5$—P), 142.0 (d, $J_{PC}$=36.2 Hz, ipso-$C_6H_5$—P), 163.7 (t, $J_{PC}$=4.5 Hz, py-C2,6).

IR (KBr pellet): 2361, 2293, 2246, 1884, 1458, 1060 $cm^{-1}$.

Anal. Calcd. for $C_{37}H_{55}BNP_3Ru$: C, 61.84; H, 7.72. Found: C, 61.98; H, 7.66.

Typical Procedures for the Catalytic Dehydrogenation of Alcohols (a) Complexes 2' (0.01 mmol), 4' (0.01 mmol) or 6' (0.01 mmol) were dissolved in the neat primary or secondary alcohol (10 mmol). The flask was equipped with a condenser and the solution was heated with stirring in an open system under argon at the specified temperature and time (Tables 18 and 19). After cooling to room temperature, the product aldehydes, esters or ketones were determined by GC, using mesitylene or (in the case of 1-butanol) benzene as internal standards, employing a Carboxen 1000 column on a HP 690 series GC system.

(b) A solution containing the catalyst (0.01 mmol) (complexes 2', 4' or 6') and the alcohol (10 mmol) in toluene (2 mL) was heated in a flask equipped with a reflux condenser under argon in an open system at the specified temperatures and times (Tables 2 and 3). After cooling to room temperature, the products were determined by GC using mesitylene or benzene (for 1-butanol) as internal standards, employing a Carboxen 1000 column on a HP 690 series GC system.

X-Ray Crystal Structure Determination of 2'.

The crystal was mounted on a nylon loop and flash frozen in a nitrogen stream at 120K. Data were collected on a Nonius Kappa CCD diffractometer mounted on a FR590 generator equipped with a sealed tube with Mo Kα radiation (λ=0.71073 Å) and a graphite monochromator. The four structures were solved using direct methods with SHELXS-97 based on $F^2$.

Complex 2':

$C_{23}H_{48}BNP_2Ru$, yellow plate, 0.40×0.40×0.30 $mm^3$, monoclinic, P2$_1$ (No. 4), a=12.541 (3) Å, b=15.314 (3) Å, c=15.131 (3) Å, β=111.85 (3)°, V=2697.3 (9) $Å^3$, Z=4, fw=512.4, F(000)=1088, $D_c$=1.262 Mg/$m^3$, μ=0.709 $mm^{-1}$. The final cycle of refinement based on $F^2$ gave an agreement factor R=0.027 for data with I>2σ(I) and R=0.030 for all data (6375 reflections) with a goodness-of-fit of 1.080. Idealized hydrogen atoms were placed and refined in the riding mode, with the exception of Hru and Hb1-Hb4 which were located in the difference map and refined independently.

Example 11

Synthesis of Complex 9 and Catalysis by It

Scheme 39

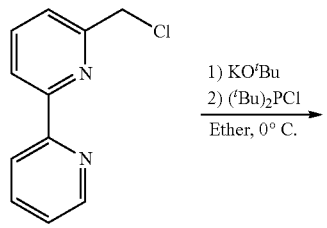

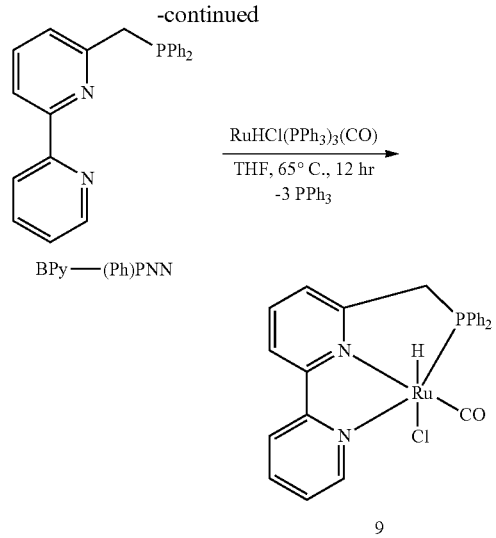

(a) Synthesis of the Ligand BPy-(Ph)PNN (10)

An oven-dried 250 mL three-necked round bottom flask equipped with an argon inlet, a stirring bar, dropping funnel and one rubber septum was cooled under a stream of argon. The flask was then charged with chlorodiphenylphosphine (1.08 g, 6 mmol) in 30 mL dry ether. The solution was cooled to 0° C. and a THF solution (5 mL) of potassium tert-butoxide (74 mg, 6.6 mmol) was added dropwise via syringe during 10 min. The resulting brown coloured mixture was stirred for 1 hr at 0° C. and then a solution of 6-chloromethyl-2,2'-bipyridine (1.02 g, 5 mmol) in 20 mL dry ether was added dropwise (~15 min) to it. The stirring was continued for a further 1 hr at the same temperature and the mixture was allowed to slowly warm up to room temperature and stirred overnight. To this reaction mixture was added 20 mL of degassed water and the ether phase was separated under $N_2$ atmosphere. The aqueous phase was extracted with ether (2×20 mL). The combined ether solutions were dried over anhydrous $Na_2SO_4$, filtered under $N_2$ pressure, and the solvent was removed under vacuum to get brownish-white solid. This was purified by column chromatography in the nitrogen glove box (basic alumina; hexane:ether (10:1) as eluent) to yield 1.08 g (61%) of 6-di-phenyphosphinomethyl-2,2'-bipyridine (BPy-(Ph)PNN) as a white crystalline solid.

$^{31}$P {1H}NMR (122 MHz, $CD_2Cl_2$): −8.28 (s). $^1$H NMR (300 MHz, $CD_2Cl_2$): 3.81 (s, 2H, P—CH2), 7.13 (d, JHH=7.5 Hz, 1H, H-5), 7.32 (ddd, JHH=7.5 Hz, JHH=4.8H, JPH=1.2 Hz, 1H, H-5'), 7.40-7.45 (m, 6H, Ph-H), 7.58-7.63 (m, 4H, Ph-H), 7.69 (t, JHH=7.8 Hz, 1H, H-4), 7.80 (dt, JHH=7.8 Hz, JHH=2.1 Hz, 1H, H-4'), 8.28 (br d, JHH=8 Hz, 2H, H-3 and 11-3'), 8.68-8.70 (m, 1H, H-6'). $^{13}$C{1H}NMR (125 MHz, CD2Cl2): 38.35 (d, JPC=16.3 Hz, P—CH2), 118.07 (s, C-3), 121.02 (s, C-3'), 123.55 (s, C-5'), 123.61 (d, JPC=8.4 Hz, C-5), 128.34 (s, Ph-C), 128.40 (Ph-C), 128.65 (s, Ph-C), 132.90 (s, Ph-C), 133.05 (s, Ph-C), 136.61, (s, C-4'), 136.97 (s, C-4), 138.72 (d, JPC=15.0 Hz, Ph-C(quar)), 149.02 (s, C-6'), 155.49 (s, C-2), 156.22 (s, C-2'), 157.64 (d, JPC=7.5, C-6). Anal. Calcd. for $C_{23}H_{19}N_2P$: C, 77.95; H, 5.40. Found: C, 78.13; H, 5.61. MS (ESI, MeOH): 355 (100%, M+1)+). Assignment of signals was confirmed by DEPT 135, COSY, and HSQC.

(b) Synthesis of Complex 9

To an oven dried 25 mL pressure vessel equipped with magnetic stirring bar was added ligand, BPy-(Ph)PNN (10)

(148 mg, 0.42 mmol), RuHCl(CO)(PPh$_3$)$_3$ (382 mg, 0.4 mmol), and 8 mL dry THF in a nitrogen glove box. The flask was sealed and heated at 65° C. for 12 hr with stirring outside the glove box, then cooled to room temperature to lead to reddish-brown solid. It was reintroduced to the glove box, and the solvent was decanted and the solid thus obtained was washed with ether (3×5 mL), then dried under vacuum to give analytically pure complex RuHCl(CO)(BPy-(Ph)PNN) (184 mg, 84%). $^{31}$P{1H}NMR (202 MHz, CD$_2$Cl$_2$): 69.44 (s). $^1$H NMR (500 MHz, CD$_2$Cl$_2$): −14.09 (d, JPH=25.5 Hz, 1H, Ru—H), 4.38-4.50 (m, 2H, P—CH2), 7.39-7.40 (m, 3H, Ph-H), 7.46-7.51 (m, 4H, Ph-H), 7.60-7.64 (m, 3H, Ph-H), 7.87-7.90 (m, 2H, H-5 and H-5'), 7.57 (d, JHH=7.8 Hz, 1H, H-5), 7.93-7.97 (m, 2H, H-4 and H-4'), 8.04 (d, JHH=8.0 Hz, 1H, H-3), 8.10 (d, JHH=8.0 Hz, 1H, H-3'), 9.22 (br s, 1H, H-6'). $^{13}$C{1H}NMR (125 MHz, CD2Cl2): 45.52 (d, JPC=26.3 Hz, P—CH2), 120.04 (s, C-3), 122.65 (s, C-3'), 123.09 (d, JPC=11.3, C-5), 126.21 (s, C-5'), 128.16 (s, Ph-C), 128.24 (s, Ph-C), 128.28 (s, Ph-C), 128.37 (s, Ph-C), 129.82 (s, Ph-C), 130.37 (s, Ph-C), 131.60 (d, JPC=11.3 Hz, Ph-Ca (ortho)), 133.46 (d, JPC=11.3 Hz, Ph-Cb(ortho)), 133.78 (d, JPC=43.8 Hz, Ph-Cb(quar)), (136.64, (s, C-4'), 137.39 (s, C-4), 139.86 (d, JPC=50.0 Hz, Ph-Ca(quar)), 153.39 (s, C-6'), 154.67 (s, C-2), 156.05 (s, C-2'), 160.04 (d, JPC=6.3, C-6). 206.53 (d, JPC=7.5 Hz, Ru—CO). IR (KBr, pellet): 1915 (vCO) cm$^{-1}$. MS (ESI, CH3CN): 519 (100%, (M−1)$^+$) and MS (ESI, CH$_3$OH): 485 (100%, (M-Cl)$^+$).

Some Examples of Reactions Catalyzed by Complex 9:

Scheme 40

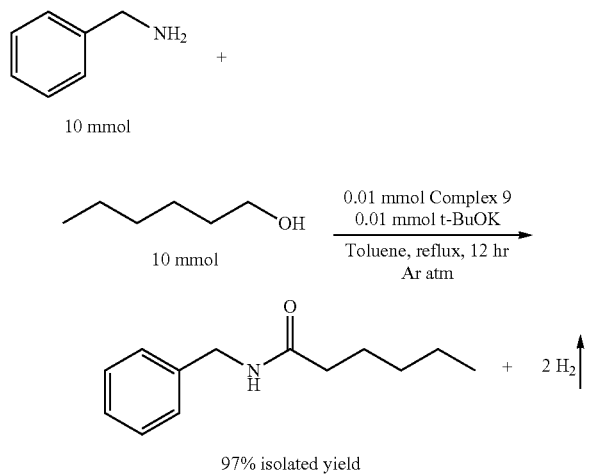

Scheme 41

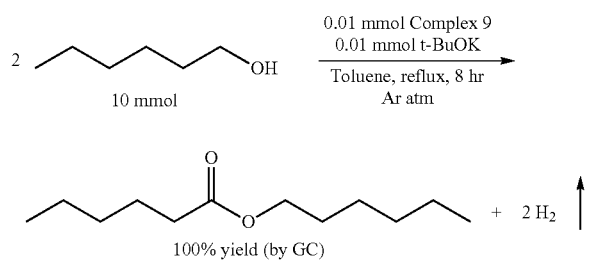

Scheme 42

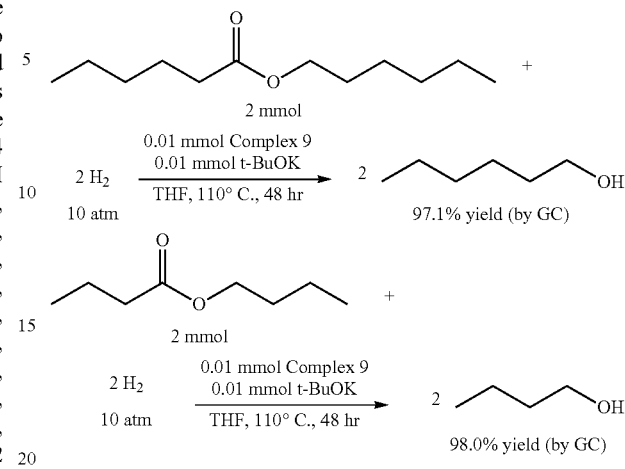

Example 12

Direct Synthesis of Amides from Esters using Ruthenium-Pincer Catalyst With Liberation of H$_2$ Under Neutral Conditions PNN-type pincer ruthenium complexes used for catalytic conversion of esters and amines into amides:

Scheme 43

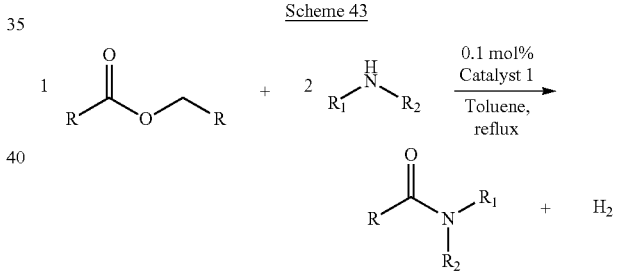

The applicants of the present invention have discovered that amide synthesis from esters and amines can be achieved using the ruthenium PNN catalyst 1. The reaction is general, efficient, environmentally benign and atom economical. It proceeds under neutral conditions without acid/base/activators/promoters. Notably, this reaction affords with amide in high TON (1000) and H$_2$ as the only byproduct (Scheme 43).

When a benzene solution containing 10 mmol of pyrrolidine, 10 mmol of ethyl acetate and 0.01 mmol of complex 1 was refluxed under Argon atmosphere, quantitative conversion of pyrrolidine was observed by GC after 28 hrs, to yield 98% of N-acetyl pyrrolidine after column purification (Table 29, entry 1). The N-acetyl pyrrolidine was characterized by NMR and GC-MS. Similar results were obtained in toluene. Reaction of ethyl acetate with morpholine in benzene under reflux resulted after 36 hrs in 79% conversion with the isolation of the corresponding amide in 77% yield (Table 29, entry 2). Refluxing of 1-methyl piperazine, ethyl acetate and benzene in the presence of complex 1 provides the corresponding amide in 56% yield with the conversion of the ester being 59% (Table 29, entry 3).

Various esters and amines reacted similarly. Refluxing a toluene solution containing butyl butyrate (5 mmol), piperidine (10 mmol) and 0.1 mol % of the PNN complex 1 under argon atmosphere for 19 hrs resulted in 100% conversion of piperidine as observed by GC analysis, with the exclusive formation of the 1-(piperidin-1-yl)butan-1-one in 94% yield after isolation from alumina column chromatography (Table 29, entry 4). The product was completely characterized by NMR spectroscopy. Unlike the traditional methods, this reaction does not form any alcohol as by-product, resulting in the irreversible, unique incorporation of both the acyl and alkoxo parts of the starting ester into the product amide. Significantly the TON of ester-amide exchange reaction was high (1000). Similarly, refluxing the toluene solution containing butyl butyrate, morpholine or N-methyl piperazine in the presence of complex 1 resulted in 100% conversion of the amine with the isolation of the amides in 95 and 94% yields, respectively. Refluxing of excess of butyl butyrate and piperazine in toluene led to bis-acylation of the piperazine, providing the corresponding amide in 61% yield.

To explore the synthetic utility of this reaction, pentyl pentanoate was reacted with various amines. The reaction of pentyl pentanoate with piperidine gave 100% conversion with the isolation of the amide in 96% yield. Morpholine and N-methyl piperazine furnished the respective amide in 96 and 94% isolated yield.

Next, reactions were studied with primary amines. The reaction of ethyl butyrate and hexyl amine in the presence of 0.1 mol % of 1 in refluxing toluene led to 100% conversion of the hexyl amine with the isolation of 97% of the corresponding amide as the only product. Similarly, reaction of pentyl pentanoate and 4-methylbenzyl amine in refluxing toluene resulted in 100% conversion with isolation of corresponding amide in 98% yield. These reactions did not lead any alcohol as waste product.

The reactions were also studied in absence of solvent. Thus, heating pentylpentanoate, piperidine and complex 1 at 135° C. resulted in 52% conversion.

TABLE 29

Amination of esters catalyzed by the ruthenium complex 1[a]

| Entry | Ester | Amine | Time (hrs) | Conv. of amine | Isolated Yield (%) |
|---|---|---|---|---|---|
| 1 | ethyl acetate | pyrrolidine | 26 | 100 | 1-(pyrrolidin-1-yl)ethan-1-one, 99 |
| 2 | ethyl acetate | morpholine | 36 | 79 | 1-morpholinoethan-1-one, 77 |
| 3 | ethyl acetate | N-methylpiperazine | 24 | 59 | 1-(4-methylpiperazin-1-yl)ethan-1-one, 56 |
| 4 | butyl butyrate | piperidine | 19 | 100 | 1-(piperidin-1-yl)butan-1-one, 94 |

TABLE 29-continued

Amination of esters catalyzed by the ruthenium complex 1[a]

| Entry | Ester | Amine | Time (hrs) | Conv. of amine | Isolated Yield (%) |
|---|---|---|---|---|---|
| 5 | butyl butanoate | morpholine | 21 | 100 | 1-(butanoyl)morpholine — 95 |
| 6 | butyl butanoate | N-methylpiperazine | 24 | 100 | 1-butanoyl-4-methylpiperazine — 94 |
| 6 | butyl butanoate | piperazine | 36 | 100 | 1,4-dibutanoylpiperazine — 61 |
| 7 | pentyl pentanoate | piperidine | 19 | 100 | 1-pentanoylpiperidine — 96 |

TABLE 29-continued
Amination of esters catalyzed by the ruthenium complex 1[a]
| Entry | Ester | Amine | Time (hrs) | Conv. of amine | Isolated Yield (%) |
|---|---|---|---|---|---|
| 8 | 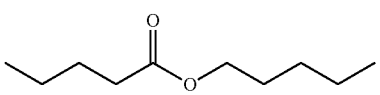 | 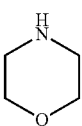 | 26 | 100 | 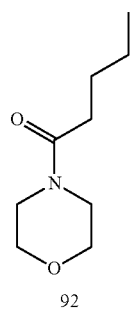 92 |
| 9 | 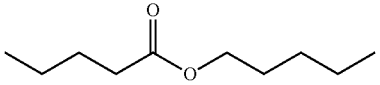 | 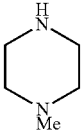 | 24 | 100 | 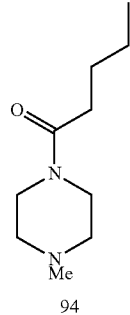 94 |
| 10 | 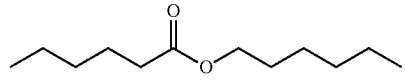 |  | 18 | 100 | 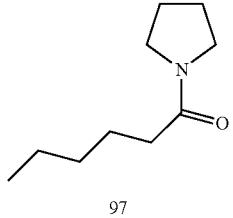 97 |
| 11 | 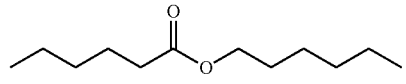 |  | 26 | 100 | 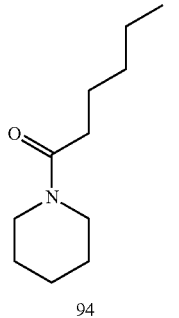 94 |

TABLE 29-continued

Amination of esters catalyzed by the ruthenium complex 1[a]

| Entry | Ester | Amine | Time (hrs) | Conv. of amine | Isolated Yield (%) |
|---|---|---|---|---|---|
| 12 | (pentanoate ester) | morpholine | 18 | 100 | (morpholine amide) 93 |
| 13 | (butanoate ester) | hexylamine | 24 | 100 | (N-hexyl butanamide) 97 |
| 14 | (pentanoate ester) | 4-methylbenzylamine | 18 | 100 | (N-(4-methylbenzyl) pentanamide) 98 |

[a]Complex 1 (0.01 mmol), ester (5 mmol), amine (10 mmol) and toluene/benzene (3 ml) were refluxed at an oil bath temperature of 135° C. in a Schlenk tube. Conversion of amine was analyzed by GC using m-xylene as internal standard.

In summary, acylation of amines using esters as the acylating partner is efficiently catalyzed by complex 1 under neutral conditions. The use of symmetrical esters results in the incorporation of both the acyl and alkoxo parts of the substrate ester into the product amide with liberation of $H_2$. This offers an environmentally benign, atom economical method for amide synthesis from esters without any waste generation. This catalytic cycle produces a high turnover number (1000) and both primary and secondary amines can be used.

Example 13

Ruthenium-Pincer Catalyzed Acylation of Alcohols Using Esters with Liberation of $H_2$ Under Neutral Conditions The acylation of esters with secondary alcohols can be carried out selectively to give the mixed ester using the PNN catalyst 1. The reaction is general, efficient, and environmentally benign. It proceeds under neutral conditions without acids or bases, activators, or molecular sieves. Uniquely, when a symmetrical ester (such as ethyl acetate) is reacted with a secondary alcohol, the only co-product is molecular hydrogen, unlike the generally employed transesterification reaction which gives an alcohol co-product (or its derivative) (Scheme 44).

Scheme 44. Acylation of alcohols using esters.

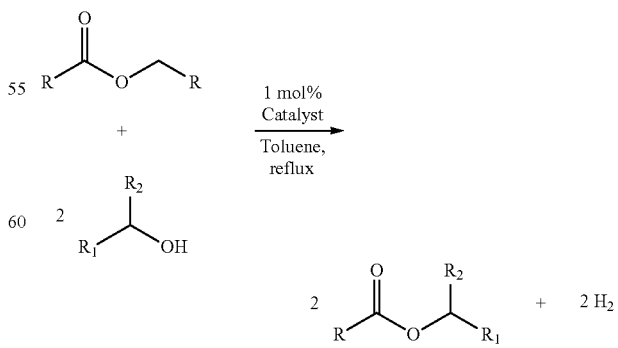

When a benzene solution containing 15 mmols of cyclohexanol, 5 mmols of ethyl acetate and 0.05 mmols of complex 1 was refluxed under argon atmosphere, GC analysis after 28 hrs showed that all of the ethyl acetate disappeared and cyclohexyl acetate was formed as a single product (Table 30, entry 1). $^1$H NMR and GC-MS of the isolated product were identical to cyclohexyl acetate prepared by refluxing neat acetic anhydride with cyclohexanol.

Likewise, refluxing a toluene solution containing one equivalent of hexyl hexanoate, 2 equivalents of cyclohexanol and 1 mol % of the PNN complex 1 under argon atmosphere for 20 h resulted in 84% conversion of hexyl hexanoate as determined by GC analysis, with the exclusive formation of the ester cyclohexyl hexanoate in 83% yield (Table 30, entry 2). Notably, unlike the traditional transesterification methods, this reaction does not form an alcohol product; rather, an irreversible incorporation of both the acyl and alkoxo parts of the starting ester into the product ester takes place. While 2 equivalents of the alcohol with respect to the ester are sufficient, somewhat higher yields are obtained when 3 equivalents of alcohol were used. Thus, reaction of 3 equivalents of cyclohexanol with hexyl hexanoate resulted after 26 h in 96% conversion with 95% yield of cyclohexyl hexanoate, as observed by GC, and confirmed by GC-MS by comparison with an authentic sample (Table 30, entry 3). The pure product was isolated by evaporation of the solvent followed by passing through a basic alumina plug and analysis by NMR and GC-MS. Use of the PNP complexes 2 or 3 resulted after 20 h in 58% or 17% yield of cyclohexyl hexanoate, respectively. Studying the scope of this new reaction with regard to the secondary alcohol, reaction of hexyl hexanoate with cyclopentanol in the presence of 1 mol % 1 was carried out. After 26 h reflux in toluene, cyclopentyl hexanoate (70% yield) was formed, with 71% conversion of hexyl hexanoate (Table 30, entry 4). Similarly, upon reaction of hexyl hexanoate with excess of 1-phenylethanol, 50% conversion of hexyl hexanoate with the formation of 49% of the acylated product was observed (Table 30, entry 5). The lower conversion of the ester is a result of facile dehydrogenation of 1-phenylethanol to acetophenone (49%). Because of the expected easy dehydrogenation of the isopropyl alcohol to acetone, transesterification with this alcohol was performed in a closed vessel, to retard this dehydrogenation process. Thus, heating hexyl hexanoate with excess of isopropyl alcohol resulted after 19 h in 83% conversion of hexyl hexanoate with the formation of isopropyl hexanoate in 67% yield (entry 6). The reaction of hexyl hexanoate and 3-pentanol led to 91% conversion of the ester with formation of 3-pentyl hexanoate in 90% yield after 26 h reflux (entry 7).

Exploring further the scope with regard to the ester substrate, pentyl pentanoate was reacted with cyclohexanol, resulting in 93% conversion with the formation of 93% cyclohexyl pentanoate (entry 8). Like in the case of hexyl hexanoate, the presumably formed pentanol intermediate is converted into pentyl pentanoate with the liberation of $H_2$. Similarly, treatment of pentyl pentanoate with cyclopentanol, 1-phenylethanol and 3-pentanol, furnished 87, 51, 91% conversion of pentyl pentanoate, respectively, with the predominant formation of the corresponding cross-ester as the product in 85, 49, 90% yields, respectively (entries 9-11).

Next we studied the reaction of butyl butyrate with various secondary alcohols. Reaction of 5 mmol of butyl butyrate with 15 mmol of cyclohexanol led to 93% conversion of the ester with the formation of 92% of cyclohexyl butyrate after 34 h (entry 12). Upon refluxing of butyl butyrate with cyclopentanol, after 28 hrs 75% conversion of the ester, with formation of 74% cyclopentyl butyrate were observed (entry 13). In a similar reaction with 1-phenylethanol or 3-pentanol, 41 and 77% conversion, respectively, into the product was noted by GC analysis after 36 h (entries 14 and 15).

These reactions were also studied with unsymmetrical esters. The reaction of ethyl butyrate with 3-pentanol in the presence of 1 mol % of 1 under refluxing toluene led to 75% conversion of ethyl butyrate with the formation of 73% of 3-pentyl butyrate as the exclusive product (entry 16). Traces of 3-pentyl acetate, resulting from reaction with the formed ethanol, were also observed. The remaining ethanol probably evaporated from the reaction mixture under the reflux conditions. Similarly, the reaction of methyl hexanoate with cyclohexanol results in 42% conversion after 17 h with the formation of 42% of cyclohexyl hexanoate (entry 17).

Since the dehydrogenation of the secondary alcohol to ketone is slower than the dehydrogenative coupling of the primary alcohol to ester, most of the secondary alcohol reacts with the ester, although some ketone resulting from excess alcohol was observed. The slow reaction of the secondary alcohol with PNN complex may be due to the steric hindrance.

TABLE 30

Acylation of alcohols catalyzed by the ruthenium complex 1[a)]

| Entry | Ester | alcohol | Time (hrs) | Conv. of ester % | Yield % |
|---|---|---|---|---|---|
| 1[b)] | 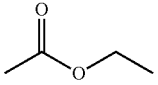 | 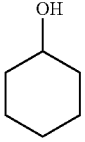 | 28 | 100 | 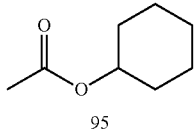 95 |
| 2[c)] | 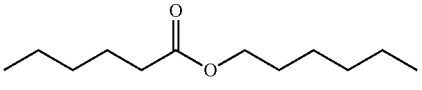 | 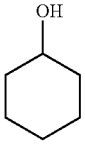 | 20 | 84 | 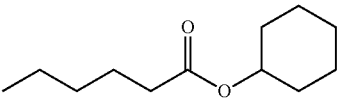 83 |

TABLE 30-continued
Acylation of alcohols catalyzed by the ruthenium complex 1[a]
| Entry | Ester | alcohol | Time (hrs) | Conv. of ester % | Yield % |
|---|---|---|---|---|---|
| 3 | 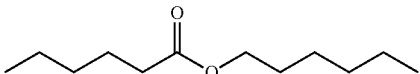 | 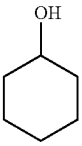 | 26 | 96 (cat 1) 58 (cat. 2) 17 (cat. 3) | 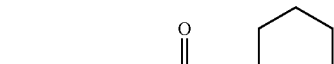 95 (cat 1) |
| 4 | 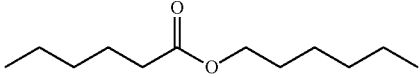 | 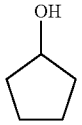 | 26 | 71 | 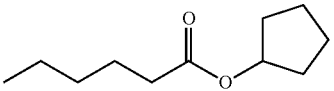 70 |
| 5 | 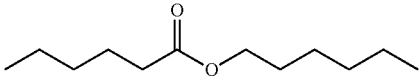 | 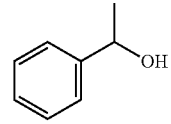 | 36 | 50 | 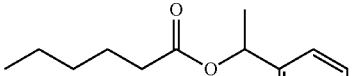 49 |
| 6[d] | 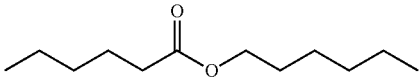 |  | 19 | 83 | 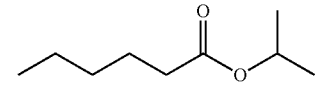 67 |
| 7 | 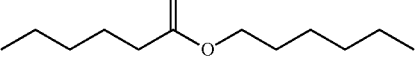 | 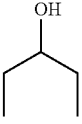 | 26 | 91 | 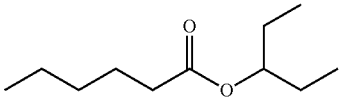 90 |
| 8 | 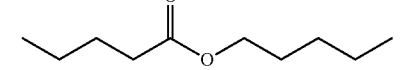 | 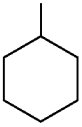 | 36 | 93 | 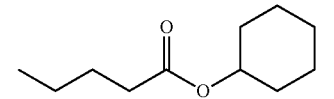 93 |
| 9 | 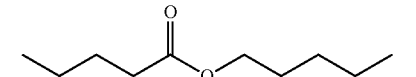 | 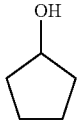 | 36 | 87 |  85 |
| 10 |  | 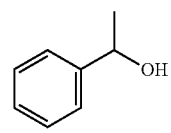 | 18 | 51 | 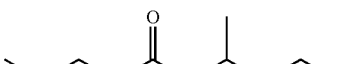 49 |
| 11 |  | 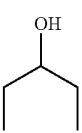 | 26 | 91 | 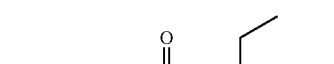 90 |

TABLE 30-continued

Acylation of alcohols catalyzed by the ruthenium complex 1[a]

| Entry | Ester | alcohol | Time (hrs) | Conv. of ester % | Yield % |
|---|---|---|---|---|---|
| 12 | butyl butyrate | cyclohexanol | 34 | 93 | cyclohexyl butyrate, 92 |
| 13 | butyl butyrate | cyclopentanol | 28 | 75 | cyclopentyl butyrate, 74 |
| 14 | butyl butyrate | 1-phenylethanol | 36 | 41 | 1-phenylethyl butyrate, 39 |
| 15 | butyl butyrate | 3-pentanol | 18 | 77 | 3-pentyl butyrate, 76 |
| 16[e] | ethyl butyrate | 3-pentanol | 20 | 75 | 3-pentyl butyrate, 73 |
| 17 | methyl hexanoate | cyclohexanol | 17 | 42 | cyclohexyl hexanoate, 42 |

[a]Complex 1 (0.05 mmol), ester (5 mmol), alcohol (15 mmol) and toluene (3 ml) were refluxed/heated at an oil bath temperature of 135° C. under argon. Conversion of ester and yield of product were analyzed by GC using m-xylene or benzene as internal standards. A small amount of the secondary alcohol was converted into the corresponding ketone.
[b]Benzene was used as solvent. Efficient cooling of the reflux condenser is required to avoid losses of ethyl formate.
[c]1 (0.05 mmol), hexyl hexanoate (5 mmol), cyclohexanol (10 mmol) and toluene (3 ml) were used.
[d]a closed system and 3 ml of 2-propanol were used. An equivalent amount of 1-hexanol (67%) was also detected.
[e]m-xylene was used as solvent and benzene as internal standard.

Experimental Section
General Procedure for the Catalytic Acylation of Alcohols:

Complex 1 (0.05 mmol), ester (5 mmol), alcohol (15 mmol) and toluene (3 mL) were added to Schlenk flask under an atmosphere of nitrogen in a glove box. The flask was equipped with a condenser and the solution was refluxed with stirring in an open system under argon for the specified time (Table 30). In the case of isopropanol, the reactions were performed in a closed system at 135° C. The reaction products were analyzed by GC-MS. After cooling to room temperature, m-xylene (1 mmol) or benzene (1 mmol) were added as internal standards to the reaction mixture and the products were quantitatively analyzed by GC using a Carboxen 1000 column on a HP 690 series GC system or HP-5 cross linked 5% PH ME Siloxane column (30 m×0.32 mm×0.25 μm film thickness) on a HP 6890 series GC system. In the reaction of cyclohexanol and esters, evaporation of the solvent, followed by purification over basic alumina column chromatography afforded the pure transesters. $^1$H NMR of the products isolated from the catalysis was identical with the literature.

Example 14

Synthesis of Cyclic Dipeptides and Pyrazines from β-Aminoalcohols

A. Formation of Cyclic Dipeptides

Dehydrogenative coupling of β-aminoalcohols can lead to cyclic dipeptide formation (Scheme 45), except in case of R=H, Me (in which case linear polypeptides are the main products; in case of R=Me, a small amount of cyclic dipeptide is also formed).

Scheme 45

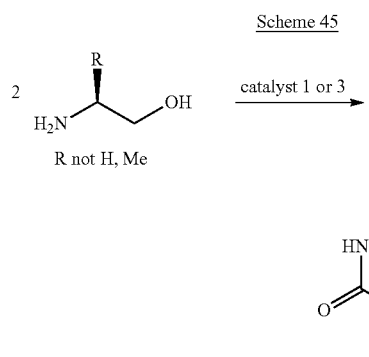

R not H, Me

Refluxing a dioxane solution of (S)-2-amino-4-methylpentan-1-ol with complex 1 (1 mol %) led to 64% isolated yield of the cyclic dipeptide, 3,6-diisobutylpiperazine-2,5-dione 7b after workup (Table 31, entry 1). The product structure was confirmed by MS, NMR spectroscopies.

Upon refluxing a dioxane solution containing 2 mmol of (2S,3S)-2-amino-3-methylpentan-1-ol and 0.02 mmol of catalyst 1 for 19 hrs and cooling the reaction mixture, the solid product precipitated and was filtered off and dried under vacuum to give pure 3-(sec-butyl)-6-(sec-butyl)piperazine-2,5-dione 7c in 72% yield (Table 31, entry 2). The structure was confirmed by NMR and MS spectroscopies. Under the same conditions, cyclic peptidation of (S)-2-amino-3-methylbutan-1-ol led to 3,6-diisopropylpiperazine-2,5-dione 7d as an insoluble solid which separated from the reaction mixture and was isolated by filtration and dried under vacuum to give 78% of (3S,6S)-3,6-diisopropylpiperazine-2,5-dione 7d (Table 31, entry 3). The optical rotation of the pure product)(−52° was essentially the same as reported in the literature)(−54°). Thus, under these experimental condition, no racemization took place.

The reaction of (S)-2-amino-3-phenylpropan-1-ol and 1 in refluxing dioxane led to 90% conversion with the isolation of the corresponding 3,6-dibenzylpiperazine-2,5-dione 7e in 72% yield (Table 31, entry 4). Reaction of 2-amino-2-methylpropan-1-ol under the same conditions yielded 100% conversion with isolation of the corresponding cyclic dipeptide 3,3,6,6-tetramethylpiperazine-2,5-dione 7f in 92% yield (Table 31, entry 5).

Tricyclic ring systems represent an important structural motif in many naturally existing alkaloids. Refluxing a dioxane solution of (S)-pyrrolidin-2-yl-methanol in the presence of catalyst 1 followed by solvent evaporation, hexane addition to the crude solid, and its isolation by filtration and washing with hexane led to octahydrodipyrrolo[1,2-a:1',2'-d]pyrazine-5,10-dione 7g in 99% isolated yield (Table 31, entry 6).

TABLE 31

Synthesis of cyclic dipeptides from β-aminoalcohols catalyzed by complex 1.

| Entry | Catalyst | Aminoalcohol | cyclic dipeptide | Isolated Yields (%) |
|---|---|---|---|---|
| 1 | 1 | | 7b | 64 |
| 2 | 1 | | 7c | 72 |
| 3 | 3 | | 7d | 87 |
| 4 | 3 | | 7e | 82 |

TABLE 31-continued

Synthesis of cyclic dipeptides from β-aminoalcohols catalyzed by complex 1.

| Entry | Catalyst | Aminoalcohol | cyclic dipeptide | Isolated Yields (%) |
|---|---|---|---|---|
| 5 | 1 | (structure) | 7f | 92 |
| 6 | 1 | (structure) | 7g | 99 |

[a] Complex 1 or 3 (0.02 mmol), aminoalcohol (2 mmol) and dioxane (2 ml) were refluxed under argon (oil bath temperature of 135° C.) for 19 h.

B. Formation of Pyrazines

Pyrazines are biologically important organic compounds and their synthesis is of industrial significance. When the RuPNP complex 2 was used as catalyst, pyrazine derivatives were obtained from β-amino alcohols (Scheme 46). Thus, a toluene solution of isoleucinol with complex 2 (1 mol %) was vigorously refluxed under argon for 24 hrs resulting in complete conversion of isoleucinol. The solvent was evaporated under vacuum and the residue was subjected to silica-gel column chromatography to afford 2,6-diiso-butyl pyrazine 8a in 53% yield (Table 32, Entry 1). $^1$H NMR exhibits the characteristic aromatic CH at 8.27 ppm and GC-MS confirms the respective molecular weight. The same reaction was also conducted by reflux under air using complex 2, resulting in 48% isolated yield of 8a. The similarity in yields of 8a under argon and under air indicates that air does not play a role as oxidant in the dehydrogenation of the presumed intermediate 1,4-dihydropyrazine to form the pyrazine. Significantly, no cyclic dipeptide was obtained under these conditions. Similar results were obtained with other aminoalcohols. Thus, toluene solutions of (S)-2-amino-3-methylbutan-1-ol, (S)-2-amino-4-methylpentan-1-ol, and (S)-2-amino-2-phenylethanol, were vigorously refluxed (bath temperature 165° C.) for 24 hrs while monitoring reaction progress by GC-MS. After complete disappearance of the amino alcohol, the crude product was purified by column chromatography to get the corresponding pyrazine products 8b-d (Table 32).

Scheme 46

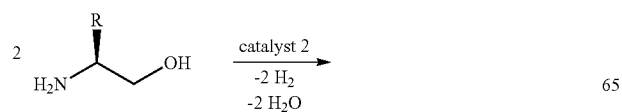

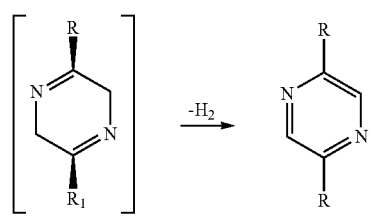

TABLE 32

Synthesis of pyrazines from β-aminoalcohols catalyzed by the ruthenium PNP complex 2.(a)

| Entry | β-Aminoalcohol | Pyrazine | Isolated Yields (%) |
|---|---|---|---|
| 1 | (structure) | 8a | 53 |
| 2 | (structure) | 8b | 35 |
| 3[b] | (structure) | 8c | 38 |

TABLE 32-continued

Synthesis of pyrazines from β-aminoalcohols catalyzed by the ruthenium PNP complex 2.(a)

| Entry | β-Aminoalcohol | Pyrazine | Isolated Yields (%) |
|---|---|---|---|
| 4 | | 8d | 45 |
| 5[c] | | 8a | 48 |

(a)Complex 2 (0.02 mmol), aminoalcohol (2 mmol) and toluene (2 ml) were vigorously refluxed (oil bath temperature at 165° C. for 24 h).
(b)Heated in absence of solvent (oil bath temperature at 165° C.).
(c)Reaction performed under air.

General Procedure for the Synthesis of Cyclic Dipeptides from β-Aminoalcohols:

Complex 1 (0.02 mmol), aminoalcohol (2 mmol) and dioxane (2 mL) were added to Schlenk flask under an atmosphere of nitrogen in a glovebox. The flask was equipped with a condenser and the solution was refluxed with stirring in an open system under argon for 19 hrs. The reaction products were analyzed by GC-MS on Agilent 7820A GC coupled with 5975 MSD system. The reaction mixture was cooled; the solid obtained was filtered off, washed with hexane and dried to give the pure cyclic dipeptide.

General Procedure for the Synthesis of Pyrazines from β-Aminoalcohols:

Complex 2 (0.02 mmol), aminoalcohol (2 mmol) and toluene (2 mL) were added to Schlenk flask under an atmosphere of nitrogen in a glovebox. The flask was equipped with a condenser and the solution was refluxed with stirring under argon in an open system for the 24 hrs. The reaction products were analyzed by GC-MS on Agilent 7820A GC coupled with 5975 MSD system. The solvent was evaporated from the reaction mixture and the crude product was subjected to silica-gel column chromatography using EtOAc:hexane to afford the pyrazine derivatives.

Characterization Data of Cyclic Dipeptides (3S,6S)-3,6-diisobutylpiperazine-2,5-dione

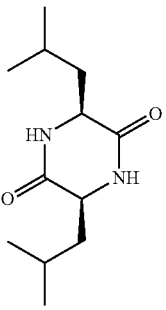 [SMILES: CC(C)C[C@@H]1NC(=O)[C@H](CC(C)C)NC1=O]

mp: 270-272° C.
$^1$H NMR (300 MHz, CD$_3$COOD): 0.84 (broad s, 12H, CH$_3$), 1.7 (broad s, 6H, CH$_2$, CH), 4.23 (broad s, 2H, NCH).
$^{13}$C{$^1$H}NMR (300 MHz, CDCl$_3$): 21.3 (CH$_3$), 21.6 (CH$_3$), 23.7 (CH$_3$), 23.8 (CH$_3$), 26.0 (CH), 26.2 (CH), 43.7 (CH$_2$), 46.4 (CH$_2$), 55.4 (NCH), 55.8 (NCH), 174.9 (C=O), 175.0 (C=O).
MS (ES$^+$, CH$_2$Cl$_2$+TFA): 227 (60%, M+H$^+$), 249 (100%, M+Na), 475 (70%, 2M+Na).

3-((R)-sec-butyl)-6-((S)-sec-butyl)piperazine-2,5-dione

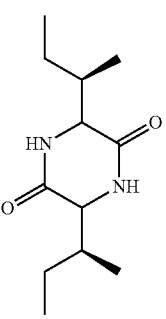 [SMILES: CC[C@@H](C)C1NC(=O)C([C@@H](C)CC)NC1=O]

mp: 276-280° C. (decompose)
$^1$H NMR (300 MHz, CDCl$_3$): 0.86-1.02 (m, 12H, CH$_3$), 1.19-1.47 (m, 4H, CH$_2$), 2.10-2.26 (m, 2H, CH$_2$), 3.91-4.07 (m, 2H, NCH), 6.11-6.31 (m, 2H, NH).
MS (ES$^+$, CH$_2$Cl$_2$+TFA): 227 (40%, M+H), 244 (100%, 249 (40%, M+Na), 467 (80%), 475 (5%, 2M+Na).

(3S,6S)-3,6-diisopropylpiperazine-2,5-dione

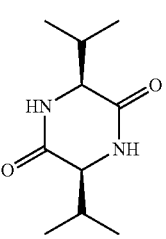

mp: 290-294° C. (decompose)
$^1$H NMR (300 MHz, CDCl$_3$ and CD$_3$COOD): 0.91 (d, J=6.6 Hz, 6H, CH$_3$), 1.01 (d, J=6.6 Hz, 6H, CH$_3$), 2.44-2.53 (m, 2H, CH), 4.11 (m, 2H, NCH).

$^{13}C\{^1H\}$NMR (300 MHz, CDCl$_3$): 15.7 (CH$_3$), 18.2 (CH$_3$), 32.3 (CH), 59.8 (NCH), 171.2 (C=O).
MS (ES$^+$, CH$_2$Cl$_2$+TFA): 199 (100%, M+H$^+$), 221 (60%, M+Na), 419 (15%, 2M+Na).
[α]=−52° (c=0.01, AcOH)

(3S,6S)-3,6-dibenzylpiperazine-2,5-dione

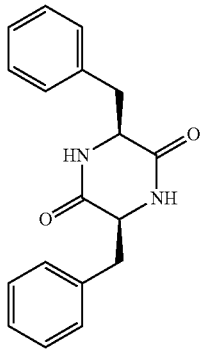 [SMILES: O=C1N[C@@H](Cc2ccccc2)C(=O)N[C@H]1Cc1ccccc1]

mp: 299-302° C. (decompose)
$^1$H NMR (300 MHz, CDCl$_3$ and CD$_3$COOD): 2.15-2.22 (m, 2H, CH$_2$), 2.95-3.01 (m, 2H, CH$_2$), 4.39-4.43 (m, 2H, NCH), 7.03 (d, J=6.9 Hz, 4H, =CH), 7.31-7.39 (m, 6H, =CH).
$^{13}C\{^1H\}$NMR (300 MHz, CD$_3$COOD): 39.6 (CH$_2$), 56.2 (NCH), 128.4 (=CH), 129.4 (=CH), 129.9 (=CH), 133.5 (quat-C), 169.9, 173.0 (C=O).
MS (ES$^+$, CH$_2$Cl$_2$+TFA): 295 (80%, M+H), 317 (100%, M+Na), 611 (60%, 2M+Na).

3,3,6,6-tetramethylpiperazine-2,5-dione

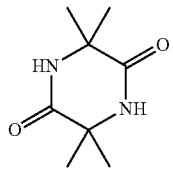

$^1$H NMR (300 MHz, DMSO-d$_6$): 1.30 (s, 12H, CH$_3$), 8.09 (s, 2H, NH).
$^{13}C\{^1H\}$NMR (300 MHz, DMSO-d$_6$): 28.6 (CH$_3$), 55.7 (quat-C), 170.2 (C=O).
MS (ES$^+$): 170 (100%, M$^+$), 192 (30%), 200 (25%).

(5aS,10aS)-octahydrodipyrrolo[1,2-a:1',2'-d]pyrazine-5,10-dione

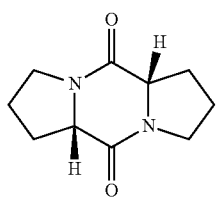 [SMILES: O=C1[C@@H]2CCCN2C(=O)[C@@H]2CCCN12]

mp: 146-148° C.
$^1$H NMR (300 MHz, CDCl$_3$): 1.88-2.33 (m, 8H, CH$_2$), 3.49-3.54 (m, 4H, NCH$_2$), 4.16 (t, 2H, NCH).

$^{13}C\{^1H\}$NMR (300 MHz, CDCl$_3$): 23.3 (CH$_2$), 27.6 (CH$_2$), 45.1 (NCH$_2$), 60.5 (NCH), 166.3 (C=O).
MS (ES): 194 (70%, M), 216 (100%, M+Na-1), 217 (10%, M+Na).

Characterization Data of Pyrazines 2,5-di-sec-butylpyrazine

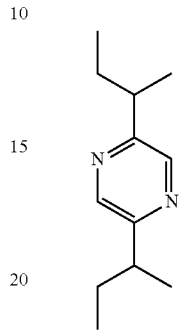

$^1$H NMR (300 MHz, CDCl$_3$): 0.77 (t, 6H, CH$_3$, J=7.2 Hz), 1.22 (d, 6H, CH$_3$, J=6.9 Hz), 1.52-1.74 (m, 4H, CH$_2$), 2.68-2.76 (m, 2H, CH), 8.27 (s, 2H, =CH).
$^{13}C\{^1H\}$NMR (300 MHz, CDCl$_3$): 11.6 (CH$_3$), 19.6 (CH$_3$), 29.3 (CH$_2$), 40.2 (CH), 142.4 (=CH), 158.1 (quat-C).

2,5-diisopropylpyrazine

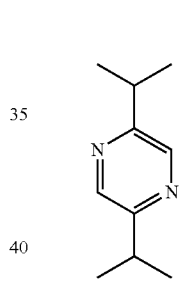

$^1$H NMR (300 MHz, CDCl$_3$): 1.23 (d, 12H, CH$_3$, J=7.2 Hz), 2.95-3.04 (m, 2H, CH), 8.30 (s, 2H, =CH).
$^{13}C\{^1H\}$NMR (300 MHz, CDCl$_3$): 21.8 (CH$_3$), 33.1 (CH), 141.4 (=CH), 158.9 (quat-C).

2,5-diisobutylpyrazine

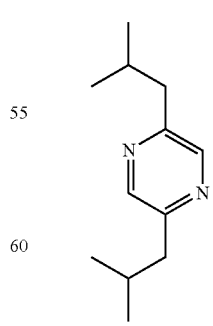

$^1$H NMR (300 MHz, CDCl$_3$): 0.94 (d, 12H, CH$_3$, J=6.6 Hz), 2.04-2.13 (m, 2H, CH), 2.63 (d, 4H, CH$_2$, J=7.2 Hz), 8.32 (s, J=6.9 Hz, 2H, =CH).

$^{13}$C{$^1$H}NMR (300 MHz, CDCl$_3$): 21.9 (CH$_3$), 28.6 (CH), 43.6 (CH$_2$), 143.5 (=CH), 153.4 (quat-C).

2,5-diphenylpyrazine

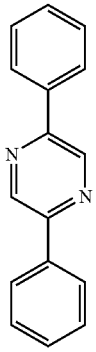 [SMILES: c1ccc(-c2cnc(-c3ccccc3)cn2)cc1]

$^1$H NMR (300 MHz, CDCl$_3$): 7.48-7.57 (m, 6H, =CH$_3$), 8.07-8.10 (m, 4H, =CH), 9.09 (s, 2H, =CH).

$^{13}$C{$^1$H}NMR (300 MHz, CDCl$_3$): 126.8 (=CH), 129.1 (=CH), 129.7 (=CH), 136.3 (quat-C), 141.2 (=CH), 150.6 (quat-C).

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

REFERENCES AND NOTES (A) References Related to Ruthenium Complexes (1) Seyden-Penne, J. *Reductions by the Alumino and Borohydrides in Organic Synthesis*; 2nd ed.; Wiley-VCH: New York, 1997.
(2) (a) Rylander, P. M. *Hydrogenation Methods*; Academic Press: London, 1985. (b) Hartwig, *J. Organotransition Metal Chemistry*; University Science Books: Sausalito, Calif., 2010; pp 651-655.
(3) (a) Hirosawa, C.; Wakasa, N.; Fuchikami, T. *Tetrahedron, Lett.* 1996, 37, 6749. (b) Núñez Magro, A. A.; Eastham, G. R.; Cole-Hamilton, D. *J. Chem. Commun.* 2007, 3154. (c) Beamson, G.; Papworth, A. J.; Philipps, C.; Smith, A. M.; Whyman, R. *Adv. Synth. Catal.* 2010, 352, 869. (d) Beamson, G.; Papworth, A. J.; Philipps, C.; Smith, A. M.; Whyman, R. *J. Catal.* 2010, 269, 93.
(4) (a) Fernandes, A. C.; Romao, C. C. *J. Mol. Catal. A.,* 2007, 272, 60. (b) Das, S.; Addis, D.; Zhou, S.; Junge, K.; Beller, M. *J. Am. Chem. Soc.* 2010, 132, 1770.
(5) Ito, M.; Koo, L. W.; Himizu, A.; Kobayashi, C.; Sakaguchi, A.; Ikariya, T. *Angew. Chem. Int. Ed.* 2009, 48, 1324.
(7) (a) Lawrence, S. A. *Amines: Synthesis, Properties and Applications*; Cambridge University Press: Cambridge, 2005. (b) Ricci, A. *Amino Group Chemistry: From Synthesis to the Life Sciences*; Wiley-VCH: Weinheim, 2008. (c) Kumara Swamy, K. C.; Bhuvan Kumar, N. N.; Balaraman, E.; Pavan Kumar, K. V. P. *Chem. Rev.* 2009, 109, 2551.
(8) (a) Zhang, J.; Gandelman, M.; Shimon, L. J. W.; Milstein, D. *Organometallics* 2004, 23, 4026. (b) Zhang, J.; Leitus, G.; Ben-David, Y.; Milstein, D. *J. Am. Chem. Soc.* 2005, 127, 10840. (c) Zhang, J.; Leitus, G.; Ben-David, Y.; Milstein, D. *Angew. Chem. Int. Ed.* 2006, 45, 1113. (d) Zhang, J.; Gandelman, M.; Shimon, L. J. W.; Milstein, D. *Dalton Trans.* 2007, 107. (e) Gunanathan, C.; Ben-David, Y.; Milstein, D. *Science* 2007, 317, 790. (f) Gnanaprakasam, B.; Zhang, J.; Milstein, D. *Angew. Chem. Int. Ed.* 2010, 49, 1. (g) Milstein, D. *Top. Catal.* 2010, 53, 915.
(9) (a) Gunanathan, C.; Shimon, L. J. W.; Milstein, D. *J. Am. Chem. Soc.* 2009, 131, 3146. (b) Gunanathan, C.; Milstein, D. *Angew. Chem. Int. Ed.* 2008, 47, 8661.
(10) Khaskin, E.; Iron, M. A.; Shimon, L. J. W.; Zhang, J.; Milstein, D. *J. Am. Chem. Soc.* 2010, 132, 8542.
(11) Kohl, S. W.; Weiner, L.; Schwartsburd, L.; Konstantinovski, L.; Shimon, L. J. W.; Ben-David, Y.; Iron, M. A.; Milstein, D. *Science* 2009, 324, 74.
(12) (a) Schubert. U.S.; Eschbaumer. C.; Heller. M. *Org. Lett.* 2000, 3373. (b) Smith. A. P.; Lamba. J. J. S.; Fraser. C. L. *Org. Synth.* 2002, 78, 82.
(13) Ahmad, N.; Levison, J. J.; Robinson, S. D.; Uttley, M. F. *Inorg. Synth.* 1974, 15, 45.
(14). Balaraman, E.; Gnanaprakasam, B.; Shimon, L. J. W.; Milstein, D. *J. Am. Chem. Soc.* 2010, 132, 16756-16758.

(B) References Relates to Formation of Amides (1) N. Sewald, H.-D. Jakubke, Peptides: *Chemistry and Biology* (Wiley-VCH, 2002).
(2a) A. Greenberg, C. M. Breneman, J. F. Liebman, *The Amide Lingkage: Selected Structural Aspects in Chemistry, Biochemistry, and Material Science* (Wiley, New York, 2000).
(2b) M. B. Smith, J. March, *Advanced Organic Chemistry* (Wiley, New York, ed. 5, 2001).
(3) B. L. Bray, *Nat. Rev.* 2, 587-93 (2003).
(4) R. C. Larock, *Comprehensive Organic Transformations* (VCH, New York, ed. 2, 1999).
(5) M. B. Smith, *Compendium of Organic Synthetic Methods* (Wiley, 2001), Vol. 9, Pp 100-116.
(6) C. J. Cobley, M. van den Heuvel, A. Abbadi, J. G. de Vries, *Tetrahedron Lett.* 41, 2467-2470 (2000).
(7) S. I. Murahashi, T. Naota, E. Saito, *J. Am. Chem. Soc.* 108, 7846-7847 (1986).
(8) S. I. Murahashi, S. Sasao, E. Saito, T. Naota, *J. Org. Chem.* 57, 2521-2523 (1992).
(9) Y. Tamaru, Y. Yamada, Z. Yoshida, *Synthesis* 1983, 474-476 (1983).
(10) A. Tillack, I. Rudloff, M. Beller, *Eur. J. Org. Chem.* 2001, 523-528 (2001).
(11) W. K. Chan, C. M, Ho, M. K. Wong, C. M. Che, *J. Am. Chem. Soc.* 128, 14796-14797 (2006).
(12) S. H. Cho, E. J. Yoo, I. Bae, S. Chang, *J. Am. Chem. Soc.* 127, 16046-16047 (2005).
(13) M. P. Cassidy, J. Raushel, V. V. Fokin, *Angew. Chem. Int. Ed.* 45, 3154-3157 (2006).
(14) Nordstrom, L. U.; Vogt, H.; Madsen, R. *J. Am. Chem. Soc.* 2008, 130, 17672
(15) Shimizu, K.; Ohshima, K.; Satsuma, A. *Chem. Eur.* 12009, 15, 9977
(16) Ghosh, S. C., Muthaia, S.; Zhang, Y.; Xu, X.; Hong, S. H; A *Adv. Synth. Catal.* 2009, 351, 2643
(17) Zweifel, T.; Naubron, J. V.; Grutzmacher, H. *Angew. Chem. Int. Ed.* 2009, 48, 559
(18) Watson, A. J. A.; Maxwell, A. C.; Williams, J. M. J. *Org. Lett.* 2009, 11, 2667.
(19) Zeng, H.; Guan, Z. *J. Am. Chem. Soc.* 2011, 133, 1159.

References Related to Borohydrides (1) a) D. G. Dick, R. Duchateau, J. H. Edema, S. Gambarotta, *Inorg. Chem.* 1993, 32, 1959-1962 and references therein; b) J. P. White III, H. Deng, S. G. Shore, *Inorg. Chem.* 1991, 30, 2337-2342.

(2) a) K. Burgess, W. A. van der Donk, *J. Am. Chem. Soc.* 1994, 116, 6561-6569; b) K. Isagawa, H. Sano, M. Hattori, Y. Otsuji, *Chem. Lett.* 1979, 1069-1072; c) H. S. Lee, I K. sagawa, Y. Otsuji, *Chem. Lett.* 1984, 363-366; d) H. S. Lee, K. Isagawa, H. Toyoda, Y. Otsuji, *Chem. Lett.* 1984, 673-676.

(3) a) D. Barbier-Baudry, O. Blacque, A. Hafid, A. Nyassi, H. Sitzmann, M. Visseaux, *Eur. J. Inorg. Chem.* 2000, 2333-2336; b) F. Bonnet, A. C. Hillier, A. Collins, S. R. Dubberley, P. Mountford, *J. Chem. Soc., Dalton Trans.* 2005, 421-423; c) T. J. Marks, J. R. Kolb, *Chem. Rev.* 1977, 77, 263-293.

(4) I. Palard, A. Soum, S. M. Guillaume, *Chem. Eur. J.* 2004, 10, 4054-4062.

(5) T. Ohkuma, M. Koizumi, K. Muniz, G. Hilt, C. Kabuto, R. Noyori, *J. Am. Chem. Soc,* 2002, 124, 6508-6509; b) C. A. Sandoval, T. Ohkuma, K. Muniz, R. Noyori, *J. Am. Chem. Soc.* 2003, 125, 13490-13503.

(6) R. Guo, X. Chen, C. Elpelt, D. Song, R Morris, *Org. Lett.* 2005, 7, 1757-1759.

(7) (a) J. A. Jensen, S. R. Wilson, G. S. Girolami, *J. Am. Chem. Soc.* 1988, 110, 4977-4982; b) J. A. Jensen, G. S. Girolami, *J. Chem. Soc., Chem. Commun.* 1986, 1160-1162.

(8) Recent reviews: a) M. E. van der Boom, D. Milstein, *Chem. Rev.* 2003, 103, 1759-1792; b) M. Albrecht, G. van Koten, *Angew. Chem. Int. Ed.* 2001, 40, 3750-3781; c) A. Vigalok, D. Milstein, *Acc. Chem. Res.* 2001, 34, 798-807; d) C. M. Jensen, *Chem. Commun.* 1999, 2443-2449; e) B. Rybtchinski, D. Milstein, *Angew. Chem. Int. Ed.* 1999, 38, 870-883.

(9) a) M. Kawatsura, J. F. Hartwig, *Organometallics* 2001, 20, 1960-1964; b) J. P. Stambuli, S. R. Shaun, K. H. Shaughnessy, J. F. Hartwig, *J. Am. Chem. Soc.,* 2001, 123, 2677-2678.

(10) D. H. Gibson, C. Pariya, M. S. Mashuta, *Organometallics* 2004, 23, 2510-2513.

(11) S. M. Kloek, M. D. Heinekey, K. I. Goldberg, *Organometallics,* 2006, 25, 3007-3011.

(12) a) D. Hermann, M. Gandelman, H. Rozenberg, L. J. W. Shimon, D. Milstein, *Organometallics* 2002, 21, 812-818; b) E. Ben-Ari, M. Gandelman, H. Rozenberg, L. J. W. Shimon, D. Milstein, *J. Am. Chem. Soc.* 2003, 125, 4714-4715; c) J. Zhang, M. Gandelman, L. J. W. Shimon, H. Rozenberg, D. Milstein, *Organometallics* 2004, 23, 4026-4033; d) J. Zhang, M. Gandelman, D. Herrman, G. Leitus, L. J. W. Shimon, Y. Ben David, D. Milstein, *Inorg. Chim. Acta* 2006, 359, 1955-1960; e) E. Ben-Ari, R. Cohen, M. Gandelman, L. J. W. Shimon, J. M. L. Martin, D. Milstein, *Organometallics* 2006, 25, 3190-3210; f) J. Zhang, G. Leitus, Y. Ben-David, D. Milstein, *Angew. Chem. Int. Ed.* 2006, 45, 1113-1115; g) M. Feller, A. Karton, G. Leitus, J. M. L. Martin, D. Milstein, *J. Am. Chem. Soc.* 2006, 127, ASAP

(13) J. Zhang, G. Leitus, Y. Ben-David, D. Milstein, *J. Am. Chem. Soc.* 2005, 127, 10840-10841.

(14) S. I. Murahashi, T. Naota, K. Ito, Y. Maeda, H. Taki, *J. Org. Chem.* 1987, 52, 4319-4327. Heating Ru(H)$_2$(PPh$_3$)$_4$ with 1-butanol at 180° C. in toluene (sealed tube) resulted in 40 turnovers of butyl butyrate after 24 hrs.

(15) a) H. B. Charman, *J. Chem. Soc. B,* 1970, 584-587; b) D. Morton, D. J. Cole-Hamilton *Chem. Comm.* 1988, 1154-1156.

(16) a) A. Dobson, S. D. Robinson, *Inorg. Chem.,* 1977, 16, 137-142; b) C. W. Jung, P. E. Garrou, *Organometallics* 1982, 1, 658-666; c) G. B. W. L. Ligthart, R. H. Meijer, M. P. Donners, J., J. Meuldijk, V. J. A. J. M. Ekemans, L. A. Hulshof, *Tetrahedron Lett.* 2003, 44, 1507-1509.

(17) (a) S. Shinoda, T. Kojima, Y. Saito, *J. Mol. Cat.,* 1983, 18, 99-104; (b) T. Matsubara, Y. Saito, *J. Mol. Cat.,* 1994, 92, 1-8.

(18) G. R. A. Adair and J. M. J. Williams, *Tetrahedron Lett.* 2005, 46, 8233-8235.

(19) Y. Lin, D. Ma, X. Lu, *Tetrahedron Lett.,* 1987, 28, 3115-3118.

(20) Y. Blum, Y. Shvo, *J. Organomet. Chem.* 1985, 282, C7-C10; Yields and reaction times were not reported.

(21) Homogeneous catalytic dehydrogenative lactonization of diols: (a) Y. Lin, X. Zhu, Y. Zhou, *J. Organometal. Chem.* 1992, 429, 269-274; Attempted use of primary alcohols resulted in no catalysis (b) J. Zhao, J. F. Hartwig, *Organometallics* 2005, 24, 2441

(22) a) J. A. Statler, G. Wilkinson, M. Thornton-Pett, M. B. Hursthousee, *J. Chem. Soc., Dalton Trans.* 1984, 1731-1738; b) J. B. Letts, T. J. Mazanec, D. W. Meek, *J. Am. Chem. Soc.* 1982, 104, 3898-3905.

(23) G. Jia, H. M. Lee, I. D. Williams, C.-P. Lau, Y. Chen, *Organometallics* 1997, 16, 3941-3949.

(24) a) R. Pierantozzi, G. L. Geoffroy, *Inorg. Chem.* 1980, 19, 1821-1822; b) G. Geoffroy, L. R. Pierantozzi, *J. Am. Chem. Soc.* 1976, 98, 8054-8059.

(25) N. Menashe, Y. Shvo, *Organometallics* 1991, 10, 3885-3891.

(26) T. Ito, H. Horino, Y. Koshiro, A. Yamamoto, *Bull. Chem. Soc. Jpn.* 1982, 55, 504-512.

(27) A. Jansen, S. Pitter, *Monatsch. Chem.* 1999, 130, 783-794.

(28) R. Holm, *Inorg. Synth.* 1970, 12, 238-240.

What is claimed is:

1. A Ruthenium complex represented by the structure of any of formulae B1, B2 or A3:

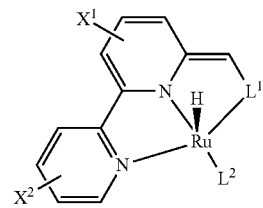

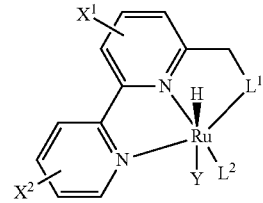

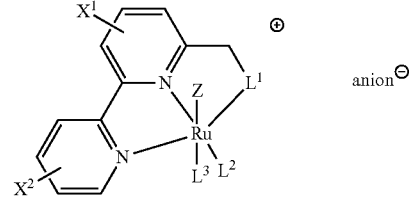

wherein

L$^1$ is selected from the group consisting of phosphine (PR$^a$R$^b$), phosphite P(OR$^a$)(OR$^b$), phosphinite P(OR$^a$)(R$^b$), amine (NR$^a$R$^b$), imine, oxazoline, sulfide (SR$^a$), sulfoxide (S(=O)R$^a$), heteroaryl containing at least one heteroatom selected from nitrogen and sulfur; arsine (AsR$^a$R$^b$), stibine (SbR$^a$R$^b$) and a N-heterocyclic carbene represented by the structures:

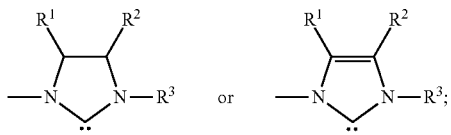

L$^2$ is a mono-dentate two-electron donor selected from the group consisting of CO, PR$^a$R$^b$R$^c$, P(OR$^a$)(OR$^b$)(OR$^c$), NO$^+$, AsR$^a$R$^b$R$^c$, SbR$^a$R$^b$R$^c$, SR$^a$R$^b$, nitrile (RCN), isonitrile (RNC), N$_2$, PF$_3$, CS, heteroaryl, tetrahydrothiophene, alkene and alkyne;

L$^3$ is absent or is L$^2$;

Y and Z are each independently H or an anionic ligand selected from the group consisting of H, halogen, OCOR, OCOCF$_3$, OSO$_2$R, OSO$_2$CF$_3$, CN, OR, N(R)$_2$ and RS;

R$^a$, R$^b$ and R$^c$ are each independently alkyl, cycloalkyl, aryl, heterocyclyl, heteroaryl, alkylcycloalkyl, alkylaryl, alkylheterocyclyl or alkylheteroaryl;

R, R$^1$, R$^2$ and R$^3$ are each independently H, alkyl, cycloalkyl, aryl, heterocyclyl, heteroaryl, alkylcycloalkyl, alkylaryl, alkylheterocyclyl or alkylheteroaryl;

X$^1$ represents zero, one, two or three substituents and X$^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; and anion represents a group bearing a single negative charge; or a borane derivative of said catalyst.

2. The complex according to claim 1,
wherein X$^1$ and X$^2$ are each absent, and the bipyridine moiety is unsubstituted; or
wherein L$^1$ is phosphine (PR$^a$R$^b$); or
wherein L$^2$ is CO; or
wherein Z and Y are H or halogen.

3. The Ruthenium complex according to claim 1, wherein the catalyst is represented by formula C1:

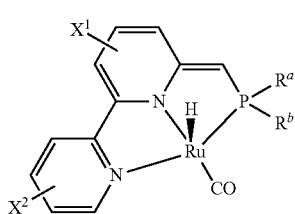

wherein each of X$^1$, X$^2$ R$^a$ and R$^b$ are as defined in claim 1.

4. The Ruthenium complex according to claim 1, wherein the catalyst is represented by formula C2:

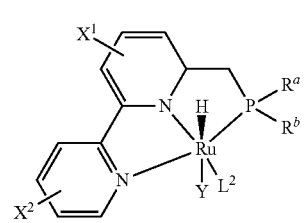

wherein each of X$^1$, X$^2$, Y, R$^a$ and R$^b$ are as defined in claim 1.

5. The Ruthenium complex according to claim 4,
wherein Y is halogen; or
wherein L$^2$ is CO; or
wherein the Ruthenium complex is represented by the structure of formulae 4, 7 or 9:

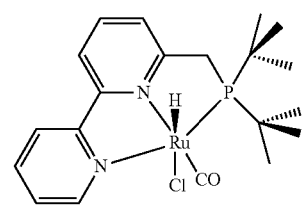

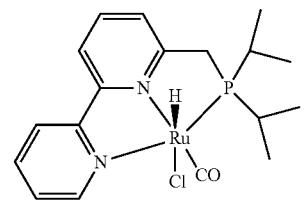

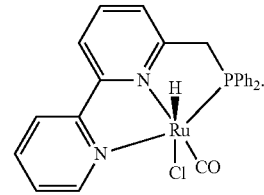

6. A borane derivative of the complex of formula A1 according to claim 1, wherein the borane derivative is represented by the structure of formula D, E or 8':

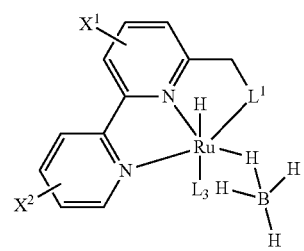

wherein L$^1$, X$^1$ and X$^2$ are as defined in claim 1;

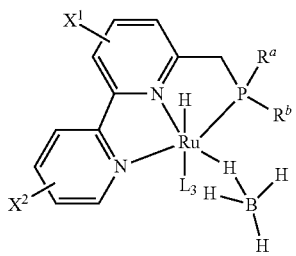

wherein each of $X^1$, $X^2$, $R^a$ and $R^b$ is as defined in claim 1;

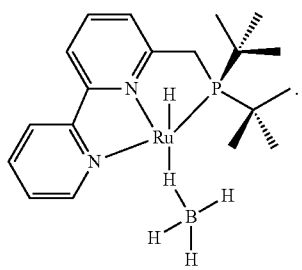

7. A process for hydrogenating an amide to an alcohol and an amine, comprising the step of reacting the amide with molecular hydrogen ($H_2$) in the presence of the Ruthenium complex according to claim 1 wherein the process comprises the step of hydrogenating an amide represented by the formula $R^4C(=O)-N-R^5R^{5'}$ to an alcohol of formula $R^4CH_2OH$ and amine of formula $R^5R^{5'}NH$:

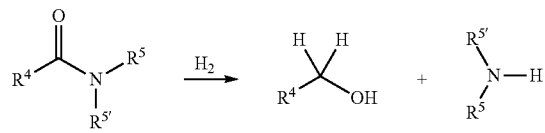

wherein $R^4$, $R^5$ and $R^{5'}$ are each independently selected from the group consisting of H, an unsubstituted or substituted alkyl, alkoxyalkyl, cycloalkyl, aryl, alkylaryl, heterocyclyl and heteroaryl.

8. A process for hydrogenating an ester, organic carbonate, carbamate or urea derivative, comprising the step of reacting the ester, organic carbonate, carbamate or urea derivative with molecular hydrogen (H2) in the presence of the Ruthenium complex according to claim 1, thereby hydrogenating the ester, organic carbonate, carbamate or urea derivative and generating at least one alcohol, amine or combination thereof.

9. The process of claim 8, comprising the step of hydrogenating an ester represented by the formula $R^6C(=O)-OR^7$ to the corresponding alcohol or alcohols:

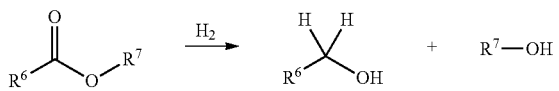

wherein
$R^6$ is selected from the group consisting of H, an unsubstituted or substituted alkyl, alkoxyalkyl, cycloalkyl, aryl, alkylaryl, heterocyclyl and heteroaryl; and $R^7$ is selected from the group consisting of an unsubstituted or substituted alkyl, alkoxyalkyl, cycloalkyl, aryl, alkylaryl, heterocyclyl and heteroaryl.

10. A process for preparing an amide, comprising the step of reacting a primary or secondary amine with a primary alcohol in the presence of the Ruthenium complex according to claim 1, thereby generating the amide and molecular hydrogen,
wherein said process comprises reacting an amine represented by formula $R^{11}R^{11'}NH$ with an alcohol represented by the formula $R^{12}CH_2OH$ to generate an amide represented by the structure $R^{12}-C(=O)-NR^{11}R^{11'}$:

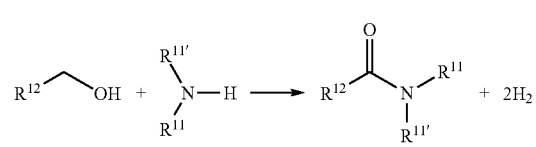

wherein $R^{10}$, $R^{11}$ and $R^{12}$ are each independently selected from the group consisting of H an unsubstituted or substituted alkyl, alkoxyalkyl, cycloalkyl, aryl, alkylaryl, heterocyclyl and heteroaryl.

11. A process for preparing a pyrazine, comprising the step of reacting a beta-amino alcohol with a Ruthenium complex according to claim 1, wherein $L^1$ is selected from a phosphine ($PR^aR^b$), and a N-heterocyclic carbene represented by the structures:

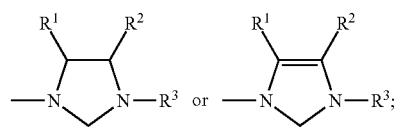

wherein $R^1$, $R^2$, $R^3$, $R^a$ and $R^b$ are as defined in claim 1.

12. A process for preparing an ester by dehydrogenative coupling of primary alcohols, comprising the step of reacting a primary alcohol or a combination of primary alcohols in the presence of the Ruthenium complex according to claim 1, thereby generating the ester and molecular hydrogen,
wherein the process comprises the step of converting a primary alcohol represented by formula $R^{13}CH_2OH$ to an ester by the structure $R^{13}-C(=O)-OCH_2R^{13}$:

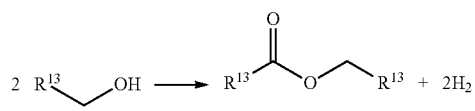

wherein $R^{13}$ is selected from the group consisting of H, an unsubstituted or substituted alkyl, alkoxyalkyl, cycloalkyl, aryl, alkylaryl, heterocyclyl and heteroaryl; or
wherein the process comprises the steps of reacting a first primary alcohol represented by formula $R^{13}CH_2OH$ with a second alcohol represented by formula $R^{13'}CH_2OH$ so as to generate an ester by the structure $R^{13}-C(=O)-OCH_2R^{13'}$ or an ester of formula $R^{13'}-C(=O)-OCH_2R^{13}$

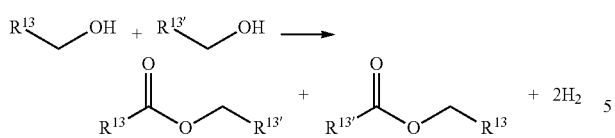

wherein $R^{13}$ and $R^{13'}$ are the same or different from each other and are each independently selected is from the group consisting of H, an unsubstituted or substituted alkyl, alkoxyalkyl, cycloalkyl, aryl, alkylaryl, heterocyclyl and heteroaryl.

13. A process for preparing an ester by dehydrogenative coupling of a primary alcohol and a secondary alcohol comprising the step of reacting the primary and secondary alcohol in the presence of the Ruthenium complex according claim 1, thereby generating the ester and molecular hydrogen, wherein the process comprises the step of reacting a primary alcohol represented by formula $R^{13}CH_2OH$ with a secondary alcohol of formula $R^{13'}R^{13''}CHOH$ so as to generate an ester by the structure $R^{13}-C(=O)-OCHR^{13'}R^{13''}$:

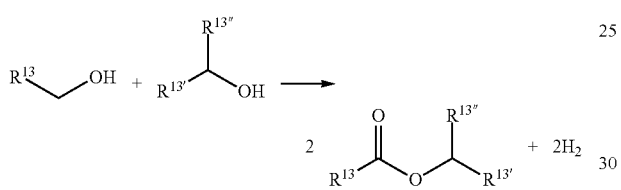

wherein $R^{13}$, $R^{13'}$ and $R^{13''}$ are each independently selected from the group consisting of H, an unsubstituted or substituted alkyl, alkoxyalkyl, cycloalkyl, aryl, alkylaryl, heterocyclyl and heteroaryl.

14. A process for preparing a ketone by dehydrogenation of a secondary alcohol, comprising the step of reacting the secondary alcohol in the presence of the Ruthenium complex according to claim 1, thereby generating the ester and molecular hydrogen, wherein the process comprises the step of converting a secondary alcohol represented by formula $R^{14}CH(OH)R^{14'}$ to a ketone represented by the structure $R^{14}-C(=O)-R^{14'}$:

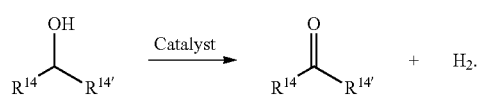

15. A process for preparing an amide, comprising the step of reacting a primary or secondary amine with an ester in the presence of the Ruthenium complex according to claim 1, thereby generating the amide and molecular hydrogen, wherein the process comprises the step of reacting an amine represented by formula $R^{15}R^{15'}NH$ with an ester represented by the formula $R^{16}-C(=O)-OCH_2R^{16'}$ to generate an amide represented by the structure $R^{16}-C(=O)-NR^{15}R^{15'}$:

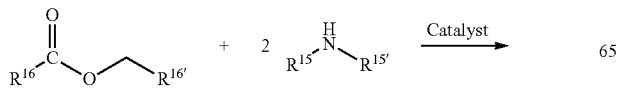

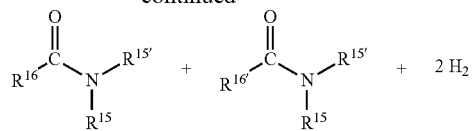

wherein $R^{15}$, $R^{15'}$, $R^{16}$ and $R^{16'}$ are each independently selected from the group consisting of H, an unsubstituted or substituted alkyl, alkoxyalkyl, cycloalkyl, aryl, alkylaryl, heterocyclyl and heteroaryl.

16. A process for modifying an ester by reacting a primary or secondary alcohol with an ester in the presence of the Ruthenium complex according to claim 1, thereby generating the ester and molecular hydrogen, wherein the process comprises the step of reacting a primary or secondary alcohol represented by formula $R^{17}R^{17'}CHOH$ with an ester by the structure $R^{18}-C(=O)-OCH_2R^{18'}$:

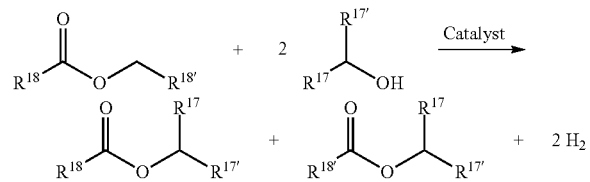

wherein $R^{17}$, $R^{17'}$, $R^{18}$ and $R^{18'}$ are each independently selected from the group consisting of H, an unsubstituted or substituted alkyl, alkoxyalkyl, cycloalkyl, aryl, alkylaryl, heterocyclyl and heteroaryl.

17. A process for preparing a carboxylic acid comprising the step of reacting a primary alcohol with water and a base in the presence of the Ruthenium complex according to claim 1, thereby generating the carboxylic acid and molecular hydrogen, wherein the process comprises the step of reacting a primary alcohol represented by formula $R^{17}CH_2OH$ with water in the presence of a base so as to generate a carboxylic acid salt represented by the structure $R^{17}-C(=O)O^-$ and, optionally, if desired, converting the carboxylic acid salt to the corresponding carboxylic acid of formula $R^{17}-C(=O)OH$.

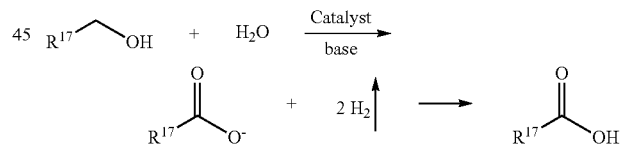

wherein $R^{17}$ is selected from the group consisting of H, an unsubstituted or substituted alkyl, alkoxyalkyl, cycloalkyl, aryl, alkylaryl, heterocyclyl and heteroaryl.

18. A process for preparing a Ruthenium complex represented by the structure of formula D according to claim 6,

D

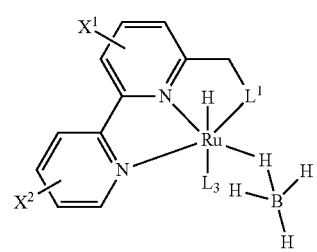

the process comprising the step of reacting sodium borohydride (NaBH$_4$) with a precursor of formula A2

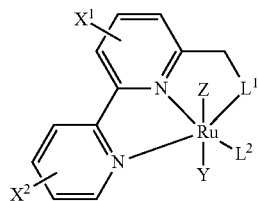

A2 wherein
L$^1$ is selected from the group consisting of phosphine (PR$^a$R$^b$), phosphite P(OR$^a$)(OR$^b$), phosphinite P(OR$^a$)(R$^b$), amine (NR$^a$R$^b$), imine, oxazoline, sulfide (SR$^a$), sulfoxide (S(=O)R$^a$), heteroaryl containing at least one heteroatom selected from nitrogen and sulfur; arsine (AsR$^a$R$^b$), stibine (SbR$^a$R$^b$) and a N-heterocyclic carbene represented by the structures:

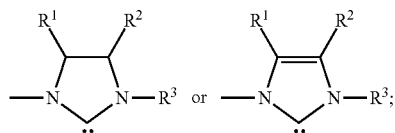

L$^2$ is a mono-dentate two-electron donor selected from the group consisting of CO, PR$^a$R$^b$R$^c$, P(OR$^a$)(OR$^b$)(OR$^c$), NO$^+$, AsR$^a$R$^b$R$^c$, SbR$^a$R$^b$R$^c$, SR$^a$R$^b$, nitrile (RCN), isonitrile (RNC), N$_2$, PF$_3$, CS, heteroaryl, tetrahydrothiophene, alkene and alkyne;

L$^3$ is absent or is L$^2$;

Y and Z are each independently halogen, OCOCF$_3$, OSO$_2$R or OSO$_2$CF$_3$,

R$^a$, R$^b$ and R$^e$ are each independently alkyl, cycloalkyl, aryl, heterocyclyl, heteroaryl, alkylcycloalkyl, alkylaryl, alkylheterocyclyl or alkylheteroaryl;

R, R$^1$, R$^2$ and R$^3$ are each independently H, alkyl, cycloalkyl, aryl, heterocyclyl, heteroaryl, alkylcycloalkyl, alkylaryl, alkylheterocyclyl or alkylheteroaryl; and X$^1$ represents zero, one, two or three substituents and X$^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety.

19. A method for preparing the Ruthenium complex according to claim 1, which comprises reacting a Ruthenium reagent with a compound represented by the structure of formula Z:

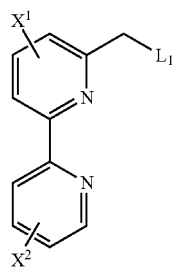

Z wherein L$^1$ is selected from the group consisting of phosphine (PR$^a$R$^b$), phosphite P(OR$^a$)(OR$^b$), phosphinite P(OR$^a$)(R$^b$), amine (NR$^a$R$^b$), imine, oxazoline, sulfide (SR$^a$), sulfoxide (S(=O)R$^a$), heteroaryl containing at least one heteroatom selected from nitrogen and sulfur; arsine (AsR$^a$R$^b$), stibine (SbR$^a$R$^b$) and a N-heterocyclic carbene represented by the structures:

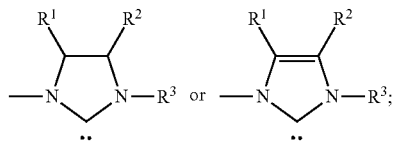

X$^1$ represents zero, one, two or three substituents and X$^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; and R$^a$ and R$^b$ are each independently alkyl, cycloalkyl, aryl, heterocyclyl, heteroaryl, alkylcycloalkyl, alkylaryl, alkylheterocyclyl or alkylheteroaryl.

20. The method of claim 19, wherein compound Z is selected from the group consisting of:

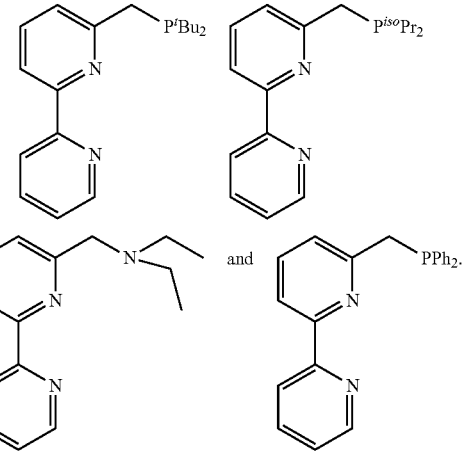

21. A Ruthenium complex represented by the structure of formula 3:

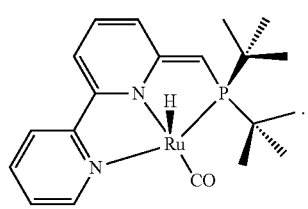

3

* * * * *

UNITED STATES PATENT AND TRADEMARK OFFICE
CERTIFICATE OF CORRECTION

PATENT NO.         : 9,045,381 B2                                  Page 1 of 1
APPLICATION NO.    : 13/880328
DATED              : June 2, 2015
INVENTOR(S)        : Milstein et al.

It is certified that error appears in the above-identified patent and that said Letters Patent is hereby corrected as shown below:

In the Claims

Column 143:
Line 67, after "wherein each of $X^1$,", delete "$X^2$ $R^a$" and insert -- $X^2$, $R^a$ --.

Column 149:
Line 34, after "$R^a$, $R^b$ and", delete "$R^e$" and insert -- $R^c$ --.

Signed and Sealed this
Twenty-ninth Day of September, 2015

Michelle K. Lee
*Director of the United States Patent and Trademark Office*